(12) United States Patent
Pei et al.

(10) Patent No.: US 11,576,946 B2
(45) Date of Patent: Feb. 14, 2023

(54) PEPTIDYL INHIBITORS OF CALCINEURIN-NFAT INTERACTION

(71) Applicant: Ohio State Innovation Foundation, Columbus, OH (US)

(72) Inventors: Dehua Pei, Columbus, OH (US); John W. Christman, Columbus, OH (US); Manjula Karpurapu, Columbus, OH (US); Patrick G. Dougherty, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/965,718

(22) PCT Filed: Jan. 29, 2019

(86) PCT No.: PCT/US2019/015695
§ 371 (c)(1),
(2) Date: Jul. 29, 2020

(87) PCT Pub. No.: WO2019/148194
PCT Pub. Date: Aug. 1, 2019

(65) Prior Publication Data
US 2021/0169966 A1 Jun. 10, 2021

Related U.S. Application Data

(60) Provisional application No. 62/623,235, filed on Jan. 29, 2018.

(51) Int. Cl.
*A61K 38/08* (2019.01)
*A61K 47/64* (2017.01)
*A61P 11/00* (2006.01)

(52) U.S. Cl.
CPC .............. *A61K 38/08* (2013.01); *A61K 47/64* (2017.08); *A61P 11/00* (2018.01)

(58) Field of Classification Search
CPC .................................. A61K 38/08; A61K 47/64
See application file for complete search history.

(56) References Cited

U.S. PATENT DOCUMENTS

| | | |
|---|---|---|
| 5,579,250 A | 11/1996 | Balaji et al. |
| 5,612,895 A | 3/1997 | Balaji et al. |
| 5,631,280 A | 5/1997 | Goldstein et al. |
| 5,965,536 A | 10/1999 | Cohen et al. |
| 6,110,889 A | 8/2000 | Miller et al. |
| 6,251,854 B1 | 6/2001 | Montal et al. |
| 6,355,619 B1 | 3/2002 | Miller et al. |
| 6,593,292 B1 | 7/2003 | Rothbard et al. |
| 6,605,115 B1 | 8/2003 | Cooke et al. |
| 6,649,587 B1 | 11/2003 | Frydman et al. |
| 6,669,951 B2 | 12/2003 | Rothbard et al. |
| 6,730,293 B1 | 5/2004 | Rothbard et al. |
| 6,759,387 B2 | 7/2004 | Rothbard et al. |
| 6,794,545 B1 | 9/2004 | Frydman et al. |
| 6,809,176 B2 | 10/2004 | Blokhin et al. |
| 6,960,648 B2 | 11/2005 | Bonny |
| 6,982,351 B2 | 1/2006 | Frydman et al. |
| 7,026,347 B2 | 4/2006 | Frydman et al. |
| 7,084,241 B2 | 8/2006 | Hogan et al. |
| 7,169,814 B2 | 1/2007 | Rothbard et al. |
| 7,186,825 B2 | 3/2007 | Frydman et al. |
| 7,229,961 B2 | 6/2007 | Rothbard et al. |
| 7,253,207 B2 | 8/2007 | Blokhin et al. |
| 7,279,502 B2 | 10/2007 | Clifford et al. |

(Continued)

FOREIGN PATENT DOCUMENTS

| | | |
|---|---|---|
| CA | 2417064 | 2/2002 |
| CA | 2455951 | 2/2003 |

(Continued)

OTHER PUBLICATIONS

International Search Report and Written Opinion issued by the International Searching Authority (ISA/US) in PCT Application No. PCT/US2019/015695 dated Jul. 25, 2019. 14 pages.
Qian, Ziqing, et al. "Structure-based optimization of a peptidyl inhibitor against calcineurin-nuclear factor of activated T cell (NFAT) interaction." Journal of medicinal chemistry 57.18 (2014): 7792-7797.
GenBank: AEV23320.1. "Beta-fibrinogen, partial [Boana albopunctata]." Feb. 13, 2012. https://www.ncbi.nlm.nih.gov/protein/AEV23320.1?report=genbank&log$=protalign&blast_rank=3&RID=FMTADBYS014. 1 page.
Alonso, A et al., Protein tyrosine phosphatases in the human genome, Cell, Jun. 2004, 117(6):699-711.
Andaloussi, S. E. L. et al., "Design of a peptide-based vector, PepFect6, for efficient delivery of siRNA in cell culture and systemically in vivo," Nucleic Acids Research, May 2011, 39(9):3972-3987.

(Continued)

*Primary Examiner* — Amber D Steele
(74) *Attorney, Agent, or Firm* — Meunier Carlin & Curfman LLC

(57) ABSTRACT

Described are peptides and peptide conjugates comprising CN binding motifs (CNBM) which inhibit the CN-NFAT interaction. In some embodiments, the peptides comprise: (i) CNBM; (ii) a hydrophobic, non-peptidic moiety (RH) which interacts with the hydrophobic pocket on a CN protein; (iii) a sequence -AAU1-AAU2-AAU3-AAU4-AAU5-AAU6-, wherein each of AAU2, AAU3, AAU4, AAU5, and AAU6, is, independently, optional, and each of AAU1, AAU2, AAU3, AAU4, AAU5, and AAU6 when present is independently an amino acid as defined herein; or (iv) combinations thereof. In some embodiments, RH is conjugated to the N- or C-terminus of the CNBM. In some embodiments, the sequence -AAU1-AAU2-AAU3-AAU4-AAU5-AAU6- is conjugated to the N- or C terminus of the CNBM. In some embodiments, the peptides comprise: CNBM and RH. In some embodiments. In some embodiments, the peptides comprise: CNBM and AAU1-AAU2-AAU3-AAU4-AAU5-AAU6-. In some embodiments, the peptides of the disclosure CNBM and RH.

21 Claims, 31 Drawing Sheets

Specification includes a Sequence Listing.

(56) References Cited

U.S. PATENT DOCUMENTS

| | | |
|---|---|---|
| 7,312,244 B2 | 12/2007 | Clifford et al. |
| 7,585,834 B2 | 9/2009 | Wender et al. |
| 7,816,490 B2 | 10/2010 | Hogan et al. |
| 8,614,290 B2 | 12/2013 | Wester et al. |
| 8,628,750 B2 | 1/2014 | Wester et al. |
| 8,629,112 B2 | 1/2014 | Gombert et al. |
| 9,169,290 B2 | 10/2015 | O'Neil |
| 10,626,147 B2 | 4/2020 | Pei et al. |
| 2002/0009491 A1 | 1/2002 | Rothbard et al. |
| 2002/0035243 A1 | 3/2002 | Imfeld et al. |
| 2002/0120100 A1 | 8/2002 | Bonny |
| 2002/0127198 A1 | 9/2002 | Rothbard et al. |
| 2003/0022831 A1 | 1/2003 | Rothbard et al. |
| 2003/0032593 A1 | 2/2003 | Wender et al. |
| 2003/0032594 A1 | 2/2003 | Bonny |
| 2003/0072715 A1 | 4/2003 | Frydman et al. |
| 2003/0130356 A1 | 7/2003 | Frydman et al. |
| 2003/0167129 A1 | 9/2003 | Nestor et al. |
| 2004/0002117 A1 | 1/2004 | Hogan et al. |
| 2004/0152687 A1 | 8/2004 | Frydman et al. |
| 2004/0192665 A1 | 9/2004 | Frydman et al. |
| 2004/0248783 A1 | 12/2004 | Kawabe et al. |
| 2005/0192210 A1 | 9/2005 | Rothbard et al. |
| 2006/0128614 A1 | 6/2006 | Cheng et al. |
| 2006/0141514 A1 | 6/2006 | Rozzelle et al. |
| 2007/0093427 A1 | 4/2007 | Matsui et al. |
| 2012/0045393 A1 | 2/2012 | Linder et al. |
| 2014/0303071 A1 | 10/2014 | O'Neil |
| 2015/0038671 A1 | 2/2015 | Parang et al. |
| 2015/0284455 A1 | 10/2015 | Springer et al. |
| 2016/0031941 A1 | 2/2016 | Eckert et al. |
| 2017/0112896 A1 | 4/2017 | Briesewitz |
| 2017/0190743 A1 | 7/2017 | Pei et al. |
| 2017/0281723 A1 | 10/2017 | Pei et al. |
| 2017/0304383 A1 | 10/2017 | Briesewitz et al. |
| 2017/0355730 A1 | 12/2017 | Pei et al. |
| 2019/0282654 A1 | 9/2019 | Pei et al. |
| 2019/0309020 A1 | 10/2019 | Pei et al. |

FOREIGN PATENT DOCUMENTS

| | | |
|---|---|---|
| CN | 105440105 | 3/2016 |
| EP | 1185493 | 7/2005 |
| EP | 1574507 | 9/2005 |
| JP | 3791981 | 6/2006 |
| JP | 2016065018 | 4/2016 |
| WO | 1999/021877 | 5/1999 |
| WO | 2000/011022 | 3/2000 |
| WO | 2001/013957 | 3/2001 |
| WO | 2002/057313 | 7/2002 |
| WO | 2002/064091 | 8/2002 |
| WO | 2002/067917 | 9/2002 |
| WO | 2002/090503 | 11/2002 |
| WO | 2003/059942 | 7/2003 |
| WO | 2003/070755 | 8/2003 |
| WO | 2003/092631 | 11/2003 |
| WO | 2003/092632 | 11/2003 |
| WO | 2004/050685 | 6/2004 |
| WO | 2006/041805 | 4/2006 |
| WO | 2006/058436 | 6/2006 |
| WO | 2006/086773 | 8/2006 |
| WO | 2007/040535 | 4/2007 |
| WO | 2007/055578 | 5/2007 |
| WO | 2007/070372 | 6/2007 |
| WO | 2007/072037 | 6/2007 |
| WO | 2007/096662 | 8/2007 |
| WO | 2007/106554 | 9/2007 |
| WO | 2007/108749 | 9/2007 |
| WO | 2007/111993 | 10/2007 |
| WO | 2008/077194 | 7/2008 |
| WO | 2009/027706 | 3/2009 |
| WO | 2009/092062 | 7/2009 |
| WO | 2010/045335 | 4/2010 |
| WO | 2010/107832 | 9/2010 |
| WO | 2011/095218 | 8/2011 |
| WO | 2011/095607 | 8/2011 |
| WO | 2013/142184 | 9/2013 |
| WO | 2014/053629 | 4/2014 |
| WO | 2015/179691 | 11/2015 |
| WO | 2016/033368 | 3/2016 |
| WO | 2016/044683 | 3/2016 |
| WO | WO 2016/033368 | * 3/2016 ............ A61K 38/03 |
| WO | 2018/089648 | 5/2018 |
| WO | 2018/098231 | 5/2018 |

OTHER PUBLICATIONS

Anderl, J. et al., "Chemical modification allows phallotoxins and amatoxins to be used as tools in cell biology," Beilstein Journal of Organic Chemistry, 2012, 8(233):2072-2084.

Appelbaum, J. S. et al., "Arginine Topology Controls Escape of Minimally Cationic Proteins from Early Endosomes to the Cytoplasm," Chemistry & Biology, Jul. 2012, 19:819-830.

Aramburu, J.; et al., "Affinity-driven peptide selection of an NFAT inhibitor more selective than cyclosporine A." Science 1999, 285, 2129-2133.

Aramburu, J.; et al., "Selective inhibition of NFAT activation by a peptide spanning the calcineurin targeting site of NFAT." Mol. Cell 1998, 1, 627-637.

Birts, C. N. et al., "A cyclic peptide inhibitor of C-terminal binding protein dimerization links metabolism with mitotic fidelity in breast cancer cells," Chem. Sci. 2013, 4, 3046-3057.

Bold, G.; et al., "New aza-dipeptide analogues as potent and orally absorbed HIV-1 protease inhibitors: candidates for clinical development." J. Med. Chem. 1998, 41, 3387-3401. abstract.

Bolte, S. et al., "A guided tour into subcellular colocalization analysis in light microscopy," J. Microsc., Dec. 2006, 224(Pt. 3), 213-232.

Burke, T.R. Jr. et al., "Potent Inhibition of Insulin Receptor Dephosphorylation by a Hexamer Peptide Containing the Phosphotyrosyl Mimetic F2Pmp," Biochem. Biophys. Res. Commun., Oct. 1994, 204(1):129-134.

Carpenter, A. E. et al., "CellProfiler: image analysis software for identifying and quantifying cell phenotypes," Genome Biology, 2006, 7:R100, 11 pages.

Cascales, L. et al., "Identification and Characterization of a New Family of Cell-Penetrating Peptides," J. Biol. Chem., Oct. 2011, 286(42):36932-36943.

Chapman, J. R. "Chronic calcineurin inhibitor nephrotoxicity—lest we forget." Am. J. Transplant 2011, 11, 693-697.

Chatterjee, J. et al., "N-Methylation of Peptides: A New Perspective in Medicinal Chemistry," Acc. Chem. Res., 2008, 41(10):1331-1342.

Chen, X. et al., "On-Bead Screening of Combinatorial Libraries: Reduction of Nonspecific Binding by Decreasing Surface Ligand Density," J. Comb. Chem. 2009, 11(4):604-611.

Cheng, S. H. et al., "Defective intracellular transport and processing of CFTR is the molecular basis of most cystic fibrosis," Cell, Nov. 1990, 63(4):827-834.

Chierici, S.; et al., "A case study of 2,2-dimethylthiazolidine as locked cis proline amide bond: synthesis, NMR and molecular modeling studies of a δ-conotoxin EVIA peptide analog." Org. Biomol. Chem. 2004, 2, 2436-2441.

Choi et al. "Cell permeable NFAT inhibitory peptide Sim-2-VIVIT inhibits sT-cell activation and alleviates allergic airways inflammation and hyper-responsiveness", Immunology Letters 143:2, 2012, pp. 170-176.

Cooley, C. B. et al., "Oligocarbonate Molecular Transporters: Oligomerization-Based Syntheses and Cell-Penetrating Studies," J. Am. Chem. Soc., 2009, 131(45):16401-16403.

Crabtree, G. R. "Generic signals and specific outcomes: signaling through $Ca^{2+}$, calcineurin, and NF-AT." Cell 1999, 96, 611-614.

Cushing, P. R. et al., "A Stabilizing Influence: CAL PDZ Inhibition Extends the Half-Life of L1F508-CFTR," Angew. Chem. Int. Ed., Dec. 2010, 49(51):9907-9911.

Cushing, P. R. et al., "The Relative Binding Affinities of PDZ Partners for CFTR: A Biochemical Basis for Efficient Endocytic Recycling," Biochemistry, 2008, 47(38): 10084-10098.

(56) References Cited

OTHER PUBLICATIONS

Davies, S. J.; et al., "Structure-activity relationships of the peptide deformylase inhibitor BB-3497: modification of the P2' and P3' side chains." Bioorg. Med. Chem. Lett. 2003, 13, 2715-2718.

Depaul, A. J.; et al., "Equilibrium conformational dynamics in an RNA tetraloop from massively parallel molecular dynamics." Nucleic Acids Res. 2010, 38, 4856-4867.

Deshayes, S. et al., "Cell-penetrating peptides: tools for intracellular delivery of therapeutics," Cell. Mol. Life Sci., Aug. 2005, 62(16):1839-1849.

Dewan, V. et al., "Cyclic Peptide Inhibitors of HIV-1 Capsid-Human Lysyl-tRNA Synthetase Interaction," ACS Chem. Biol., 2012, 7(4):761-769.

Doyle, D. A et al., "Crystal Structures of a Complexed and Peptide-Free Membrane Protein-Binding Domain: Molecular Basis of Peptide Recognition by PDZ," Cell, Jun. 1996, 85(7):1067-1076.

Driggers, E. M. et al., "The exploration of macrocycles for drug discovery—an underexploited structural class," Nat. Rev. Drug Discov., Jul. 2008, 7:608-624.

Duchardt, F. et al., "A Cell-penetrating Peptide Derived from Human Lactoferrin with Conformation-dependent Uptake Efficiency," J. Biol. Chem., Dec. 2009, 284(52):36099-36108.

Duchardt, F. et al., "A Comprehensive Model for the Cellular Uptake of Cationic Cell-penetrating Peptides," Traffic, Jul. 2007, 8(7):848-866.

Dumy, P.; et al., "Pseudo-prolines as a molecular hinge: reversible induction of cis amide bonds into peptide backbones." J. Am. Chem. Soc. 1997, 119, 918-925.

Eguchi, A. et al., "Protein Transduction Domain of HIV-1 Tat Protein Promotes Efficient Delivery of DNA into Mammalian Cells," J. Biol. Chem., Jul. 2001, 276:26204-26210.

Eichler, J. et al., "Novel a-glucosidase inhibitors identified using multiple cyclic peptide combinatorial libraries," Molecular Diversity, Aug. 1996, 1(4):233-240.

Eisenberg, David, Robert M. Weiss, and Thomas C. Terwilliger. "The hydrophobic moment detects periodicity in protein hydrophobicity." Proceedings of the National Academy of Sciences 81.1 (1984): 140-144.

Elchelby, M. et al., "Increased insulin sensitivity and obesity resistance in mice lacking the protein tyrosine phosphatase-18 gene," Science, Mar. 1999, 283(5407):1544-1548.

El-Sayed, A et al., "Delivery of Macromolecules Using Arginine-Rich Cell-Penetrating Peptides: Ways to Overcome Endosomal Entrapment," The AAPS Journal, Mar. 2009, 11(1):13-22.

Engelman, D. M., T. A. Steitz, and A. Goldman. "Identifying nonpolar trans bilayer helices in amino acid sequences of membrane proteins." Annual review of biophysics and biophysical chemistry 15.1 (1986): 321-353.

Extend European Search Report issued for Application No. 15835788.9, dated Jun. 1, 2018.

Extended European Search Report issued for Application No. 15796259.8, dated Jan. 22, 2018, 6 pages.

Fernandez-Lopez, S. et al., "Antibacterial agents based on the cyclic D,L-alpha-peptide architecture," Nature, Jul. 2001, 412:452-455 and Correction page, Nature, Nov. 2001, 414:329.

Ferrari, A. et al., "Caveolae-Mediated Internalization of Extracellular HIV-1 Tat Fusion Proteins Visualized in Real Time," Molecular Therapy, 2003, 8:284-294.

Fittipaldi, A. et al., "Cell Membrane Lipid Rafts Mediate Caveolar Endocytosis of HIV-1 Tat Fusion Proteins," J. Biol. Chem., Sep. 2003, 278:34141-34149.

Frackenpohl, J. et al., "The Outstanding Biological Stability of - and y-Peptides toward Proteolytic Enzymes: An In Vitro Investigation with Fifteen Peptidases," Chembiochem, Jun. 2001, 2(6):445-455.

Frankel, A D. et al., "Cellular uptake of the tat protein from human immunodeficiency virus," Cell, Dec. 1988, 55(6):1189-1193.

Frost, J. R. et al., "Macrocyclization of Organo-Peptide Hybrids through a Dual Bio-orthogonal Ligation: Insights from Structure-Reactivity Studies," ChemBioChem, Jan. 2013, 14(1):147-160.

Futaki, S. et al., "Arginine-rich peptides. An abundant source of membrane-permeable peptides having potential as carriers for intracellular protein delivery." The Journal of Biological Chemistry, 2001, 276(8):5836-5840.

Futaki, S., "Membrane-permeable arginine-rich peptides and the translocation mechanisms," Advanced Drug Delivery Reviews, Feb. 2005, 57(4): 547-558.

Giebel, L. B. et al., "Screening of cyclic peptide phage libraries identifies ligands that bind streptavidin with high affinities," Biochemistry, 1995, 34(47):15430-15435.

Gobbo, M. et al., "Synthesis and biological activity of some linear and cyclic kinin analogues,"International Journal of Peptide & Protein Research, Jul. 1994, 44(1):1-9.

Goncalves, E. et al., "Binding of Oligoarginine to Membrane Lipids and Heparan Sulfate: Structural and Thermodynamic Characterization of a Cell-Penetrating Peptide," Biochemistry, 2005, 44(7):2692-2702.

Goun, E. A et al., "Molecular Transporters: Synthesis of Oligoguanidinium Transporters and Their Application to Drug Delivery and Real-Time Imaging," ChemBioChem, Oct. 2006, 7(10):1497-1515.

Green, M. et al., "Autonomous functional domains of chemically synthesized human immunodeficiency virus Tat trans-activator protein," Cell, Dec. 1988, 55(6): 1179-1188.

Grigoriu, S.; et al., "The molecular mechanism of substrate engagement and immunosuppressant inhibition of calcineurin." PLoS Biol. 2013, 11, e1001492.

Gupta, B. et al., "Intracellular delivery of large molecules and small particles by cell-penetrating proteins and peptides," Advanced Drug Delivery Reviews, Feb. 2005, 57(4):637-651.

Gwack, Y.; et al., "A genome-wide *Drosophila* RNAi screen identifies DYRK-family kinases as regulators of NFAT." Nature 2006, 441, 646-650.

Hamill, K. M. et al., "Polymyxins facilitate entry into mammalian cells" Chem. Sci., 2016, 7:5059-5068.

Hariton-Gazal, E. et al., "Functional Analysis of Backbone Cyclic Peptides Bearing the Arm Domain of the HIV-1 Rev Protein: Characterization of the Karyophilic Properties and Inhibition of Rev-Induced Gene Expression," Biochemistry, 2005, 44(34): 11555-11566.

He, R et al., "Recent Advances in PTP1B Inhibitor Development for the Treatment of Type 2 Diabetes and Obesity," Chapter 6 In: New Therapeutic Strategies for Type 2 Diabetes: Small Molecule Approaches, Jones, R. M. (ed.), RSC Drug Discovery Series No. 27, The Royal Society of Chemistry, 2012, pp. 142-176.

Heinis, C. et al., "Phage-encoded combinatorial chemical libraries based on bicyclic peptides," Nat. Chem. Biol., 2009, 5:502-507.

Herce, H. D. et al., "Arginine-Rich Peptides Destabilize the Plasma Membrane, Consistent with a Pore Formation Translocation Mechanism of Cell-Penetrating Peptides," Biophys. J., Oct. 2009, 97(7): 1917-1925.

Herce, H. D. et al., "Molecular dynamics simulations suggest a mechanism for translocation of the HIV-1 Tat peptide across lipid membranes," Proc. Natl. Acad. Sci. U. S. A., Dec. 2007, 104(52):20805-20810.

Hili, R. et al., "Macrocyclization of Linear Peptides Enabled by Amphoteric Molecules," J. Am. Chem. Soc., 2010, 132(9):2889-2891.

Hirose, H. et al., "Transient Focal Membrane Deformation Induced by Arginine-rich Peptides Leads to Their Direct Penetration into Cells," Mol. Ther., 2012, 20(5):984-993.

Hojo, M.; et al., "Cyclosporine induces cancer progression by a cell-autonomous mechanism." Nature 1999, 397, 530-534.

Holub, J. M. et al., "Improved assays for determining the cytosolic access of peptides, proteins, and their mimetics," Biochemistry, Dec. 2013, 52(50):9036-9046.

Hopp, Thomas P., and Kenneth R. Woods. "Prediction of protein antigenic determinants from amino acid sequences." Proceedings of the National Academy of Sciences 78.6 (1981): 3824-3828.

Horn, M. et al., "Tuning the properties of a novel short cell-penetrating peptide by intramolecular cyclization with a triazole bridge," Chem. Commun. 2016, 52:2261-2264.

(56) References Cited

OTHER PUBLICATIONS

Hoyer, J. et al., "Peptide Vectors for the Nonviral Delivery of Nucleic Acids," Acc. Chem. Res., 2012, 45(7): 1048-1056.
Humphrey, W.; et al., "VMD: visual molecular dynamics." J. Mol. Graphics 1996, 14, 33-38.
Illsley, N. P. et al., "Membrane chloride transport measured using a chloride-sensitive fluorescent probe," Biochemistry, 1987, 26(5):1215-1219.
International Preliminary Report on Patentability for International Application No. PCT/US2015/032043, dated Nov. 22, 2016, 8 pages.
International Preliminary report on Patentability issued for Application No. PCT/US2019/015695, dated Aug. 13, 2020.
International Preliminary Report on Patentability issued in issued in International Application No. PCT/US2015/47267, dated Mar. 9, 2017.
International Search Report and Written Opinion for International Application No. PCT/US2015/032043, dated Jan. 14, 2016, 11 pages.
International Search Report and Written Opinion issued in International Application No. PCT/US2015/47267, dated Dec. 7, 2015.
Jang, S. et al., "Cell-Penetrating, Dimeric a-Helical Peptides: Nanomolar Inhibitors of HIV-1 Transcription", Angew. Chem. Int. Ed. 2014, 53, 10086-10089.
Janin, J. O. E. L. "Surface and inside volumes in globular proteins." Nature 277.5696 (1979): 491-492.
Jeong, J. H. et al., "siRNA Conjugate Delivery Systems," Bioconjugate Chem., 2009, 20(1):5-14.
Jha, D. et al., "CyLoP-1: A Novel Cysteine-Rich Cell-Penetrating Peptide for Cytosolic Delivery of Cargoes," Bioconj. Chem., 2011, 22(3):319-328.
Jiang, B. et al., "A Selective, Cell-Permeable Nonphosphorylated Bicyclic Peptidyl Inhibitor against Peptidyl-Prolyl Isomerase Pin1," J. Med. Chem., 58:6306-6312 (2015). Published Online: Jul. 21, 2015.
Jójárt, B.; et al., "Performance of the general amber force field in modeling aqueous POPC membrane bilayers." J. Comput. Chem. 2007, 28, 2051-2058.
Joo, S. H. et al., "High-Throughput Sequence Determination of Cyclic Peptide Library Members by Partial Edman Degradation/Mass Spectrometry," J. Am. Chem. Soc., 2006, 128(39):13000-13009.
Jorgensen, W. L.; et al., "Solvation and Conformation of Methanol in Water." J. Am. Chem. Soc. 1983, 105, 1407-1413.
Josephson, L. et al., "High-Efficiency Intracellular Magnetic Labeling with Novel Superparamagnetic-Tat Peptide Conjugates," Bioconjugate Chem., 1999, 10(2):186-191.
Junkes, C. et al., "Cyclic antimicrobial R-, W-rich peptides: the role of peptide structure and E. coli outer and inner membranes in activity and the mode of action," European Biophysics Journal, 2011, 40(4):515-528.
Kaduk, C.; et al., "Synthesis of Fmoc-amino acid fluorides via DAST, an alternative fluoridation agent." Lett. Pep. Sci. 1995, 2, 285-288.
Kang, S.; et al., "Inhibition of the calcineurin-NFAT interaction by small organic molecules reflects binding at an allosteric site." J. Biol. Chem. 2005, 280, 37698-37706.
Kaplan, I. M. et al., "Cationic TAT peptide transduction domain enters cells by macropinocytosis," Journal of Controlled Release, Jan. 2005, 102(1):247-253.
Kawakami, T. et al., "In Vitro Selection of Multiple Libraries Created by Genetic Code Reprogramming to Discover Macrocyclic Peptides That Antagonize VEGFR2 Activity in Living Cells," ACS Chem. Biol., Apr. 2013, 8(6):1205-1214.
Kerem, B. et al., "Identification of the cystic fibrosis gene: genetic analysis," Science, Sep. 1989, 245(4922):1073-1080.
Kiani, A.; et al., "Manipulating immune responses with immunosuppressive agents the target NFAT." Immunity 2000, 12, 359-372.
Kohli, R. M. et al., "Biomimetic synthesis and optimization of cyclic peptide antibiotics," Nature, Aug. 2002, 418:658-661.
Kritzer, J. A. et al., "Rapid selection of cyclic peptides that reduce a-synuclein toxicity in yeast and animal models," Nature Chemical Biology, Sep. 2009, 5(9):655-663.
Kundu, R. et al., "Hybrid Organic-Inorganic Inhibitors of a PDZ Interaction that Regulates the Endocytic Fate of CFTR," Angew. Chem. Int. Ed., Jul. 2012, 51(29):7217-7220.
Kwon, Y-U et al., "Quantitative Comparison of the Relative Cell Permeability of Cyclic and Linear Peptides," Chemistry & Biology, Jun. 2007, 14(6):671-677.
Kyte, Jack, and Russell F. Doolittle. "A simple method for displaying the hydropathic character of a protein." Journal of molecular biology 157.1 (1982): 105-132.
Lalonde, M.S. et al., "Inhibition of Both HIV-1 Reverse Transcription and Gene Expression by a Cyclic Peptide that Binds the Tat-Transactivating Response Element (TAR) RNA", PLoS Pathogenes May 2011, 7(5) e1002038.
LaMontagne, K. R. Jr. et al., "Protein tyrosine phosphatase PTP1B suppresses p210 bcr-abl-induced transformation of Rat-1 fibroblasts and promotes differentiation of K562 cells," Proc. Natl. Acad. Sci. U. S. A., Nov. 1998, 95(24):14094-14099.
LaRochelle, J. R. et al., "Fluorescence Correlation Spectroscopy Reveals Highly Efficient Cytosolic Delivery of Certain Penta-Arg Proteins and Stapled Peptides," Journal of the American Chemical Society, 2015, 137:2536-2541.
Lattig-Tunnemann, G. et al., "Backbone rigidity and static presentation of guanidinium groups increases cellular uptake of arginine-rich cell-penetrating peptides," Nature Communications, 2011, 2:453. 6 pages.
Leduc, A-M et al., "Helix-stabilized cyclic peptides as selective inhibitors of steroid receptor-coactivator interactions," Proc. Natl. Acad. Sci. U.S.A., Sep. 2003, 100(20): 11273-11278.
Lee, H. J. et al., "PDZ domains and their binding partners: structure, specificity, and modification," Cell Communication and Signaling, 2010, 8:8, 18 pages.
Lee, J. et al., "Using marine natural products to discover a protease that catalyzes peptide macrocyclization of diverse substrates," J. Am. Chem. Soc., Feb. 2009, 131(6):2122-2124.
Lessard, L. et al., "The two faces of PTP1B in cancer," Biochim. Biophys. Acta, Mar. 2010, 1804(3):613-619.
Li, H.; et al., "Interaction of calcineurin with substrates and targeting proteins." Trends Cell Biol. 2011, 21, 91-103.
Li, H.; et al., "Structural delineation of the calcineurin-NFAT interaction and its parallels to PPI targeting interactions." J. Mol. Biol. 2004, 342, 1659-1674.
Li, H.; et al., "Structure of calcineurin in complex with PVIVIT peptide: portrait of a low-affinity signaling interaction." J. Mol. Biol. 2007, 369, 1296-1306.
Li, S. et al., "Photolithographic synthesis of cyclic peptide arrays using a differential deprotection strategy," Chem. Commun., 2005, 5:581-583.
Li, S. et al., "Fluoride enhances the activity of fungicides that destabilize cell membranes," Bioorganic & Medicinal Chemistry Letters, 2012, 22(9):3317-3322.
Lian, W. et al., "Cell-permeable bicyclic peptide inhibitors against intracellular proteins," J. Am. Chem. Soc., Jul. 2014, 136(28):9830-9833.
Lian, W. et al., "Screening Bicyclic Peptide Libraries for Protein-Protein Interaction Inhibitors: Discovery of a Tumor Necrosis Factor-a Antagonist," J. Am. Chem. Soc., 2013, 135(32): 11990-11995.
Liao et al., Cell-premeable bicyclic peptidyl inhibitors against T-cell protein tyrosine phosphates from a combinatorial library, Organic & Biomolecular Chemistry, vol. 15, pp. 9595-9598, 2017.
Lin, K-J, et al., "QSAR studies of antimicrobial alpha, beta-polypeptides," Pharmaceutical Biotechnology, 2003, 10(5):299-303 (with English Abstract).
Lindgren M. et al., "Classes and Prediction of Cell-Penetrating Peptides," Chapter 1 In: Cell-Penetrating Peptides: Methods and Protocols, Methods in Molecular Biology, vol. 683, pp. 3-19, Springer Science+Business Media, LLC 2011.
Liu, J. et al., "Nanostructured Materials Designed for Cell Binding and Transduction," Biomacromolecules, 2001, 2(2):362-368.

(56) References Cited

OTHER PUBLICATIONS

Liu, J.; et al., "Calcineurin is a common target of cyclophilin-cyclosporine A and FKBP-FK506 complexes." Cell 1991, 66, 807-815.
Liu, R. et al., "A Novel Peptide-Based Encoding System for "One-Bead One-Compound" Peptidomimetic and Small Molecule Combinatorial Libraries," J. Am. Chem. Soc., 2002, 124(26):7678-7680.
Liu, T. et al., "High-Throughput Screening of One-Bead-One-Compound Libraries: Identification of Cyclic Peptidyl Inhibitors against Calcineurin/NFAT Interaction," ACS Comb. Sci., 2011, 13(5):537-546.
Liu, T. et al., "Membrane Permeable Cyclic Peptidyl Inhibitors against Human Peptidylprolyl Isomerase Pin1," J. Med. Chem., 2010, 53(6):2494-2501.
Liu, Y. et al., "Multifunctional Tandem Peptide Modified Paclitaxel-Loaded Liposomes for the Treatment of Vasculogenic Mimicry and Cancer Stem Cells in Malignant Glioma," ACS Applied Materials & Interfaces, 2015, 7(30):16792-16801.
Llinas-Brunet, M.; et al., "A systematic approach to the optimization of substrate-based inhibitors of the hepatitis C virus NS3 protease: discovery of potent and specific tripeptide inhibitors." J. Med. Chem. 2004, 47, 6584-6594.
Lu, K. P. et al., "The prolyl isomerase PIN1: a pivotal new twist in phosphorylation signalling and disease," Nat. Rev. Mol. Cell Biol., Nov. 2007, 8:904-916.
Luechapanichkul, R.; et al., "Specificity profiling of dual specificity phosphatase vaccinia VH1-related (VHR) reveals two distinct substrate binding modes." J. Biol. Chem. 2013, 288, 6498-6510.
Magzoub, M. et al., "Conformational states of the cell-penetrating peptide penetratin when interacting with phospholipid vesicles: effects of surface charge and peptide concentration," Biochim. Biophys. Acta, Jun. 2002, 1563(1-2):53-63.
Maiolo, J. R. et al., "Effects of cargo molecules on the cellular uptake of arginine-rich cell-penetrating peptides," Biochim. Biophys. Acta., Jul. 2005, 1712(2): 161-172.
Majer et al., Structure-based subsite specificity mapping of human cathespin D using statine-based inhibitors, Protein Science, vol. 6, pp. 1458-1466, 1997.
Maly, D. J. et al., "Combinatorial Strategies for Targeting Protein Families: Application to the Proteases," Chembiochem, Jan. 2002, 3(1):16-37.
Maly, D. J. et al., "Expedient Solid-Phase Synthesis of Fluorogenic Protease Substrates Using the 7-Amino-4-carbamoylmethylcoumarin (ACC) Fluorophore," J. Org. Chem., 2002, 67(3):910-915.
Mandal, D. et al., "Cell-Penetrating Homochiral Cyclic Peptides as Nuclear-Targeting Molecular Transporters," Angew. Chem. Int. Ed., 2011, 50:9633-9637.
Marsault, E. et al., "Macrocycles Are Great Cycles: Applications, Opportunities, and Challenges of Synthetic Macrocycles in Drug Discovery," J. Med. Chem., 2011, 54(7): 1961-2004.
Meutermans, W. D. F. et al., "Synthesis of Difficult Cyclic Peptides by Inclusion of a Novel Photolabile Auxiliary in a Ring Contraction Strategy," J. Am. Chem. Soc., 1999, 121(42):9790-9796. Published Online: Oct. 8, 1999.
Millward, S. W. et al., "A General Route for Post-Translational Cyclization of mRNA Display Libraries," J. Am. Chem. Soc., 2005, 127(41):14142-14143. Published Online: Sep. 27, 2005.
Millward, S. W. et al., "Design of Cyclic Peptides That Bind Protein Surfaces with Antibody-Like Affinity," ACS Chem Biol., 2007, 2(9):625-634. Published Online: Sep. 21, 2007.
Ming, Z. et al., "Synthesis of RGD containing peptides and their vasodilation effect," Preparative Biochemistry 8 Biotechnology, 2000, 30(3):247-256.
Miranda, E. et al., "A Cyclic Peptide Inhibitor of HIF-1 Heterodimerization That Inhibits Hypoxia Signaling in Cancer Cells," Journal of the American Chemical Society, 2013, 135(28): 10418-10425.
Miskolzie, M. et al., "An NMR conformational analysis of cyclic bradykinin mimics. Evidence for a-turn," Journal of Biomolecular Structure & Dynamics, 2000, 17(6):947-955.

Mitra, S. et al., "Highly sensitive peptide-based probes for protein tyrosine phosphatase activity utilizing a fluorogenic mimic of phosphotyrosine," Bioorg. Med. Chem. Lett., Dec. 2005, 15(23):5142-5145.
Moore, J. D. et al., "Pin1 inhibitors: Pitfalls, progress and cellular pharmacology," Bioorg. Med. Chem. Lett., Aug. 2013, 23(15):4283-4291.
Morais Cabral, J. H. et al., "Crystal structure of a PDZ domain," Nature, Aug. 1996, 382:649-652.
Mosmann, T., "Rapid colorimetric assay for cellular growth and survival: Application to proliferation and cytotoxicity assays," J. Immunol. Methods, Dec. 1983, 65(1-2):55-63.
Mueller, J. et al., "Comparison of Cellular Uptake Using 22 CPPs in 4 Different Cell Lines," Bioconjugate Chem., 2008, 19(12):2363-2374.
Muratovska, A. et al., "Conjugate for efficient delivery of short interfering RNA (siRNA) into mammalian cells," FEBS Lett., Jan. 2004, 558(1-3):63-68.
Nakase, I. et al., "Efficient Intracellular Delivery of Nucleic Acid Pharmaceuticals Using Cell-Penetrating Peptides," Acc. Chem. Res., 2012, 45(7):1132-1139.
Nakase, I. et al., "Interaction of arginine-rich peptides with membrane-associated proteoglycans is crucial for induction of actin organization and macropinocytosis," Biochemistry, 2007, 46:492-501.
Ngu-Schwemlein, M. et al., "In vitro synergy between some cationic amphipathic cyclooctapeptides and antibiotics," Australian Journal of Chemistry, 2015, 68(2):218-223.
Nguyen, L. T.; et al., "Serum stabilities of short tryptophan- and arginine-rich antimicrobial peptide analogs." PLoS One 2010, 5, e12684.
Nischan, N. et al., "Covalent Attachment of Cyclic TAT Peptides to GFP Results in Protein Delivery into Live Cells with Immediate Bioavailability," Angew. Chem. Int. Ed., 2015, 54:1950-1953, with Supporting Information pp. S1-S26.
Noguchi, H.; et al., "A new cell-permeable peptide allows successful allogeneic islet transplantation in mice." Nat. Med. 2004, 10, 305-309.
Nori, A. et al., "Tat-conjugated synthetic macromolecules facilitate cytoplasmic drug delivery to human ovarian carcinoma cells," Bioconjugate Chem., Jan.-Feb. 2003, 14(1):44-50.
Ocampo-Garcia, B. E. et al., "Design and biological evaluation of 99mTc-N2S2-Tat(49-57)-c(RGDyK): A hybrid radiopharmaceutical for tumors expressing a(v)(3) integrins," Nuclear Medicine and Biology (2013), 40(4):481-487.
Oh, D. et al., "Enhanced Cellular Uptake of Short Polyarginine Peptides through Fatty Acylation and Cyclization," Molecular Pharmaceutics, 2014, 11(8):2845-2854.
Oh, D. et al., "Amphiphilic Bicyclic Peptides as Cellular Delivery Agents," ChemMedChem, 2014, 9(11):2449-2453.
Oh, D. et al., "Antibacterial activities of amphiphilic cyclic cell-penetrating peptides against multidrug-resistant pathogens," Molecular Pharmaceutics, 2014, 11(10):3528-3536.
Okamoto, H. et al., "Conformational transitions of cyclic D,L-Peptides," Journal of Computational Chemistry, 2009, 30(6):962-973.
Palm-Apergi, C. et al., "The membrane repair response masks membrane disturbances caused by cell-penetrating peptide uptake," FASEB J., Jan. 2009, 23(1):214-223.
Pawson, T. et al., "Assembly of Cell Regulatory Systems Through Protein Interaction Domains," Science, Apr. 2003, 300(5618) :445-452.
Perni, R. B.; et al., "Preclinical profile of VX-950, a potent, selective, and orally bioavailable inhibitor of hepatitis C Virus NS3-4A serine protease." Antimicrob. Agents Chemother. 2006, 50, 899-909.
Pettersen, E. F.; et al., "UCSF Chimera—a visualization system for exploratory research and analysis." J. Comput. Chem. 2004, 13, 1605-1612.
Pham, W. et al., "Enhancing Membrane Permeability by Fatty Acylation of Oligoarginine Peptides," Chembiochem, Aug. 2004, 5(8): 1148-1151.

(56) References Cited

OTHER PUBLICATIONS

Platz, K. P.; et al., "Nephrotoxicity following orthotopic liver transplantation. A comparison between cyclosporine and FK506." Transplantation 1994, 58, 170-178.
Pomilio, A B. et al., "Naturally-Occurring Cyclopeptides: Structures and Bioactivity," Current Organic Chemistry, Nov. 2006, 10(16):2075-2121.
Pooga, M. et al., "Cellular translocation of proteins by transportation," FASEB J., 2001, 15(8):1451-1453.
Pritz, S. et al., "Synthesis of Biologically Active Peptide Nucleic Acid-Peptide Conjugates by Sortase-Mediated Ligation," Journal of Organic Chemistry, 2007, 72(10):3909-3912.
Qian et al., "Structure-Based Optimization of a Peptidyl Inhibitor against Calcineurin-Nuclear Factor of Activated T Cell (NFAT) Interaction." J. Med. Chem. 2014, 57, 7792-7797.
Qian, Z. et al., "Discovery and Mechanism of Highly Efficient Cyclic Cell-Penetrating Peptides," Biochemistry, 2016, 55:2601-2612.
Qian, Z. et al., "Early endosomal escape of a cyclic cell-penetrating peptide allows effective cytosolic cargo delivery," Biochemistry, 2014, 53:4034-4046.
Qian, Z. et al., "Efficient delivery of cyclic peptides into mammalian cells with short sequence motifs," ACS Chem. Biol., 2013, 8:423-431.
Qian, Z. et al., "Intracellular Delivery of Peptidyl Ligands by Reversible Cyclization: Discovery of a PDZ Domain Inhibitor that Rescues CFTR Activity," Angew. Chem. Int. Ed., 2015, 54:5874-5878.
Qian, Z. et al., "Monitoring the cytosolic entry of cell-penetrating peptides using a pH-sensitive fluorophore," Chem. Commun., 2015, 51:2162-2165.
Qian, Ziqing, et al. "Discovery and mechanism of highly efficient cyclic cell-penetrating peptides." Biochemistry 55.18 (2016): 2601-2612.
Qin, C. et al., "Optimization of Antibacterial Cyclic Decapeptides," J. Comb. Chem., 2004, 6(3):398-406.
Rao, A.; et al., "Transcription factors of the NFAT family: regulation and function." Annu. Rev. Immunol. 1997, 15, 707-747.
Ren, L. et al., "Substrate Specificity of Protein Tyrosine Phosphatases 18, RPTPa, SHP-1, and SHP-2," Biochemistry, 2011, 50(12):2339-2356.
Rezai, T. et al., "Conformational Flexibility, Internal Hydrogen Bonding, and Passive Membrane Permeability: Successful in Silico Prediction of the Relative Permeabilities of Cyclic Peptides," J. Am. Chem. Soc., 2006, 128(43): 14073-14080.
Rezai, T. et al., "Testing the Conformational Hypothesis of Passive Membrane Permeability Using Synthetic Cyclic Peptide Diastereomers," J. Am. Chem. Soc., 2006, 128(8):2510-2511.
Richard, J. P. et al., "Cellular uptake of unconjugated TAT peptide involves clathrin-dependent endocytosis and heparan sulfate receptors," J. Biol. Chem., 2005, 280:15300-15306.
Ricouart, A et al., "Design of potent protein kinases inhibitors using the bisubstrate approach," Journal of Medicinal Chemistry, 1991, 34(1):73-78.
Riedl, S. J. et al., "Molecular mechanisms of caspase regulation during apoptosis," Nat. Rev. Mol. Cell Biol., Nov. 2004, 5:897-907.
Roberts, K. D. et al., "Efficient synthesis of thioether-based cyclic peptide libraries," Tetrahedron Letters, Nov. 1998, 39(45):8357-8360.
Roberts, K. E. et al., "Computational Design of a PDZ Domain Peptide Inhibitor that Rescues CFTR Activity," Plos Computational Biology, Apr. 2012, 8(4): e1002477, 12 pages.
Rothbard, J. B. et al., "Conjugation of arginine oligomers to cyclosporin A facilitates topical delivery and inhibition of inflammation," Nature Medicine, 2000, 6(11):1253-1257.
Rotstein, B. H. et al., "Solvatochromic Reagents for Multicomponent Reactions and their Utility in the Development of Cell-Permeable Macrocyclic Peptide Vectors," 2011, Chem. Eur. J., 17:12257-12261.

Roy, J.; et al., "Cracking the phosphatase code: Docking interactions determine substrate specificity." Sci. Signal. 2009, 2, re9, 1-7.
Rueping, M. et al., "Cellular Uptake Studies with beta-Peptides," ChemBioChem, Mar. 2002, 3(2-3):257-259.
Rusnati, M. et al., "Multiple Interactions of HIV-I Tat Protein with Size-defined Heparin Oligosaccharides," J. Biol. Chem., Oct. 1999, 274(40):28198-28205.
Saar, K. et al., "Cell-penetrating peptides: A comparative membrane toxicity study," Anal. Biochem., 2005, 345:55-65.
Sako, Y. et al., "Ribosomal synthesis of bicyclic peptides via two orthogonal inter-side-chain reactions," J. Am. Chem. Soc., Jun. 2008, 130(23):7232-7234.
Salvado, I. et al., "Membrane-disrupting iridium(III) oligocationic organometallopeptides," Chemical Communications, 2016, 52(73): 11008-11011.
Schafmeister, C. E. et al., "An All-Hydrocarbon Cross-Linking System for Enhancing the Helicity and Metabolic Stability of Peptides," J. Am. Chem. Soc., 2000, 122(24):5891-5892.
Schmidt, N. et al., "Arginine-rich cell-penetrating peptides," FEBS Lett., 2010, 584: 1806-1813.
Schwarze, S. R. et al., "In vivo protein transduction: delivery of a biologically active protein into the mouse," Science, Sep. 1999, 285(5433):1569-1572.
Scott, C. P. et al., "Production of cyclic peptides and proteins in vivo," Proc. Natl. Acad. Sci. U. S. A., Nov. 1999, 96(24):13638-13643.
Shirazi, A. N. et al, "Cysteine and arginine-rich peptides as molecular carriers," Bioorg. Med. Chem. Lett., 2016, 26:656-661.
Shirazi, A. N. et al, "Cyclic peptides containing tryptophan and arginine as Src kinase inhibitors", Bioorganic & Medicinal Chemistry Letters 23 (2013) 3230-3234.
Shirazi, A. N. et al., "Cyclic Peptide-Capped Gold Nanoparticles as Drug Delivery Systems," Molecular Pharmaceutics, 2013, 11:500-511.
Shirazi, A. N. et al., "Design and Biological Evaluation of Cell-Penetrating Peptide-Doxorubicin Conjugates as Prodrugs," Molecular Pharmaceutics, 2013, 10:488-499.
Shrake, Andrew, and John A. Rupley. "Environment and exposure to solvent of protein atoms. Lysozyme and insulin." Journal of molecular biology 79.2 (1973): 351-371.
Sieber, M.; et al., "Novel inhibitors of the calcineurin/NFATc hub-alternatives to CsA and FK506?" Cell Commun. Signal. 2009, 7, 25.
Sigal, N. H.; et al., "Is cyclophilin involved in the immunosuppressive and nephrotoxic mechanism of action of cyclosporine A?" J. Exp. Med. 1991, 173, 619-628.
Sigman, M. S.; et al., "Schiff base catalysts for the asymmetric Strecker reaction identified and optimized from parallel synthetic libraries." J. Am. Chem. Soc. 1998, 120, 4901-4902.
Slee, E. A. et al., "Benzyloxycarbonyl-Val-Ala-Asp (OMe) fluoromethylketone (Z-VAD.FMK) inhibits apoptosis by blocking the processing of CPP32," Biochemical Journal, Apr. 1996, 315(1):21-24.
Songyang, Z. et al., "Recognition of Unique Carboxyl-Terminal Motifs by Distinct PDZ Domains," Science, Jan. 1997, 275(5296):73-77.
Sorin, E. J.; et al., "Exploring the helix-coil transition via all-atom equilibrium ensemble simulations." Biophys. J. 2005, 88, 2472-2493.
Sousa Da Silva, A. W.; et al., "ACPYPE—AnteChamberPYthon Parser interfacE." BMC Res. Notes 2012, 5, 367.
Stanford, S. M. et al., "High-throughput screen using a single-cell tyrosine phosphatase assay reveals biologically active inhibitors of tyrosine phosphatase CD45," Proc. Natl. Acad. Sci. U. S. A., Aug. 2012, 109(35):13972-13977.
Stewart, J. M. et al., "Bradykinin antagonists: Anti-cancer drugs for the new millennium?" Peptides for the New Millennium, Proceedings of the American Peptide Symposium, 16th, Minneapolis, MN, United States, Jun. 26-Jul. 1, 1999 (2000), Meeting Date 1999, 219-221. Fields, G. B. et al., (eds.), Kluwer Academic Publishers, Dordrecht, Neth.

(56) References Cited

OTHER PUBLICATIONS

Stewart, K. M. et al., "Cell-penetrating peptides as delivery vehicles for biology and medicine," Org. Biomol. Chem., Jul. 2008, 6(13):2242-2255.
Suhorutsenko, J. et al., "Cell-penetrating peptides, PepFects, show no evidence of toxicity and immunogenicity in vitro and in vivo," Bioconjugate Chem., Nov. 2011, 22(11):2255-2262.
Sun, Y. et al., "A thioester ligation approach to amphipathic bicyclic peptide library," Org. Lett., May 2001, 3(11):1681-1684.
Takeuchi, K.; et al., "Structure of the calcineurin-NFAT complex: defining a T cell activation switch using solution NMR and crystal coordinates." Structure 2007, 15, 587-597.
Tam, J. P. et al., "Disulfide bond formation in peptides by dimethyl sulfoxide. Scope and applications," J. Am. Chem. Soc., 1991, 113(17):6657-6662.
Tavassoli, A. et al., "Inhibition of HIV Budding by a Genetically Selected Cyclic Peptide Targeting the Gag-TSG101 Interaction," ACS Chemical Biology, 2008, 3(12):757-764.
Thakkar, A. et al., "Traceless Capping Agent for Peptide Sequencing by Partial Edman Degradation and Mass Spectrometry," Anal. Chem., 2006, 78(16):5935-5939.
Thornberry, N. A. et al., "A Combinatorial Approach Defines Specificities of Members of the Caspase Family and Granzyme B. Functional Relationships Established for Key Mediators of Apoptosis," J. Biol. Chem., Jul. 1997, 272(29):17907-17911.
Tien, Matthew Z., et al. "Maximum allowed solvent accessibilities of residues in proteins." PloS one 8.11 (2013): e80635.
Traboulsi, H. et al., "Macrocyclic Cell Penetrating Peptides: A Study of Structure-Penetration Properties," Bioconjugate Chemistry, 2015, 26:405-411.
Trinh, T. B. et al., "Discovery of a Direct Ras Inhibitor by Screening a Combinatorial Library of Cell-Permeable Bicyclic Peptides," ACS Comb Sci., 2016, 18:75-85. Published Online: Dec. 8, 2015.
Tse, B. N. et al., "Translation of DNA into a Library of 13 000 Synthetic Small-Molecule Macrocycles Suitable for in Vitro Selection," J. Am. Chem. Soc., 2008, 130(46):15611-15626.
Turner, R. A. et al., "Click chemistry as a macrocyclization tool in the solid-phase synthesis of small cyclic peptides," Org. Lett., Nov. 2007, 9(24): 5011-5014. Epub Oct. 23, 2007.
Tyagi, M. et al., "Internalization of HIV-1 Tat requires cell surface heparan sulfate proteoglycans," J. Biol. Chem., Feb. 2001, 276(5):3254-3261. Epub Oct. 6, 2000.
Upadhyaya, P. et al., "Inhibition of Ras signaling by blocking Ras-effector interactions with cyclic peptide," Angew. Chem. Int. Ed., May 2015, 54:7602-7606. Published Online: May 7, 2015.
Van Goor, F. et al., "Correction of the F508del-CFTR protein processing defect in vitro by the investigational drug VX-809," Proc. Natl. Acad. Sci. U. S. A., Nov. 2011, 108(46):18843-18848.
Varkouhi, A. K. et al., "Endosomal escape pathways for delivery of biologicals," J. Controlled Release, May 2011, 151(3):220-228. Epub Nov. 13, 2010.
Wadia, J. S. et al., "Transmembrane delivery of protein and peptide drugs by TAT-mediated transduction in the treatment of cancer," Advanced Drug Delivery Reviews, Feb. 2005, 57(4):579-596. Epub Dec. 19, 2004.
Wallbrecher, R. et al., "Exploration of the Design Principles of a Cell-Penetrating Bicylic Peptide Scaffold," Bioconjugate Chemistry, 2014, 25(5):955-964. Published Online: Apr. 3, 2014.
Wang, C-W. et al., "Increased potency of a novel D-beta-naphthylalanine-substituted antimicrobial peptide against fluconazole-resistant fungal pathogens," FEMS Yeast Research, 2009, 9(6):967-970.
Wang, J.; et al., "Automatic atom type and bond type perception in molecular mechanical calculations." J. Mol. Graphic. Model. 2006, 25, 247-260.
Wang, J.; et al., "Development and testing of a general AMBER force field." J. Comput. Chem. 2004, 25, 1157-1174.
Wedemeyer, W. J.; et al., "Proline cis-trans isomerization and protein folding." Biochemistry 2002, 41, 14637-14644.
Wender, P. A. et al., "The design, synthesis, and evaluation of molecules that enable or enhance cellular uptake: Peptoid molecular transporters," Proc. Natl. Acad. Sci. U. S. A., Nov. 2000, 97(24):13003-13008.
White, T. R. et al., "On-resin N-methylation of cyclic peptides for discovery of orally bioavailable scaffolds," Nat. Chem. Biol., Sep. 2011, 7(11): 810-817.
Wohr, T.; et al., "Pseudo-prolines as a solubilizing, structure-disrupting protection technique in peptide synthesis." J. Am. Chem. Soc. 1996, 118, 9218-9227.
Wolde, M. et al., "Targeting CAL as a negative regulator of DeltaF508-CFTR cell-surface expression: an RNA interference and structure-based mutagenetic approach," J. Biol. Chem., Mar. 2007, 282(11):8099-8109. Epub Dec. 11, 2006.
Wu, G. et al., "Structural basis of IAP recognition by Smac/DIABLO," Nature, Dec. 2000, 408(6815):1008-1012.
Wu, X. et al., "Inhibition of Ras-effector interactions by cyclic peptides," Med. Chem. Commun., 2013, 4:378-382. Published Online: Nov. 27, 2012.
Xie, L. et al., "Cellular Effects of Small Molecule PTP1B Inhibitors on Insulin Signaling," Biochemistry, 2003, 42(44):12792-12804.
Yin, J. et al., "Genetically encoded short peptide tag for versatile protein labeling by Sfp phosphopantetheinyl transferase," Proc. Natl. Acad. Sci. U. S. A., Nov. 2005, 102(44): 15815-15820.
Yu, H., "Therapeutic potential of VIVIT, a selective peptide inhibitor of nuclear factor of activated T cells, in cardiovascular disorders." Cardiovasc Drug Rev. 2007 Summer;25(2):175-87.
Zabolotny, J. M. et al., "PTP1B regulates leptin signal transduction in vivo," Dev. Cell, Apr. 2002, 2(4):489-495.
Zhao, K. et al., "Enhanced activity of cyclic transporter sequences driven by phase behavior of peptide-liquid complexes," Soft Matter, 2012, 8(24): 6430-6433.
Ziegler, A. et al., "Interaction of the protein transduction domain of HIV-1 TAT with heparan sulfate: binding mechanism and thermodynamic parameters," Biophys. J., Jan. 2004, 86(1):254-263.
Ziegler, A., "Thermodynamic studies and binding mechanisms of cell-penetrating peptides with lipids and glycosaminoglycans," Advanced Drug Delivery Reviews, Mar. 2008, 60(4-5):580-597. Epub Oct. 22, 2007.
Extended European Search Report issued for European Application No. 19743545.6, dated Dec. 13, 2021.
Yu, Haixiang, et al. "Selective modulation of nuclear factor of activated T-cell function in restenosis by a potent bipartite peptide inhibitor." Circulation research 110.2 (2012): 200-210.
Karpurapu, M., et al. "Inhibition of nuclear factor of activated T cells (NFAT) c3 activation attenuates acute lung injury and pulmonary edema in murine models of sepsis" Oncotarget 9(12):10606-10620, 2018.

* cited by examiner

Compound 41 (CNI101)

Compound 42 (CNI102)

Compound 43 (CNI103)

FIG. 29 (Con't)
Compound 44 (CNI104)
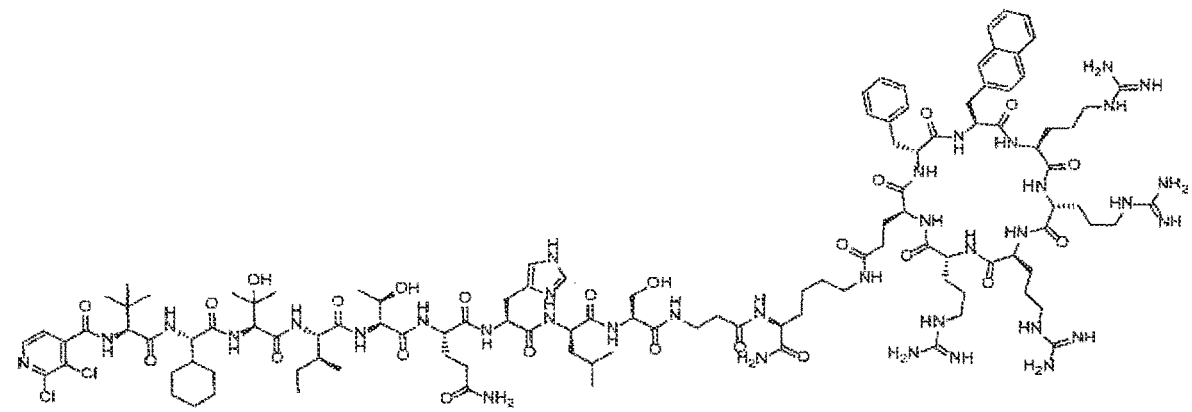
Compound 45 (CNI105)
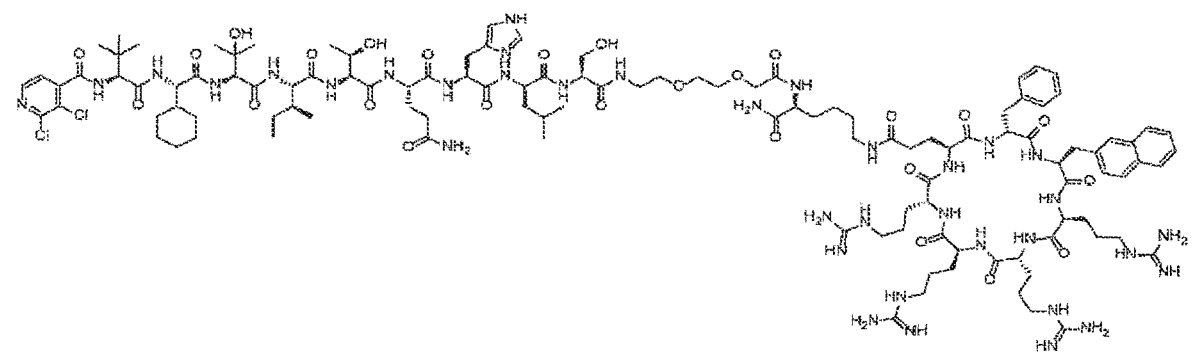

FIG. 29 (Con't)
Compound 46 (CNI106)
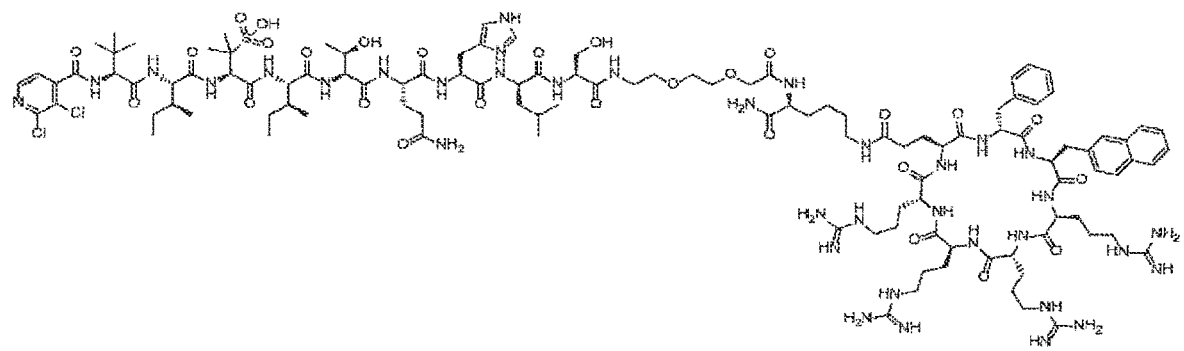
Compound 47 (CNI107)
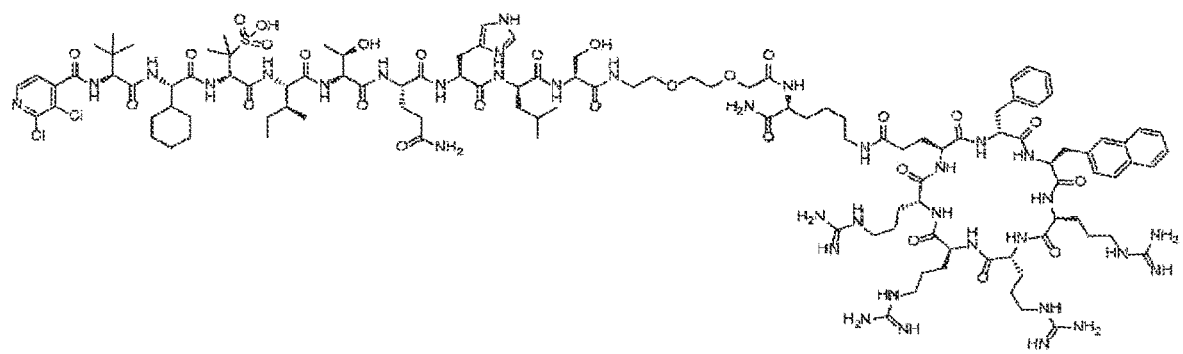
Compound 48 (CNI108)
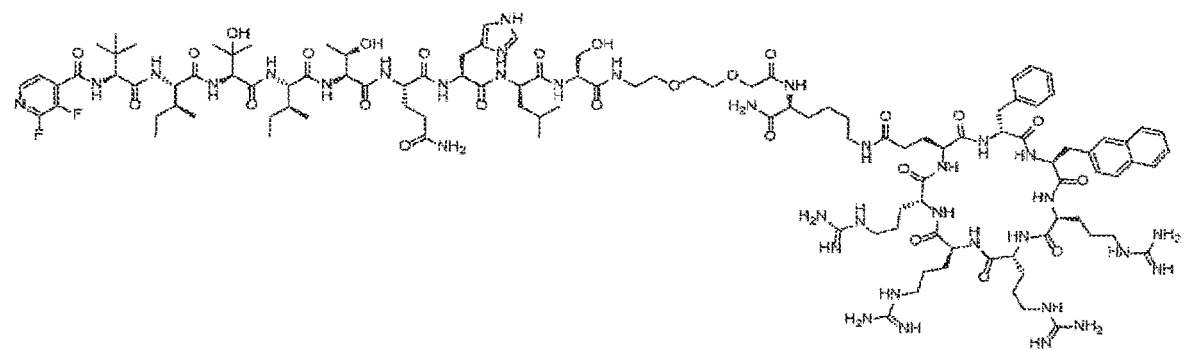

FIG. 29 (Con't)
Compound 49 (CNI109)
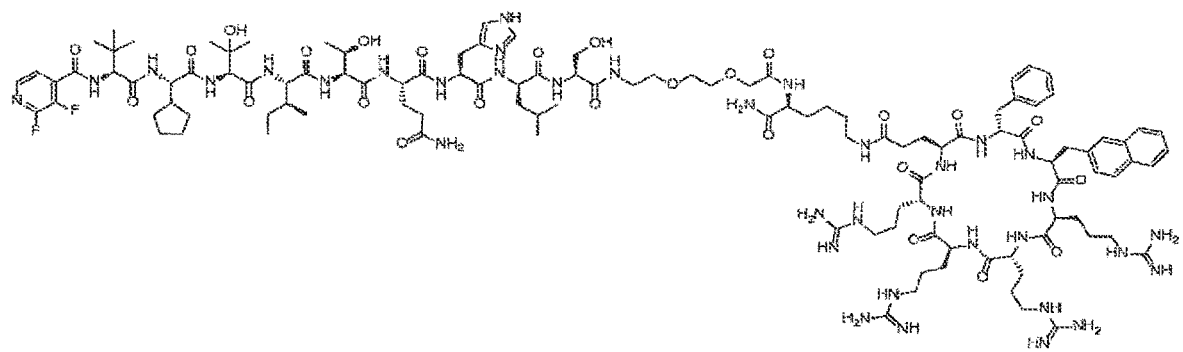
Compound 50 (CNI110)
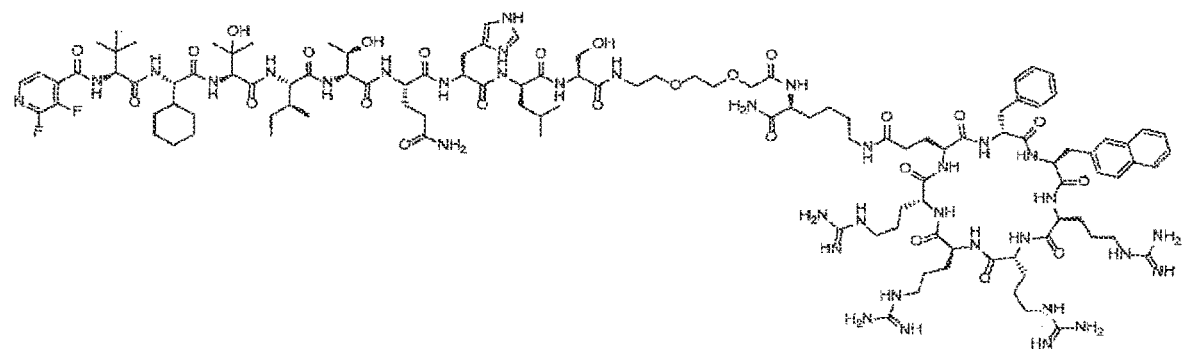

FIG. 29 (Con't)
Compound 51 (CNI111)
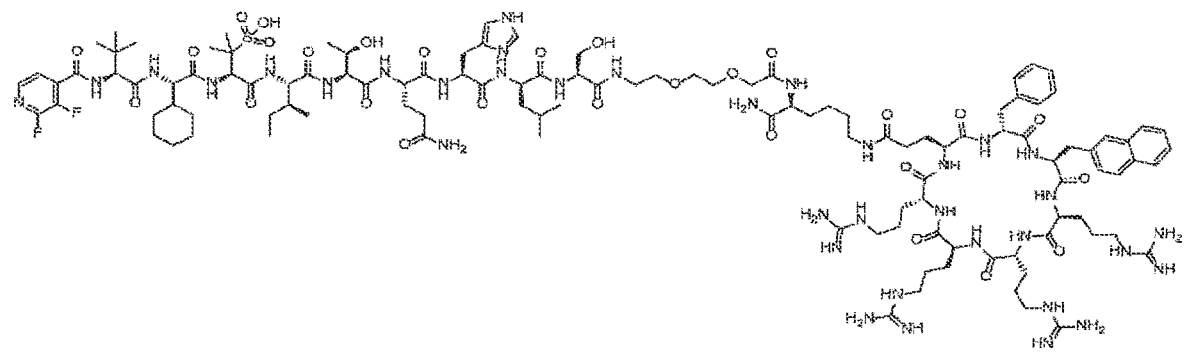
Compound 52 (CNI103 degradation fragment 1)
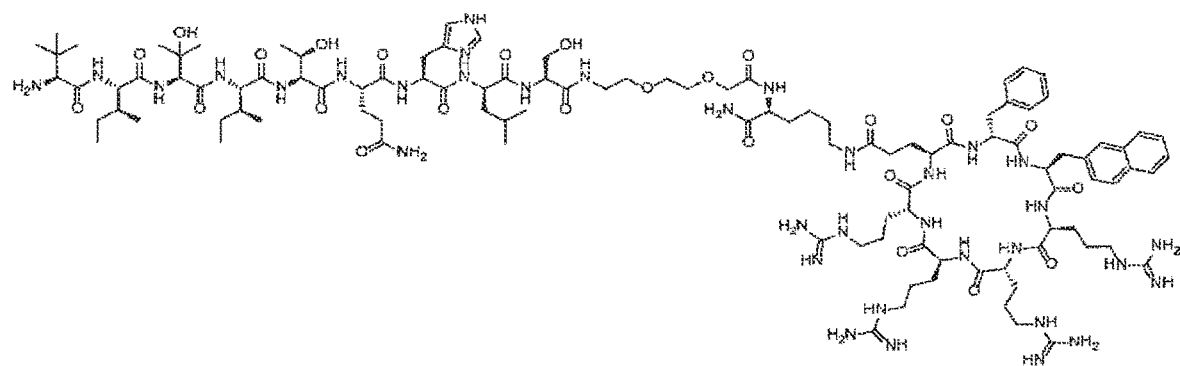
Compound 53 (CNI103 degradation fragment 2)
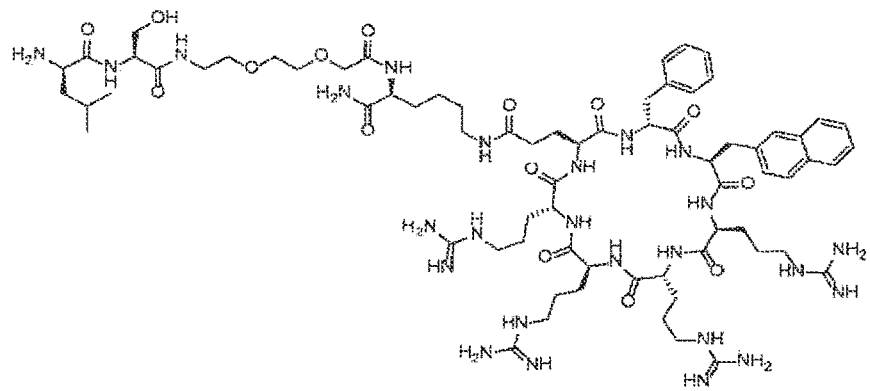

FIG. 29 (Con't)
Compound 54 (CNI103 degradation fragment 3)
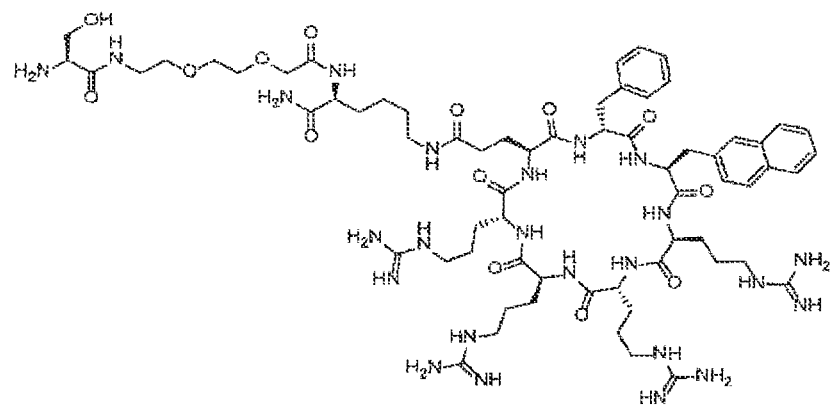

SEQUENCE LISTING

```
<160> NUMBER OF SEQ ID NOS: 221

<210> SEQ ID NO 1
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine

<400> SEQUENCE: 1

Xaa Ile Xaa Ile Thr
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic construct

<400> SEQUENCE: 2

Val Ile Val Ile Thr
1               5

<210> SEQ ID NO 3
<211> LENGTH: 5
<212> TYPE: PRT
<213> ORGANISM: Artificial Sequence
```

```
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: tert-butyl-alanine

<400> SEQUENCE: 3

Val Ile Xaa Ile Thr
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: homovaline

<400> SEQUENCE: 4

Xaa Ile Xaa Ile Thr
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: tert-butyl-alanine

<400> SEQUENCE: 5

Xaa Ile Val Ile Thr
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Beta-hydroxyvaline

<400> SEQUENCE: 6

Xaa Ile Xaa Ile Thr
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic construct
<220> FEATURE:
```

```
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (2)..(2)
<223> OTHER INFORMATION: cyclohexylglycine
<220> FEATURE:
<221> NAME/KEY: MOD_RES
<222> LOCATION: (3)..(3)
<223> OTHER INFORMATION: Beta-hydroxyvaline

<400> SEQUENCE: 7

Xaa Xaa Xaa Ile Thr
1               5

<210> SEQ ID NO 8
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: penicillamine sulfonic acid

<400> SEQUENCE: 8

Xaa Ile Xaa Ile Thr
1               5

<210> SEQ ID NO 9
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (2)..(2)
<223> OTHER INFORMATION: cyclohexylglycine
<220> FEATURE:
<221> NAME/KEY: MOD_RES
<222> LOCATION: (3)..(3)
<223> OTHER INFORMATION: penicillamine sulfonic acid

<400> SEQUENCE: 9

Xaa Xaa Xaa Ile Thr
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine
<220> FEATURE:
```

```
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (8)..(8)
<223> OTHER INFORMATION: 4-fluorophenylalanine

<400> SEQUENCE: 10

Xaa Ile Xaa Ile Thr Tyr Glu Xaa Gly
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine
<220> FEATURE:
<221> NAME/KEY: MOD_RES
<222> LOCATION: (8)..(8)
<223> OTHER INFORMATION: D-amino acid

<400> SEQUENCE: 11

Xaa Ile Xaa Ile Thr Gln His Leu His
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine

<400> SEQUENCE: 12

Xaa Ile Xaa Ile Thr Asp Gln Tyr Arg
1               5

<210> SEQ ID NO 13
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine
<220> FEATURE:
<221> NAME/KEY: MOD_RES
<222> LOCATION: (8)..(8)
<223> OTHER INFORMATION: D-amino acid
```

-continued

<400> SEQUENCE: 13

Xaa Ile Xaa Ile Thr Gln His Leu Ser
1               5

<210> SEQ ID NO 14
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine
<220> FEATURE:
<221> NAME/KEY: MOD_RES
<222> LOCATION: (9)..(9)
<223> OTHER INFORMATION: D-amino acid

<400> SEQUENCE: 14

Xaa Ile Xaa Ile Thr Asp Gln Tyr Lys
1               5

<210> SEQ ID NO 15
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 15

Lys Phe Phe Arg Arg Arg Arg Asp
1               5

<210> SEQ ID NO 16
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-diaminopropionic acid
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

```
<400> SEQUENCE: 16

Xaa Phe Phe Arg Arg Arg Arg Asp
1               5

<210> SEQ ID NO 17
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (13)..(13)
<223> OTHER INFORMATION: D-amino acid

<400> SEQUENCE: 17

Arg Val Arg Thr Arg Gly Lys Arg Arg Ile Arg Arg Pro Pro
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (13)..(13)
<223> OTHER INFORMATION: D-amino acid

<400> SEQUENCE: 18

Arg Thr Arg Thr Arg Gly Lys Arg Arg Ile Arg Val Pro Pro
1               5                   10

<210> SEQ ID NO 19
<211> LENGTH: 8
<212> TYPE: PRT
<213> ORGANISM: Artificial Sequence
<220> FEATURE:
<223> OTHER INFORMATION: synthetic construct

<400> SEQUENCE: 19

Trp Arg Trp Arg Trp Arg Trp Arg
1               5

<210> SEQ ID NO 20
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(2)
<223> OTHER INFORMATION: linked by dodecanoyl moiety

<400> SEQUENCE: 20

Lys Arg Arg Arg Arg
1               5

<210> SEQ ID NO 21
<211> LENGTH: 8
<212> TYPE: PRT
<213> ORGANISM: Artificial Sequence
<220> FEATURE:
<223> OTHER INFORMATION: synthetic construct

<400> SEQUENCE: 21
```

-continued

```
Cys Arg Cys Arg Cys Arg Cys Arg
1               5

<210> SEQ ID NO 22
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(4)
<223> OTHER INFORMATION: L-2,3-diaminopropionic acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(8)
<223> OTHER INFORMATION: L-2,3-diaminopropionic acid

<400> SEQUENCE: 22

Thr Xaa Xaa Xaa Phe Leu Xaa Xaa Thr
1               5

<210> SEQ ID NO 23
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: L-2-amino-3-guanidinylpropionic acid
<220> FEATURE:
<221> NAME/KEY: MOD_RES
<222> LOCATION: (3)..(3)
<223> OTHER INFORMATION: L-2,3-diaminopropionic acid
<220> FEATURE:
<221> NAME/KEY: MOD_RES
<222> LOCATION: (4)..(4)
<223> OTHER INFORMATION: L-2-amino-3-guanidinylpropionic acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(8)
<223> OTHER INFORMATION: L-2-amino-3-guanidinylpropionic acid

<400> SEQUENCE: 23

Thr Xaa Xaa Xaa Phe Leu Xaa Xaa Thr
1               5

<210> SEQ ID NO 24
<211> LENGTH: 4
<212> TYPE: PRT
<213> ORGANISM: Artificial Sequence
<220> FEATURE:
<223> OTHER INFORMATION: synthetic construct

<400> SEQUENCE: 24

Gly Pro His Pro
1

<210> SEQ ID NO 25
<211> LENGTH: 5
<212> TYPE: PRT
<213> ORGANISM: Artificial Sequence
```

```
<220> FEATURE:
<223> OTHER INFORMATION: synthetic construct

<400> SEQUENCE: 25

Gly Pro His Glu Glu
1               5

<210> SEQ ID NO 26
<211> LENGTH: 16
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: Tert-butyl-alanine
<220> FEATURE:
<221> NAME/KEY: MOD_RES
<222> LOCATION: (7)..(7)
<223> OTHER INFORMATION: Tert-butyl-alanine

<400> SEQUENCE: 26

Gly Pro His Pro Xaa Ile Xaa Ile Thr Gly Pro His Glu Glu Tyr Lys
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine

<400> SEQUENCE: 27

Xaa Ile Xaa Ile Thr Gly Pro
1               5

<210> SEQ ID NO 28
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine

<400> SEQUENCE: 28

Xaa Ile Xaa Ile Thr Gly Pro His Glu Glu Tyr Lys
1               5                   10

<210> SEQ ID NO 29
<211> LENGTH: 4
<212> TYPE: PRT
<213> ORGANISM: Artificial Sequence
<220> FEATURE:
<223> OTHER INFORMATION: synthetic construct
<220> FEATURE:
```

```
<221> NAME/KEY: MOD_RES
<222> LOCATION: (1)..(1)
<223> OTHER INFORMATION: D-amino acid

<400> SEQUENCE: 29

Asp Gly Trp Leu
1

<210> SEQ ID NO 30
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: 4-fluorophenylalanine

<400> SEQUENCE: 30

Tyr Glu Xaa His
1

<210> SEQ ID NO 31
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: beta-D-homoalanine
<220> FEATURE:
<221> NAME/KEY: MOD_RES
<222> LOCATION: (3)..(3)
<223> OTHER INFORMATION: beta-D-homoalanine

<400> SEQUENCE: 31

Tyr Trp Xaa Pro
1

<210> SEQ ID NO 32
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2-naphthylalanine
<220> FEATURE:
<221> NAME/KEY: MOD_RES
<222> LOCATION: (3)..(3)
<223> OTHER INFORMATION: (1S,2R)-2-aminocyclopentane carboxylic acid

<400> SEQUENCE: 32

Xaa Gln Xaa Trp
1

<210> SEQ ID NO 33
<211> LENGTH: 4
<212> TYPE: PRT
<213> ORGANISM: Artificial Sequence
<220> FEATURE:
<223> OTHER INFORMATION: synthetic construct
```

```
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 2-naphthylalanine

<400> SEQUENCE: 33

Gln Tyr Asn Xaa
1

<210> SEQ ID NO 34
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: D-amino acid

<400> SEQUENCE: 34

Gln His Leu His
1

<210> SEQ ID NO 35
<211> LENGTH: 4
<212> TYPE: PRT
<213> ORGANISM: Artificial Sequence
<220> FEATURE:
<223> OTHER INFORMATION: synthetic construct

<400> SEQUENCE: 35

Asp Gln Tyr Arg
1

<210> SEQ ID NO 36
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: isoaspartic acid

<400> SEQUENCE: 36

Xaa Gln Trp Arg
1

<210> SEQ ID NO 37
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: (1S,2R)-2-aminocyclopentane carboxylic acid

<400> SEQUENCE: 37

Tyr Xaa Gly Trp
1
```

```
<210> SEQ ID NO 38
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: 2-naphthylalanine

<400> SEQUENCE: 38

Ser Gly His Xaa
1

<210> SEQ ID NO 39
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: 2-naphthylalanine
<220> FEATURE:
<221> NAME/KEY: MOD_RES
<222> LOCATION: (4)..(4)
<223> OTHER INFORMATION: beta-D-homoalanine

<400> SEQUENCE: 39

Pro Xaa Arg Xaa
1

<210> SEQ ID NO 40
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: ornithine
<220> FEATURE:
<221> NAME/KEY: MOD_RES
<222> LOCATION: (4)..(4)
<223> OTHER INFORMATION: D-amino acid

<400> SEQUENCE: 40

His Glu Xaa Ala
1

<210> SEQ ID NO 41
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: D-amino acid

<400> SEQUENCE: 41

Gln His Leu Ser
1
```

```
<210> SEQ ID NO 42
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: norleucine
<220> FEATURE:
<221> NAME/KEY: MOD_RES
<222> LOCATION: (3)..(3)
<223> OTHER INFORMATION: 2-naphthylalanine

<400> SEQUENCE: 42

Xaa Ala Xaa Tyr
1

<210> SEQ ID NO 43
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: 2-naphthylalanine

<400> SEQUENCE: 43

Lys His Xaa Asp
1

<210> SEQ ID NO 44
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: ornithine
<220> FEATURE:
<221> NAME/KEY: MOD_RES
<222> LOCATION: (2)..(2)
<223> OTHER INFORMATION: norleucine
<220> FEATURE:
<221> NAME/KEY: MOD_RES
<222> LOCATION: (4)..(4)
<223> OTHER INFORMATION: 2-naphthylalanine

<400> SEQUENCE: 44

Xaa Xaa His Xaa
1

<210> SEQ ID NO 45
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid
<220> FEATURE:
```

```
<221> NAME/KEY: MOD_RES
<222> LOCATION: (4)..(4)
<223> OTHER INFORMATION: 2-naphthylalanine

<400> SEQUENCE: 45

Tyr Asn Ser Xaa
1

<210> SEQ ID NO 46
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: 2-naphthylalanine

<400> SEQUENCE: 46

Gly Tyr Gly Xaa
1

<210> SEQ ID NO 47
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: D-amino acid

<400> SEQUENCE: 47

Asp His Lys Tyr
1

<210> SEQ ID NO 48
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: beta-alanine
<220> FEATURE:
<221> NAME/KEY: MOD_RES
<222> LOCATION: (4)..(4)
<223> OTHER INFORMATION: 2-naphthylalanine

<400> SEQUENCE: 48

Gln Tyr Xaa Xaa
1

<210> SEQ ID NO 49
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: D-amino acid

<400> SEQUENCE: 49

His His Phe Trp
```

```
<210> SEQ ID NO 50
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: D-amino acid

<400> SEQUENCE: 50

Arg Tyr Glu Tyr
1

<210> SEQ ID NO 51
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: 2-naphthylalanine
<220> FEATURE:
<221> NAME/KEY: MOD_RES
<222> LOCATION: (4)..(4)
<223> OTHER INFORMATION: beta-D-homoalanine

<400> SEQUENCE: 51

Ala His Xaa Xaa
1

<210> SEQ ID NO 52
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: beta-aspartate
<220> FEATURE:
<221> NAME/KEY: MOD_RES
<222> LOCATION: (4)..(4)
<223> OTHER INFORMATION: 2-naphthylalanine

<400> SEQUENCE: 52

Pro Xaa His Xaa
1

<210> SEQ ID NO 53
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: norleucine

<400> SEQUENCE: 53

Gln His Tyr Xaa
1
```

```
<210> SEQ ID NO 54
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid

<400> SEQUENCE: 54

Gln Phe Arg Asp
1

<210> SEQ ID NO 55
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid

<400> SEQUENCE: 55

Trp Glu Gly Arg
1

<210> SEQ ID NO 56
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: 2-naphthylalanine

<400> SEQUENCE: 56

Pro Glu Xaa Arg
1

<210> SEQ ID NO 57
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: beta-alanine

<400> SEQUENCE: 57

Gln His Gly Xaa
1

<210> SEQ ID NO 58
<211> LENGTH: 4
<212> TYPE: PRT
<213> ORGANISM: Artificial Sequence
<220> FEATURE:
<223> OTHER INFORMATION: synthetic construct
<220> FEATURE:
```

```
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: 4-fluorophenylalanine

<400> SEQUENCE: 58

Tyr Glu Xaa Gly
1

<210> SEQ ID NO 59
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: 2-naphthylalanine
<220> FEATURE:
<221> NAME/KEY: MOD_RES
<222> LOCATION: (4)..(4)
<223> OTHER INFORMATION: phenylglycine

<400> SEQUENCE: 59

Ala His Xaa Xaa
1

<210> SEQ ID NO 60
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2-naphthylalanine
<220> FEATURE:
<221> NAME/KEY: MOD_RES
<222> LOCATION: (4)..(4)
<223> OTHER INFORMATION: (1S,2R)-2-aminocyclopentane carboxylic acid

<400> SEQUENCE: 60

Xaa His Tyr Xaa
1

<210> SEQ ID NO 61
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (2)..(2)
<223> OTHER INFORMATION: D-amino acid

<400> SEQUENCE: 61

His Ala Ser Tyr
1

<210> SEQ ID NO 62
<211> LENGTH: 4
<212> TYPE: PRT
<213> ORGANISM: Artificial Sequence
<220> FEATURE:
<223> OTHER INFORMATION: synthetic construct
```

```
<220> FEATURE:
<221> NAME/KEY: MOD_RES
<222> LOCATION: (1)..(1)
<223> OTHER INFORMATION: beta-alanine
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: 2-naphthylalanine

<400> SEQUENCE: 62

Xaa Glu Xaa Arg
1

<210> SEQ ID NO 63
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: 2-naphthylalanine

<400> SEQUENCE: 63

Thr Pro Ala Xaa
1

<210> SEQ ID NO 64
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: 2-naphthylalanine

<400> SEQUENCE: 64

Ile His Xaa His
1

<210> SEQ ID NO 65
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: D-amino acid

<400> SEQUENCE: 65

Asp Gln Tyr Lys
1

<210> SEQ ID NO 66
```

```
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: beta-alanine
<220> FEATURE:
<221> NAME/KEY: MOD_RES
<222> LOCATION: (2)..(2)
<223> OTHER INFORMATION: D-amino acid

<400> SEQUENCE: 66

Xaa Glu Arg Tyr
1

<210> SEQ ID NO 67
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: D-amino acid

<400> SEQUENCE: 67

Thr Leu Tyr Phe
1

<210> SEQ ID NO 68
<211> LENGTH: 4
<212> TYPE: PRT
<213> ORGANISM: Artificial Sequence
<220> FEATURE:
<223> OTHER INFORMATION: synthetic construct

<400> SEQUENCE: 68

Tyr His Pro Trp
1

<210> SEQ ID NO 69
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-amino acid

<400> SEQUENCE: 69

Asn Pro Tyr Trp
1

<210> SEQ ID NO 70
<211> LENGTH: 4
<212> TYPE: PRT
<213> ORGANISM: Artificial Sequence
```

```
<220> FEATURE:
<223> OTHER INFORMATION: synthetic construct

<400> SEQUENCE: 70

Ser Tyr Ser Trp
1

<210> SEQ ID NO 71
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: 2-naphthylalanine

<400> SEQUENCE: 71

Gln Tyr Xaa Ser
1

<210> SEQ ID NO 72
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (4)..(4)
<223> OTHER INFORMATION: D-amino acid

<400> SEQUENCE: 72

Tyr His Gly Phe
1

<210> SEQ ID NO 73
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: (1S,2R)-2-aminocyclopentane carboxylic acid
<220> FEATURE:
<221> NAME/KEY: MOD_RES
<222> LOCATION: (3)..(3)
<223> OTHER INFORMATION: 2-naphthylalanine

<400> SEQUENCE: 73

Xaa Gly Xaa His
1

<210> SEQ ID NO 74
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-piperidine-2-carboxylic acid
<220> FEATURE:
```

```
<221> NAME/KEY: MOD_RES
<222> LOCATION: (3)..(3)
<223> OTHER INFORMATION: 2-naphthylalanine

<400> SEQUENCE: 74

Glu Xaa Xaa His
1

<210> SEQ ID NO 75
<211> LENGTH: 4
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (3)..(3)
<223> OTHER INFORMATION: D-amino acid

<400> SEQUENCE: 75

Gln His Leu Ser
1

<210> SEQ ID NO 76
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 76

Phe Xaa Arg Arg Arg Arg Gln
1               5

<210> SEQ ID NO 77
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (2)..(2)
<223> OTHER INFORMATION: L-2-naphthylalanine

<400> SEQUENCE: 77

Phe Xaa Arg Arg Arg Arg Gln
1               5
```

```
<210> SEQ ID NO 78
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MOD_RES
<222> LOCATION: (2)..(2)
<223> OTHER INFORMATION: L-2-naphthylalanine

<400> SEQUENCE: 78

Phe Xaa Arg Arg Arg Gln
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine

<400> SEQUENCE: 79

Phe Xaa Arg Arg Arg Cys
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (6)..(6)
<223> OTHER INFORMATION: selenocysteine

<400> SEQUENCE: 80

Phe Xaa Arg Arg Arg Xaa
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
```

```
<220> FEATURE:
<221> NAME/KEY: MOD_RES
<222> LOCATION: (4)..(4)
<223> OTHER INFORMATION: L-napthylalanine

<400> SEQUENCE: 81

Arg Arg Arg Xaa Phe Gln
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (5)..(5)
<223> OTHER INFORMATION: L-napthylalanine

<400> SEQUENCE: 82

Arg Arg Arg Arg Xaa Phe
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine

<400> SEQUENCE: 83

Phe Xaa Arg Arg Arg Arg
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (2)..(2)
<223> OTHER INFORMATION: D-napthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid
```

<400> SEQUENCE: 84

Phe Xaa Arg Arg Arg Arg Gln
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (2)..(2)
<223> OTHER INFORMATION: D-napthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 85

Phe Xaa Arg Arg Arg Arg Gln
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine

<400> SEQUENCE: 86

Phe Xaa Arg Arg Arg Arg Gln
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (4)..(4)
<223> OTHER INFORMATION: D-amino acid

```
<220> FEATURE:
<221> NAME/KEY: MOD_RES
<222> LOCATION: (6)..(6)
<223> OTHER INFORMATION: D-amino acid

<400> SEQUENCE: 87

Phe Xaa Arg Arg Arg Arg Gln
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (5)..(5)
<223> OTHER INFORMATION: L-napthylalanine

<400> SEQUENCE: 88

Arg Arg Phe Arg Xaa Arg Gln
1               5

<210> SEQ ID NO 89
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (6)..(6)
<223> OTHER INFORMATION: L-napthylalanine

<400> SEQUENCE: 89

Phe Arg Arg Arg Arg Xaa Gln
1               5

<210> SEQ ID NO 90
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (5)..(5)
<223> OTHER INFORMATION: L-napthylalanine

<400> SEQUENCE: 90

Arg Arg Phe Arg Xaa Arg Gln
1               5

<210> SEQ ID NO 91
```

```
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (3)..(3)
<223> OTHER INFORMATION: L-napthylalanine

<400> SEQUENCE: 91

Arg Arg Xaa Phe Arg Arg Gln
1               5

<210> SEQ ID NO 92
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide

<400> SEQUENCE: 92

Cys Arg Arg Arg Arg Phe Trp Gln
1               5

<210> SEQ ID NO 93
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: L-napthylalanine
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 93

Phe Phe Xaa Arg Arg Arg Arg Gln
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
```

```
<223> OTHER INFORMATION: forms a cyclic peptide
<220> FEATURE:
<221> NAME/KEY: MOD_RES
<222> LOCATION: (3)..(3)
<223> OTHER INFORMATION: L-napthylalanine

<400> SEQUENCE: 94

Phe Phe Xaa Arg Arg Arg Arg Gln
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MOD_RES
<222> LOCATION: (6)..(6)
<223> OTHER INFORMATION: L-napthylalanine

<400> SEQUENCE: 95

Arg Phe Arg Phe Arg Xaa Arg Gln
1               5

<210> SEQ ID NO 96
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MOD_RES
<222> LOCATION: (1)..(1)
<223> OTHER INFORMATION: selenocysteine

<400> SEQUENCE: 96

Xaa Arg Arg Arg Arg Phe Trp Gln
1               5

<210> SEQ ID NO 97
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine

<400> SEQUENCE: 97

Phe Xaa Arg Arg Arg Arg Gln Lys
1               5

<210> SEQ ID NO 98
<211> LENGTH: 8
<212> TYPE: PRT
<213> ORGANISM: Artificial Sequence
```

<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine

<400> SEQUENCE: 98

Phe Xaa Arg Arg Arg Arg Gln Cys
1               5

<210> SEQ ID NO 99
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 99

Phe Xaa Arg Arg Arg Arg Arg Gln
1               5

<210> SEQ ID NO 100
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine

<400> SEQUENCE: 100

Phe Xaa Arg Arg Arg Arg Arg Gln
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE

```
<222> LOCATION: (1)..(9)
<223> OTHER INFORMATION: forms a cyclic peptide
<220> FEATURE:
<221> NAME/KEY: MOD_RES
<222> LOCATION: (5)..(5)
<223> OTHER INFORMATION: L-napthylalanine
<220> FEATURE:
<221> NAME/KEY: MOD_RES
<222> LOCATION: (8)..(8)
<223> OTHER INFORMATION: L-norleucine

<400> SEQUENCE: 101

Arg Arg Arg Arg Xaa Phe Asp Xaa Cys
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide
<220> FEATURE:
<221> NAME/KEY: MOD_RES
<222> LOCATION: (2)..(2)
<223> OTHER INFORMATION: L-napthylalanine

<400> SEQUENCE: 102

Phe Xaa Arg Arg Arg
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide

<400> SEQUENCE: 103

Phe Trp Arg Arg Arg
1               5

<210> SEQ ID NO 104
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide
<220> FEATURE:
<221> NAME/KEY: MOD_RES
<222> LOCATION: (4)..(4)
<223> OTHER INFORMATION: L-napthylalanine

<400> SEQUENCE: 104

Arg Arg Arg Xaa Phe
1               5

<210> SEQ ID NO 105
<211> LENGTH: 5
<212> TYPE: PRT
```

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(5)
<223> OTHER INFORMATION: forms a cyclic peptide

<400> SEQUENCE: 105

Arg Arg Arg Trp Phe
1               5

<210> SEQ ID NO 106
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 106

Phe Phe Arg Arg Arg Gln
1               5

<210> SEQ ID NO 107
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 107

Phe Phe Arg Arg Arg Gln
1               5

<210> SEQ ID NO 108
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (4)..(4)
<223> OTHER INFORMATION: D-amino acid

<400> SEQUENCE: 108

Phe Phe Arg Arg Arg Gln
1               5

<210> SEQ ID NO 109
<211> LENGTH: 6
```

```
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 109

Phe Arg Phe Arg Arg Gln
1               5

<210> SEQ ID NO 110
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 110

Phe Arg Arg Phe Arg Gln
1               5

<210> SEQ ID NO 111
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 111

Phe Arg Arg Arg Phe Gln
1               5

<210> SEQ ID NO 112
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (2)..(2)
<223> OTHER INFORMATION: L-naphthylalanine

<400> SEQUENCE: 112

Gly Xaa Arg Arg Arg Gln
1               5

<210> SEQ ID NO 113
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
```

<223> OTHER INFORMATION: forms a cyclic peptide

<400> SEQUENCE: 113

Phe Phe Phe Arg Ala Gln
1               5

<210> SEQ ID NO 114
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide

<400> SEQUENCE: 114

Phe Phe Phe Arg Arg Gln
1               5

<210> SEQ ID NO 115
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 115

Phe Phe Arg Arg Arg Arg Gln
1               5

<210> SEQ ID NO 116
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 116

Phe Arg Arg Phe Arg Arg Gln
1               5

<210> SEQ ID NO 117
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 117

Phe Arg Arg Arg Phe Arg Gln
1               5

<210> SEQ ID NO 118
<211> LENGTH: 7
<212> TYPE: PRT

```
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 118

Arg Phe Phe Arg Arg Arg Gln
1               5

<210> SEQ ID NO 119
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 119

Arg Phe Arg Arg Phe Arg Gln
1               5

<210> SEQ ID NO 120
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 120

Phe Arg Phe Arg Arg Arg Gln
1               5

<210> SEQ ID NO 121
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 121

Phe Phe Phe Arg Arg Arg Gln
1               5

<210> SEQ ID NO 122
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 122

Phe Phe Arg Arg Arg Phe Gln
```

<210> SEQ ID NO 123
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 123

Phe Arg Phe Phe Arg Arg Gln
1               5

<210> SEQ ID NO 124
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 124

Arg Arg Phe Phe Phe Arg Gln
1               5

<210> SEQ ID NO 125
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 125

Phe Phe Arg Phe Arg Arg Gln
1               5

<210> SEQ ID NO 126
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 126

Phe Phe Arg Arg Phe Arg Gln
1               5

<210> SEQ ID NO 127
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE

```
<222> LOCATION: (1)..(7)
<223> OTHER INFORMATION: forms a cyclic peptide

<400> SEQUENCE: 127

Phe Arg Arg Phe Phe Arg Gln
1               5

<210> SEQ ID NO 128
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 128

Phe Arg Arg Phe Arg Phe Gln
1               5

<210> SEQ ID NO 129
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 129

Phe Arg Phe Arg Phe Arg Gln
1               5

<210> SEQ ID NO 130
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide

<400> SEQUENCE: 130

Arg Phe Phe Arg Phe Arg Gln
1               5

<210> SEQ ID NO 131
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (2)..(2)
<223> OTHER INFORMATION: L-naphthylalanine

<400> SEQUENCE: 131

Gly Xaa Arg Arg Arg Arg Gln
1               5
```

<210> SEQ ID NO 132
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 132

Phe Phe Phe Arg Arg Arg Arg Gln
1               5

<210> SEQ ID NO 133
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 133

Arg Phe Phe Arg Arg Arg Arg Gln
1               5

<210> SEQ ID NO 134
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 134

Arg Arg Phe Phe Arg Arg Arg Gln
1               5

<210> SEQ ID NO 135
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 135

Arg Phe Phe Phe Arg Arg Arg Gln
1               5

<210> SEQ ID NO 136
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)

```
<223> OTHER INFORMATION: forms a cyclic peptide

<400> SEQUENCE: 136

Arg Arg Phe Phe Phe Arg Arg Gln
1               5

<210> SEQ ID NO 137
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 137

Phe Phe Arg Arg Phe Arg Arg Gln
1               5

<210> SEQ ID NO 138
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 138

Phe Phe Arg Arg Arg Arg Phe Gln
1               5

<210> SEQ ID NO 139
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(8)
<223> OTHER INFORMATION: forms a cyclic peptide

<400> SEQUENCE: 139

Phe Arg Arg Phe Phe Arg Arg Gln
1               5

<210> SEQ ID NO 140
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(9)
<223> OTHER INFORMATION: forms a cyclic peptide

<400> SEQUENCE: 140

Phe Phe Phe Arg Arg Arg Arg Arg Gln
1               5

<210> SEQ ID NO 141
<211> LENGTH: 10
<212> TYPE: PRT
```

```
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(10)
<223> OTHER INFORMATION: forms a cyclic peptide

<400> SEQUENCE: 141

Phe Phe Phe Arg Arg Arg Arg Arg Arg Gln
1               5                   10

<210> SEQ ID NO 142
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (2)..(2)
<223> OTHER INFORMATION: L-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 142

Phe Xaa Arg Arg Arg Arg Gln
1               5

<210> SEQ ID NO 143
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(2)
<223> OTHER INFORMATION: L-4-fluorophenylalanine

<400> SEQUENCE: 143

Xaa Xaa Arg Arg Arg Arg Gln
1               5

<210> SEQ ID NO 144
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (2)..(2)
<223> OTHER INFORMATION: D-amino acid
<220> FEATURE:
```

```
<221> NAME/KEY: MOD_RES
<222> LOCATION: (5)..(5)
<223> OTHER INFORMATION: D-amino acid

<400> SEQUENCE: 144

Phe Phe Phe Arg Arg Arg Gln
1               5

<210> SEQ ID NO 145
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 145

Phe Phe Phe Arg Arg Arg Gln
1               5

<210> SEQ ID NO 146
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 146

Phe Phe Phe Arg Arg Arg Gln
1               5

<210> SEQ ID NO 147
<211> LENGTH: 7
<212> TYPE: PRT
<213> ORGANISM: Artificial Sequence
<220> FEATURE:
<223> OTHER INFORMATION: synthetic construct
<220> FEATURE:
```

<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 147

Phe Phe Phe Arg Arg Arg Gln
1               5

<210> SEQ ID NO 148
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: L-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 148

Phe Phe Xaa Arg Arg Arg Gln
1               5

<210> SEQ ID NO 149
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES

```
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 149

Phe Xaa Phe Arg Arg Arg Gln
1               5

<210> SEQ ID NO 150
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MISC_FEATURE
<222> LOCATION: (1)..(1)
<223> OTHER INFORMATION: L-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 150

Xaa Phe Phe Arg Arg Arg Gln
1               5

<210> SEQ ID NO 151
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (2)..(2)
<223> OTHER INFORMATION: L-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 151

Phe Xaa Arg Arg Arg Gln
1               5

<210> SEQ ID NO 152
<211> LENGTH: 6
<212> TYPE: PRT
<213> ORGANISM: Artificial Sequence
```

```
<220> FEATURE:
<223> OTHER INFORMATION: synthetic construct
<220> FEATURE:
<221> NAME/KEY: MISC_FEATURE
<222> LOCATION: (1)..(6)
<223> OTHER INFORMATION: forms a cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid

<400> SEQUENCE: 152

Phe Xaa Arg Arg Arg Gln
1               5

<210> SEQ ID NO 153
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 153

Cys Trp Trp Arg Arg Arg Arg Cys
1               5

<210> SEQ ID NO 154
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(9)
<223> OTHER INFORMATION: Cys residues jopined by disulfide bond

<400> SEQUENCE: 154

Cys Trp Trp Val Arg Arg Arg Arg Cys
1               5

<210> SEQ ID NO 155
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 155

Cys Phe Trp Arg Arg Arg Arg Cys
1               5
```

```
<210> SEQ ID NO 156
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (1)..(8)
<223> OTHER INFORMATION: Cys residues jopined by disulfide bond

<400> SEQUENCE: 156

Cys Trp Trp Trp Arg Arg Arg Cys
1               5

<210> SEQ ID NO 157
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homeoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (5)..(7)
<223> OTHER INFORMATION: D-amino acid

<400> SEQUENCE: 157

Xaa Xaa Arg Glu Arg Arg Glu
1               5

<210> SEQ ID NO 158
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homeoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (5)..(7)
<223> OTHER INFORMATION: D-amino acid

<400> SEQUENCE: 158

Xaa Xaa Arg Arg Arg Arg Glu
1               5

<210> SEQ ID NO 159
<211> LENGTH: 7
<212> TYPE: PRT
```

```
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(3)
<223> OTHER INFORMATION: L-napthylalanine
<220> FEATURE:
<221> NAME/KEY: MOD_RES
<222> LOCATION: (5)..(7)
<223> OTHER INFORMATION: D-amino acid

<400> SEQUENCE: 159

Xaa Xaa Xaa Arg Arg Arg Glu
1               5

<210> SEQ ID NO 160
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(3)
<223> OTHER INFORMATION: L-napthylalanine
<220> FEATURE:
<221> NAME/KEY: MOD_RES
<222> LOCATION: (5)..(6)
<223> OTHER INFORMATION: D-amino acid

<400> SEQUENCE: 160

Xaa Xaa Xaa Arg Arg Arg Glu
1               5

<210> SEQ ID NO 161
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (5)..(7)
<223> OTHER INFORMATION: D-amino acid

<400> SEQUENCE: 161
```

```
Xaa Xaa Phe Arg Arg Arg Glu
1               5

<210> SEQ ID NO 162
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homeoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (5)..(6)
<223> OTHER INFORMATION: D-amino acid

<400> SEQUENCE: 162

Xaa Xaa Phe Arg Arg Arg Glu
1               5

<210> SEQ ID NO 163
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homeoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(7)
<223> OTHER INFORMATION: D-amino acid

<400> SEQUENCE: 163

Xaa Xaa Phe Arg Arg Arg Glu
1               5

<210> SEQ ID NO 164
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
```

```
<222> LOCATION: (1)..(1)
<223> OTHER INFORMATION: L-homeoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(6)
<223> OTHER INFORMATION: D-amino acid

<400> SEQUENCE: 164

Xaa Xaa Phe Arg Arg Arg Glu
1               5

<210> SEQ ID NO 165
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homeoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (3)..(3)
<223> OTHER INFORMATION: D-napthylalanine
<220> FEATURE:
<221> NAME/KEY: MOD_RES
<222> LOCATION: (5)..(6)
<223> OTHER INFORMATION: D-amino acid

<400> SEQUENCE: 165

Xaa Xaa Xaa Arg Arg Arg Glu
1               5

<210> SEQ ID NO 166
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(7)
<223> OTHER INFORMATION: forms a cyclic peptide
<220> FEATURE:
<221> NAME/KEY: MOD_RES
<222> LOCATION: (1)..(1)
<223> OTHER INFORMATION: L-homeoproline
<220> FEATURE:
<221> NAME/KEY: MOD_RES
<222> LOCATION: (2)..(2)
<223> OTHER INFORMATION: L-napthylalanine
<220> FEATURE:
<221> NAME/KEY: MOD_RES
<222> LOCATION: (3)..(3)
<223> OTHER INFORMATION: D-napthylalanine
<220> FEATURE:
<221> NAME/KEY: MOD_RES
<222> LOCATION: (5)..(7)
```

```
<223> OTHER INFORMATION: D-amino acid

<400> SEQUENCE: 166

Xaa Xaa Xaa Arg Arg Arg Glu
1               5

<210> SEQ ID NO 167
<211> LENGTH: 8
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Arg is modified with pimelic acid
<220> FEATURE:
<221> NAME/KEY: MISC_FEATURE
<222> LOCATION: (1)..(4)
<223> OTHER INFORMATION: Cyclization between Arg is modified with
      pimelic acid and Arg is modified with lysine peptoid residue
<220> FEATURE:
<221> NAME/KEY: MOD_RES
<222> LOCATION: (4)..(4)
<223> OTHER INFORMATION: Arg is modified with lysine peptoid residue

<400> SEQUENCE: 167

Arg Gln Arg Arg Gly Arg Arg Arg
1               5

<210> SEQ ID NO 168
<211> LENGTH: 19
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (2)..(19)
<223> OTHER INFORMATION: Cys residues jopined by disulfide bond

<400> SEQUENCE: 168

Lys Cys Phe Gln Trp Gln Arg Asn Met Arg Lys Val Arg Gly Pro Pro
1               5                   10                  15

Val Ser Cys

<210> SEQ ID NO 169
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(11)
<223> OTHER INFORMATION: Cyclization between Lys and Glu
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
```

```
<220> FEATURE:
<221> NAME/KEY: MOD_RES
<222> LOCATION: (10)..(10)
<223> OTHER INFORMATION: D-amino acid

<400> SEQUENCE: 169

Lys Arg Arg Arg Gly Arg Lys Lys Arg Glu
1               5                   10

<210> SEQ ID NO 170
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(12)
<223> OTHER INFORMATION: Cyclization between Lys and Glu
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: D-amino acid

<400> SEQUENCE: 170

Lys Arg Arg Arg Arg Arg Arg Arg Arg Glu
1               5                   10

<210> SEQ ID NO 171
<211> LENGTH: 34
<212> TYPE: PRT
<213> ORGANISM: Artificial Sequence
<220> FEATURE:
<223> OTHER INFORMATION: synthetic construct
<220> FEATURE:
<221> NAME/KEY: DISULFID
<222> LOCATION: (4)..(21)
<223> OTHER INFORMATION: Cys residues jopined by disulfide bond
<220> FEATURE:
<221> NAME/KEY: DISULFID
<222> LOCATION: (11)..(23)
<223> OTHER INFORMATION: Cys residues jopined by disulfide bond
<220> FEATURE:
<221> NAME/KEY: DISULFID
<222> LOCATION: (17)..(29)
<223> OTHER INFORMATION: Cys residues jopined by disulfide bond

<400> SEQUENCE: 171

Gly Gly Val Cys Pro Lys Ile Leu Lys Lys Cys Arg Arg Asp Ser Asp
1               5                   10                  15

Cys Pro Gly Ala Cys Ile Cys Arg Gly Asn Gly Tyr Cys Gly Ser Gly
            20                  25                  30

Ser Asp

<210> SEQ ID NO 172
```

```
<211> LENGTH: 10
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (1)..(10)
<223> OTHER INFORMATION: Macrocyclization by multicomponent reaction
      with aziridine aldehyde and isocyanide
<220> FEATURE:
<221> NAME/KEY: MOD_RES
<222> LOCATION: (2)..(2)
<223> OTHER INFORMATION: L-3-cyclohexyl-alanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (4)..(4)
<223> OTHER INFORMATION: L-cyclohexylalanine
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (6)..(6)
<223> OTHER INFORMATION: L-cyclohexylalanine
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (8)..(8)
<223> OTHER INFORMATION: L-cyclohexylalanine
<220> FEATURE:
<221> NAME/KEY: MOD_RES
<222> LOCATION: (9)..(9)
<223> OTHER INFORMATION: D-amino acid

<400> SEQUENCE: 172

Pro Xaa Arg Xaa Arg Xaa Arg Xaa Arg Gly
1               5                   10

<210> SEQ ID NO 173
<211> LENGTH: 13
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: Ser is modified with trimesic acid
<220> FEATURE:
<221> NAME/KEY: MISC_FEATURE
<222> LOCATION: (1)..(13)
<223> OTHER INFORMATION: N-terminal amine and side chains of two
      L-2,3-diaminopropionic acid residues bicyclized with trimesic acid
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (4)..(4)
<223> OTHER INFORMATION: L-4-(phosphonodifluoromethyl)phenylalanine
<220> FEATURE:
<221> NAME/KEY: MOD_RES
<222> LOCATION: (6)..(6)
<223> OTHER INFORMATION: L-2,3-diaminopropionic acid
<220> FEATURE:
<221> NAME/KEY: MOD_RES
<222> LOCATION: (8)..(8)
```

```
<223> OTHER INFORMATION: L-naphthylalanine
<220> FEATURE:
<221> NAME/KEY: MOD_RES
<222> LOCATION: (13)..(13)
<223> OTHER INFORMATION: L-2,3-diaminopropionic acid

<400> SEQUENCE: 173

Ser Val Pro Xaa His Xaa Phe Xaa Arg Arg Arg Arg Xaa
1               5                   10

<210> SEQ ID NO 174
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: D-alanine is modified with trimesic acid
<220> FEATURE:
<221> NAME/KEY: MOD_RES
<222> LOCATION: (1)..(1)
<223> OTHER INFORMATION: D-amino acid
<220> FEATURE:
<221> NAME/KEY: MISC_FEATURE
<222> LOCATION: (1)..(17)
<223> OTHER INFORMATION: N-terminal amine and side chains of two
      L-2,3-diaminopropionic acid residues bicyclized with trimesic acid
<220> FEATURE:
<221> NAME/KEY: MOD_RES
<222> LOCATION: (2)..(2)
<223> OTHER INFORMATION: sarcosine
<220> FEATURE:
<221> NAME/KEY: MOD_RES
<222> LOCATION: (4)..(4)
<223> OTHER INFORMATION: D-phosphothreonine
<220> FEATURE:
<221> NAME/KEY: MOD_RES
<222> LOCATION: (5)..(5)
<223> OTHER INFORMATION: L-homoproline
<220> FEATURE:
<221> NAME/KEY: MOD_RES
<222> LOCATION: (6)..(6)
<223> OTHER INFORMATION: L-naphthylalanine
<220> FEATURE:
<221> NAME/KEY: MOD_RES
<222> LOCATION: (9)..(9)
<223> OTHER INFORMATION: D-alanine
<220> FEATURE:
<221> NAME/KEY: MOD_RES
<222> LOCATION: (10)..(10)
<223> OTHER INFORMATION: L-2,3-diaminopropionic acid
<220> FEATURE:
<221> NAME/KEY: MOD_RES
<222> LOCATION: (12)..(12)
<223> OTHER INFORMATION: L-naphthylalanine
<220> FEATURE:
<221> NAME/KEY: MOD_RES
<222> LOCATION: (17)..(17)
<223> OTHER INFORMATION: L-2,3-diaminopropionic acid

<400> SEQUENCE: 174

Ala Xaa Asp Xaa Xaa Xaa Arg Ala Xaa Xaa Phe Xaa Arg Arg Arg Arg
1               5                   10                  15

Xaa

<210> SEQ ID NO 175
<211> LENGTH: 16
<212> TYPE: PRT
<213> ORGANISM: Artificial Sequence
<220> FEATURE:
<223> OTHER INFORMATION: synthetic construct
<220> FEATURE:
```

```
<221> NAME/KEY: MISC_FEATURE
<222> LOCATION: (1)..(15)
<223> OTHER INFORMATION: Three Cys side chains bicyclized with
      tris(bromomethyl)benzene

<400> SEQUENCE: 175

Cys Arg Arg Ser Arg Arg Gly Cys Gly Arg Arg Ser Arg Arg Cys Gly
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: synthetic construct

<400> SEQUENCE: 176

Leu Lys Lys Leu Cys Lys Leu Leu Lys Lys Leu Cys Lys Leu Ala Gly
1               5                   10                  15

<210> SEQ ID NO 177
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (5)..(9)
<223> OTHER INFORMATION: Cyclization between Lys and Glu

<400> SEQUENCE: 177

Arg Arg Arg Arg Lys Arg Arg Arg Glu
1               5

<210> SEQ ID NO 178
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(9)
<223> OTHER INFORMATION: Cyclization between Lys and Glu

<400> SEQUENCE: 178

Arg Arg Arg Lys Arg Arg Arg Arg Glu
1               5

<210> SEQ ID NO 179
<211> LENGTH: 9
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (3)..(9)
<223> OTHER INFORMATION: Cyclization between Lys and Glu

<400> SEQUENCE: 179

Arg Arg Lys Arg Arg Arg Arg Arg Glu
1               5

<210> SEQ ID NO 180
<211> LENGTH: 9
<212> TYPE: PRT
<213> ORGANISM: Artificial Sequence
```

```
<220> FEATURE:
<223> OTHER INFORMATION: synthetic construct
<220> FEATURE:
<221> NAME/KEY: MISC_FEATURE
<222> LOCATION: (2)..(9)
<223> OTHER INFORMATION: Cyclization between Lys and Glu

<400> SEQUENCE: 180

Arg Lys Arg Arg Arg Arg Arg Arg Glu
1               5

<210> SEQ ID NO 181
<211> LENGTH: 12
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: L-propargylglycine
<220> FEATURE:
<221> NAME/KEY: MISC_FEATURE
<222> LOCATION: (1)..(12)
<223> OTHER INFORMATION: Cyclization by the click reaction between
      L-propargylglycine and L-6-Azido-2-amino-hexanoic
<220> FEATURE:
<221> NAME/KEY: MOD_RES
<222> LOCATION: (12)..(12)
<223> OTHER INFORMATION: L-6-Azido-2-amino-hexanoic

<400> SEQUENCE: 181

Xaa Leu Arg Lys Arg Leu Arg Lys Phe Arg Asn Xaa
1               5                   10

<210> SEQ ID NO 182
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: cyclic peptide
<220> FEATURE:
<221> NAME/KEY: MOD_RES
<222> LOCATION: (2)..(2)
<223> OTHER INFORMATION: D-amino acid
<220> FEATURE:
<221> NAME/KEY: MOD_RES
<222> LOCATION: (3)..(3)
<223> OTHER INFORMATION: L-2-naphthylalanine
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 182

Phe Phe Xaa Arg Arg Arg Arg Gln
1               5

<210> SEQ ID NO 183
<211> LENGTH: 8
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (1)..(8)
<223> OTHER INFORMATION: cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (4)..(4)
<223> OTHER INFORMATION: D-amino acid
<220> FEATURE:
<221> NAME/KEY: MOD_RES
<222> LOCATION: (6)..(6)
<223> OTHER INFORMATION: D-amino acid

<400> SEQUENCE: 183

Phe Xaa Arg Arg Arg Arg Gln
1               5

<210> SEQ ID NO 184
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (2)..(2)
<223> OTHER INFORMATION: D-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (5)..(5)
<223> OTHER INFORMATION: D-amino acid
<220> FEATURE:
<221> NAME/KEY: MOD_RES
<222> LOCATION: (7)..(7)
<223> OTHER INFORMATION: D-amino acid

<400> SEQUENCE: 184

Phe Xaa Arg Arg Arg Arg Gln
1               5

<210> SEQ ID NO 185
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (2)..(2)
<223> OTHER INFORMATION: L-2-naphthylalanine
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
```

```
<222> LOCATION: (5)..(5)
<223> OTHER INFORMATION: D-amino acid

<400> SEQUENCE: 185

Phe Xaa Arg Arg Arg Arg Gln
1               5

<210> SEQ ID NO 186
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: cyclic peptide
<220> FEATURE:
<221> NAME/KEY: MOD_RES
<222> LOCATION: (2)..(2)
<223> OTHER INFORMATION: L-2-naphthylalanine

<400> SEQUENCE: 186

Phe Xaa Arg Arg Arg Arg Arg Gln
1               5

<210> SEQ ID NO 187
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (5)..(5)
<223> OTHER INFORMATION: L-2-naphthylalanine

<400> SEQUENCE: 187

Arg Arg Phe Arg Xaa Arg Gln
1               5

<210> SEQ ID NO 188
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: cyclic peptide
<220> FEATURE:
<221> NAME/KEY: MOD_RES
<222> LOCATION: (3)..(3)
<223> OTHER INFORMATION: L-2-naphthylalanine

<400> SEQUENCE: 188

Phe Phe Xaa Arg Arg Arg Arg Gln
1               5

<210> SEQ ID NO 189
<211> LENGTH: 8
<212> TYPE: PRT
<213> ORGANISM: Artificial Sequence
<220> FEATURE:
<223> OTHER INFORMATION: Synthetic Construct
<220> FEATURE:
```

```
<221> NAME/KEY: MISC_FEATURE
<222> LOCATION: (1)..(8)
<223> OTHER INFORMATION: cyclic peptide
<220> FEATURE:
<221> NAME/KEY: MOD_RES
<222> LOCATION: (6)..(6)
<223> OTHER INFORMATION: L-2-naphthylalanine

<400> SEQUENCE: 189

Arg Phe Arg Phe Arg Xaa Arg Gln
1               5

<210> SEQ ID NO 190
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(6)
<223> OTHER INFORMATION: cyclic peptide
<220> FEATURE:
<221> NAME/KEY: MOD_RES
<222> LOCATION: (2)..(2)
<223> OTHER INFORMATION: L-2-naphthylalanine

<400> SEQUENCE: 190

Phe Xaa Arg Arg Arg Gln
1               5

<210> SEQ ID NO 191
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<220> FEATURE:
<221> NAME/KEY: MOD_RES
<222> LOCATION: (6)..(6)
<223> OTHER INFORMATION: L-2-naphthylalanine

<400> SEQUENCE: 191

Phe Arg Arg Arg Arg Xaa Gln
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (5)..(5)
<223> OTHER INFORMATION: L-2-naphthylalanine

<400> SEQUENCE: 192

Arg Arg Phe Arg Xaa Arg Gln
1               5
```

-continued

```
<210> SEQ ID NO 193
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: cyclic peptide
<220> FEATURE:
<221> NAME/KEY: MOD_RES
<222> LOCATION: (3)..(3)
<223> OTHER INFORMATION: L-2-naphthylalanine

<400> SEQUENCE: 193

Arg Arg Xaa Phe Arg Arg Gln
1               5

<210> SEQ ID NO 194
<211> LENGTH: 4
<212> TYPE: PRT
<213> ORGANISM: Unknown
<220> FEATURE:
<223> OTHER INFORMATION: N-terminal tetrapeptide

<400> SEQUENCE: 194

Gly Pro His Pro
1

<210> SEQ ID NO 195
<211> LENGTH: 4
<212> TYPE: PRT
<213> ORGANISM: Unknown
<220> FEATURE:
<223> OTHER INFORMATION: N-terminal tetrapeptide
<220> FEATURE:
<221> NAME/KEY: MOD_RES
<222> LOCATION: (1)..(1)
<223> OTHER INFORMATION: ACETYLATION

<400> SEQUENCE: 195

Gly Pro His Pro
1

<210> SEQ ID NO 196
<211> LENGTH: 6
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MISC_FEATURE
<222> LOCATION: (5)..(6)
<223> OTHER INFORMATION: linked by 2-(2-(2-aminoethoxy)ethoxy)acetamide
      (miniPEG)
<220> FEATURE:
<221> NAME/KEY: MOD_RES
<222> LOCATION: (6)..(6)
<223> OTHER INFORMATION: fluorescein isothiocyanate (FITC) attached
```

```
<400> SEQUENCE: 196

Xaa Ile Xaa Ile Thr Lys
1               5

<210> SEQ ID NO 197
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (8)..(8)
<223> OTHER INFORMATION: 4-fluorophenylalanine
<220> FEATURE:
<221> NAME/KEY: MOD_RES
<222> LOCATION: (10)..(10)
<223> OTHER INFORMATION: beta-alanine
<220> FEATURE:
<221> NAME/KEY: MOD_RES
<222> LOCATION: (11)..(11)
<223> OTHER INFORMATION: fluorescein isothiocyanate (FITC) attached

<400> SEQUENCE: 197

Xaa Ile Xaa Ile Thr Tyr Glu Xaa Gly Ala Lys
1               5                   10

<210> SEQ ID NO 198
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: beta-alanine
<220> FEATURE:
<221> NAME/KEY: MOD_RES
<222> LOCATION: (11)..(11)
<223> OTHER INFORMATION: fluorescein isothiocyanate (FITC) attached
```

<400> SEQUENCE: 198

Xaa Ile Xaa Ile Thr Gln His Leu Ser Xaa Lys
1               5                   10

<210> SEQ ID NO 199
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: beta-alanine
<220> FEATURE:
<221> NAME/KEY: MOD_RES
<222> LOCATION: (11)..(11)
<223> OTHER INFORMATION: fluorescein isothiocyanate (FITC) attached

<400> SEQUENCE: 199

Xaa Ile Xaa Ile Thr Gln His Leu His Xaa Lys
1               5                   10

<210> SEQ ID NO 200
<211> LENGTH: 11
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (10)..(10)
<223> OTHER INFORMATION: beta-alanine
<220> FEATURE:
<221> NAME/KEY: MOD_RES
<222> LOCATION: (11)..(11)
<223> OTHER INFORMATION: fluorescein isothiocyanate (FITC) attached

<400> SEQUENCE: 200

Xaa Ile Xaa Ile Thr Asp Gln Tyr Arg Xaa Lys
1               5                   10

<210> SEQ ID NO 201
<211> LENGTH: 11
<212> TYPE: PRT

```
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (9)..(9)
<223> OTHER INFORMATION: D-amino acid
<220> FEATURE:
<221> NAME/KEY: MOD_RES
<222> LOCATION: (10)..(10)
<223> OTHER INFORMATION: beta-alanine
<220> FEATURE:
<221> NAME/KEY: MOD_RES
<222> LOCATION: (11)..(11)
<223> OTHER INFORMATION: fluorescein isothiocyanate (FITC) attached

<400> SEQUENCE: 201

Xaa Ile Xaa Ile Thr Asp Gln Tyr Lys Xaa Lys
1               5                   10

<210> SEQ ID NO 202
<211> LENGTH: 5
<212> TYPE: PRT
<213> ORGANISM: Artificial Sequence
<220> FEATURE:
<223> OTHER INFORMATION: linker sequence
<220> FEATURE:
<221> NAME/KEY: MOD_RES
<222> LOCATION: (1)..(2)
<223> OTHER INFORMATION: beta-alanine

<400> SEQUENCE: 202

Xaa Xaa Arg Arg Met
1               5

<210> SEQ ID NO 203
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: beta-alanine
<220> FEATURE:
<221> NAME/KEY: MISC_FEATURE
```

```
<222> LOCATION: (12)..(18)
<223> OTHER INFORMATION: cyclic peptide
<220> FEATURE:
<221> NAME/KEY: MOD_RES
<222> LOCATION: (13)..(13)
<223> OTHER INFORMATION: D-amino acid
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (17)..(17)
<223> OTHER INFORMATION: 3-(2-Naphthyl)-L-alanine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (18)..(18)
<223> OTHER INFORMATION: AMIDATION

<400> SEQUENCE: 203

Xaa Ile Xaa Ile Thr Gln His Leu Ser Xaa Lys Gln Arg Arg Arg Arg
1               5                   10                  15

Xaa Phe

<210> SEQ ID NO 204
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichloro-4-pyridinyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
    (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
```

```
<221> NAME/KEY: MOD_RES
<222> LOCATION: (17)..(17)
<223> OTHER INFORMATION: AMIDATION

<400> SEQUENCE: 204

Xaa Ile Xaa Ile Thr Gln His Leu Ser Lys Gln Arg Arg Arg Xaa
1               5                   10                  15

Phe

<210> SEQ ID NO 205
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichloro-4-pyridinyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: homovaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 205

Xaa Ile Xaa Ile Thr Gln His Leu Ser Lys Gln Arg Arg Arg Xaa
1               5                   10                  15

Phe

<210> SEQ ID NO 206
<211> LENGTH: 17
<212> TYPE: PRT
<213> ORGANISM: Artificial Sequence
<220> FEATURE:
<223> OTHER INFORMATION: synthetic construct
<220> FEATURE:
```

```
<221> NAME/KEY: MOD_RES
<222> LOCATION: (1)..(1)
<223> OTHER INFORMATION: 2,3-dichlorisonicotinamide moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 206

Xaa Ile Xaa Ile Thr Gln His Leu Ser Lys Gln Arg Arg Arg Arg Xaa
1               5                   10                  15

Phe

<210> SEQ ID NO 207
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzamide moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: L-beta-hydroxyvaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
```

```
        (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 207

Xaa Ile Xaa Ile Thr Gln His Leu Ser Lys Gln Arg Arg Arg Arg Xaa
1               5                   10                  15

Phe

<210> SEQ ID NO 208
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: L-beta-hydroxyvaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
        (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
```

```
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 208

Xaa Ile Xaa Ile Thr Gln His Leu Ser Lys Gln Arg Arg Arg Xaa
1               5                   10                  15

Phe

<210> SEQ ID NO 209
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (2)..(2)
<223> OTHER INFORMATION: L-cyclohexylglycine
<220> FEATURE:
<221> NAME/KEY: MOD_RES
<222> LOCATION: (3)..(3)
<223> OTHER INFORMATION: L-beta-hydroxyvaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: beta-alanine
<220> FEATURE:
<221> NAME/KEY: MISC_FEATURE
<222> LOCATION: (12)..(18)
<223> OTHER INFORMATION: cyclic peptide
<220> FEATURE:
<221> NAME/KEY: MOD_RES
<222> LOCATION: (13)..(13)
<223> OTHER INFORMATION: D-amino acid
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (17)..(17)
<223> OTHER INFORMATION: 3-(2-Naphthyl)-L-alanine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (18)..(18)
<223> OTHER INFORMATION: AMIDATION

<400> SEQUENCE: 209

Xaa Xaa Xaa Ile Thr Gln His Leu Ser Xaa Lys Gln Arg Arg Arg Arg
1               5                   10                  15

Xaa Phe

<210> SEQ ID NO 210
```

```
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (2)..(2)
<223> OTHER INFORMATION: L-cyclohexylglycine
<220> FEATURE:
<221> NAME/KEY: MOD_RES
<222> LOCATION: (3)..(3)
<223> OTHER INFORMATION: L-beta-hydroxyvaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 210

Xaa Xaa Xaa Ile Thr Gln His Leu Ser Lys Gln Arg Arg Arg Arg Xaa
1               5                   10                  15

Phe

<210> SEQ ID NO 211
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
```

```
<222> LOCATION: (3)..(3)
<223> OTHER INFORMATION: L-penicillamine sulfonic acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 211

Xaa Ile Xaa Ile Thr Gln His Leu Ser Lys Gln Arg Arg Arg Arg Xaa
1               5                   10                  15

Phe

<210> SEQ ID NO 212
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (2)..(2)
<223> OTHER INFORMATION: L-cyclohexylglycine
<220> FEATURE:
<221> NAME/KEY: MOD_RES
<222> LOCATION: (3)..(3)
<223> OTHER INFORMATION: L-penicillamine sulfonic acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
```

<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 212

Xaa Xaa Xaa Ile Thr Gln His Leu Ser Lys Gln Arg Arg Arg Arg Xaa
1               5                   10                  15

Phe

<210> SEQ ID NO 213
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-difluoroisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: L-beta-hydroxyvaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
    (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)

<223> OTHER INFORMATION: AMIDATION

<400> SEQUENCE: 213

Xaa Ile Xaa Ile Thr Gln His Leu Ser Lys Gln Arg Arg Arg Arg Xaa
1               5                   10                  15
Phe

<210> SEQ ID NO 214
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-difluoroisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (2)..(2)
<223> OTHER INFORMATION: L-cyclopentylglycine
<220> FEATURE:
<221> NAME/KEY: MOD_RES
<222> LOCATION: (3)..(3)
<223> OTHER INFORMATION: L-beta-hydroxyvaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 214

Xaa Xaa Xaa Ile Thr Gln His Leu Ser Lys Gln Arg Arg Arg Arg Xaa
1               5                   10                  15
Phe

<210> SEQ ID NO 215
<211> LENGTH: 17
<212> TYPE: PRT
<213> ORGANISM: Artificial Sequence
<220> FEATURE:

```
<223> OTHER INFORMATION: synthetic construct
<220> FEATURE:
<221> NAME/KEY: MOD_RES
<222> LOCATION: (1)..(1)
<223> OTHER INFORMATION: 2,3-difluoroisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (2)..(2)
<223> OTHER INFORMATION: L-cyclohexylglycine
<220> FEATURE:
<221> NAME/KEY: MOD_RES
<222> LOCATION: (3)..(3)
<223> OTHER INFORMATION: L-beta-hydroxyvaline
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 215

Xaa Xaa Xaa Ile Thr Gln His Leu Ser Lys Gln Arg Arg Arg Arg Xaa
1               5                   10                  15

Phe

<210> SEQ ID NO 216
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-difluoroisonicotinamide
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (2)..(2)
<223> OTHER INFORMATION: L-cyclohexylglycine
<220> FEATURE:
<221> NAME/KEY: MOD_RES
```

```
<222> LOCATION: (3)..(3)
<223> OTHER INFORMATION: L-penicillamine sulfonic acid
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
<222> LOCATION: (11)..(17)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: 3-(2-Naphthyl)-L-alanine
<220> FEATURE:
<221> NAME/KEY: MOD_RES
<222> LOCATION: (17)..(17)
<223> OTHER INFORMATION: D-amino acid
<220> FEATURE:
<221> NAME/KEY: MOD_RES
<222> LOCATION: (17)..(17)
<223> OTHER INFORMATION: AMIDATION

<400> SEQUENCE: 216

Xaa Xaa Xaa Ile Thr Gln His Leu Ser Lys Gln Arg Arg Arg Xaa
1               5                   10                  15

Phe

<210> SEQ ID NO 217
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzamide
<220> FEATURE:
<221> NAME/KEY: MOD_RES
<222> LOCATION: (1)..(1)
<223> OTHER INFORMATION: Tert-butyl-alanine
<220> FEATURE:
<221> NAME/KEY: MOD_RES
<222> LOCATION: (3)..(3)
<223> OTHER INFORMATION: Tert-butyl-alanine

<400> SEQUENCE: 217

Xaa Ile Xaa Ile Thr Gly Pro
1               5

<210> SEQ ID NO 218
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (5)..(5)
<223> OTHER INFORMATION: tert-butyl-alanine
```

```
<220> FEATURE:
<221> NAME/KEY: MOD_RES
<222> LOCATION: (5)..(5)
<223> OTHER INFORMATION: tert-butyl-alanine
<220> FEATURE:
<221> NAME/KEY: misc_feature
<222> LOCATION: (7)..(7)
<223> OTHER INFORMATION: Xaa can be any naturally occurring amino acid

<400> SEQUENCE: 218

Gly Pro His Pro Xaa Ile Xaa Ile Thr Gly Pro His Glu Glu
1               5                   10

<210> SEQ ID NO 219
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (7)..(7)
<223> OTHER INFORMATION: D-amino acid
<220> FEATURE:
<221> NAME/KEY: MOD_RES
<222> LOCATION: (8)..(8)
<223> OTHER INFORMATION: 4-fluorophenylalanine
<220> FEATURE:
<221> NAME/KEY: MOD_RES
<222> LOCATION: (10)..(10)
<223> OTHER INFORMATION: beta-alanine
<220> FEATURE:
<221> NAME/KEY: MISC_FEATURE
<222> LOCATION: (12)..(18)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (13)..(13)
<223> OTHER INFORMATION: L-2-naphthylalanine
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (17)..(17)
<223> OTHER INFORMATION: D-amino acid

<400> SEQUENCE: 219

Xaa Ile Xaa Ile Thr Tyr Glu Xaa Gly Ala Lys Phe Xaa Arg Arg Arg
1               5                   10                  15

Arg Gln

<210> SEQ ID NO 220
<211> LENGTH: 18
<212> TYPE: PRT
<213> ORGANISM: Artificial Sequence
<220> FEATURE:
```

```
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MOD_RES
<222> LOCATION: (10)..(10)
<223> OTHER INFORMATION: beta-alanine
<220> FEATURE:
<221> NAME/KEY: MISC_FEATURE
<222> LOCATION: (12)..(18)
<223> OTHER INFORMATION: cyclic peptide
<220> FEATURE:
<221> NAME/KEY: MOD_RES
<222> LOCATION: (12)..(12)
<223> OTHER INFORMATION: D-amino acid
<220> FEATURE:
<221> NAME/KEY: MOD_RES
<222> LOCATION: (13)..(13)
<223> OTHER INFORMATION: L-2-naphthylalanine
<220> FEATURE:
<221> NAME/KEY: MOD_RES
<222> LOCATION: (15)..(15)
<223> OTHER INFORMATION: D-amino acid
<220> FEATURE:
<221> NAME/KEY: MOD_RES
<222> LOCATION: (17)..(17)
<223> OTHER INFORMATION: D-amino acid

<400> SEQUENCE: 220

Xaa Ile Xaa Ile Thr Gln His Leu Ser Xaa Lys Phe Xaa Arg Arg Arg
1               5                   10                  15

Arg Gln

<210> SEQ ID NO 221
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: MOD_RES
<222> LOCATION: (1)..(1)
<223> OTHER INFORMATION: 2,3-dichlorobenzoyl moiety attached
<220> FEATURE:
<221> NAME/KEY: MOD_RES
<222> LOCATION: (1)..(1)
<223> OTHER INFORMATION: tert-butyl-alanine
<220> FEATURE:
<221> NAME/KEY: MOD_RES
<222> LOCATION: (3)..(3)
<223> OTHER INFORMATION: tert-butyl-alanine
<220> FEATURE:
<221> NAME/KEY: MOD_RES
<222> LOCATION: (8)..(8)
<223> OTHER INFORMATION: D-amino acid
<220> FEATURE:
<221> NAME/KEY: MISC_FEATURE
<222> LOCATION: (9)..(10)
<223> OTHER INFORMATION: linked by 2-(2-(2-aminoethoxy)ethoxy)acetamide
      (miniPEG)
<220> FEATURE:
<221> NAME/KEY: MISC_FEATURE
```

```
<222> LOCATION: (11)..(17)
<223> OTHER INFORMATION: cyclic peptide
<220> FEATURE:
<221> NAME/KEY: MOD_RES
<222> LOCATION: (11)..(11)
<223> OTHER INFORMATION: D-amino acid
<220> FEATURE:
<221> NAME/KEY: MOD_RES
<222> LOCATION: (12)..(12)
<223> OTHER INFORMATION: L-2-naphthylalanine
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (16)..(16)
<223> OTHER INFORMATION: D-amino acid

<400> SEQUENCE: 221

Xaa Ile Xaa Ile Thr Gln His Leu Ser Lys Phe Xaa Arg Arg Arg Arg
1               5                   10                  15

Gln
```

PEPTIDYL INHIBITORS OF CALCINEURIN-NFAT INTERACTION

CROSS-REFERENCE TO RELATED APPLICATIONS

This application is a national stage application filed under 35 U.S.C. § 371 of PCT/US2019/015695 filed Jan. 29, 2019, which claims priority to U.S. Provisional Application No. 62/623,235, filed on Jan. 29, 2018, which is incorporated by reference in its entirety for all purposes.

STATEMENT REGARDING FEDERALLY FUNDED RESEARCH

This invention was made with government support under GM110208, GM122459 and HL137224 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Apr. 10, 2022, is named SeqList_16965718_ST25.txt and is 89,438 bytes in size.

BACKGROUND

Activation of NFAT c3 influences the inflammatory phenotype of lung macrophages that contributes to the development of acute respiratory distress syndrome (ARDS). ARDS is a common, acute inflammatory lung disease (~200,000 cases/year in the US) with high morbidity and mortality rates (~40% mortality).

Calcineurin (CN) is a calmodulin (CaM)-dependent protein serine/threonine phosphatase that participates in activation of nuclear factor of activated T cells (NFAT) during T-cell signaling. During T cell activation, an increase in the cytoplasmic level of calcium activates CN, which subsequently dephosphorylates multiple phosphoseryl residues on NFATs, thereby activing NFAT. The dephosphorylated (activated) NFATs translocate into the nucleus and up-regulate the expression of interleukin 2 (IL-2), which in turn activates T-helper lymphocytes, induces the production of other cytokines, and stimulates the immune response. It was later found that CN also functions similarly in many other cell types including macrophages, where activation of NFATc3 by CN is required for inflammatory responses.

Thus, there exists a need for therapeutic agents which inhibit the Calcineurin-NFAT interaction. The present disclosure addresses this need.

SUMMARY

Described herein, in various embodiments, are peptides and peptide conjugates comprising CN binding motifs (CNBM) which inhibit the CN-NFAT interaction. In some embodiments, the peptides of the disclosure comprise: (i) CNBM; (ii) a hydrophobic, non-peptidic moiety ($R^H$) which interacts with the hydrophobic pocket on a CN protein; (iii) a sequence $-AA_{U1}-AA_{U2}-AA_{U3}-AA_{U4}-AA_{U5}-AA_{U6}$-, wherein each of $AA_{U2}$, $AA_{U3}$, $AA_{U4}$, $AA_{U5}$, and $AA_{U6}$, is, independently, optional, and each of $AA_{U1}$, $AA_{U2}$, $AA_{U3}$, $AA_{U4}$, $AA_{U5}$, and $AA_{U6}$ when present is independently an amino acid as defined herein; or (iv) combinations thereof.

In some embodiments, $R^H$ is conjugated to the N- or C-terminus of the CNBM. In some embodiments, the sequence $-AA_{U1}-AA_{U2}-AA_{U3}-AA_{U4}-AA_{U5}-AA_{U6}$- is conjugated to the N- or C terminus of the CNBM. In some embodiments, the peptides of the disclosure comprise: CNBM and $R^H$. In some embodiments. In some embodiments, the peptides of the disclosure comprise: CNBM and $AA_{U1}-AA_{U2}-AA_{U3}-AA_{U4}-AA_{U5}-AA_{U6}$-. In some embodiments, the peptides of the disclosure CNBM and $R^H$.

In some embodiments, the CNBM described herein comprises any combination of at least five amino acids selected from the group consisting of: tert-butyl-alanine (Tle or tle); isoleucine (Ile or ile); threonine (Thr or thr); valine (Val or val); homovaline (Hva or hva); β-hydroxyvaline (Bhv or bhv); cyclohexylglycine (Chg or chg); penicillamine sulfonic acid (Psa or psa). In some embodiments, the CNBM comprises one of the following sequences: (i) Tle-Ile-Tle-Ile-Thr (ZIZIT) (SEQ ID NO:1); (ii) Val-Ile-Val-Ile-Thr (VIVIT) (SEQ ID NO:2); (iii) Val-Ile-Tle-Ile-Thr (VIZIT) (SEQ ID NO:3); (iv) Tle-Ile-Hva-Ile-Thr (SEQ ID NO:4); (v) Tle-Ile-Val-Ile-Thr (ZIVIT) (SEQ ID NO:5); (vi) Tle-Ile-Bhv-Ile-Thr (SEQ ID NO:6); (vii) Tle-Chg-Bhv-Ile-Thr (SEQ ID NO:7); (viii) Tle-Ile-Psa-Ile-Thr (SEQ ID NO:8); or (ix) Tle-Chg-Psa-Ile-Thr (SEQ ID NO:9).

In some embodiments, $R^H$ is selected from acyl, carbocyclyl, heterocyclyl, formyl, and acetyl, each of which are optionally substituted. In some embodiments, R is an aryl or heteroaryl, each of which is optionally substituted. In some embodiments, R is pyridinyl, benzoyl, cyclopentylcarbonyl, or cyclohexylcarbonyl, each of which are optionally substituted. In some embodiments, R is a pyridinyl or benzoyl, each of which is optionally substituted with one or more substituents selected from halogen and alkyl. In some embodiments, the pyridinyl or benzoyl is substituted at the ortho position, the meta position, or a combination thereof with a halogen or an alkyl. In some embodiments, $R^H$ is 2,3-dichlorobenzoyl or 2,3-dichloro-4-pyridinyl.

In some embodiments, each of $AA_{U1}$, $AA_{U2}$, $AA_{U3}$, $AA_{U4}$, $AA_{U5}$, and $AA_{U6}$ are selected from the following amino acids:

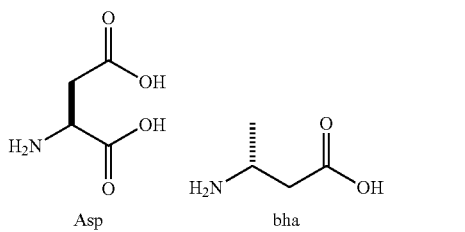

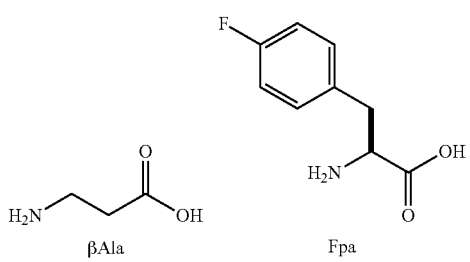

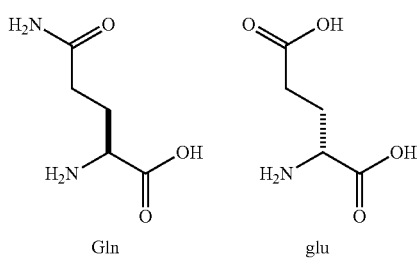

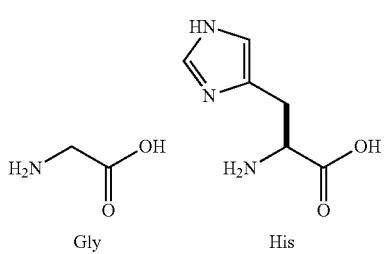

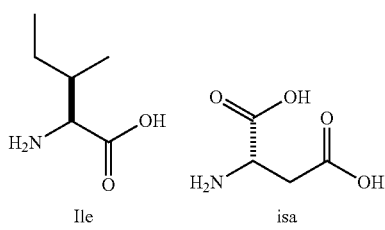

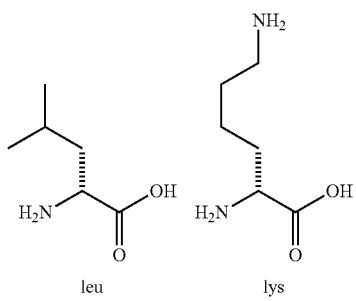

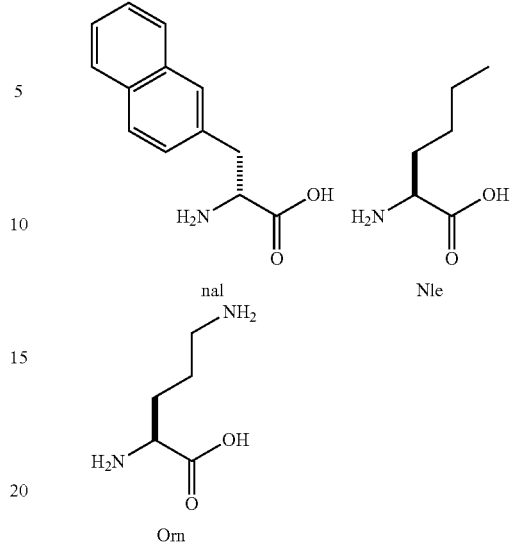

wherein the N- and/or the C-terminus of the above amino acids independently form peptide bonds. In some embodiments, $AA_{U1}$, $AA_{U2}$, $AA_{U3}$, and $AA_{U4}$ are selected from No. 1-47 below, and each of $AA_{U5}$ and $AA_{U6}$ are absent.

| No. | $AA_{U1}$ | $AA_{U2}$ | $AA_{U3}$ | $AA_{U4}$ |
|---|---|---|---|---|
| 1 | Asp | Gly | Trp | leu |
| 2 | Tyr | glu | Fpa | His |
| 3 | Tyr | Trp | Bha | Pro |
| 4 | Nal | Gln | AcP | Trp |
| 5 | Gln | Tyr | asn | Nal |
| 6 | Gln | His | leu | His |
| 7 | Asp | Gln | Tyr | Arg |
| 8 | Ias | Gln | Trp | Arg |
| 9 | Tyr | Acp | Gly | Trp |
| 10 | Ser | Gly | His | Nal |
| 11 | Pro | Nal | Arg | Bha |
| 12 | His | glu | Orn | ala |
| 13 | Gln | His | leu | Ser |
| 14 | Nle | Ala | Nal | Tyr |
| 15 | lys | His | Nal | Asp |
| 16 | Orn | Nle | His | Nal |
| 17 | Tyr | asn | Ser | Nal |
| 18 | Gly | Tyr | Gly | Nal |
| 19 | Asp | His | lys | Tyr |
| 20 | Gln | Tyr | βAla | Nal |
| 21 | His | His | phe | Trp |
| 22 | Arg | Tyr | glu | Tyr |
| 23 | Ala | His | Nal | Bha |
| 24 | Pro | βAsp | His | Nal |
| 25 | Gln | His | Tyr | Nle |
| 26 | Gln | phe | Arg | Asp |
| 27 | Trp | glu | Gly | Arg |
| 28 | Pro | glu | Nal | Arg |
| 29 | Gln | His | Gly | βAla |
| 30 | Tyr | glu | Fpa | Gly |
| 31 | Ala | His | Nal | Phg |
| 32 | Nal | His | Tyr | Acp |
| 33 | His | ala | Ser | Tyr |
| 34 | βAla | glu | Nal | Arg |
| 35 | thr | Pro | ala | Nal |
| 36 | Ile | His | Nal | His |
| 37 | Asp | Gln | Tyr | lys |
| 38 | βAla | glu | Arg | Tyr |
| 39 | thr | leu | Tyr | phe |
| 40 | Tyr | His | Pro | Trp |
| 41 | asn | Pro | Tyr | Trp |
| 42 | Ser | Tyr | Ser | Trp |
| 43 | Gln | Tyr | Nal | Ser |
| 44 | Tyr | His | Gly | phe |

-continued

| No. | AA$_{U1}$ | AA$_{U2}$ | AA$_{U3}$ | AA$_{U4}$ |
|---|---|---|---|---|
| 45 | Acp | Gly | Nal | His |
| 46 | glu | Pip | Nal | His |
| 47 | Gln | His | leu | Ser |

In some embodiments, the peptides described herein further comprise a cell penetrating peptide sequence conjugated to the peptide, e.g., at the N-termini, the C-termini, or a side chain of the amino acid in the peptide. In some embodiments, the cell penetrating peptide sequence is a cyclic, cell penetrating peptide sequence, e.g., any of those disclosed herein.

In some embodiments, the disclosure provides for polypeptide conjugates according to Formula I, II, or III:

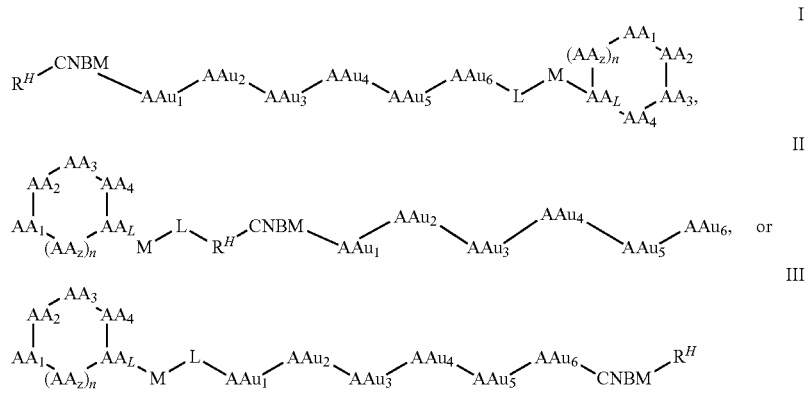

chain are independently selected from 3-benzothienyl-L-alanine, phenylalanine, naphthylalanine, and tryptophan, each of which is optionally substituted.

In some embodiments, M is a covalent bond, a disulfide, an amide, a thioether, or a triazolyl.

In some embodiments, L is a linking moiety selected from at least one amino acid, alkylene, alkenylene, alkynylene, aryl, cycloalkyl, cycloalkenyl, cycloalkynyl, heterocyclyl, heteroaryl, ether, βAla-Lys, mini-PEG-Lys, and combinations thereof, each of which are optionally substituted. In particular embodiments, is βAla-Lys, mini-PEG-Lys, or combinations thereof.

In some embodiments, the disclosure provides for pharmaceutical compositions comprising one or more peptides and/or peptide conjugates disclosed herein. In some embodiments, the disclosure also provides for methods of inhibiting the binding between CN and one or more ligands, comprising contacting the CN with a peptide or peptide conjugate disclosed herein. In other embodiments, the disclosure provides for a method for treating a subject having acute respiratory distress syndrome (ARDS) comprising administering a therapeutically effective amount of a peptide or polypeptide conjugate disclosed herein. In still other embodiments, the disclosure provides for peptides and peptide conjugates for use as a medicament in the treatment of ARDS.

In some embodiments, the disclosure provides for a cell comprising a peptide and/or polypeptide conjugate described herein.

In other embodiments, the disclosure provides for method of making a peptide or polypeptide conjugate disclosed herein.

wherein:
each of AA$_1$, AA$_2$, AA$_3$, and AA$_4$ are independently an amino acid which is optionally substituted;

AA$_Z$, at each instance and when present, is independently an amino acid which is optionally substituted;

n is an integer from 0 to 6;

AA$_L$ is an amino acid;

M is a bonding moiety;

L is a linking moiety;

AA$_{U1}$, AA$_{U2}$, AA$_{U3}$, AA$_{U4}$, AA$_{U5}$, and AA$_{U6}$, is, independently, optional, and when present, is an amino acid which is optionally substituted;

CNBM is a CN-binding motif having the following sequence: (i) Tle-Ile-Tle-Ile-Thr (ZIZIT) (SEQ ID NO:1); (ii) Val-Ile-Val-Ile-Thr (VIVIT) (SEQ ID NO:2); (iii) Val-Ile-Tle-Ile-Thr (VIZIT) (SEQ ID NO:3); (iv) Tle-Ile-Hva-Ile-Thr (SEQ ID NO:4); (v) Tle-Ile-Val-Ile-Thr (ZIVIT) (SEQ ID NO:5); (vi) Tle-Ile-Bhv-Ile-Thr (SEQ ID NO:6); (vii) Tle-Chg-Bhv-Ile-Thr (SEQ ID NO:7); (viii) Tle-Ile-Psa-Ile-Thr (SEQ ID NO:8); or (ix) Tle-Chg-Psa-Ile-Thr (SEQ ID NO: 9); and R$^H$ is a hydrophobic non-peptidyl moiety which interacts with the hydrophobic pocket in a CN protein;
wherein:
at least two of AA$_1$, AA$_2$, AA$_3$, AA$_4$ and AA$_Z$ are arginines; and
at least two of AA$_1$, AA$_2$, AA$_3$, AA$_4$ and AA$_Z$ are independently amino acids having a hydrophobic side chain.

In some embodiments, the at least one hydrophobic side chain comprises an aromatic ring. In particular embodiments, wherein the amino acids having a hydrophobic side

n=5). (a) TNFα, IL-6, and total protein levels in BALF 4 h after treatment. (b) TNFα, IL-6, and total protein levels in BALF 24 h after treatment.

Figure 26:
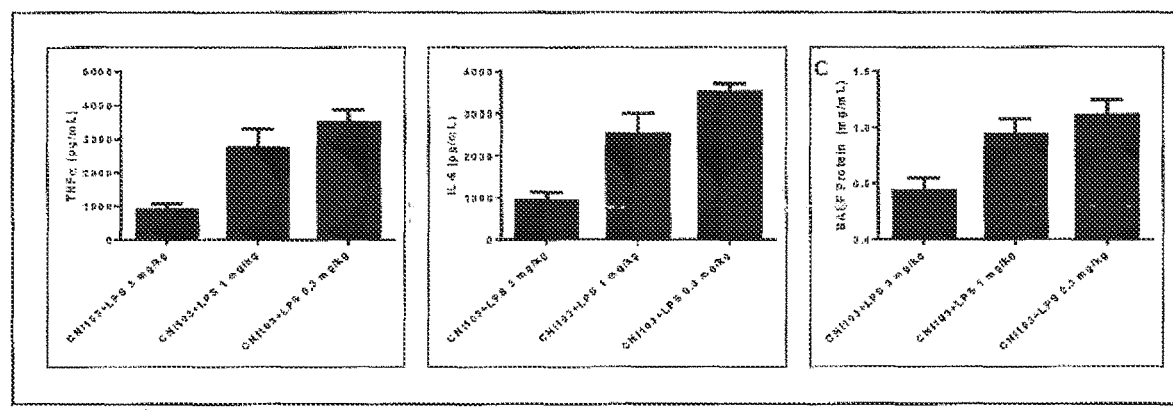

FIG. 26 Dose response of intranasally administered CNI103 (SEQ ID NO: 208) for prevention of cytokine secretion in a mouse ALI model (n=5). (a) TNFα (b) IL-6, and (c) total protein levels in BALF.

Figure 27:
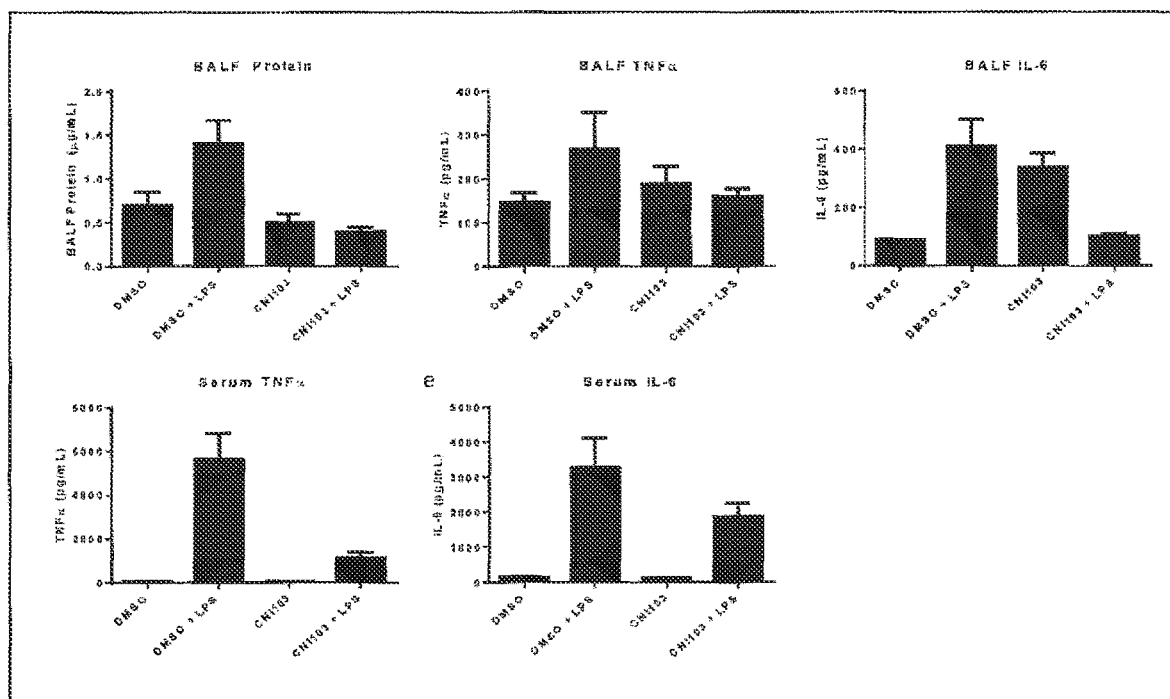

FIG. 27 Reduction of LPS-induced cytokine secretion in mice dosed intravenously with CNI103 (SEQ ID NO: 208) (5 mg/kg; n=5). (a) Total protein levels in BALF; (b) TNFα levels in BALF; (c) IL-6 levels in BALF; (d) TNFα levels in serum; and (e) IL-6 levels in serum.

Figure 28:
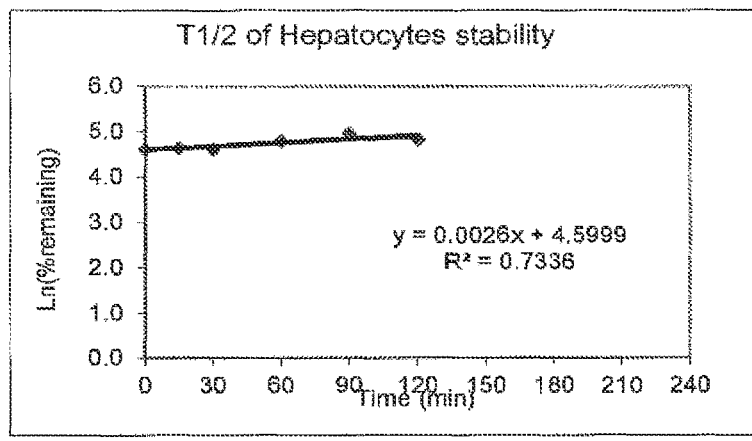

FIG. 28. Half-life ($T_{1/2}$) of hepatocytes stability.

Figure 29:
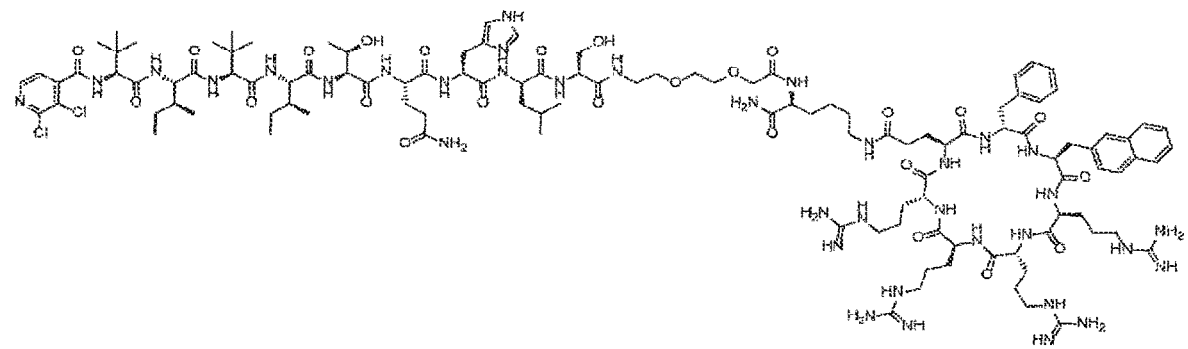
Figure 29:
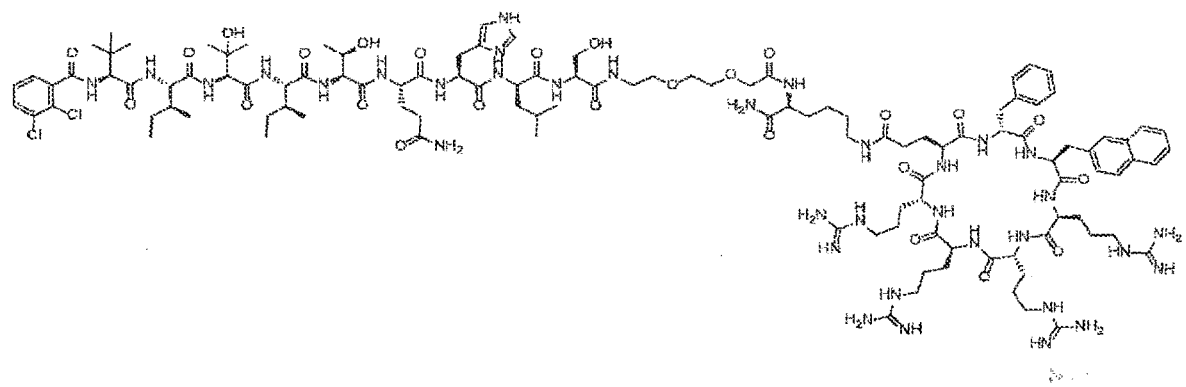
Figure 29:
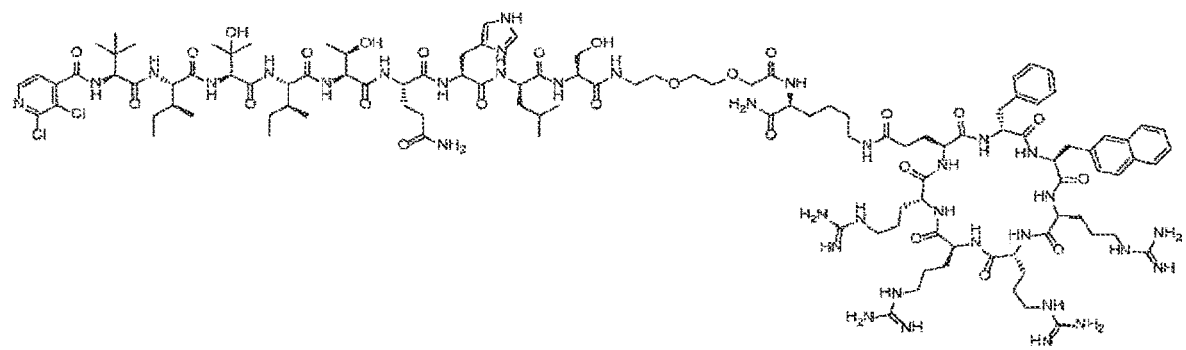

FIG. 29. Depicts the structure of compounds 41-54, which correspond to CNI101-CNI111 (SEQ ID NOs: 206-216).

DETAILED DESCRIPTION

"Peptide", "polypeptide", and "peptide conjugate" are used interchangeably herein to refer to a natural or synthetic molecule comprising two or more amino acids linked together by peptide (amide) bonds. The term(s), as used herein, refer to proteins, polypeptides, and peptide of any size, structure, or function. In addition, such terms encompass amino acids joined to each other by peptide bonds or modified peptide bonds, e.g., peptide isosteres, etc., and may contain modified amino acids other than the 20 gene-encoded amino acids. The polypeptides of the instant disclosure may contain natural amino acids and/or non-natural amino acids (i.e., compounds that do not occur in nature but that can be incorporated into a polypeptide chain). Amino acid analogs as are known in the art may alternatively be employed. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyrog!utamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T, E. Creighton, W.H. Freeman and Company, New York (1993); Posttranslational Covalent Modification of Proteins, B.C. Johnson, Ed., Academic Press, New York, pp. 1-12 (1983), each of which are herein incorporated by reference its entirety for all purposes).

The above terms also encompass modifications of one or more amino acids that enhance a property of the original peptide, such as increase stability, increased efficacy, enhanced delivery, increased half life, etc. Methods of making such modifications based upon a known polypeptide sequence are described, for example, in U.S. Pat. Nos. 5,631,280; 5,612,895; and 5,579,250, each of which are herein incorporated by reference in its entirety for all purposes. For example, modifications can involve the incorporation of a non-amino acid residue and/or non-amide linkages at a given position. Some non-limiting examples of unnatural amino acids which may be suitable amino acid mimics include β-alanine, L-α-amino butyric acid, L-γ-ammo butyric acid, L-α-amino isobutyric acid, L-ε-amino caproic acid, 7-amino heptanoic acid, L-aspartic acid, L-glutamic acid, N-ε-Boe-N-α-CBZ-L-lysine, N-ε-Boc-N-α-Fmoc-L-lysine, L-rnethionine sulfone, L-norleucine, L-norvaline, N-α-Boc-N-δCBZ-L-ornithine, N-δ-Boc-N-α-CBZ-L-oraithine, Boc-p-nitro-L-phenylaianine, Boc-hydroxyproline, and Boc-L-thioproline.

"Acyl" refers to a radical of the formula —C(=O)$R_a$, wherein $R_a$ is an $C_{1-40}$ alkyl, $C_{2-40}$ alkenyl, $C_{2-40}$ alkynyl, carbocyclyl, or heterocyclyl.

"Alkylene" or "alkylene chain" refers to a fully saturated, straight or branched divalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. The alkylene chain is attached, directly or indirectly, to the cCPP through a single bond and, directly or indirectly, to the CNBM through a single bond. Unless stated otherwise specifically in the specification, an alkylene chain can be optionally substituted as described herein.

"Alkenylene" or "alkenylene chain" refers to a straight or branched divalent hydrocarbon chain radical, having from two to forty carbon atoms, and having one or more carbon-carbon double bonds. Non-limiting examples of $C_2$-$C_{40}$ alkenylene include ethene, propene, butene, and the like. The alkenylene chain is attached, directly or indirectly, to the cCPP through a single bond and, directly or indirectly, to the CNBM through a single bond. Unless stated otherwise specifically in the specification, an alkenylene chain can be optionally substituted.

"Alkynylene" or "alkynylene chain" refers to a straight or branched divalent hydrocarbon chain radical, having from two to forty carbon atoms, and having one or more carbon-carbon triple bonds. Non-limiting examples of $C_2$-$C_{40}$ alkynylene include ethynylene, propargylene and the like. The alkynylene chain is attached, directly or indirectly, to the cCPP through a single bond and, directly or indirectly, to the CNBM through a single bond. Unless stated otherwise specifically in the specification, an alkynylene chain can be optionally substituted.

"Aryl" refers to a hydrocarbon ring system comprising hydrogen, 6 to 40 carbon atoms and at least one aromatic ring. For purposes of this invention, the aryl can be a monovalent radical (e.g., when R is an aryl) or a divalent radical (e.g., when the linker is an aryl). Further, the aryl can be a monocyclic, bicyclic, tricyclic or tetracyclic ring system, which can include fused or bridged ring systems. Aryls include, but are not limited to, aryl divalent radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. When the aryl is a monovalent radical (i.e., when R is an aryl), the aryl is attached to the CNBM through a single bond. When the aryl is a divalent radical (i.e., when the aryl comprises a linker), the aryl is attached, directly or indirectly, to the cCPP through a single bond and, directly or indirectly, to the CNBM through a single bond. Unless stated otherwise specifically in the specification, an aryl group can be optionally substituted.

"Carbocyclyl," "carbocyclic ring" or "carbocycle" refers to a rings structure, wherein the atoms which form the ring are each carbon. Carbocyclic rings can comprise from 3 to 20 carbon atoms in the ring. Carbocyclic rings include aryls and cycloalkyl, cycloalkenyl and cycloalkynyl as defined herein. For purposes of this invention, the carbocyclyl may be a monovalent radical (e.g., when R is a carbocyclyl) or a divalent radical (e.g., when the linker comprises a carbocyclyl). Unless stated otherwise specifically in the specification, a carbocyclyl group can be optionally substituted.

"Cycloalkyl" refers to a stable non-aromatic monocyclic or polycyclic fully saturated hydrocarbon divalent radical having from 3 to 40 carbon atoms and at least one ring, wherein the ring consists solely of carbon and hydrogen atoms, which can include fused or bridged ring systems. Monocyclic cycloalkyl divalent radicals include, for example, cyclopropyl, cyclobutyl, cyclopentyl, cyclohexyl, cycloheptyl, and cyclooctyl. Polycyclic cycloalkyl divalent radicals include, for example, adamantyl, norbornyl, decalinyl, 7,7-dimethyl-bicyclo[2.2.1]heptanyl, and the like. The cycloalkyl divalent radical is attached, directly or indirectly, to the cCPP through a single bond and, directly or indirectly, to CNBM through a single bond. Unless otherwise stated specifically in the specification, a cycloalkyl group can be optionally substituted.

"Cycloalkenyl" refers to a stable non-aromatic monocyclic or polycyclic hydrocarbon divalent radical having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. The cycloalkenyl divalent radical is attached, directly or indirectly, to the cCPP through a single bond and, directly or indirectly, to the CNBM through a single bond. Unless otherwise stated specifically in the specification, a cycloalkenyl group can be optionally substituted.

"Cycloalkynyl" refers to a stable non-aromatic monocyclic or polycyclic hydrocarbon divalent radical having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyl radicals include, for example, cycloheptynyl, cyclooctynyl, and the like. The cycloalkynyl divalent radical is attached, directly or indirectly, to the cCPP through a single bond and, directly or indirectly, to the CNBM through a single bond. Unless otherwise stated specifically in the specification, a cycloalkynyl group can be optionally substituted.

"Formyl" refers to a radical of the formula —C(=O)H.

"Heterocyclyl," "heterocyclic ring" or "heterocycle" refers to a stable 3- to 20-membered ring which consists of two to twelve carbon atoms and from one to six heteroatoms selected from the group consisting of nitrogen, oxygen and sulfur. For purposes of this invention, the heterocyclyl can be a monovalent radical (e.g., when R is a heterocyclyl) or a divalent radical (e.g., when the linker is a heterocyclyl) Heterocyclycl or heterocyclic rings include heteroaryls as defined below. Unless stated otherwise specifically in the specification, the heterocyclyl can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. When the heterocyclyl is a monovalent radical (e.g., when R is a heterocyclyl), said heterocyclyl is attached to the CNBM through a single bond. When the heterocyclyl is a divalent radical (e.g., when the linker comprises a heterocyclyl), said heterocyclyl is attached, directly or indirectly, to the cCPP through a single bond and, directly or indirectly, to the CNBM through a single bond. Unless stated otherwise specifically in the specification, a heterocyclyl group can be optionally substituted.

"Heteroaryl" refers to a 5- to 20-membered ring system comprising hydrogen atoms, one to thirteen carbon atoms, one to six heteroatoms selected from the group consisting of nitrogen, oxygen and sulfur, and at least one aromatic ring. For purposes of this invention, the heteroaryl can be a monovalent radical (e.g., when R is a heteroaryl) or a divalent radical (e.g., when the linker is a heteroaryl). Further, the heteroaryl can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). When the heteroaryl is a monovalent radical (e.g., when R is a heteroaryl), said heteroaryl is attached to the CNBM through a single bond. When the heteroaryl is a divalent radical (e.g., when the linker comprises a heteroaryl), said heteroaryl is attached, directly or indirectly, to the cCPP through a single bond and, directly or indirectly, to the CNBM through a single bond. Unless stated otherwise specifically in the specification, a heteroaryl group can be optionally substituted.

The term "ether" used herein refers to a straight or branched divalent radical moiety having the following structure: —$R_1$—O—$R_2$—, wherein $R_1$ and $R_2$ are independently selected from alkyl, carbocyclyl, or heterocyclyl. In some embodiments, the ether is —$[(CH_2)_m—O—(CH_2)_n]_z$— wherein each of m, n, and z are independently selected from 1 to 40. Examples include polyethylene glycol. The ether is attached, directly or indirectly, to the cCPP through a single bond and, directly or indirectly, to the CNBM through a single bond. Unless stated otherwise specifically in the specification, the ether can be optionally substituted.

The term "substituted" used herein means any amino acid disclosed herein wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, "substituted" also encompasses instances in which one or more carbon atoms on an amino acid side chain are replaced by a heteroatom.

As used herein the terms "treating" or "treatment" includes prevention; delay in onset; diminution, eradication, or delay in exacerbation of signs or symptoms after onset; prevention of relapse; and ameliorating one or more conditions associated with a disease or illness disclosed herein.

The amino acids in the polypeptide conjugates disclosed herein may be independently selected from any natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, 2,3-diaminopropionic acid a derivative, or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| Alanine | Ala (A) | ala (a) |
| Allosoleucine | AIle | aile |
| Arginine | Arg (R) | arg (r) |
| Asparagine | Asn (N) | asn (n) |
| Aspartic acid | Asp (D) | asp (d) |
| Cysteine | Cys (C) | cys (c) |
| Cyclohexylalanine | Cha | cha |
| 2,3-diaminopropionic acid | Dap | dap |
| 4-fluorophenylalanine | Fpa (Σ) | pfa |
| Glutamic acid | Glu (E) | glu (e) |
| Glutamine | Gln (Q) | gln (q) |
| Glycine | Gly (G) | gly (g) |
| Histidine | His (H) | his (h) |
| Homoproline (aka pipecolic acid) | Pip (Θ) | pip (θ) |
| Isoleucine | Ile (I) | ile (i) |
| Leucine | Leu (L) | leu (l) |
| Lysine | Lys (K) | lys (k) |
| Methionine | Met (M) | met (m) |
| Napthylalanine | Nal (Φ) | nal (φ) |
| Norleucine | Nle (Ω) | nle |
| Phenylalanine | Phe (F) | phe (F) |
| Phenylglycine | Phg (Ψ) | phg |
| 4-(phosphonodifluoromethyl) phenylalanine | F₂Pmp (Λ) | f₂pmp |
| Proline | Pro (P) | pro (p) |
| Sarcosine | Sar (Ξ) | sar |
| Selenocysteine | Sec (U) | sec (u) |
| Serine | Ser (S) | ser (s) |
| Threonine | Thr (T) | thr (y) |
| Tyrosine | Tyr (Y) | tyr (y) |
| Tryptophan | Trp (W) | trp (w) |
| Valine | Val (V) | val (v) |
| Tert-butyl-alanine | Tle | tle |
| Penicillamine | Pen | pen |
| Homoarginine | HomoArg | homoarg |
| Nicotinyl-lysine | Lys (NIC) | lys (NIC) |
| Triflouroacetyl-lysine | Lys (TFA) | lys (TFA) |
| Methyl-leucine | MeLeu | meLeu |
| 3-(3-benzothienyl)-alanine | Bta | Bta |

*single letter abbreviations: when shown in capital letters herein it indicates the L-amino acid form, when shown in lower case herein it indicates the D-amino acid.

Calcineurin Binding Motifs and Peptides Comprising the Same

Described herein, in various embodiments, are peptides and peptide conjugates comprising CN binding motifs (CNBM).

The CNBM may be any sequence of amino acids which binds to CN. In some embodiments, the CNBM comprises any combination of at least five amino acids selected from the group consisting of: tert-butyl-alanine (Tle or tle), isoleucine (Ile or ile), threonine (Thr or thr), valine (Val or val), homovaline (Hva or hva), β-hydroxyvaline (Bhv or bhv); cyclohexylglycine (Chg or chg); penicillamine sulfonic acid (Psa or psa). In some embodiments, the CNBM comprises two Ile amino acids. In some embodiments, the Ile amino acids are separated by a different amino acid, e.g., -Ile-Xaa-Ile-, wherein Xaa is Tle, tle, Thr, thr, Val, val Hva, hva, Bhv bhv, Chg, chg, Psa or psa. In some embodiments, the C-termini of the CNBM is Thr. In some embodiments, the CNBM comprises -Ile-Xaa-Ile-Thr, wherein Xaa is defined above. In some embodiments, the CNBM comprises one of the following sequences: i) Tle-Ile-Tle-Ile-Thr (ZIZIT) (SEQ ID NO:1); (ii) Val-Ile-Val-Ile-Thr (VIVIT) (SEQ ID NO:2); (iii) Val-Ile-Tle-Ile-Thr (VIZIT) (SEQ ID NO:3); (iv) Tle-Ile-Hva-Ile-Thr (SEQ ID NO:4); (v) Tle-Ile-Val-Ile-Thr (ZIVIT) (SEQ ID NO:5); (vi) Tle-Ile-Bhv-Ile-Thr (SEQ ID NO:6); (vii) Tle-Chg-Bhv-Ile-Thr (SEQ ID NO:7); (viii) Tle-Ile-Psa-Ile-Thr (SEQ ID NO:8); or (ix) Tle-Chg-Psa-Ile-Thr (SEQ ID NO:9).

Without being bound by theory, the $R^H$ groups described herein improve binding affinity by interacting with the hydrophobic pocket on a CN protein (e.g., compared to an otherwise identical CNBM which does not have and $R^H$ group). The hydrophobic pocket on CN is has a volume of approximately 73 $Å^3$. R can be any hydrophobic, non-peptidyl moiety which fits in the hydrophobic pocket on CN. In some embodiments, R has a volume of less than or equal to about 73 $Å^3$, e.g., 73 $Å^3$, 72 $Å^3$, 70 $Å^3$, 71 $Å^3$, 70 $Å^3$, 65 $Å^3$, 60 $Å^3$, 55 $Å^3$, 50 $Å^3$, 45 $Å^3$, 40 $Å^3$, 35 $Å^3$, 30 $Å^3$, 25 $Å^3$, and 20 $Å^3$ or less. In some embodiments, $R^H$ is selected from acyl, carbocyclyl, heterocyclyl, formyl, and acetyl, each of which are optionally substituted. In other embodiments, $R^H$ is an aryl or heteroaryl, each of which is optionally substituted. $R^H$ is pyridinyl, benzoyl, cyclopentylcarbonyl, or cyclohexylcarbonyl, each of which are optionally substituted. In some embodiments, $R^H$ is a pyridinyl or benzoyl which is optionally substituted with one or more substituents selected from halogen and alkyl. In particular embodiments, the pyridinyl or benzoyl is substituted at the ortho position, the meta position, or a combination thereof, with a halogen or an alkyl.

$R^H$ groups may also improve proteolytic stability of the peptide and peptide conjugates compared to an otherwise identical peptide or peptide conjugate that does not have the $R^H$ group. Proteolytic stability may be increased by about 1% to about 100%, e.g., 1, 5, 10, 15, 20, 25, 30, 35, 40, 45, 50, 55, 60, 65, 70, 75, 80, 85, 90, 95, 100%, inclusive of all values and subranges therebetween. Methods of measuring proteolytic stability are known in the art. In some embodiments, proteolytic stability is measured according to the method provided in these examples.

In some embodiments, $R^H$ is selected from 2,3-dichlorobenzoyl, 3-chloro-4-methylbenzoyl, 2,6-dichloro-3-fluorobenzoyl, 2-trifluoromethylbenzoyl, formyl, 2-fluoro-6-methylbenzoyl, acetyl, 4-chloro-2-methylbenzoyl, 3-chloro-5-methylbenzoyl, 3-(1-chloromethyl)benzoyl, 3,5-dibromobenzoyl, 4-tertbutylbenzoyl, 3-methylbenzoyl, 2-chlorobenzoyl, 3-iodobenzoyl, 2-chloro-4-iodobenzoyl, 4-methylbenzoyl, 2-bromobenzoyl, 2-fluorobenzoyl, 2,4,6-trimethylbenzoyl, 2-chloro-5-fluorobenzoyl, 2-chlorobenzoyl, 2-bromo-4-chlorobenzoyl, 2-fluoro-4-methylbenzoyl, 4-isopropylbenzoyl, 4-fluoro-2-methylbenzoyl, 4-(1-bromomethyl)benzoyl, 2-methylbenzoyl, 4-bromobenzoyl, 4-trifluoromethylbenzoyl, 2-fluoro-4-chlorobenzoyl, 2,6-dimethylbenzoyl, 4-butylbenzoyl, 3-bromobenzoyl, 3,5-dimethylbenzoyl, 2-iodobenzoyl, cyclopropylcarbonyl, 2-chloro-3-methylbenzoyl, 3-ethynylbenzoyl, 2,4-dimethylbenzoyl, 3,5-trifluoromethylbenzoyl, 2-chloro-4-fluorobenzoyl, 4-fluorobenzoyl, 5-chloro-2-methylbenzoyl, 2-(1-chloromethyl)benzoyl, 4-(2-chloroethyl)benzoyl, 2-chloro-6-fluorobenzoyl, 4-chloro-2-methylbenzoyl, 3-fluorobenzoyl, cyclohexylcarbonyl, 2-naphthoic acid, 4-iodobenzoyl, 3,4-dimethylbenzoyl, 2,4-dichloro-3-fluorobenzoyl, 2,3,4-trifluorobenzoyl, 4-ethylnylbenzoyl, 2-chloro-4-iodobenzoyl, or 2,3-dichloro-4-pyridinyl.

In particular embodiments, $R^H$ is 2,3-dichlorobenzoyl or 2,3-dichloro-4-pyridinyl.

As discussed herein, in various embodiments, the peptides described herein comprise the sequence $AA_{U1}$-$AA_{U2}$-$AA_{U3}$-$AA_{U4}$-$AA_{U5}$-$AA_{U6}$, wherein each of $AA_{U2}$, $AA_{U3}$, $AA_{U4}$, $AA_{U5}$, and $AA_{U6}$ is, independently, optional. In some embodiments, each of $AA_{U1}$, $AA_{U2}$, $AA_{U3}$, $AA_{U4}$, $AA_{U5}$, and $AA_{U6}$ is, independently, when present, an amino acid which is optionally substituted. In some embodiments, each of $AA_{U1}$, $AA_{U2}$, $AA_{U3}$, $AA_{U4}$, $AA_{U5}$, and $AA_{U6}$, when present are independently selected from the following amino acids:

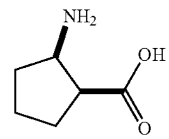

Acp

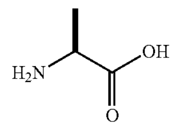

Ala 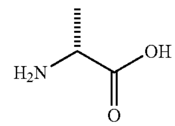 ala

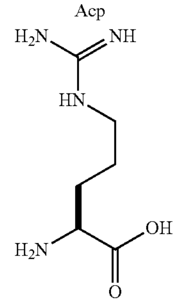

Arg 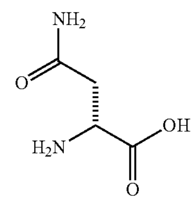 asn

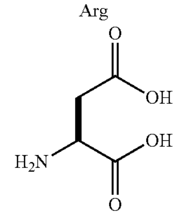

Asp 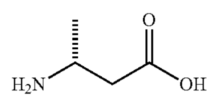 bha

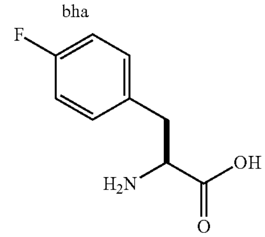

Fpa

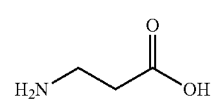

βAla

Gln 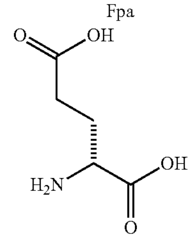 glu

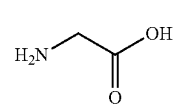

Gly

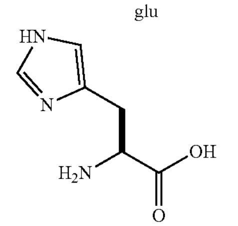

His

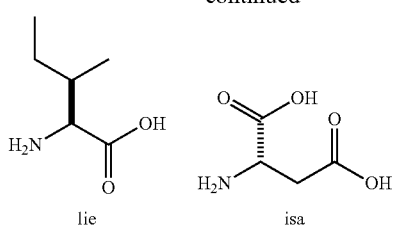

Ile / Isa

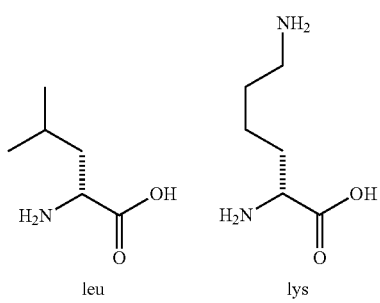

leu / lys

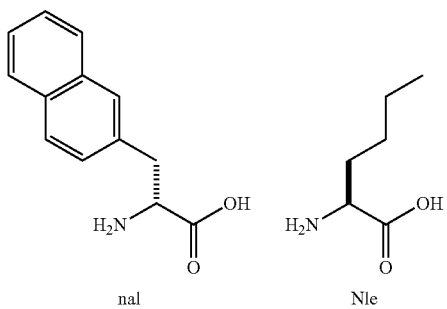

nal / Nle

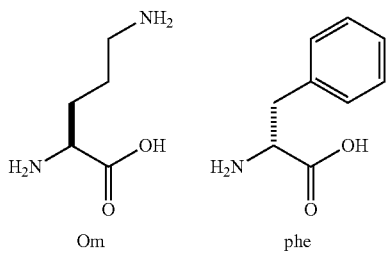

Orn / phe

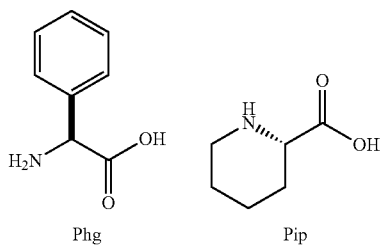

Phg / Pip

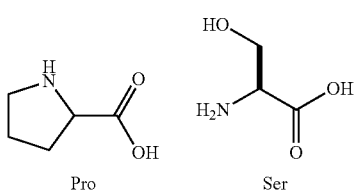

Pro / Ser

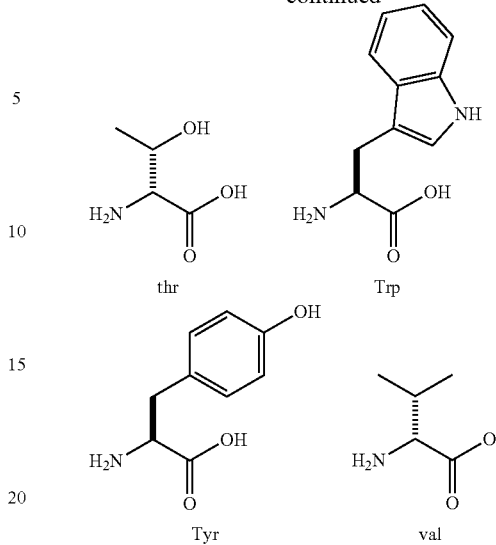

thr / Trp / Tyr / val wherein at least one of the amino group or the carboxylic acid group on the above amino acids forms a peptide bond, e.g., to any of the groups described herein. In some embodiments, the amino group forms a peptide bond. In some embodiments, the carboxylic acid forms a peptide bond. In some embodiments, both the amino group and the carboxylic acid group independently form a peptide bond.

In some embodiments, $AA_{U1}$, $AA_{U2}$, $AA_{U3}$, and $AA_{U4}$ are selected from No. 1-47 below, and each of $AA_{U5}$ and $AA_{U6}$ are absent.

| No. | $AA_{U1}$ | $AA_{U2}$ | $AA_{U3}$ | $AA_{U4}$ |
|---|---|---|---|---|
| 1 | Asp | Gly | Trp | leu |
| 2 | Tyr | glu | Fpa | His |
| 3 | Tyr | Trp | Bha | Pro |
| 4 | Nal | Gln | AcP | Trp |
| 5 | Gln | Tyr | asn | Nal |
| 6 | Gln | His | leu | His |
| 7 | Asp | Gln | Tyr | Arg |
| 8 | Ias | Gln | Trp | Arg |
| 9 | Tyr | Acp | Gly | Trp |
| 10 | Ser | Gly | His | Nal |
| 11 | Pro | Nal | Arg | Bha |
| 12 | His | glu | Orn | ala |
| 13 | Gln | His | leu | Ser |
| 14 | Nle | Ala | Nal | Tyr |
| 15 | lys | His | Nal | Asp |
| 16 | Orn | Nle | His | Nal |
| 17 | Tyr | asn | Ser | Nal |
| 18 | Gly | Tyr | Gly | Nal |
| 19 | Asp | His | lys | Tyr |
| 20 | Gln | Tyr | βAla | Nal |
| 21 | His | His | phe | Trp |
| 22 | Arg | Tyr | glu | Tyr |
| 23 | Ala | His | Nal | Bha |
| 24 | Pro | βAsp | His | Nal |
| 25 | Gln | His | Tyr | Nle |
| 26 | Gln | phe | Arg | Asp |
| 27 | Trp | glu | Gly | Arg |
| 28 | Pro | glu | Nal | Arg |
| 29 | Gln | His | Gly | βAla |
| 30 | Tyr | glu | Fpa | Gly |
| 31 | Ala | His | Nal | Phg |
| 32 | Nal | His | Tyr | Acp |
| 33 | His | ala | Ser | Tyr |
| 34 | βAla | glu | Nal | Arg |
| 35 | thr | Pro | ala | Nal |
| 36 | Ile | His | Nal | His |

-continued

| No. | $AA_{U1}$ | $AA_{U2}$ | $AA_{U3}$ | $AA_{U4}$ |
|---|---|---|---|---|
| 37 | Asp | Gln | Tyr | lys |
| 38 | βAla | glu | Arg | Tyr |
| 39 | thr | leu | Tyr | phe |
| 40 | Tyr | His | Pro | Trp |
| 41 | asn | Pro | Tyr | Trp |
| 42 | Ser | Tyr | Ser | Trp |
| 43 | Gln | Tyr | Nal | Ser |
| 44 | Tyr | His | Gly | phe |
| 45 | Acp | Gly | Nal | His |
| 46 | glu | Pip | Nal | His |
| 47 | Glu | His | leu | Ser |

The peptides and polypeptide conjugates disclosed herein inhibit the CN-NFAT interaction. In some embodiments, said polypeptide conjugates bind (covalently or non-covalently) to the NFAT docking site on CN, thereby inhibiting NFAT binding. As used herein, "inhibit" or "inhibiting" refers to a complete ablation of binding of NFAT to CN, or a reduction in such binding e.g., by an amount in the range of from about 1% to about 100%, such as about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, and about 100%, inclusive of all values and subranges therebetween. In some embodiments, inhibition can be measured based on a reduction in dephosphorylation of NFAT, e.g., by an amount in the range of from about 1% to about 100%, such as about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, and about 100%, inclusive of all values and subranges therebetween.

In some embodiments, the peptides disclosed herein have a dissociation constant ($K_D$; nM) in the range of from about 1000 nM to about 0.1 nM, e.g., about 100 nM, about 900 nM, about 800 nM, about 700 nM, about 600 nM, about 500 nM, about 400 nM, about 300 nM, about 200 nM, about 100 nM, about 90 nM, about 80 nM, about 70 nM, about 60 nM, about 50 nM, about 40 nM, about 30 nM, about 20 nM, about 10 nM, about 1 nM, and about 0.1 nM, inclusive of all values and subranges therebetween.

In other embodiments, inhibition can be measured in terms of the concentration of polypeptide where the binding of NFAT is reduced by half (i.e., $IC_{50}$) In some embodiments, the polypeptide conjugates of the present disclosure have an $IC_{50}$ value in the range of from about 1,000 nM to about 0.1 nM, e.g., about 1000 nM, about 950 nM, about 900 nM, about 850 nM, about 800 nM, about 750 nM, about 700 nM, about 650 nM, about 600 nM, about 550 nM, about 500 nM, about 450 nM, about 400 nM, about 350 nM, about 300 nM, about 250 nM, about 200 nM, about 150 nM, about 100 nM, about 90 nM, about 80 nM, about 70 nM, about 60 nM, about 50 nM, about 40 nM, about 30 nM, about 20 nM, about 10 nM, about 5 nM, about 1 nM, and about 0.1 nM, inclusive of all values and subranges therebetween. In particular embodiments, the $IC_{50}$ value is in the range of from about 500 to about 10 nM, e.g., from about 426 to about 127 nM, or about 426 nM to about 45.6 nM.

Polypeptide Conjugates

To mediate intercellular delivery, the peptides described above may further comprise a cell-penetrating peptide (CPP). Such constructs are referred to as polypeptide conjugates. Accordingly, in various embodiments, the polypeptide conjugates comprise (a) a first peptide comprising a calcineurin (CN) binding motif (CNBM) as described herein, an N-terminus, and a C-terminus; and (b) a second peptide comprising a cell-penetrating peptide (CPP) as described herein conjugated, directly or indirectly, to the first peptide. In some embodiments, the CPP is cyclic and is referred to herein as "cCCP". In some embodiments, the second peptide is conjugated, directly or indirectly, to the C-terminus of the first peptide.

In further embodiments, the polypeptide conjugates described herein further comprise (c) the hydrophobic non-peptidyl moiety "$R^H$". In some embodiments, R is conjugated, directly or indirectly, to the first peptide. In some embodiments, second peptide is conjugated, directly or indirectly, to the C-terminus of the first peptide, and $R^H$ is conjugated, directly or indirectly, to the N-terminus of the first peptide. In other embodiments, the second peptide is conjugated, directly or indirectly to the N-terminus of the first peptide, and $R^H$ is conjugated, directly or indirectly, to the C-terminus of the first peptide. In some embodiments, the second peptide is conjugated (directly or indirectly) to $R^H$, and $R^H$ is conjugated (directly or indirectly) to the N- or C-terminus of the first peptide. In still other embodiments, In additional or alternative embodiments, the peptide conjugate comprises (d) $AA_{U1}$-$AA_{U2}$-$AA_{U3}$-$AA_{U4}$-$AA_{U5}$-$AA_{U6}$, as defined herein, wherein each of $AA_{U2}$, $AA_{U3}$, $AA_{U4}$, $AA_{U5}$, and $AA_{U6}$ are optional. In some embodiments, the sequence comprising $AA_{U1}$-$AA_{U2}$-$AA_{U3}$-$AA_{U4}$-$AA_{U5}$-$AA_{U6}$ is conjugated (directly or indirectly) to the N- or C-terminus of CNMB.

The polypeptide conjugates disclosed herein exclude those exemplified in U.S. Patent App. Pub. US2017/0281723.

Cell-Penetrating Peptide

Cell-penetrating peptides (CPPs) allow for otherwise impermeable CNBM (including CNBM, R and/or $AA_{U1}$-$AA_{U2}$-$AA_{U3}$-$AA_{U4}$-$AA_{U5}$-$AA_{U6}$) to be efficiently delivered to the cytosol of a cell. The CPP of the peptides disclosed herein may be or include any amino sequence which facilitates cellular uptake of a CNBM, and may be linear or cyclic ("cCCP"). Suitable CPPs include naturally occurring sequences, modified sequences, and synthetic sequences. In embodiments, the total number of amino acids in the CPP may be in the range of from 4 to about 20 amino acids, e.g., about 5, about 6, about 7, about 8, about 9, about 10, about 11, about 12, about 13, about 14, about 15, about 16, about 17, about 18, and about 19 amino acids, inclusive of all ranges and subranges therebetween. Non-limiting examples of cell penetrating moieties include Polyarginine (e.g., $R_9$ or $R_{11}$), Antennapedia sequences, HIV-TAT, Penetratin, Antp-3A (Antp mutant), Buforin II. Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol).

In some embodiments, the CPP is a cCPPs and comprises about 4 to about to about 13 amino acids. In particular embodiments, the cCPPs disclosed herein comprise about 6 to about 10 amino acids, or about 6 to about 8 amino acids.

Each amino acid in the cCPP may be a natural or non-natural amino acid, such as a D or L amino acid, or a naturally occurring or synthetic amino acid.

In some embodiments, the cCPP comprises the following sequence: -AA$_1$-AA$_2$-AA$_3$-AA$_4$-(AA$_Z$)$_n$-, wherein: AA$_1$, AA$_2$, AA$_3$, and AA$_4$ are independently selected from an amino acid, which is optionally substituted with one or more substituents; AA$_Z$ at each instance and when present, is independently selected from an amino acid, which is optionally substituted with one or more substituents; m is a number in the range of from 0 to 10 (e.g., 0, 1, 2, 3, 4, 5, 6, 7, 8, 9, and 10, inclusive of all ranges and subranges therebetween).

In particular embodiments, at least two of AA$_1$, AA$_2$, AA$_3$, AA$_4$ and AA$_Z$ are arginine. In other particular embodiments, and at least two of AA$_1$, AA$_2$, AA$_3$, AA$_4$ and AA$_Z$ are independently a hydrophobic amino acid which is optionally substituted. Thus, in certain embodiments, the cCPPs may include any combination of at least two arginines and at least two hydrophobic amino acids. In other embodiments, the cCPPs may include any combination of two to three arginines and at least two hydrophobic amino acids.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. The structures of a few of these non-natural aromatic hydrophobic amino acids (prior to incorporation into the peptides disclosed herein) are provided below.

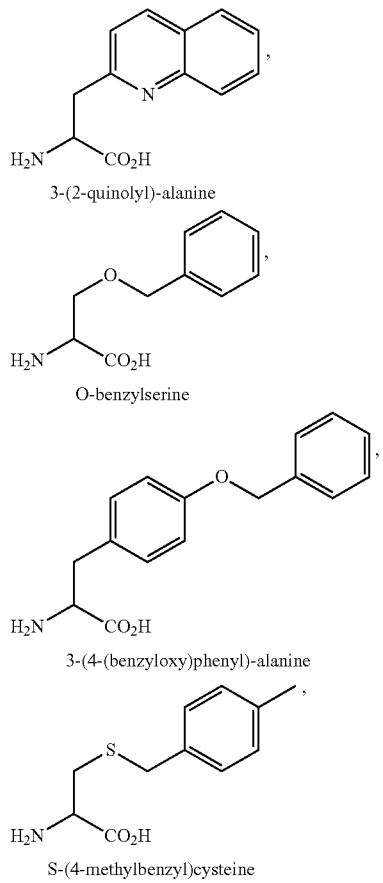

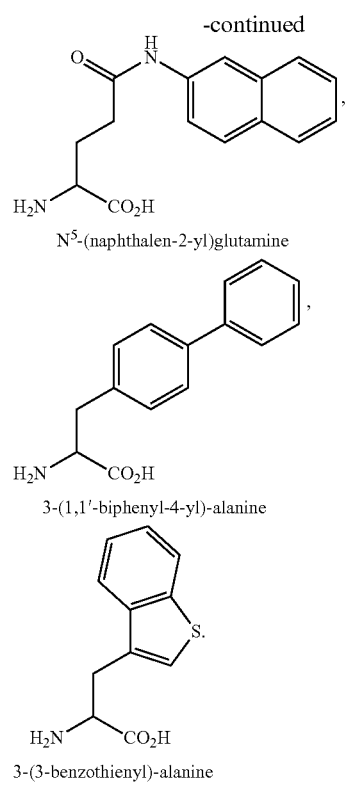

In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents. In particular embodiments, the hydrophobic amino acid is naphthylalanine or 3-(3-benzothienyl)-alanine, each of which is optionally substituted with one or more substituents. In other particular embodiments, any two hydrophobic amino acids are naphthylalanine and 3-(3-benzothienyl)-alanine, each of which is optionally substituted with one or more substituents.

The optional substituent can be any atom or group which does not significantly reduce the cytosolic delivery efficiency of the cCPP, e.g., compared to an otherwise identical cCCP which does not include the optional substituent. In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a cCPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A 1981; 78(6): 3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 2

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating chirality relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the cCPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the cCPPs described herein comprise at least two consecutive hydrophobic amino acids and at least two consecutive arginines. In further embodiments, one hydrophobic amino acid is adjacent to one of the arginines. In still other embodiments, the cCPPs described herein comprise at least three consecutive hydrophobic amino acids and three consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the cCPPs described herein (e.g., $AA_1$, $AA_2$, $AA_3$, $AA_4$ and $AA_Z$ at each instance and when present) can have one of the following sequences: $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid.

Each of $AA_{H1}$ and $AA_{H2}$ are independently selected from any hydrophobic amino acid, e.g., glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, tert-leucine, or nicotinoyl lysine, each of which is optionally substituted with one or more substituents. In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents. In particular embodiments, the hydrophobic amino acid is naphthylalanine or 3-(3-benzothienyl)-alanine, each of which is optionally substituted with one or more substituents. In other particular embodiments, any two hydrophobic amino acids are naphthylalanine and 3-(3-benzothienyl)-alanine, each of which is optionally substituted with one or more substituents.

In some embodiments, each of the hydrophobic amino acids in the peptides disclosed herein (e.g., $AA_{H1}$ and $AA_{H2}$) are independently a hydrophobic amino acid having a hydrophobicity value which is greater than that of glycine. In other embodiments, each of the hydrophobic amino acids in the peptides disclosed herein (e.g., $AA_{H1}$ and $AA_{H2}$) are independently a hydrophobic amino acid having a hydrophobicity value which is greater than that of alanine. In still other embodiments, each of the hydrophobic amino acids in the peptides disclosed herein (e.g., $AA_{H1}$ and $AA_{H2}$) are independently an hydrophobic amino acid having a hydrophobicity value which is greater than that of phenylalanine, e.g., as measured using the hydrophobicity scales described above, including Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also been found to improve the cytosolic uptake of the cCPP (and the attached cargo). For example, in some embodiments, the cCPPs disclosed herein may include $AA_{H1}$-D-Arg or D-Arg-$AA_{H1}$. In other embodiments, the cCPPs disclosed herein may include $AA_{H1}$-L-Arg or L-Arg-$AA_{H1}$. In some embodiments, the presence of the hydrophobic amino acid on the N- or C-terminal of the D-Arg or L-Arg, or a combination thereof, in the CPP improves the cytosolic delivery efficiency.

The size of the hydrophobic amino acid on the N- or C-terminal of the D-Arg or an L-Arg, or a combination thereof (e.g., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, $AA_{H2}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of $AA_{H1}$ and $AA_{H2}$ have a combined SASA of at least about 350 Å$^2$, at least about 360 Å$^2$, at least about 370 Å$^2$, at least about 380 Å$_2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, $AA_{H2}$ is a hydrophobic amino acid with a side chain having a SASA that is less than or equal to the SASA of the hydrophobic side chain of $AA_{H1}$. By way of example, and not by limitation, a cCPP having a Nal-Arg motif exhibits improved cytosolic delivery efficiency compared to an otherwise identical CPP having a Phe-Arg motif; a cCPP having a Phe-Nal-Arg motif exhibits improved cytosolic delivery efficiency compared to an otherwise identical cCPP having a Nal-Phe-Arg motif; and a phe-Nal-Arg motif exhibits improved cytosolic delivery efficiency compared to an otherwise identical cCPP having a nal-Phe-Arg motif. In some embodiments, the presence of the larger hydrophobic amino acid on the N- or C-terminal of the D-Arg or L-Arg, or a combination thereof, in the cCPP improves cytosolic delivery efficiency.

As used herein, "hydrophobic surface area" or "SASA" refers to the surface area (reported as square Ångstroms; Å$^2$) of an amino acid side chain that is accessible to a solvent. In particular embodiments, SASA is calculated using the 'rolling ball' algorithm developed by Shrake & Rupley (*J Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al. (PLOS ONE 8(11): e80635, which is herein incorporated by reference in its entirety for all purposes.

TABLE 3

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the cCPP does not include a hydrophobic amino acid on the N- and/or C-terminal of $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$. In alternative embodiments, the cCPP does not include a hydrophobic amino acid having a side chain which is larger (as described herein) than at least one of $AA_{H1}$ or $AA_{H2}$. In further embodiments, the cCPP does not include a hydrophobic amino acid with a side chain having a surface area greater than $AA_{H1}$. For example, in embodiments in which at least one of $AA_{H1}$ or $AA_{H2}$ is phenylalanine, the cCPP does not further include a naphthylalanine (although the cCPP include at least one hydrophobic amino acid which is smaller than $AA_{H1}$ and $AA_{H2}$, e.g., leucine). In still other embodiments, the cCPP does not include a naphthylalanine in addition to the hydrophobic amino acids in $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$.

The chirality of the amino acids (i.e., D or L amino acids) can be selected to improve cytosolic delivery efficiency of the cCPP (and the attached cargo as described below). In some embodiments, the hydrophobic amino acid on the N- or C-terminal of an arginine (e.g., $AA_{H1}$) has the same or opposite chirality as the adjacent arginine. In some embodiments, $AA_{H1}$ has the opposite chirality as the adjacent arginine. For example, when the arginine is D-arg (i.e. "r"), $AA_{H1}$ is a D-$AA_{H1}$, and when the arginine is L-Arg (i.e., "R"), $AA_{H1}$ is a L-$AA_{H1}$. Accordingly, in some embodiments, the cCPPs disclosed herein may include at least one of the following motifs: D-$AA_{H1}$-D-arg, D-arg-D-$AA_{H1}$, L-$AA_{H1}$-L-Arg, or L-Arg-L$AA_{H1}$. In particular embodiments, when arginine is D-arg, $AA_H$ can be D-nal, D-trp, or D-phe. In another non-limiting example, when arginine is L-Arg, $AA_H$ can be L-Nal, L-Trp, or L-Phe. In some embodiments, the presence of the hydrophobic amino acid having the same chirality as the adjacent arginine improves cytosolic delivery efficiency.

In some embodiments, the cCPPs described herein include three arginines. Accordingly, in some embodiments, the cCPPs described herein include one of the following sequences: $AA_{H2}$-$AA_{H1}$-R-r-R, $AA_{H2}$-$AA_{H1}$-R-r-r, $AA_{H2}$-$AA_{H1}$-r-R-R, $AA_{H2}$-$AA_{H1}$-r-R-r, R-R-r-$AA_{H1}$-$AA_{H2}$, r-R-r-$AA_{H1}$-$AA_{H2}$, r-r-R-$AA_{H1}$-$AA_{H2}$, or, R-r-R-$AA_{H1}$-$AA_{H2}$. In particular embodiments, the cCPPS have one of the following sequences $AA_{H2}$-$AA_{H1}$-R-r-R, $AA_{H2}$-$AA_{H1}$-r-R-r, r-R-r-$AA_{H1}$-$AA_{H2}$, or R-r-R-$AA_{H1}$-$AA_{H2}$. In some embodiments, the chirality of $AA_{H1}$ and $AA_{H2}$ can be selected to improve cytosolic uptake efficiency, e.g., as described above, where $AA_{H1}$ has the same chirality as the adjacent arginine, and $AA_{H1}$ and $AA_{H2}$ have the opposite chirality.

In some embodiments, the cCPPs described herein include three hydrophobic amino acids. Accordingly, in some embodiments, the cCPPs described herein include one of the following sequences: $AA_{H3}$-$AA_{H2}$-$AA_{H1}$-R-r, $AA_{H3}$-$AA_{H2}$-$AA_{H1}$-R-r, $AA_{H3}$-$AA_{H2}$-$AA_{H1}$-r-R, $AA_{H3}$-$AA_{H2}$-$AA_{H1}$-r-R, R-r-$AA_{H1}$-$AA_{H2}$-$AA_{H3}$, R-r-$AA_{H1}$-$AA_{H2}$-$AA_{H3}$, r-R-$AA_{H1}$-$AA_{H2}$-$AA_{H3}$, or, r-R-$AA_{H1}$-$AA_{H2}$-$AA_{H3}$, wherein $AA_{H3}$ is any hydrophobic amino acid described above, e.g., piperidine-2-carboxylic acid, naphthylalanine, 3-(3-benzothienyl)-alanine, tryptophan, or phenylalanine. In some embodiments, the chirality of $AA_{H1}$, $AA_{H2}$, and $AA_{H3}$ can be selected to improve cytosolic uptake efficiency, e.g., as described above, where $AA_{H1}$ has the same chirality as the adjacent arginine, and $AA_{H1}$ and $AA_{H2}$ have the opposite chirality. In other embodiments, the size of $AA_{H1}$, $AA_{H2}$, and $AA_{H3}$ can be selected to improve cytosolic uptake efficiency, e.g., as described above, where $AA_{H3}$ has a SAS of less than or equal to $AA_{H1}$ and/or $AA_{H2}$.

In some embodiments, $AA_{H1}$ and $AA_{H2}$ have the same or opposite chirality. In certain embodiments, $AA_{H1}$ and $AA_{H2}$ have the opposite chirality. Accordingly, in some embodiments, the cCPPs disclosed herein include at least one of the following sequences: D-$AA_{H2}$-L-$AA_{H1}$-R-r; L-$AA_{H2}$-D-$AA_{H1}$-r-R; R-r-D-$AA_{H1}$-L-$AA_{H2}$; or r-R-L-$AA_{H1}$-D-$AA_{H1}$, wherein each of D-$AA_{H1}$ and D-$AA_{H2}$ is a hydrophobic amino acid having a D configuration, and each of L-$AA_{H1}$ and L-$AA_{H2}$ is a hydrophobic amino acid having an L configuration. In some embodiments, each of D-$AA_{H1}$ and D-$AA_{H2}$ is independently selected from the group consisting of D-pip, D-nal, D-trp, and D-phe. In particular embodiments, D-$AA_{H1}$ or D-$AA_{H2}$ is D-nal. In other particular embodiments, D-$AA_{H1}$ is D-nal. In some embodiments, each of L-$AA_{H1}$ and L-$AA_{H2}$ is independently selected from the group consisting of L-Pip, L-Nal, L-Trp, and L-Phe. In particular embodiments, each of L-$AA_{H1}$ and L-$AA_{H2}$ is L-Nal. In other particular embodiments, L-$AA_{H1}$ is L-Nal. In some embodiments, the presence of an $AA_{H1}$ and $AA_{H2}$ having an opposite chirality improves the cytosolic delivery efficiency.

As used herein cytosolic delivery efficiency refers to the ability of a peptide (e.g., cCPP conjugated, directly or indirectly, to the CNBM) to traverse a cell membrane and enter the cytosol. In some embodiments, cytosolic delivery efficiency of the peptide is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a peptide over the concentration of the peptide in the growth medium. Relative cytosolic delivery efficiency refers to the concentration of a peptide in the cytosol compared to the concentration of a control peptide in the cytosol. Quantification can be achieved by fluorescently labeling the peptide (e.g., with a FITC dye) and measuring the fluorescence intensity using techniques well-known in the art.

In particular embodiments, relative cytosolic delivery efficiency is determined by comparing (i) the amount of a peptide of the invention internalized by a cell type (e.g., HeLa cells) to (ii) the amount of the control peptide internalized by the same cell type. To measure relative cytosolic delivery efficiency, the cell type may be incubated in the presence of a peptide of the invention for a specified period of time (e.g., 30 minutes, 1 hour, 2 hours, etc.) after which the amount of the peptide internalized by the cell is quantified using methods known in the art, e.g., fluorescence microscopy. Separately, the same concentration of the control peptide is incubated in the presence of the cell type over the same period of time, and the amount of the control peptide internalized by the cell is quantified.

Those skilled in the art can determine the appropriate control sequence. In some embodiments, the control sequence does not include a particular modification (e.g., matching chirality of arginine and $AA_{H1}$) but is otherwise identical to the modified sequence. In some embodiments, the control sequence does not have a CNBM, $R^H$, $AA_{U1}$-$AA_{U2}$-$AA_{U3}$-$AA_{U5}$-$AA_{U6}$, or combinations thereof. In some embodiments, the control is the CPP (or cCPP). In some embodiments, the control has the following sequence: cyclic(fΦRrRrQ) (SEQ ID NO: 76) (also referred to as cCPP9). In some embodiments, the control has the following sequence: cyclic(FΦRRRRQ) (SEQ ID NO: 77) (also referred to as cCPP1)

In other embodiments, relative cytosolic delivery efficiency can be determined by measuring the $IC_{50}$ of a peptide having a modified sequence for an intracellular target, and comparing the $IC_{50}$ of said peptide to a proper control sequence (as described herein, e.g., cCPP9).

In some embodiments, the relative cytosolic delivery efficiency of the described herein in the range of from about 1% to about 5000% compared to cyclo(fΦRrRrQ) (SEQ ID NO: 76) or compared to cyclo(FΦRRRRQ) (SEQ ID NO: 77), e.g., about 5%, about 10%, about 20%, about 30%, about 40%, about 50%, about 60%, about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, about 500%, about 510%, about 520%, about 530%, about 540%, about 550%, about 560%, about 570%, about 580%, or about 590%, about 600%, about 610%, about 620%, about 630%, about 640%, about 650%, about 660%, about 670%, about 680%, or about 690%, about 700%, about 710%, about 720%, about 730%, about 740%, about 750%, about 760%, about 770%, about 780%, about 790%, about 800%, about 810%, about 820%, about 830%, about 840%, about 850%, about 860%, about 870%, about 880%, or about 890%, about 900%, about 910%, about 920%, about 930%, about 940%, about 950%, about 960%, about 970%, about 980%, or about 990%, about 1000%, about 1100%, about 1200%, about 1300%, about 1400%, about 1500%, about 1600%, about 1700%, about 1800%, about 1900%, about 2000%, about 2100%, about 2200%, about 2300%, about 2400%, about 2500%, about 2600%, about 2700%, about 2800%, about 2900%, about 3000%, about 3100%, about 3200%, about 3300%, about 3400%, about 3500%, about 3600%, about 3700%, about 3800%, about 3900%, about 4000%, about 4100%, about 4200%, about 4300%, about 4400%, about 4500%, about 4600%, about 4700%, about 4800%, about 4900%, and about 5000%, about inclusive of all values and subranges therebetween.

In other embodiments, the absolute cytosolic delivery efficacy of from about 40% to about 100%, e.g., about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, inclusive of all values and subranges therebetween.

Non-limiting examples of suitable cyclic cell penetrating peptides are provided in Table 4.

TABLE 4

Examples of cyclic cell penetrating peptides.

| ID | cCPP Sequence | |
|---|---|---|
| PCT 1 | cyclo(FΦRRRQ) | (SEQ ID NO: 78) |
| PCT 2 | cyclo(FΦRRRC) | (SEQ ID NO: 79) |
| PCT 3 | cyclo(FΦRRRU) | (SEQ ID NO: 80) |
| PCT 4 | cyclo(RRRΦFQ) | (SEQ ID NO: 81) |
| PCT 5 | cyclo(RRRRΦF) | (SEQ ID NO: 82) |
| PCT 6 | cyclo(FΦRRRR) | (SEQ ID NO: 83) |
| PCT 7 | cyclo(FϕrRrRq) | (SEQ ID NO: 84) |
| PCT 8 | cyclo(FϕrRrRQ) | (SEQ ID NO: 85) |
| PCT 9 | cyclo(FΦRRRRQ) | (SEQ ID NO: 86) |
| PCT 10 | cyclo(fΦRrRrQ) | (SEQ ID NO: 87) |
| PCT 11 | cyclo(RRFRΦRQ) | (SEQ ID NO: 88) |
| PCT 12 | cyclo(FRRRRΦQ) | (SEQ ID NO: 89) |
| PCT 13 | cyclo(rRFRΦRQ) | (SEQ ID NO: 90) |
| PCT 14 | cyclo(RRΦFRRQ) | (SEQ ID NO: 91) |
| PCT 15 | cyclo(CRRRRFWQ) | (SEQ ID NO: 92) |
| PCT 16 | cyclo(FfΦRrRrQ) | (SEQ ID NO: 93) |
| PCT 17 | cyclo(FFΦRRRRQ) | (SEQ ID NO: 94) |
| PCT 18 | cyclo(RFRFRΦRQ) | (SEQ ID NO: 95) |
| PCT 19 | cyclo(URRRRFWQ) | (SEQ ID NO: 96) |
| PCT 20 | cyclo(CRRRRFWQ) | (SEQ ID NO: 92) |
| PCT 21 | cyclo(FΦRRRRQK) | (SEQ ID NO: 97) |
| PCT 22 | cyclo(FΦRRRRQC) | (SEQ ID NO: 98) |
| PCT 23 | cyclo(fΦRrRrRQ) | (SEQ ID NO: 99) |
| PCT 24 | cyclo(FΦRRRRRQ) | (SEQ ID NO: 100) |
| PCT 25 | cyclo(RRRRΦFDΩC) | (SEQ ID NO: 101) |
| PCT 26 | cyclo(FΦRRR) | (SEQ ID NO: 102) |
| PCT 27 | cyclo(FWRRR) | (SEQ ID NO: 103) |
| PCT 28 | cyclo(RRRΦF) | (SEQ ID NO: 104) |
| PCT 29 | cyclo(RRRWF) | (SEQ ID NO: 105) |

TABLE 4-continued

Examples of cyclic cell penetrating peptides.

| ID | cCPP Sequence | |
|---|---|---|
| SAR 1 | cyclo(FΦRRRRQ) | (SEQ ID NO: 86) |
| SAR 19 | cyclo(FFRRRQ) | (SEQ ID NO: 106) |
| SAR 20 | cyclo(FFrRrQ) | (SEQ ID NO: 107) |
| SAR 21 | cyclo(FFRrRQ) | (SEQ ID NO: 108) |
| SAR 22 | cyclo(FRFRRQ) | (SEQ ID NO: 109) |
| SAR 23 | cyclo(FRRFRQ) | (SEQ ID NO: 110) |
| SAR 24 | cyclo(FRRRFQ) | (SEQ ID NO: 111) |
| SAR 25 | cyclo(GΦRRRQ) | (SEQ ID NO: 112) |
| SAR 26 | cyclo(FFFRAQ) | (SEQ ID NO: 113) |
| SAR 27 | cyclo(FFFRRQ) | (SEQ ID NO: 114) |
| SAR 28 | cyclo(FFRRRRQ) | (SEQ ID NO: 115) |
| SAR 29 | cyclo(FRRFRRQ) | (SEQ ID NO: 116) |
| SAR 30 | cyclo(FRRRFRQ) | (SEQ ID NO: 117) |
| SAR 31 | cyclo(RFFRRRQ) | (SEQ ID NO: 118) |
| SAR 32 | cyclo(RFRRFRQ) | (SEQ ID NO: 119) |
| SAR 33 | cyclo(FRFRRRQ) | (SEQ ID NO: 120) |
| SAR 34 | cyclo(FFFRRRQ) | (SEQ ID NO: 121) |
| SAR 35 | cyclo(FFRRRFQ) | (SEQ ID NO: 122) |
| SAR 36 | cyclo(FRFFRRQ) | (SEQ ID NO: 123) |
| SAR 37 | cyclo(RRFFFRQ) | (SEQ ID NO: 124) |
| SAR 38 | cyclo(FFRFRRQ) | (SEQ ID NO: 125) |
| SAR 39 | cyclo(FFRRFRQ) | (SEQ ID NO: 126) |
| SAR 40 | cyclo(FRRFFRQ) | (SEQ ID NO: 127) |
| SAR 41 | cyclo(FRRFRFQ) | (SEQ ID NO: 128) |
| SAR 42 | cyclo(FRFRFRQ) | (SEQ ID NO: 129) |
| SAR 43 | cyclo(RFFRFRQ) | (SEQ ID NO: 130) |
| SAR 44 | cyclo(GΦRRRRQ) | (SEQ ID NO: 131) |
| SAR 45 | cyclo(FFFRRRRQ) | (SEQ ID NO: 132) |
| SAR 46 | cyclo(RFFRRRRQ) | (SEQ ID NO: 133) |
| SAR 47 | cyclo(RRFFRRRQ) | (SEQ ID NO: 134) |
| SAR 48 | cyclo(RFFFRRRQ) | (SEQ ID NO: 135) |
| SAR 49 | cyclo(RRFFFRRQ) | (SEQ ID NO: 136) |
| SAR 50 | cyclo(FFRRFRRQ) | (SEQ ID NO: 137) |
| SAR 51 | cyclo(FFRRRRFQ) | (SEQ ID NO: 138) |
| SAR 52 | cyclo(FRRFFRRQ) | (SEQ ID NO: 139) |
| SAR 53 | cyclo(FFFRRRRRQ) | (SEQ ID NO: 140) |
| SAR 54 | cyclo(FFFRRRRRRQ) | (SEQ ID NO: 141) |
| SAR 55 | cyclo(FΦRrRrQ) | (SEQ ID NO: 142) |

TABLE 4-continued

Examples of cyclic cell penetrating peptides.

| ID | cCPP Sequence | |
|---|---|---|
| SAR 56 | cyclo(XXRRRRQ) | (SEQ ID NO: 143) |
| SAR 57 | cyclo(FfFRrRQ) | (SEQ ID NO: 144) |
| SAR 58 | cyclo(fFfrRrQ) | (SEQ ID NO: 145) |
| SAR 59 | cyclo(fFfRrRQ) | (SEQ ID NO: 146) |
| SAR 60 | cyclo(FfFrRrQ) | (SEQ ID NO: 147) |
| SAR 61 | cyclo(fFφrRrQ) | (SEQ ID NO: 148) |
| SAR 62 | cyclo(fΦfrRrQ) | (SEQ ID NO: 149) |
| SAR 63 | cyclo(φFfrRrQ) | (SEQ ID NO: 150) |
| SAR 64 | cyclo(FΦrRrQ) | (SEQ ID NO: 151) |
| SAR 65 | cyclo(fΦrRrQ) | (SEQ ID NO: 152) |
| SAR 66 | Ac-(Lys-fFRrRrD) | (SEQ ID NO: 15, underlined portion) |
| SAR 67 | Ac-(Dap-fFRrRrD) | (SEQ ID NO: 16, underlined portion) |
| SAR 68 | CWWRRRRC (S—S) | (SEQ ID NO: 153) |
| SAR 69 | CWWWRRRRC (S—S) | (SEQ ID NO: 154) |
| SAR 70 | CFWRRRRC (S—S) | (SEQ ID NO: 155) |
| SAR 71 | CWWWRRRC (S—S) | (SEQ ID NO: 156) |
| Pin1 15 | cyclo(Pip-Nal-Arg-Glu-arg-arg-glu) | (SEQ ID NO: 157) |
| Pin1 16 | cyclo(Pip-Nal-Arg-Arg-arg-arg-glu) | (SEQ ID NO: 158) |
| Pin1 17 | cyclo(Pip-Nal-Nal-Arg-arg-arg-glu) | (SEQ ID NO: 159) |
| Pin1 18 | cyclo(Pip-Nal-Nal-Arg-arg-arg-Glu) | (SEQ ID NO: 160) |
| Pin1 19 | cyclo(Pip-Nal-Phe-Arg-arg-arg-glu) | (SEQ ID NO: 161) |
| Pin1 20 | cyclo(Pip-Nal-Phe-Arg-arg-arg-Glu) | (SEQ ID NO: 162) |
| Pin1 21 | cyclo(Pip-Nal-phe-Arg-arg-arg-glu) | (SEQ ID NO: 163) |
| Pin1 22 | cyclo(Pip-Nal-phe-Arg-arg-arg-Glu) | (SEQ ID NO: 164) |
| Pin1 23 | cyclo(Pip-Nal-nal-Arg-arg-arg-Glu) | (SEQ ID NO: 165) |
| Pin1 24 | cyclo(Pip-Nal-nal-Arg-arg-arg-glu) | (SEQ ID NO: 166) |
| Rev-13 | [Pim-RQRR-Nlys]GRRR[b] | (SEQ ID NO: 167) |
| hLF | KCFQWQRNMRKVRGPPVSC | (SEQ ID NO: 168) |
| cTat | [KrRrGrKkRrE][c] | (SEQ ID NO: 169) |

TABLE 4-continued

Examples of cyclic cell penetrating peptides.

| ID | cCPP Sequence | |
|---|---|---|
| cR10 | [KrRrRrRrRrRE]$^c$ | (SEQ ID NO: 170) |
| L-50 | [RVRTRGKRRIRRpP] | (SEQ ID NO: 17) |
| L-51 | [RTRTRGKRRIRVpP] | (SEQ ID NO: 18) |
| [WR]$_4$ | [WRWRWRWR] | (SEQ ID NO: 19) |
| MCoTI-II | [GGVCPKILKKCRRDSDCPGACICRGNGYCGSGSD] | (SEQ ID NO: 171) |
| Rotstein et al. Chem. Eur. J. 2011 | [P-Cha-r-Cha-r-Cha-r-Cha-r-G]$^d$ | (SEQ ID NO: 172) |
| Lian et al. J. Am. Chem. Soc. 2014 | Tm(SvP-F$_2$Pmp-H)-Dap-(FΦRRRR-Dap)]$^f$ | (SEQ ID NO: 173) |
| Lian et al. J. Am. Chem. Soc. 2014 | [Tm(a-Sar-D-pThr-Pip-ΦRAa)-Dap-(FΦRRRR-Dap)]$^f$ | (SEQ ID NO: 174) |
| IA8b | [CRRSRRGCGRRSRRCG]$^g$ | (SEQ ID NO: 175) |
| Dod[R$_5$] | [K(Dod)RRRR] | (SEQ ID NO: 20) |
| LK-3 | | (SEQ ID NO: 176) |
| | RRRR-[KRRRE]$^e$ | (SEQ ID NO: 177) |
| | RRR-[KRRRRE]$^e$ | (SEQ ID NO: 178) |
| | RR-[KRRRRRE]$^e$ | (SEQ ID NO: 179) |
| | R-[KRRRRRRE]$^e$ | (SEQ ID NO: 180) |
| [CR]$_4$ | [CRCRCRCR] | (SEQ ID NO: 21) |
| cyc3 | [Pra-LRKRLRKFRN-AzK]$^h$ | (SEQ ID NO: 181) |
| PMB | T-Dap-[Dap-Dap-f-L-Dap-Dap-T] | (SEQ ID NO: 22) |
| GPMB | T-Agp-[Dap-Agp-f-L-Agp-Agp-T] | (SEQ ID NO: 23) |
| cCPP1 | cyclo(FΦRRRRQ) | (SEQ ID NO: 77) |
| cCPP12 | cyclo(FfΦRrRrQ) | (SEQ ID NO: 182) |
| cCPP9 | cyclo(fΦRrRrQ) | (SEQ ID NO: 76) |
| cCPP11 | cyclo(fΦRrRrRQ) | (SEQ ID NO: 183) |
| cCPP18 | cyclo(FΦrRrRq) | (SEQ ID NO: 184) |
| cCPP13 | cyclo(FΦrRrRQ) | (SEQ ID NO: 185) |
| cCPP6 | cyclo(FΦRRRRRQ) | (SEQ ID NO: 186) |
| cCPP3 | cyclo(RRFRΦRQ) | (SEQ ID NO: 187) |
| cCPP7 | cyclo(FFΦRRRRQ) | (SEQ ID NO: 188) |
| cCPP8 | cyclo(RFRFRΦRQ) | (SEQ ID NO: 189) |
| cCPP5 | cyclo(FΦRRRQ) | (SEQ ID NO: 190) |
| cCPP4 | cyclo(FRRRRΦQ) | (SEQ ID NO: 191) |

TABLE 4-continued

Examples of cyclic cell penetrating peptides.

| ID | cCPP Sequence | |
|---|---|---|
| cCPP10 | cyclo(rRFRΦRQ) | (SEQ ID NO: 192) |
| cCPP2 | cyclo(RRΦPRRQ) | (SEQ ID NO: 193) |

Φ, L-2-naphthylalanine; Pim, pimelic acid; Nlys, lysine peptoid residue; D-pThr, D-phosphothreonine; Pip, L-piperidine-2-carboxylic acid; Cha, L-3-cyclohexyl-alanine; Tm, trimesic acid; Dap, L-2,3-diaminopropionic acid; Sar, sarcosine; $F_2$Pmp, L-difluorophosphonomethyl phenylalanine; Dod, dodecanoyl; Pra, L-propargylglycine; AzK, L-6-Azido-2-amino-hexanoic; Agp, L-2-amino-3-guanidinyl-propionic acid; [b]Cyclization between Pim and Nlys; [c]Cyclization between Lys and Glu; [d]Macrocyclization by multicomponent reaction with aziridine aldehyde and isocyanide; [e]Cyclization between the main-chain of Gln residue; [f]N-terminal amine and side chains of two Dap residues bicyclized with Tm; [g]Three Cys side chains bicyclized with tris(bromomethyl)benzene; [h]Cyclization by the click reaction between Pra and Azk.

Additionally, the cCPP used in the polypeptide conjugates and methods described herein can include any sequence disclosed in: U.S. application Ser. No. 15/312,878; U.S. application Ser. No. 15/360,719; International PCT Application No. PCT/US2017/060881 (including the corresponding U.S. Publication); and International Application Publication No. WO 2018/098231 (including the corresponding U.S. Publication), each of which is incorporated by reference in its entirety for all purposes.

Linker

In some embodiments, a linking group or linker may be used to indirectly connect any of the components described herein, e.g., the first and the second peptide, the CNMB, or $R^H$. For example, in certain embodiments, the first peptide is conjugated to the second peptide through a linking moiety.

The linking group can be any suitable moiety which can covalently bond the first peptide to the second peptide and/or $R^H$ to the first peptide. Further, the linking group can be any length which does not adversely affect cytosolic delivery and/or CN binding of the polypeptide conjugates disclosed herein. The linking group can also be selected to improve solubility (e.g., at physiological conditions or in a formulation), In some embodiments, the linking group comprises from about 1 to about 100 atoms in length. In some embodiments, the linking moiety is selected from at least one amino acid, alkylene, alkenylene, alkynylene, aryl, cycloalkyl, cycloalkenyl, cycloalkynyl, heterocyclyl, heteroaryl, ether, βAla-Lys, mini-PEG-Lys, and combinations thereof, each of which are optionally substituted. In some embodiments, the linking group comprises from one to 10 amino acids.

In some embodiments, the polypeptide conjugates of the disclosure have a structure according to Formula I, II, or III

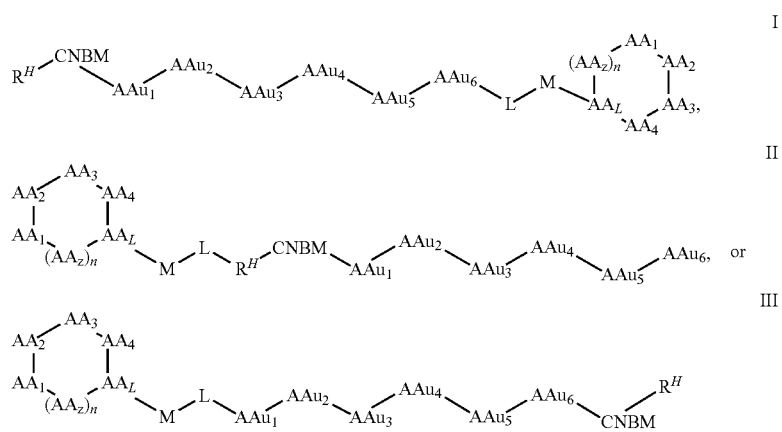

In some embodiments, each of $AA_1$, $AA_2$, $AA_3$, and $AA_4$ are independently an amino acid which is optionally substituted. In some embodiments, $AA_Z$, at each instance and when present, is independently an amino acid which is optionally substituted. In some embodiments, $AA_1$, $AA_2$, $AA_3$, $AA_4$ and $AA_Z$ at each instance and when present, are independently selected from a peptide sequence which is capable of traversing the cell membrane and entering the cytosol of a cell. Thus, in certain embodiments, $AA_1$, $AA_2$, $AA_3$, $AA_4$, and $AA_Z$ are referred to as a "cyclic, cell-penetrating peptide sequence" or "cCCP". In certain embodiments, at least two of $AA_1$, $AA_2$, $AA_3$, $AA_4$ and $AA_Z$ are arginines. In certain other embodiments, at least two of $AA_1$, $AA_2$, $AA_3$, $AA_4$ and $AA_Z$ are amino acids having a hydrophobic side chain.

In some embodiments, n is an integer in the range of from 0 to 6, e.g., 0, 1, 2, 3, 4, 5, and 6, inclusive of all values and subranges therebetween.

In some embodiments, $AA_L$ is an amino acid having a side chain on to which the linker/CBMN is conjugated, e.g., trough the formation of a bonding moiety, M. That is, before conjugation, the precursor to $AA_L$ is an amino acid having a side chain containing an amino group, a hydroxyl group, or a thiol group. Non-limiting examples of suitable amino acids include glutamine, aspartic acid, serine, threonine, asparagine, glutamine, lysine, and cysteine, include analogs and derivatives thereof.

In some embodiments, M is a bonding moiety. As used herein, a bonding moiety refers to a group which is formed when the cCCP sequence is covalently attached to the linking moiety. In certain embodiments, M is a disulfide, an amide, a thioether, or a triazolyl.

In some embodiments, each of $AA_{U1}$, $AA_{U2}$, $AA_{U3}$, $AA_{U4}$, $AA_{U5}$, and $AA_{U6}$ is, independently, optional, and when present, is an amino acid which is optionally substituted. In some embodiments each of $AA_{U1}$, $AA_{U2}$, $AA_{U3}$, $AA_{U4}$, $AA_{U5}$, and $AA_{U6}$, when present are independently selected from the following amino acid:

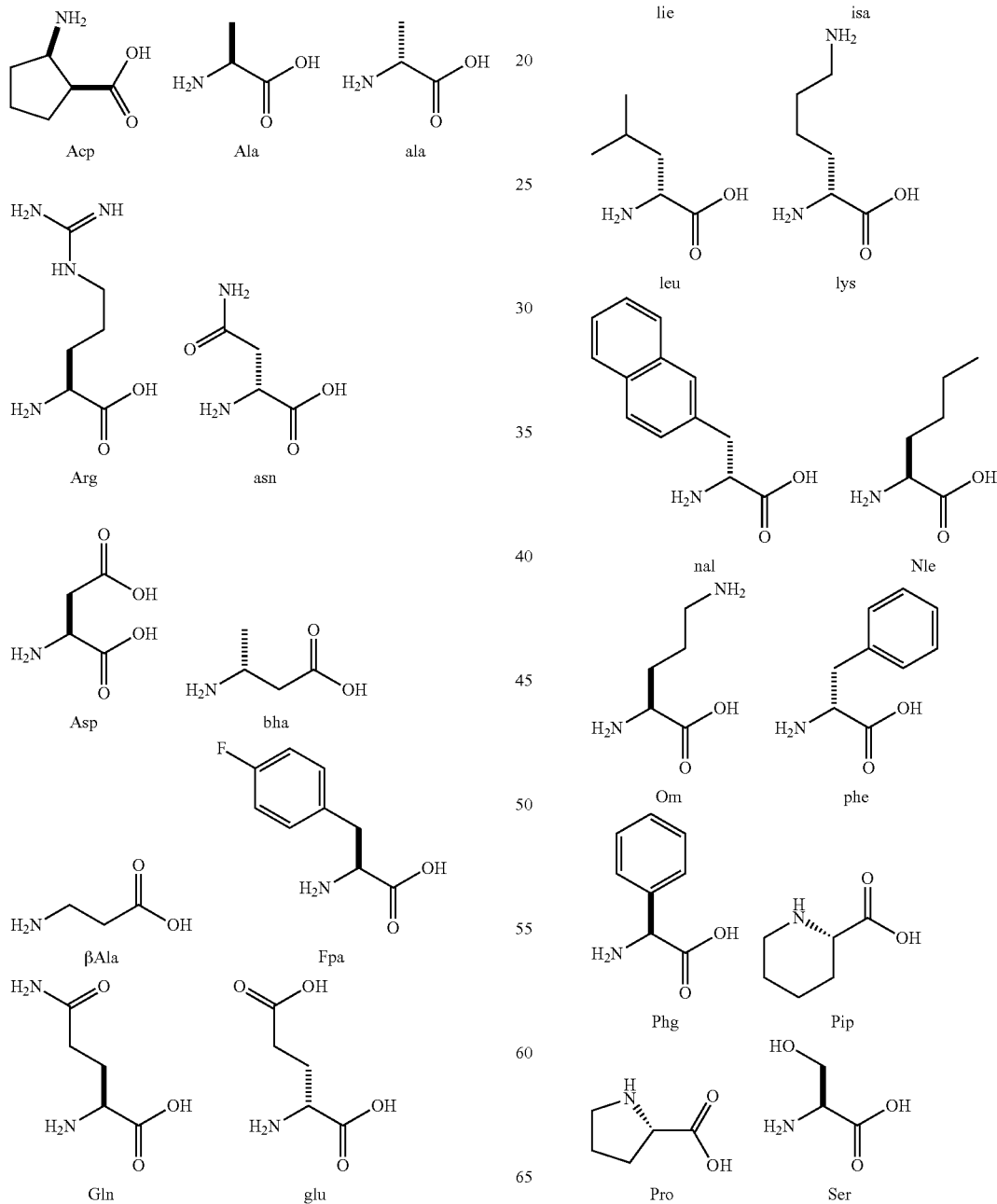

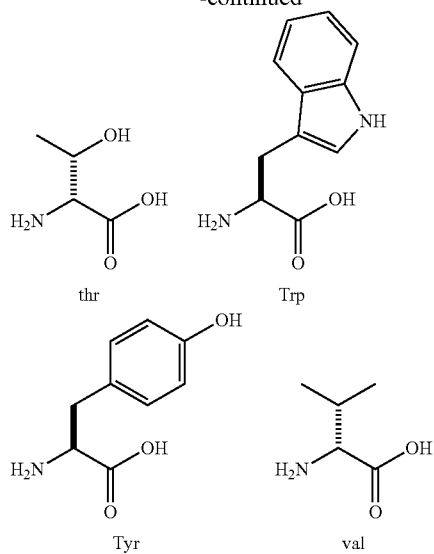

wherein at least one of the amino group or the carboxylic acid group form a peptide bond.

In certain embodiments, $AA_{U1}$ and $AA_{U2}$ are independently an amino acid which is optionally substituted, and $AA_{U3}$, $AA_{U4}$, $AA_{U5}$, and $AA_{U6}$ are absent. In other embodiments, $AA_{U1}$, $AA_{U2}$, $AA_{U3}$, and $AA_{U4}$ are independently an amino acid which is optionally substituted, and $AA_{U5}$ and $AA_{U6}$ are absent. In still other embodiments, $AA_{U1}$ on the C-terminus of CNBM in Formula I or II is an L-amino acid. In some such embodiments, the L-amino acid is selected from glutamine, tyrosine, aspartic acid, and histidine. In some embodiments, $AA_{U2}$ is selected from histidine, tyrosine, or glutamic acid. In some embodiments, at least one of the $AA_{U3}$ and $AA_{U4}$ is an aromatic hydrophobic amino acid, e.g., naphthylalanine, 3-(3-benzothienyl)-alanine, phenylglycine, homophenylalanine, phenylalanine, tryptophan, or tyrosine, each of which is optionally substituted with one or more substituents. In some embodiments, at least one of $AA_{U1}$, $AA_{U2}$, $AA_{U3}$, $AA_{U4}$, $AA_{U5}$, and $AA_{U6}$ is a D-amino acid.

In some embodiments, CNBM is a CN-binding motif as described herein.

In some embodiments, $R^H$ is a hydrophobic non-peptidyl moiety which interacts with the hydrophobic pocket in a CN protein as described herein.

In some embodiments, L is a linking moiety as described herein.

The terminal amino or carboxyl groups (e.g., in CNMB, or when present, $AA_{U1}$, $AA_{U2}$, $AA_{U3}$, $AA_{U4}$, $AA_{U5}$, or $AA_{U6}$ in Formula II) may be modified by alkylation, amidation, acylation, etc to provide esters, amides, or substituted amino groups. Further any one or more of the amino acids may be modified by acetylation, methylation, or the like to alter the chemical properties, for example lipophilicity Methods of Making The polypeptides conjugates described herein can be prepared using synthetic techniques known to one skilled in the art of organic synthesis and peptide synthesis, or variations thereon as appreciated by those skilled in the art. The polypeptides conjugates described herein can be prepared from readily available starting materials. Optimum reaction conditions can vary with the particular reactants or solvents used, but such conditions can be determined by one skilled in the art.

Variations on the peptides described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5- dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif.). The α-C-terminal amino acid is coupled to the resin by means of N,N'-dicyclohexylcarbodiimide (DCC), N,N'-diisopropylcarbodiimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazolidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N,N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Compositions, Formulations and Methods of Administration

In vivo application of the disclosed peptides, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The peptides disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Compounds can also be incorporated into polymers, examples of which include poly (D-L lactide-co-glycolide) polymer; poly[bis(p-carboxyphenoxy) propane:sebacic acid] in a 20:80 molar ratio (as used in GLIADEL); chondroitin; chitin; and chitosan.

In certain examples, the peptides and compositions disclosed herein can be locally administered at one or more anatomical sites, optionally in combination with a pharmaceutically acceptable carrier such as an inert diluent. Peptides and compositions disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the peptide can be combined with one or more excipients and used in the form of ingestible tablets, buccal tablets, troches, capsules, elixirs, suspensions, syrups, wafers, aerosol sprays, and the like.

In some embodiments, the disclosed polypeptides conjugates and compositions are bioavailable and can be delivered orally. Oral compositions can be tablets, troches, pills, capsules, and the like, and can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the peptide, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the peptide can be incorporated into sustained-release preparations and devices.

Polypeptide conjugates and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a peptide disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, polypeptide conjugates disclosed herein can be applied in as a liquid or solid. However, it will generally be desirable to administer them topically to the skin as compositions, in combination with a dermatologically acceptable carrier, which can be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the polypeptide conjugates and compositions disclosed herein can be determined by comparing their in vitro activity, and in vivo activity in animal models. Methods for the extrapolation of effective dosages in mice, and other animals, to humans are known to the art.

The dosage ranges for the administration of the polypeptide conjugates are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise one or more polypeptide conjugates disclosed herein in one or more containers. The disclosed kits can optionally include pharmaceutically acceptable carriers and/or diluents. In one embodiment, a kit includes one or more other components, adjuncts, or adjuvants as described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a polypeptide conjugate disclosed herein is provided in the kit as a solid, such as a tablet, pill, or powder form. In another embodiment, a polypeptide conjugate disclosed herein is provided in the kit as a liquid or solution. In one embodiment, the kit comprises an ampoule or syringe containing a compound and/or agent disclosed herein in liquid or solution form.

Methods of Treatment

In some embodiments, the disclosed polypeptide conjugates (e.g., the peptides according to Formulae I-III) inhibit CN-NFAT signalling. In some embodiments, the disclosed polypeptide conjugates (e.g., the peptides according to Formulae I-III) inhibit CN-mediated dephosphorylation of NFAT. In some embodiments, the disclosed polypeptide conjugates (e.g., the peptides according to Formulae I-III) inhibit recruitment of NFAT to the nucleus of the cell. In some embodiments, the disclosed polypeptide conjugates (e.g., the peptides according to Formulae I-III) inhibit NFAT-dependent gene transcription.

The disclosed methods comprise contacting the cell with a polypeptide conjugate described herein. For example, the disclosed method of inhibiting CN-NFAT signaling in a cell, comprising contacting the cell with one or more polypeptide conjugates disclosed herein. Also disclosed is a method of treating a disease in a subject that involves administering to the subject one or more polypeptide conjugates disclosed herein.

The disclosed CN inhibitors are useful in the treatment of a number of diseases wherein it is desired to decrease the activity of CN-NFAT signaling. Examples of diseases/conditions associated with CN-NFAT signaling include inflammatory diseases, autoimmune disorders, cardiovascular diseases, neurodegenerative diseases, cancer, alopecia, diseases occurring with unwanted angiogenesis, and diseases occurring with unwanted polimorphonuclear (PMN) infiltration.

The term "immune disorder" or "immune disease" refers to a condition in a subject characterized by cellular, tissue and/or organ injury caused by an immunological reaction of the subject. The term "autoimmune disorder" or "autoimmune disease" refers to a condition in a subject characterized by cellular, tissue and/or organ injury caused by an immunological reaction of the subject to its own cells, tissues and/or organs. Illustrative, non-limiting examples of autoimmune diseases which can be treated with the disclosed CN inhibitor include alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CF1DS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibro myositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, Meniere's disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, sarcoidosis, scleroderma, progressive systemic sclerosis, Sjogren's syndrome, Good pasture's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener's granulomatosis, Anti-Glomerular Basement Membrane Disease, Antiphospho lipid Syndrome, Autoimmune Diseases of the Nervous System, Familial Mediterranean Fever, Lambert-Eaton Myasthenic Syndrome, Sympathetic Ophthalmia, polyendocrinopathies, psoriasis, etc.

The term "immune mediated inflammatory disease" shall be taken to mean any disease mediated by the immune system and characterized by chronic or acute inflammation, resulting from, associated with or triggered by, a dysregulation of the normal immune response e.g. Crohn's disease, type 1 diabetes mellitus, rheumatoid arthritis, inflammatory bowel disease, psoriasis, psoriatic arthritis, ankylosing spondylitis, systemic lupus erythematosus, Hashimoto's disease, graft-versus-host disease, Sjogren's syndrome, pernicious anemia, Addison disease, scleroderma, Goodpasture's syndrome, ulcerative colitis, autoimmune hemolytic anemia, sterility, myasthenia gravis, multiple sclerosis, Basedow's disease, thrombopenia purpura, Guillain-Barre syndrome, allergy, asthma, atopic disease, arteriosclerosis, myocarditis, cardiomyopathy, glomerular nephritis, hypoplastic anemia, and rejection after organ transplantation.

For the purposes of the methods described herein, "immune disorders" include autoimmune diseases and immunologically mediated diseases. The term "inflammatory disease" refers to a condition in a subject characterized by inflammation, e.g., chronic inflammation. Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vacultides (e.g., polyarteritis nodosa, Wegner's granulomatosis, Takayasu's arteritis, temporal arteritis, and lymphomatoid granulomatosus), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The term "cardiovascular disease or disorder", as used herein, relates to diseases affecting the heart or blood vessels or both or associated with the cardiopulmonary and circulatory systems including but not limited to ischemia, angina, edematous conditions, artherosclerosis, Coronary Heart Disease, LDL oxidation, adhesion of monocytes to endothelial cells, foam-cell formation, fatty-streak development, platelet adherence, and aggregation, smooth muscle cell proliferation, reperfusion injury, high blood pressure, thrombotic disease, arrhythmia (atrial or ventricular or both); cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue, endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

The term "neurodegenerative disease", as it is used herein, refers to diseases which result from the degeneration or deterioration of nervous tissue, particularly of neurons, leading over time to a dysfunction or to a disability; the term degeneration includes loss of cell viability, loss of cell function and/or loss of the number of cells (neurons or others). Illustrative, non-limiting, examples of neurodegenerative diseases include Alzheimer's disease, Huntington's disease, Parkinson's disease, amyotrophic lateral sclerosis (ALS), multiple sclerosis, etc. In a particular embodiment, said neurodegenerative disease is a disease related to neuronal death caused by a substance which, for example, causes oxidative stress or endoplasmic reticulum stress or apoptosis or excitotoxicity or neuronal death in general. The term "cancer" refers to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumors are classified as being either benign or malignant: benign tumors are tumors that cannot spread by invasion or metastasis, i.e., they only grow locally; whereas malignant tumors are tumors that are capable of spreading by invasion and metastasis. Biological processes known to be related to cancer include angiogenesis, immune cell infiltration, cell migration and metastasis. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodglun's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; slun cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill in the art.

The term "angiogenesis", also known as vascularisation, refers to the process of formation of new blood vessels from other pre-existing ones. The role of the angiogenesis switch is not limited to the neoplasic diseases pathogenesis, but it has also been related to other non-neoplasic diseases including wet macular degeneration, diabetic retinopathies, diabetes, psoriasis and rheumatoid arthritis. The term "alopecia" includes the involuntary complete or partial hair loss from the head or body of an individual and includes alopecia areata (AA), alopecia totalis (AT), alopecia universalis (AU), androgenetic alopecia (alopecia androgenetica, or male baldness) or post-chemotherapy alopecia (PCA) or chemotherapy-induced alopecia (CIA). Alopecia areata may include diffuse alopecia areata, alopecia areata monolocularis, alopecia areata multilocuiaris, and alopecia areata barbae.

The term "polimorfonuclear (PMN) infiltration" relates to the process of infiltration of polymorphonuclear neutrophils into tissues during inflammation. Upon pathogen infection or irritant infliction, local macrophages and other cells sense the insult and produce a panel of inflammatory mediators such as cytokines and chemokines that stimulate the nearby micro vasculature and attract large numbers of PMN to migrate across the vascular wall and infiltrate into tissues. After arrival at the inflammatory site, PMN perform phagocytosis and also release powerful anti-pathogen and tissue-damaging reagents to kill pathogens and aberrant cells. Thus, the activity of PMN cells is extremely important for host defense. However, PMN activity can also induce adverse effects. The term "diseases occurring with unwanted polymorphonuclear (PMN) infiltration" relates to diseases due to the adverse effect of PMN infiltration including, without being limited to, inflammatory bowel diseases (IBD), arthritis, some cardiovascular conditions, inflammatory pulmonary and renal diseases, viral/bacterial infection-associated damage, graft versus host disease, transplantation therapy and diseases occurring with unwanted inflammatory diseases.

In some embodiments, the disclosed polypeptide conjugates compositions can be used in the prevention or treatment of the Acute Respiratory Distress Syndrome (ARDS) or milder forms of Acute Lung injury (ALI) and Hypoxemic Respirator}' Failure. In some cases, the disclosed compositions can be used for preserving or protecting or improving the quality of donor lungs for transplantation either in situ or ex vivo.

Blocking NFAT with a CNBM, VIVIT (SEQ ID NO: 2), was shown to protect against experimental colitis in mice, improve immunosuppression during fully mismatched islet allografts between B6 and C3H/HeN mouse strains, and attenuate both microgliosis and Amyloid 13 peptide (Aβ) plaque load in treated mice compared to controls in models of Alzheimers disease. Also, treatment with a CNMB has been shown to markedly attenuate albuminuria in diabetic db/db mice and alleviate niesangial matrix expansion and podocyte injury. Studies indicate that NFATc3 and NFATc4 are involved in TLR2 and TLR.4 activated TNFα induction. Furthermore, blocking the NFAT function was found to be beneficial in inflammatory bowel disease and pulmonary arterial hypertension.

In some embodiments, the polypeptide conjugates (e.g., the peptides according to Formulae I-III) and methods disclosed herein can be used in the treatment of acute respiratory distress syndrome (ARDS), including pulmonary edema.

In other embodiments, the polypeptide conjugates (e.g., the peptides according to Formulae I-III) and methods disclosed herein can be used as a therapeutic for allograft transplantation, colitis, restenosis, inflammatory bowel disease, pulmonary arterial hypertension, diabetic nephropathy and podocyte injury.

EXAMPLES

Materials. Reagents for peptide synthesis were purchased from Advanced ChemTech (Louisville, Ky.), Chem-Impex (Louisville, Ky.). 5-Fluorescein isothiocyanate (5-FITC) was purchased from Chem-Impex (Louisville, Ky.) and 5(6)-carboxynaphthlofluorescein, succinidmyl ester (NHS-NF) was purchased from Molecular Probes (Eugene, Oreg.). 2,3-Dichlorobenzoic acid, 4-bromo-3-chlorobenzoic acid, and 2,3,4,5-tetrafluorobenzoic acid was purchased from Matrix Scientific (Elgin, S.C.). Phorbol 12-myristate 13-acetate and ionomycin, calcium salt were purchased from Cayman Chemical (Ann Arbor, Mich.). Solvents for synthesis and HPLC purification were purchased from Avantor Performance Materials (Paris, Ky.). Fetal bovine serum was obtained from VWR (Radnor, Pa.). Dulbecco's Modified Eagle Medium and Dulbecco's Modified Phosphate-Buffered Saline were purchased from Gibco (Gaithersburg, Md.). Jurkat-Lucia, Quanti-LUC assay solution, normocin and Zeocin were acquired from Invivogen (San Diego, Calif.). 96- and 384-well microplates were purchased from Greiner Bio-One North America (Monroe, N.C.). All other reagents, solvents and disposable consumables were purchased from Sigma-Aldrich (St. Louis, Mo.).

Antibodies, Chemicals and Kits. Antibodies for immunoblotting, immunofluorescence and flow cytometry were purchased from different companies as indicated: NFATc3-R&D systems #AF5834; PerCP/Cy5.5 anti-mouse CD45 Antibody-Fisher #NC0217834; Anti-rabbit Alexa Fluor® 488 Conjugate-Cell signaling #4412S; Alexa Fluor® 594 Streptavidin-Biolegend #405240. Different biomolecules, fine chemicals and kits were purchased from vendors as indicated: Recombinant mouse M-CSF-PeproTech #315-02; Collagenase-Sigma #11088793001 and DNase-Sigma #D4263; ELISA kits for mouse IL6, TNFα R&D systems #DY406-05 and DY410; in 1×RIPA buffer-Cell signaling Technologies #9806; Hema 3 Stat Pack Thermo Fisher Scientific #122-911; ProteoExtract subcellular proteome extraction kit-EMD Millipore #539790.

Example 1. Peptide Synthesis

Peptide Synthesis, Labeling and Purification. Peptides (e.g., cCPPs; and/or cCPP+CNBM) were synthesized on Rink Resin LS (0.48 mmol/g) using standard fluorenylmethyloxycarbonyl (Fmoc) chemistry. Typical Fmoc deprotections were performed using 20% piperidine by volume in dimethylformamide (DMF) twice for 5 min at room temperature (RT) while mixing. Typical couplings were performed using 5 eq. of Fmoc-amino acid, 5 eq. 1-[Bis(dimethylamino)methylene]-1H-1,2,3 triazolo[4,5-b] pyridinium. 3-oxid hexafluoro phosphate (HATU), 5 eq. Hydroxybenzotriazole (HOBO, and 10 eq. diisopropylethylamine (DIPEA) for 1 h with mixing in 70:30 DMF/dichloromethane (DCM) (v/v) at RT. N-Terminal acyl groups were coupled using 5 eq. of the corresponding carboxylic acid, 5 eq. benzotriazol-1-yl-oxytripyrrolidino-phosphonium hexafluorophosphate (PyBOP), 5 eq. HOBt and 10 eq. DIPEA in 1:1 DMF/DCM (v/v) twice for 1 h with mixing at RT. The Mtt protecting group on the C-terminal lysine was removed using 50 mL of 97:2:1 DCM/TFA/TIPS for 5 min at RT (repeated 5 times) and synthesis was continued to prepare the CPP sequence. The allyl protecting group was removed by treatment in the dark with 0.3 eq. tetrakis(triphenylphosphine)palladium(0) with 10 eq. phenylsilane in dry DCM (repeated three times). The N-terminal Fmoc group was then removed with 20% piperidine in DMF. The resin was incubated in 1 M HOBt in DMF and washed with DMF and the peptide was cyclized by using 5 eq. PyBOP, 5 eq. HOBt, 10 eq. DIPEA for 30 min at RT (repeated twice). Cleavage and deprotection of the completed peptide sequences was performed on resin using 92.5:2.5:2.5:2.5 TFA/TIPS/DMB/H$_2$O for 3 h at RT. All of the peptides were labeled on solid-phase with protected side-chains using either 1 eq. 5-FITC, 5 eq. DIPEA in DMF overnight at RT or using 1 eq. NF-NHS, 5 eq. DIPEA in DMF overnight at RT. Crude peptide solutions were concentrated under a stream of inert gas and then triturated three times using chilled ether and the precipitate was isolated by centrifugation at 20K RCF, 4° C. The crude peptide was then dissolved and purified using RP-HPLC using a linear gradient beginning at 95% A (0.05% TFA in ddH$_2$O) and 5% B (0.05% TFA in acetonitrile) increasing at 1% B/min using a Waters 2458 Binary Pump paired with a Waters 2457 UV/Vis spectrometer equipped with a Waters X-Bridge C18 semi-preparative column. Peptide authenticity was confirmed using HRMS and all peptides were determined to have 95% or higher purity by analytical HPLC using a Waters X-Bridge C18 analytical column Protein Expression, Purification and Labeling. Calcineurin was expressed as the glutathione S-transferase fusion protein in BL21 *Escherichia coli* cells and purified on a glutathione sepharose column as previously mentioned. For library screening, GST-CN was biotinylated as previously mentioned. Briefly, 100 μL of GST-CN in pH 7.4 PBS with 20% glycerol (v/v) was incubated with 2 eq. NHS-biotin for 2 h at 4° C., after which the reaction was quenched with 50 μL of 1 M Tris-HCl, pH 8.0.

Example 2. ZIZIT Optimization Strategy

Figure 1A:
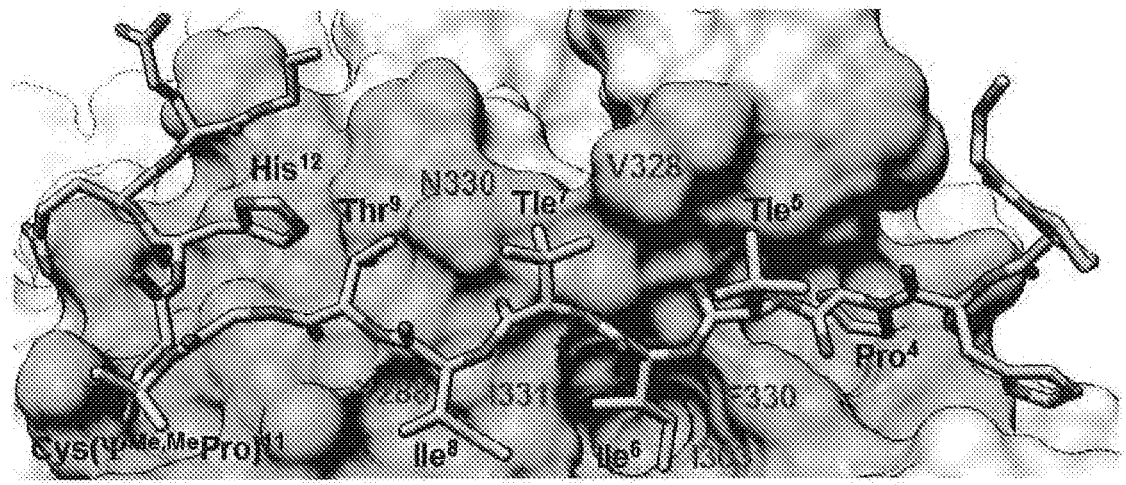
FIG. 1A illustrates binding of peptide ZIZIT-cisPro (SEQ ID NO: 218) to CN.
Figure 1B:
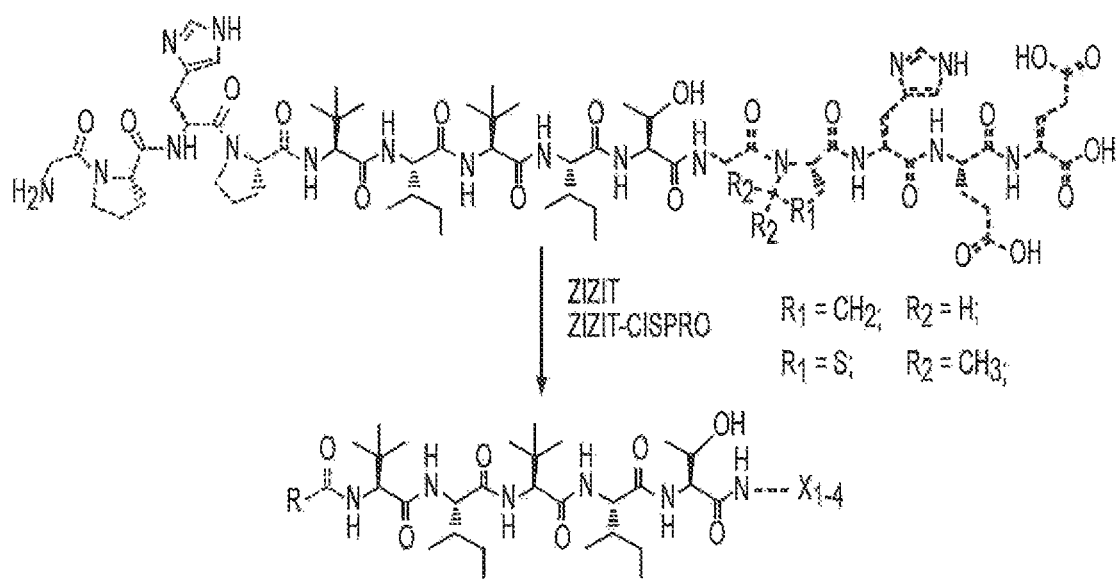
FIG. 1B shows the structure of peptide ZIZIT-cisPro and the optimized peptide conjugates, with the N- and C-terminal regions in red and blue colors, respectively.

ZIZIT-cisPro (SEQ ID NO: 218) is a potent CN inhibitor ($K_D$=2.6 nM). The structure of ZIZIT-cisPro (FIG. 1) suggests that its N-terminal (Gly-Pro-His-Pro (SEQ ID NO:24)) and C-terminal sequences (Gly-cisPro-His-Glu-Glu (SEQ ID NO:25)) are likely susceptible to proteolytic degradation, whereas the core CN-binding motif, Tle-Ile-Tle-Ile-Thr (ZIZIT) (SEQ ID NO:1), should be more protease resistant, due to the presence of multiple β-branched amino acids. The cis-proline analog, 2,2-dimethyl-1,3-thiazolidine-4-carboxylic acid, in ZIZIT-cisPro, once incorporated into a peptide, sterically blocks further elongation of the peptide chain. In addition, cisPro is acid labile to the acidic condition during peptide deprotection. Replacement of the N-terminal tetrapeptide (GPHP (SEQ ID NO:24)) with a non-peptidyl moiety (e.g., an acyl group) substantially improves the proteolytic stability of the peptide. We optimized the C-terminal sequence by a combinatorial library approach. The pentapeptide was replaced with a library of short peptides enriched in D-amino acids and screened for new CN binders.

Example 3. Replacement of the N-Terminal Sequence of ZIZIT with an Acyl Group To facilitate concentration determination and binding analysis by fluorescence anisotropy (FA), a dipeptide Tyr-Lys was added to the C-terminus of ZIZIT (SEQ ID NO:1) and the lysine side chain was labeled with fluorescein isothiocyanate (FITC). The resulting peptide, Ac-GPHPZIZITGPHEEYK(FITC)-NH$_2$ (SEQ ID NO:26, underlined portion) (Table 1, peptide 1), bound to CN with a $K_D$ value of 92 nM. Next, the N-terminal four residues (Ac-GPHP (SEQ ID NO: 195)) were replaced with benzoyl, cyclopentylcarbonyl, cyclohexylcarbonyl, acetyl, or formyl group and the resulting peptides (Table 1, peptide 2-6) were subjected to in silico rigid receptor/flexible ligand docking using a fixed core sequence (ZIZITGP (SEQ ID NO:27)) and program Glide. The benzoyl, cyclopentylcarbonyl, cyclohexylcarbonyl groups were intended to mimic the prolyl residue at position 4 of ZIZIT (SEQ ID NO:1) (FIG. 1), whereas the acetyl and formyl groups were included as negative controls to validate the in silico model. In silico docking indicated that the benzoyl group was most effective, with a binding energy of −12.8 kcal/mol for peptide 2, whereas the formyl group was least effective with a binding energy of −9.5 kcal/mol for peptide 6 (Table 5). Experimental analysis by FA revealed that the benzoyl and cyclohexylcarbonyl groups are the most effective surrogates of the tetrapeptide ($K_D$ values of 224 and 207 nM for peptides 2 and 4, respectively), largely confirming the in silico docking results.

TABLE 5

N-Terminally Acylated Peptides and Their Predicted Binding Energies and Experimental CN-Binding Affinities

| Peptide | Acyl Group | Docking Score (kcal/mol) | $K_D$ (nM) |
|---|---|---|---|
| 1 | Ac-GPHP | | 92 ± 12 |
| 2 | 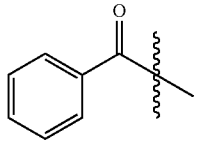 [SMILES: *C(=O)c1ccccc1] | −12.786 | 224 ± 56 |
| 3 | 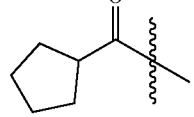 | −11.613 | 357 ± 22 |

TABLE 5-continued

N-Terminally Acylated Peptides and Their Predicted Binding Energies and Experimental CN-Binding Affinities

| Peptide | Acyl Group | Docking Score (kcal/mol) | $K_D$ (nM) |
|---|---|---|---|
| 4 | 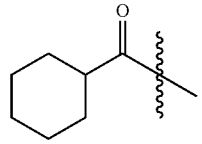 [SMILES: *C(=O)C1CCCCC1] | −12.125 | 207 ± 40 |
| 5 | 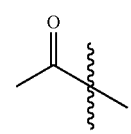 [SMILES: *C(C)=O] | −10.005 | >5400 |
| 6 | 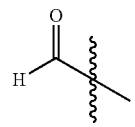 | −9.512 | >5800 |
| 7 | 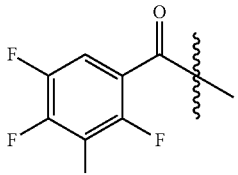 | −12.810 | 32 ± 12 |
| 8 | 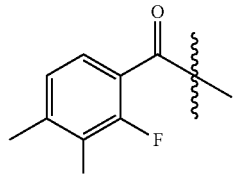 | −12.871 | 74 ± 15 |
| 9 | 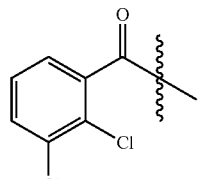 | −13.355 | 41 ± 9 |
| 10 | 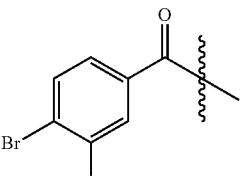 | −12.893 | 189 ± 10 |
| 11 | 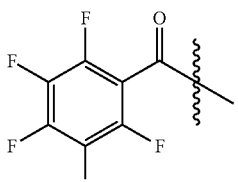 | −13.264 | 77 ± 27 |

Figure 2:
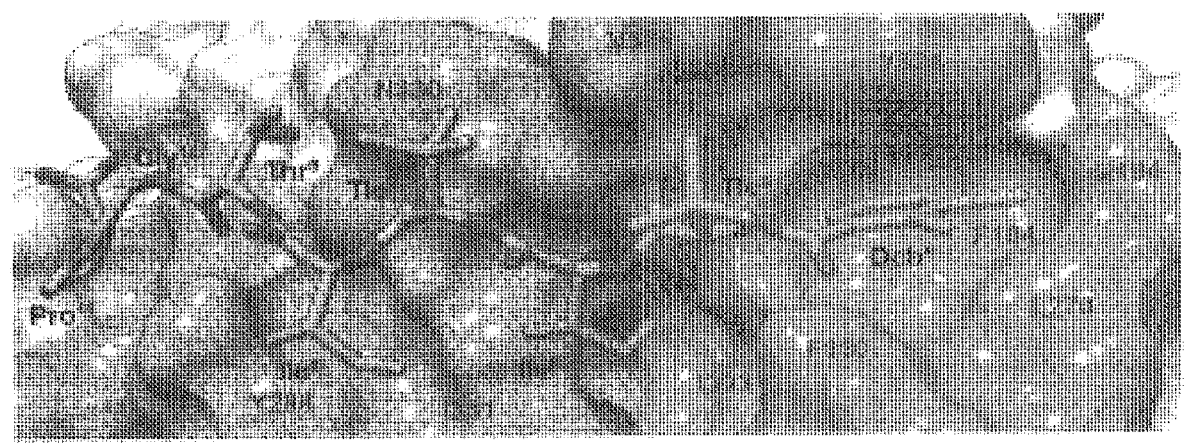
FIG. 2 is a docking model showing the binding interaction between Dcb-ZIZITGP (SEQ ID NO: 217) and CN. The peptide ligand is shown as sticks, whereas the ligand-binding surface of CN is shown in orange. Peptide atoms are shown in yellow (carbon), blue (nitrogen), red (oxygen), and green colors (chlorine).
Figure 3:
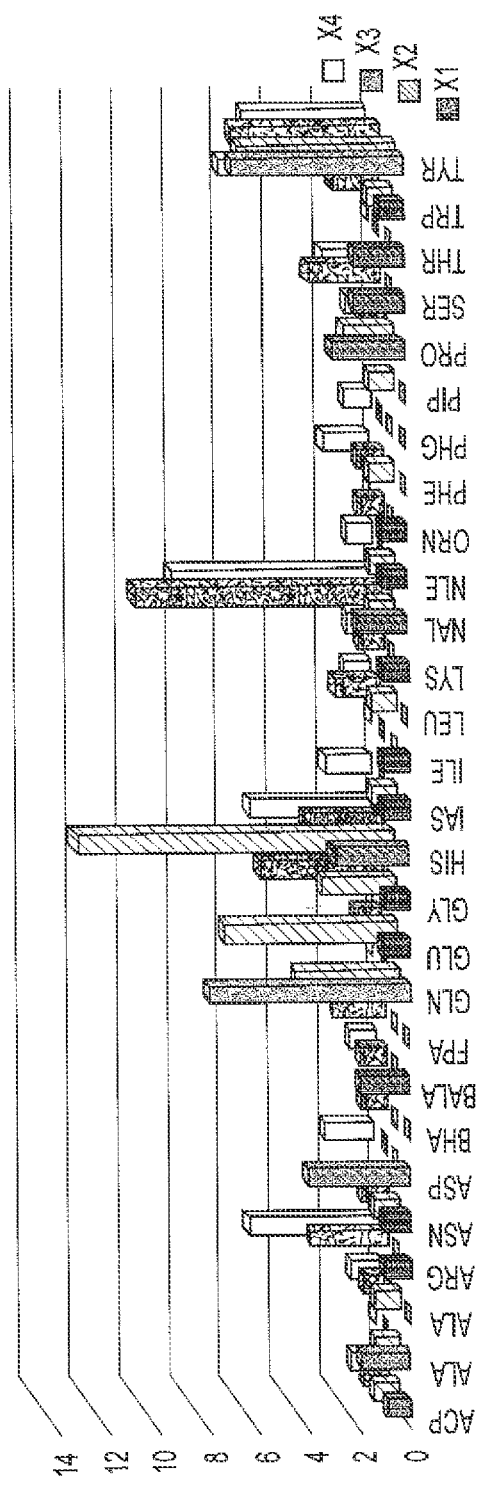
FIG. 3 is a histogram showing the sequence selectivity of CN C-terminal to the ZIZIT motif (SEQ ID NO:1). Data shown are number of occurrence (y axis) of a particular amino acid (x axis) at a given peptide position $X^{1-4}$ (z axis).

The benzoyl group was selected for further optimization. Additional in silico docking analysis was performed for a focused library of halogenated and/or alkylated benzoic acid derivatives (total 61 compounds, Table 6). Synthesis and FA analysis of the corresponding acyl-ZIZITGPHEEYK(FITC)-NH$_2$ (SEQ ID NO:28, underlined portion) peptides (Table 1, peptides 7-11) confirmed that halogenation and/or alkylation can further improve CN-binding affinity ($K_D$ values of 32 to 189 nM). Peptide 9, which contains an N-terminal 2,3-dichlorobenzoyl (Dcb) group ($K_D$=41 nM), was selected for C-terminal optimization. Molecular dynamics docking revealed that the benzoyl group fits snugly into the proline-4 binding pocket, with the two chlorine atoms facing the solvent (FIG. 2). It appears that the presence of ortho-substitution twists the benzoyl carbonyl moiety out of the benzene plane, allowing the benzene ring to optimally insert into the hydrophobic pocket.

TABLE 6

Additional Acyl Groups Subjected to In Silico Screening and Their Calculated Binding Energies to Calcineurin

| Acyl group | Docking score (kcal/mol) |
|---|---|
| 3-chloro-4-methylbenzoyl | −6.129 |
| 2,6-dichloro-3-fluorobenzoyl | −6.637 |
| 2-trifluoromethylbenzoyl | −8.857 |
| formyl | −9.512 |
| 2-fluoro-6-methylbenzoyl | −9.954 |
| acetyl | −10.005 |
| 4-chloro-2-methylbenzoyl | −10.131 |
| 3-chloro-5-methylbenzoyl | −10.303 |
| 3-(1-chloromethyl)benzoyl | −10.470 |
| 3,5-dibromobenzoyl | −10.511 |
| 4-tertbutylbenzoyl | −10.612 |
| 3-methylbenzoyl | −10.634 |
| 2-chlorobenzoyl | −10.667 |
| 3-iodobenzoyl | −10.678 |
| 2-chloro-4-iodobenzoyl | −10.732 |
| 4-methylbenzoyl | −10.768 |
| 2-bromobenzoyl | −10.784 |
| 2-fluorobenzoyl | −10.794 |
| 2,4,6-trimethylbenzoyl | −10.806 |
| 2-chloro-5-fluorobenzoyl | −10.902 |
| 2-chlorobenzoyl | −10.915 |
| 2-bromo-4-chlorobenzoyl | −11.081 |
| 2-fluoro-4-methylbenzoyl | −11.112 |
| 4-isopropylbenzoyl | −11.121 |
| 4-fluoro-2-methylbenzoyl | −11.167 |
| 4-(1-bromomethyl)benzoyl | −11.167 |
| 2-methylbenzoyl | −11.244 |
| 4-bromobenzoyl | −11.291 |
| 4-trifluoromethylbenzoyl | −11.347 |
| 2-fluoro-4-chlorobenzoyl | −11.381 |
| 2,6-dimethylbenzoyl | −11.384 |
| 4-butylbenzoyl | −11.407 |
| 3-bromobenzoyl | −11.467 |
| 3,5-dimethylbenzoyl | −11.473 |
| 2-iodobenzoyl | −11.560 |
| cyclopropylcarbonyl | −11.582 |
| 2-chloro-3-methylbenzoyl | −11.596 |
| 3-ethynylbenzoyl | −11.610 |
| 2,4-dimethylbenzoyl | −11.632 |
| 3,5-trifluoromethylbenzoyl | −11.647 |
| 2-chloro-4-fluorobenzoyl | −11.742 |
| 4-fluorobenzoyl | −11.756 |
| 5-chloro-2-methylbenzoyl | −11.783 |
| 2-(1-chloromethyl)benzoyl | −11.799 |
| 4-(2-chloroethyl)benzoyl | −11.916 |
| 2-chloro-6-fluorobenzoyl | −11.919 |
| 4-chloro-2-methylbenzoyl | −12.039 |
| 3-fluorobenzoyl | −12.061 |
| cyclohexylcarbonyl | −12.125 |
| 2-naphthoic acid | −12.237 |

TABLE 6-continued

Additional Acyl Groups Subjected to In Silico Screening and Their Calculated Binding Energies to Calcineurin

| Acyl group | Docking score (kcal/mol) |
|---|---|
| 4-iodobenzoyl | −12.328 |
| 3,4-dimethylbenzoyl | −12.438 |
| 2,4-dichloro-3-fluorobenzoyl | −12.486 |
| 2,3,4-trifluorobenzoyl | −12.573 |
| 4-ethylnylbenzoyl | −12.620 |
| 2-chloro-4-iodobenzoyl | −12.659 |

Molecular Dynamics. MD was employed to provide clustered structures for docking using Schrodinger Glide. Simulation was first prepared by editing the crystal structure of VIVIT(SEQ ID NO: 2)/CN (pdbID: 2p6b) in UCSF Chimera software suite to include ZIZIT(SEQ ID NO: 1) structural modifications. All charges and protonation sites were calculated at pH 7.4. The system was placed within a dodecahedral periodic box, each dimension 9.091 nm long, filled with copies of 216 equilibrated TIP3P water molecules and sufficient counter-ions for system neutralization. The system underwent two steps of energy minimization using steepest decent, first with only solvent relaxing, then the entire system followed by a heating process for which the temperature is increased from 0 to 300K. The system then underwent two more phases of equilibration via MD, first using NVT (isothermal) conditions for 200 ps and then NPT (isothermal-isobaric with pressure control via the Parrinello-Rahman algorithm) conditions for 200 ps. The production MD simulations were performed under NPT conditions for 20 ns. Following the simulation, trajectory clustering was performed using gmx cluster using the gromos algorithm. Structures were clustered based on RMSD from the structure extracted from the 20 ns frame of the trajectory based on the RMSD of heavy atoms from CN residues F194, L270 and Y324 as these residues form the majority of the hydrophobic N-terminal proline pocket. Snapshots every 4 ps from the trajectory were used for clustering, with the largest cluster representing ~90% of all structures sampled in the trajectory. A representative structure was produced for this cluster and served as the input receptor conformation for docking.

Docking. Compounds for screening were constructed in Maestro and then prepared for docking using LigPrep, with all ligands ionized to pH 7.4 with all tautomers generated and stereochemistry retained from the input structures. The receptor for docking was obtained from the clustered MD trajectory and was prepared using the Protein Preparation Wizard in Maestro to remove remaining water and counter-ions. The docking grid was generated using the Receptor Grid Generation tool in Maestro with no constraints input.

Docking was performed using Glide with XP precision with modified settings. The position of the C-terminal GP moiety in the original ligand was retained and used as a positional constraint for docking with a tolerance of 0.5 Å to reject poses as not conforming to the constraint. Each compound was docked using flexible ligand docking with nitrogen inversions and ring conformations sampled, amides penalized for nonplanar conformations and the planarity of conjugated π groups enhanced. For conformer generation, enhanced sampling was used and during initial pose selection 200,000 poses per ligand were retained with the top 5000 poses per ligand kept for energy minimization combined with expanded sampling. Energy minimization was performed over 5000 steps and halogens were counted as hydrogen bond acceptors. Final docked compounds were ranked by their docking score and visualized using Maestro or UCSF Chimera.

Example 4. Optimization of the C-Terminal Sequence of ZIZIT by Library Screening The C-terminal pentapeptide (GPHEE) contributes significantly to the overall CN-binding affinity, as its removal decreased the binding affinity by 17-fold ($K_D$=700 nM for peptide 12; Table 2). To replace the pentapeptide with a more proteolytically stable and tighter binding sequence, we designed a one bead-one compound (OBOC) peptide library in the form of Dcb-ZIZIT(SEQ ID NO: 1)-$X_n$-BBRRM-resin, where $X_n$ represents a random peptide sequence of 1 to 4 residues (Scheme 1). Each random position ($X^1$ to $X^4$) was constructed with a set of 28 different amino acids, including 11 proteinogenic amino acids (Ala, Arg, Asp, Gln, Gly, His, Ile, Pro, Ser, Trp, and Tyr), 6 unnatural α-L-amino acids [4-fluorophenylalanine (Fpa), 2-naphthylalanine (Nal), norleucine (Nle), ornithine (Orn), phenylglycine (Phg), and pipecolic acid (Pip)], 7 α-D-amino acids (ala, asn, glu, leu, lys, phe, thr), and 4 β-amino acids [(1S,2R)-2-aminocyclopentane carboxylic acid (Acp), β-alanine (β Ala), β-D-homoalanine (bha), and isoaspartic acid (Ias)]. The library has a theoretical diversity of $6.5\times10^5$ unique compounds and was synthesized on 1 g of TentaGel resin (90 μm). The library (200 mg or ~600,000 compounds) was screened against biotinylated GST-CN and the positive beads were stained by incubation with a streptavidin-alkaline phosphatase conjugate (SA-AP) and 5-bromo-4-chloro-3-indolylphosphate. The colored beads were isolated from the library, and the peptides were individually released from the beads by CNBr treatment and analyzed by MALDI-TOF mass spectrometry. Interestingly, all of the selected peptides contained four random residues, indicating that all four residues interact with the CN protein surface and contribute to the overall binding affinity. Inspection of the selected sequences revealed that CN strongly prefers an L-amino acid at the $X^1$ position (which is immediately C-terminal to ZIZIT), especially glutamine and tyrosine and, to a lesser extent, aspartic acid and histidine (FIG. 3). It also has a strong selectivity for histidine, tyrosine, or D-glutamic acid at the $X^2$ position. At the $X^3$ and $X^4$ positions, CN has a general preference for aromatic hydrophobic residues (especially Nal), although a variety of other amino acids (including D-amino acids) are tolerated.

Scheme 1

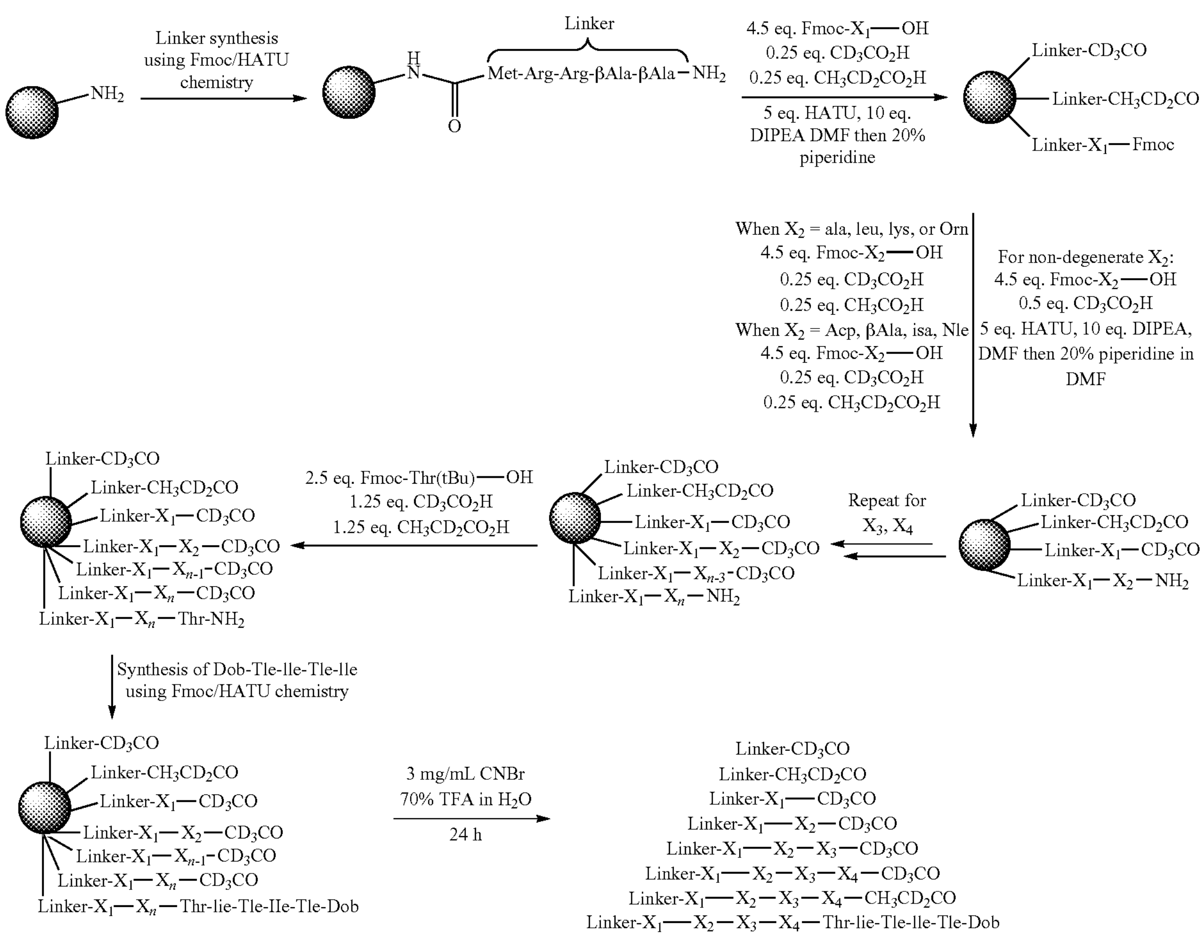

Tle-Ile-Tle-Ile-Thr = (ZIZIT) (SEQ ID NO: 1)

Five representative sequences were resynthesized, labeled at their C-termini with a βAla-Lys(FITC) moiety, and tested for CN binding by FA (Table 7, peptides 13-17). All five peptides bound to CN with high affinity ($K_D$ values of 4.7 to 64 nM). Peptides 13 (which has a C-terminal sequence of Tyr-glu-Fpa-Gly and a $K_D$ value of 12 nM) and 14 (Gln-His-leu-Ser; $K_D$=9.1 nM) were selected for further studies because of their high potency, good aqueous solubility, and the presence of a D-amino acid in the selected sequence (which improves proteolytic stability). Peptide 15, despite its excellent potency ($K_D$=4.7 nM), had lower solubility and was not further evaluated.

TABLE 7

CN-Binding Affinity of Peptides Selected from the Peptide Library

| Peptide | Sequence[a] | $K_D$ (nM)[b] |
|---|---|---|
| 12 | Dcb-ZIZIT-miniPEG-Lys (FITC) | 700 ± 150 |
| 13 | Dcb-ZIZIT-Tyr-glu-Fpa-Gly-βAla-Lys (FITC) | 12 ± 4 |
| 14 | Dcb-ZIZIT-Gln-His-leu-Ser-βAla-Lys (FITC) | 9.1 ± 3.9 |
| 15 | Dcb-ZIZIT-Gln-His-leu-His-βAla-Lys (FITC) | 4.7 ± 1.4 |
| 16 | Dcb-ZIZIT-Asp-Gln-Tyr-Arg-βAla-Lys (FITC) | 64 ± 31 |
| 17 | Dcb-ZIZIT-Asp-Gln-Tyr-lys-βAla-Lys (FITC) | 22 ± 3 |

[a]Dcb, 2,3-dichlorobenzoyl; βAla, β-alanine, FITC, fluorescein isothiocyanate; Fpa, 4-fluorophenylalanine. D-amino acids were shown in all-lowercase letters.
[b]Data represent the mean ± SD of three or more independent experiments.

Library Synthesis. The library was synthesized on 1 g of TentaGel S $NH_2$ Resin (90 μm, 0.28 mmol/g). Synthesis began by coupling the common linker sequence, β-Ala-β-Ala-Arg-Arg-Met (SEQ ID NO: 202) to the resin by following the peptide synthesis conditions mentioned above. Following N-terminal Fmoc removal, the resin (as a suspension in DMF) was volumetrically divided into 28 equal portions and placed into separate reaction vessels, to each of which a different Fmoc-amino acid ($X^4$ position) was coupled. The coupling reaction employed 4.5 eq. of Fmoc-amino acid, 0.25 eq. $CD_3CO_2H$, 0.25 eq. $CH_3CD_2CO_2H$, 5 eq. HATU, and 5 eq. HOBt. The presence of the carboxylic acids resulted in chain termination for ~10% of the library peptides, facilitating later peptide sequence determination by MS. To synthesize the remaining random positions ($X^1$-$X^3$), the resin was combined, mixed, and washed. Approximately 5 mg of the resin was set aside and the remaining resin (0.995 g) was treated with 20% piperidine in DMF to remove the N-terminal Fmoc group. The resin (0.995 g) was again split into 28 equal aliquots and to each aliquot a different Fmoc-amino acid was coupled, by using 4.5 eq. of Fmoc-amino acid, 5 eq. HATU, and 5 eq. HOBt. Additionally, 0.25 eq. of $CH_3CD_2CO_2H$+0.25 eq. of $CD_3CO_2H$ were added into the coupling reactions of Acp, βAsp, βAla, and Nle, whereas 0.25 eq. of $CH_3CO_2H$+0.25 eq. of $CD_3CO_2H$ were included during the coupling reactions of ala, leu, lys, and Orn. For all other amino acids, 0.5 eq. of $CD_3CO_2H$ was added into their coupling reactions. The above split-and-pool procedure was repeated twice to synthesize the $X^2$ and $X^1$ positions. After all 4 random positions ($X^1$-$X^4$) were added, the 4 groups of resin (3×5 mg+0.985 g) were pooled, washed, and the N-terminal Fmoc group was removed and the peptide sequence Dcb-ZIZIT was coupled to all peptides by standard peptide chemistry. To increase the stringency of library screening and select for the most potent CN binders, the loading density of full-length peptides on the resin was reduced by ~50%, by using 2.5 equiv of Fmoc-Thr(tBu)-OH, 1.25 equiv of $CD_3CO_2H$, 1.25 equiv of $CH_3CD_2CO_2H$, 5 eq. HATU, 5 eq. HOBT, and 10 eq. DIPEA during the addition of the threonine residue (30 min). Side chain deprotection was achieved by treatment with a modified reagent K (TFA/thioanisole/water/phenol/1,2-ethanedithiol, 82.5:5:5:5:2.5 v/v) for 3 h. The resulting library was exhaustively washed with DCM, DMF, 5% DIPEA in DMF, and 1:1 (v/v) DCM/diethyl ether and stored at −20° C. until use.

Library Screening. A portion of the peptide library (200 mg) was placed in a 1.5-mL Micro-Spin column and washed extensively with MeOH, $ddH_2O$ and PBS and blocked for 1 h with PBS containing 0.1% gelatin. Biotinylated GST-CN was diluted in 1 mL of blocking buffer [PBS, pH 7.4, 0.05% Tween-20, 0.1% gelatin (v/v)] supplemented with 5 mM TCEP to a final concentration of 50 nM and incubated on ice for 1 h. The resin was drained, resuspended in 1 mL of the GST-CN solution, and incubated overnight at 4° C. The resin was gently drained and quickly resuspended (without washing) in 1 mL of SA-AP buffer (30 mM Tris, pH 7.6, 1 M NaCl, 10 mM $MgCl_2$, 70 μM $ZnCl_2$, and 20 mM potassium phosphate) containing 1 μL of 1 mg/mL streptavidin-alkaline phosphatase. After incubation with mixing for 10 min at 4° C., the resin was drained and washed with SA-AP buffer, PBS, and finally staining buffer (30 mM Tris, pH 8.5, 100 mM NaCl, 5 mM $MgCl_2$, and 20 μM $ZnCl_2$). The resin was transferred into a glass-bottomed petri dish by washing with staining buffer (total 1 mL final volume) and 80 μL of 5 mg/mL BCIP in staining buffer was added. The mixture was incubated at RT on a rocking mixer and intense turquoise color developed on positive beads in ~45 min, when the staining reaction was quenched by the addition of 1 mL of 1 M HCl. The positive beads (total 89 beads) were manually isolated with a micropipette under a dissecting microscope and separated into "intensely" (49 beads), "medium" (26 beads), and "lightly" colored categories (17 beads).

The hit beads were placed into individual 1-mL Eppendorf tubes (1 bead/tube) and the peptides were released from each bead by incubating the bead in 25 μL of 3 M CNBr dissolved in 70% TFA/$H_2O$ (v/v) overnight at RT. The peptide solution was dried under vacuum and dissolved in 10 μL of 1:1 acetonitrile/$H_2O$ (v/v). One μL of the peptide solution was mixed with 1 μL of saturated α-cyano-4-hydroxycinnamic acid dissolved in 1:1 acetonitrile/$H_2O$ and 1 μL of the mixture was spotted onto a Bruker 96-spot polished steel MALDI plate. MALDI spectra were recorded using a Bruker FLEX MALDI-TOF and analyzed using Bruker FlexAnalysis. Peptide sequence was determined from the m/z ladder in the MS spectrum (FIGS. 13A-E).

Figure 4:
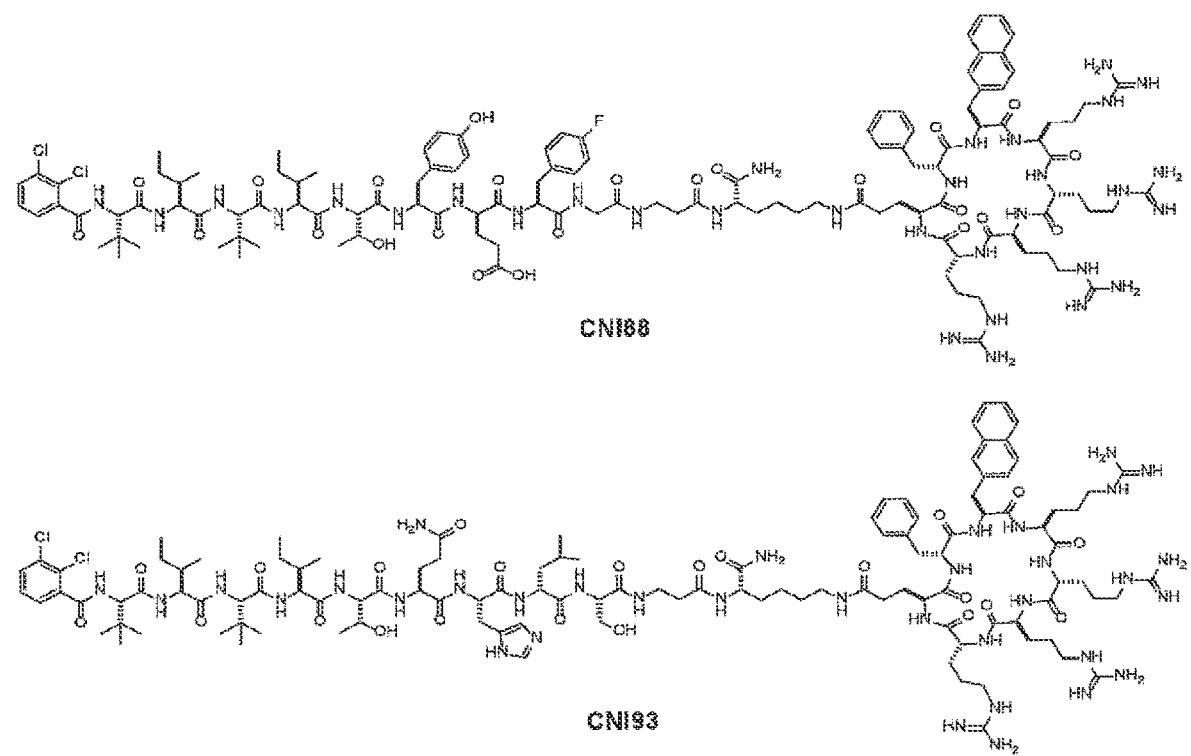
FIG. 4 illustrates the structures of calcineurin inhibitors CNI88 (SEQ ID NO. 219) and CNI93 (SEQ ID NO: 220).
Figure 5:
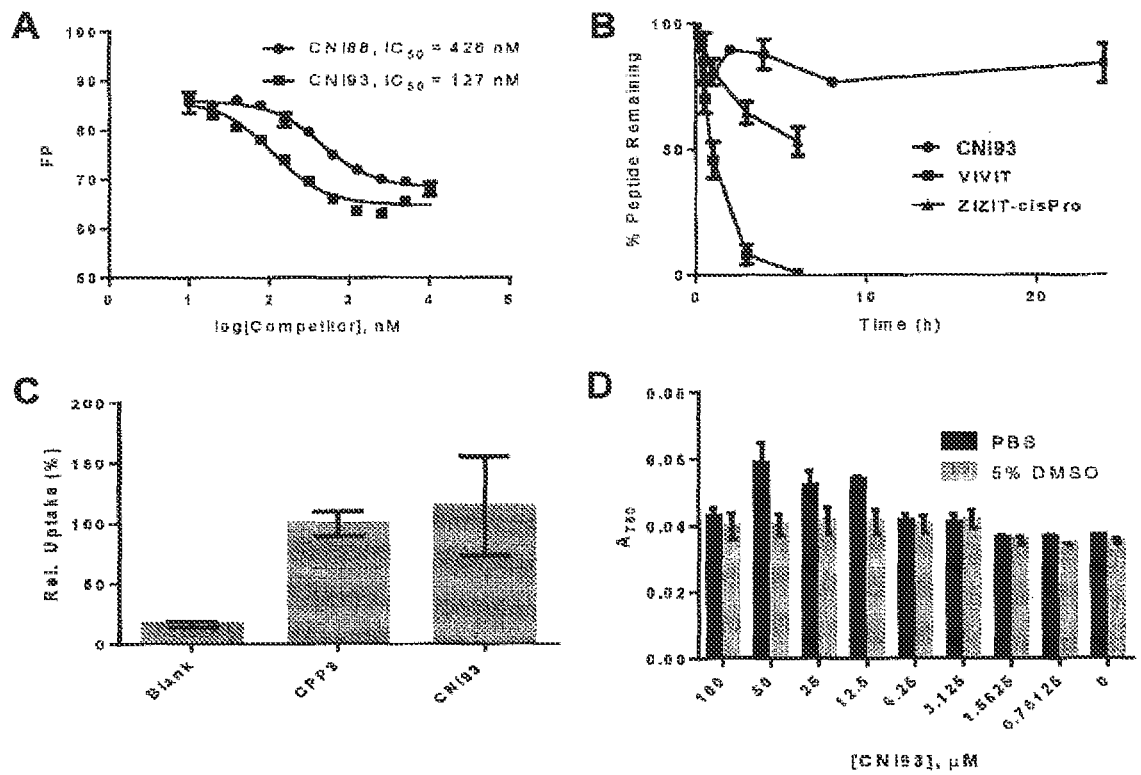
FIG. 5A illustrates inhibition of interaction of peptide 14 with CN by CNI88 and CNI93 as monitored by FP.
FIG. 5B shows a comparison of the serum stability of VIVIT (SEQ ID NO:2), ZIZIT-cisPro (SEQ ID NO: 218), and CNI93 (SEQ ID NO: 220).
FIG. 5C illustrates cytosolic entry of NF-labeled CPP9 (SEQ ID NO: 76) and CNI93 into HeLa cells (after treatment with 5 µM peptides for 2 h) as determined by flow cytometry analysis.
FIG. 5D illustrates the results of a turbidity test of CNI93 in PBS in the absence and presence of 5% DMSO.

Example 5. Generation of Cell-Permeable CN Inhibitors by Conjugation to Cyclic CPP To render peptides 13 and 14 cell-permeable, a cyclic CPP (CPP9) was covalently attached to their C-termini through an amide bond and a βAla-Lys linker, resulting in peptides CNI88 (SEQ ID NO. 219) and CNI93 (SEQ ID NO. 220), respectively (FIG. 4). CPP9 is a highly active and metabolically stable CPP, having an absolute cytosolic delivery efficiency of 62% (100% efficiency is defined as resulting in equal cargo concentration in the cytosol and the extracellular medium). To ascertain that CNI88 and CNI93 retain the ability of binding to the NFAT-docking site on CN, they were tested for competition with FITC-labeled peptide 14 for binding to CN in an FA-based assay (FP). CNI88 and CNI93 dose-dependently inhibited the binding of peptide 14 to CN, with $IC_{50}$ values of 426 and 127 nM, respectively (FIG. 5A). CNI93 was selected as the lead compound for further characterization because of its higher potency (than CNI88). In a direct binding assay by FA, CNI93 showed a $K_D$ value of 75 nM for CN.

CNI93 has excellent serum stability; incubation of CNI93 in human serum at 37° C. for 24 h resulted in no significant degradation (<10%; FIG. 5B). Under the same condition, ZIZIT-cisPro (SEQ ID NO: 218) was degraded with a half-life of ~6 h, while the VIVIT (SEQ ID NO: 2) peptide was completely degraded within 6 h ($t_{1/2}$~1 h). The aqueous solubility of CNI93 was assessed by measuring turbidity in solution. The peptide was serially diluted from a DMSO stock into PBS (pH 7.4) containing 5% DMSO and the optical density of the resulting solutions were measured at 780 nm. In the presence of 5% DMSO, CNI93 did not significantly increase the turbidity up to 100 µM (the highest concentration tested), suggesting that CNI93 has an aqueous solubility of at least 100 µM (FIG. 5C).

Figure 6:
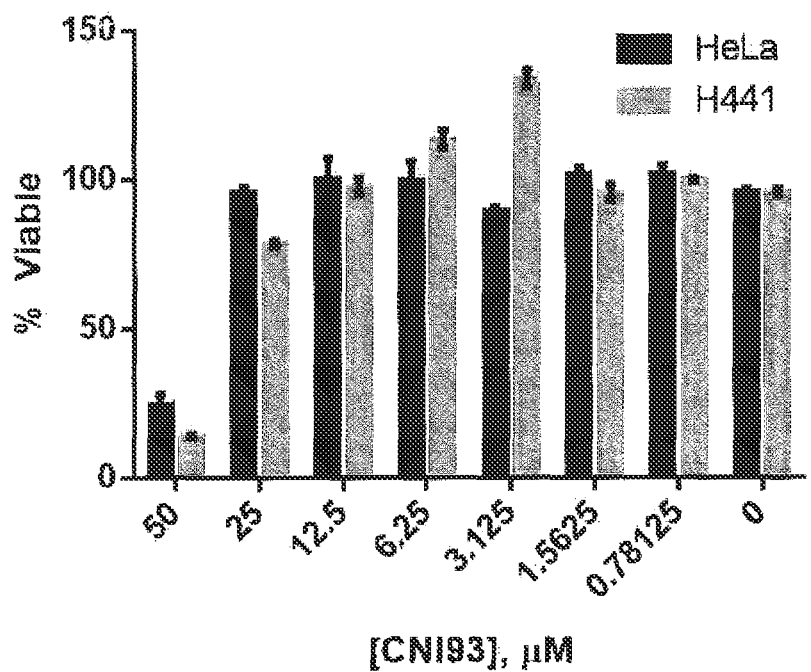
FIG. 6 illustrates that effect of CNI93 (SEQ ID NO: 220) on the viability of HeLa and H441 (lung cancer) cells as monitored by the MTT assay (72 h).

The cell-permeability of CNI93 (SEQ ID NO. 220) was estimated by labeling it with naphthofluorescein (NF) and quantitating the mean fluorescence intensity of HeLa cells treated with the peptide by flow cytometry. NF is a pH-sensitive dye (pKa=7.8) and is non-fluorescent in the acidic environments of endosomes/lysosomes. The NF fluorescence intensity of the treated cells therefore reflects the amount of the peptide that has reached the cytosol and nucleus of the cells. Flow cytometry analysis revealed that CNI93 entered HeLa cells with a relative cytosolic delivery efficiency of 109% (relative to that of CPP9, which is defined as 100%; FIG. 5D). Live-cell confocal microscopic analysis confirmed that CNI93 reached the interior of HeLa cells. Finally, CNI93 was assessed for general cytotoxicity against two different cell lines by using the MTT assay. No significant cytotoxicity was observed with any of the cell lines after treatment with 25 µM CNI93 for 72 h (FIG. 6). Reduction in cell viability was observed at 50 µM, which may be caused by compound binding to and precipitation of medium components.

Fluorescence Polarization. Fluorescence polarization (FP) experiments were carried out to measure binding affinity in both direct and competitive binding experiments using GST-CN and peptides prepared as mentioned previously. For direct binding, 50 nM FITC-labeled peptide was prepared in PBS, pH 7.4 containing 5 mM DTT and 0.01% Triton-X100 and then added to GST-CN diluted in PBS containing 0.01% Triton-X100. Solutions were incubated for 1 h at RT with gentle mixing and then pipetted into black 384-well microplates. Fluorescence polarization was measured on a TECAN Infinite M1000 plate reader and titration curves were fitted using both KaelidaGraph v 3.6 and GraphPad PRISM to the equation:

$$FP = \frac{\left(A_{min} + \left(A_{max} \times \frac{Q_b}{Q_f} - A_{min}\right)\left(\frac{(L+x+K_d) - \sqrt{((L+x+K_d)^2 - 4Lx)}}{2L}\right)\right)}{\left(1 + \left(\frac{Q_b}{Q_f} - 1\right)\left(\frac{(L+x+K_d) - \sqrt{((L+x+K_d)^2 - 4Lx)}}{2L}\right)\right)}$$

where FP is the measured fluorescence polarization, Amin is the minimum FP value, $A_{max}$ is the maximum FP signal, Qb is the quantum yield of the bound fluorophore, $Q_f$ is the quantum yield of the free fluorophore, L is the ligand concentration, $K_D$ is the dissociation constant and x is the protein concentration.

For competition assays to determine $IC_{50}$, 50 nM FITC-labeled probe was incubated with 100 nM GST-CN in PBS with 5 mM DTT and 0.01% Triton-X100 for 1 h at RT with gentle mixing. Serial dilutions of competitor peptides were prepared in PBS with 0.01% Triton-X100 and then added to the incubation solution and equilibrated at RT with gentle mixing for 1 h. Samples were pipetted into 384-well black microplates and FP signal was measured using a TECAN Infinite M1000 plate reader and analyzed using GraphPad PRISM v.6.

Serum Stability Assay. Diluted human serum (25%) (H4522 human serum, Sigma) was centrifuged at 15,000 rpm for 10 min, and the supernatant was collected. A peptide stock solution was diluted into the supernatant to a final concentration of 5 µM and incubated at 37° C. At various time points (0-24 h), 200-µL aliquots were withdrawn and mixed with 100 µL of 15% trichloroacetic acid and incubated at 4° C. overnight. The final mixture was centrifuged at 15,000 rpm for 10 min in a microcentrifuge, and the supernatant was analyzed by reversed-phase HPLC equipped with a C18 column. The amount of remaining peptide (%) was determined by integrating the area underneath the peptide peak (monitored at 214 nm) and comparing with that from the peptide at time 0.

Cytosolic Delivery Assay. HeLa cells maintained in DMEM supplemented with 10% FBS and 1% penicillin/streptomycin were seeded into 12-well plates ($1.5 \times 10^5$ cells per well) and incubated overnight at 37° C., 5% $CO_2$. The following day, the cells were washed with DPBS and incubated with 5 µM NF-labeled peptides dissolved in DMEM containing 10% FBS, 1% penicllin/streptomycin for 2 h at 37° C. in the presence of 5% $CO_2$. After that, the cells were washed with DPBS and harvested from the plate by treatment with 0.25% trypsin for 5 min Cells were centrifuged at 300×RCF, washed twice with cold DPBS, and resuspended in cold DPBS for flow cytometry analysis on a BD LSR II flow cytometer followed by data analysis and gating using Flowjo. Calculation of cytosolic uptake efficiencies was carried out as previously described by Qian, Z., et al., Discovery and Mechanism of Highly Efficient Cyclic Cell-Penetrating Peptides. Biochemistry 2016, 55, 2601-2612.

MTT Proliferation Assay. HeLa, Jurkat-Lucia, or H441 cells were seeded into a 96-well microplate (5000 cells per well) in full growth media and incubated at 37° C. overnight. A serial dilution of each compound was prepared in DPBS and then added to each well. The treated cells were incubated at 37° C. with 5% $CO_2$ for 72 h. Following compound treatment, 10 µL of MTT stock solution was added to each well. After an additional 4 h at 37° C., 100 µL of SDS-HCl solubilizing solution was added to each well and the plate was returned to the incubator overnight at 37° C. A Tecan Infinite M1000 Pro microplate reader was used the following morning to measure the absorbance of the formazan product at 565 nm.

Example 6. CNI93 Inhibits Activation and Nuclear Translocation of NFATc3

Figure 7:
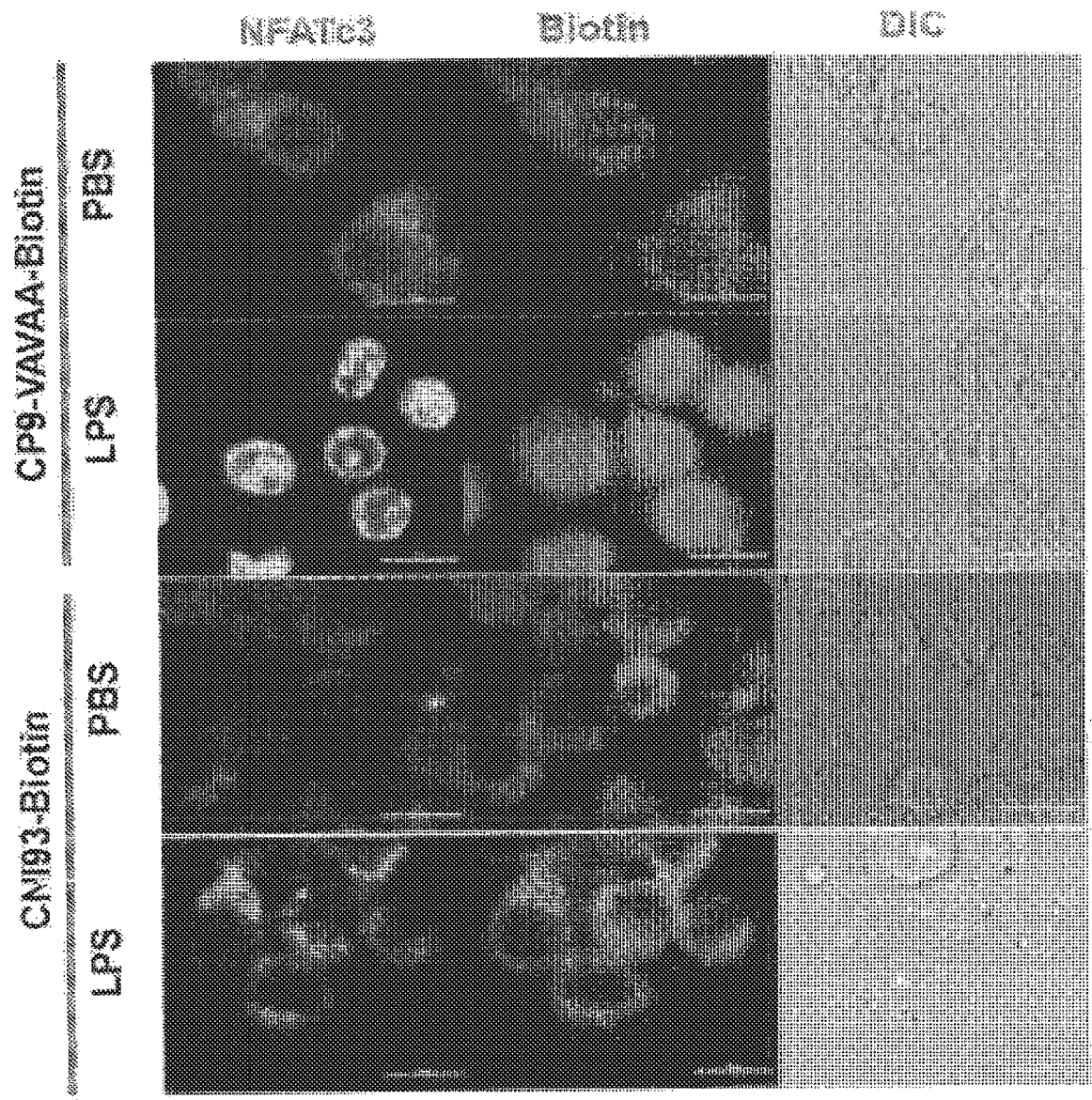
FIG. 7 illustrates inhibition of NFATc3 nuclear translocation by CNI93 (SEQ ID NO: 220). Single confocal optical sections (pinhole set to achieve 1 Airy unit) are shown (n=7-10 cells/group). Scale bars, 10 µm.

Endotoxin lipopolysaccharide (LPS) was previously shown to induce NFATc3 translocation from the cytoplasm into the nucleus and upregulation of NFATc3 target genes in macrophages. Since nuclear translocation of NFATs requires prior dephosphorylation by CN, we tested whether CNI93 can block the activation and nuclear translocation of NFATc3 in macrophages. Lung macrophages derived from collagenase treated lung tissue from healthy mice were pretreated with biotinylated CNI93 (SEQ ID NO. 220) or a non-binding control peptide, CPP9-VAVAA, and then stimulated with LPS (or PBS). The intracellular localization of NFATc3 and biotinylated CNI93 (or CPP9-VAVAA) was visualized by immunofluorescence staining with Alexa Fluor® 488 conjugated anti-NFATc3 antibody and Alexa Fluor® 594-conjugated streptavidin, respectively, and imaged by confocal microscopy. In cells treated with CPP9-VAVAA and PBS, NFATc3 was predominantly localized in the cytoplasm, whereas LPS stimulation resulted in almost complete nuclear localization of NFATc3 (FIG. 7). However, pretreatment of the cells with 1 µM CNI93 completely blocked the LPS-induced nuclear translocation of NFATc3.

Figure 8:
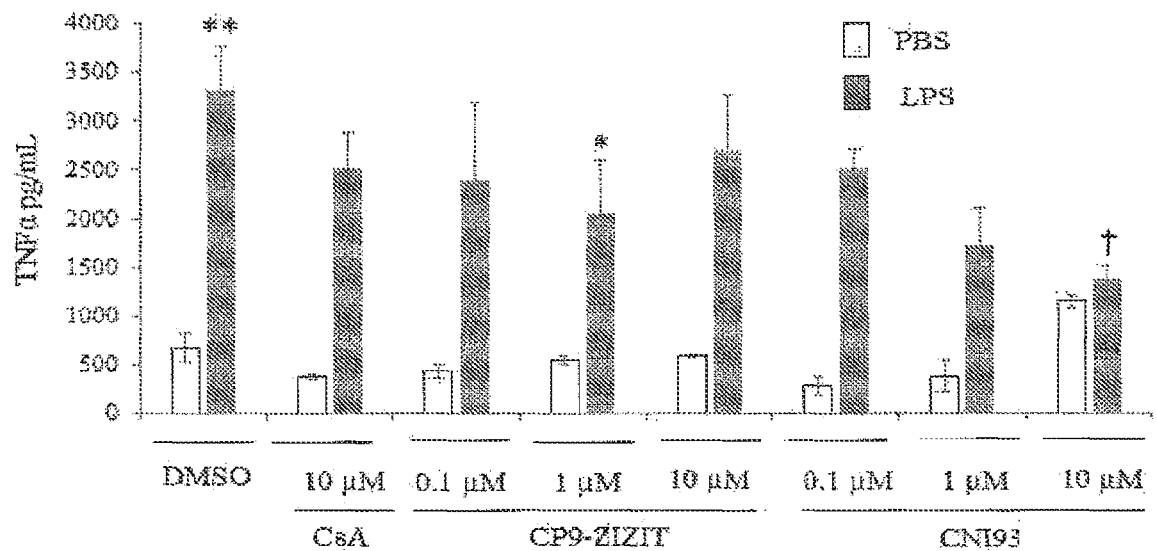
FIG. 8 illustrates inhibition of LPS-induced TNFα secretion by CNI93 (SEQ ID NO: 220). PBS, phosphate buffered saline; LPS, lipopolysaccharide.

We next examined the effect of CNI93 (SEQ ID NO. 220) on NFATc3 target gene expression in macrophages. Lung macrophages from healthy mice were untreated or treated with different concentrations of CsA, CPP9-ZIZIT, or CNI93 and then stimulated with lipopolysaccharide (LPS; 100 ng/mL for 16 h), and the amount of tumor necrosis factor-α (TNFα) released was quantitated by ELISA. Stimulation of untreated cells with 100 ng/mL LPS resulted in a 6-fold increase in TNFα production (FIG. 8). Prior treatment of macrophages with CNI93 dose-dependently decreased the LPS -induced TNFα production by 24-59%. As a positive control, treatment with 10 µM CsA reduced the TNFα production by 24%. These data indicate that CNI93 is ~10-fold more potent immunosuppressant than CsA in this ex vivo assay. In a separate experiment, CNI93 was also tested against Jurkat cells expressing a luciferase gene under the transcriptional control of NFAT. Again, 10 µM CNI93 potently inhibited phorbol ester- and ionomycin-induced expression of luciferase. The lower potency of CNI93 against Jurkat cells is likely due to the lower endocytosis rates of T cells compared to primary lung macrophages.

Immunofluorescence. Mouse BMDM were pretreated with 1 µM of control CPP9(SEQ ID NO. 76)-VAVAA-Biotin or CNI93-Biotin peptides for 5 min and stimulated with PBS or LPS (100 ng/mL) for 1 h. Treated cells were washed, fixed in 4% paraformaldehyde and incubated sequentially with anti-rabbit NFATc3, Anti-rabbit Alexa Fluor™ 488 Conjugate and Alexa Fluor™ 594 Streptavidin. Cells were washed three times in 1×PBS after incubation with each antibody. Localization of NFATc3 (Alexa Fluor™ 488-green) and peptides (CPP9-VAVAA or CNI93 in Alexa Fluor® 594-red) with PBS/LPS stimulation is determined using Zeiss LSM 510 Meta microscope (Carl Zeiss Micro-Imaging, Inc.) equipped with 488 nm and 543 nm excitation lasers.

CNI93 inhibitory activity on macrophage TNFα secretion. Mouse total lung macrophages were pretreated with 100 nM, 1 µM, 10 µM of CPP9(SEQ ID NO. 76)-VAVAA or CNI93 (SEQ ID NO. 220) for 5 min and stimulated with LPS (100 ng/mL) or PBS for 16 h. Cell supernatants were collected and analyzed for TNFα levels by R&D systems TNFα ELISA kit.

Example 7. In Vivo Uptake and Distribution of CNI93

Figure 9:
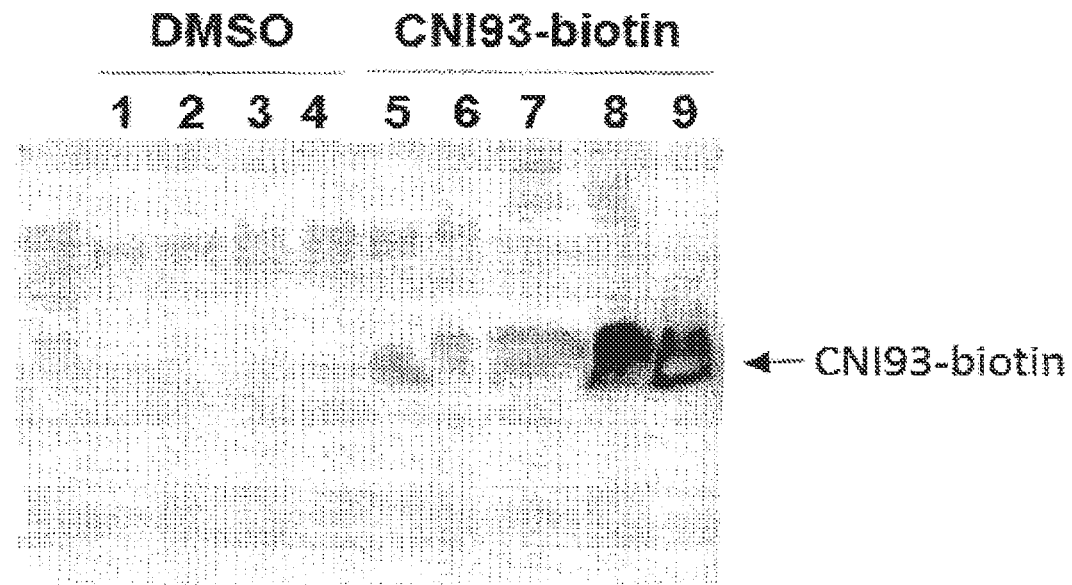
FIG. 9 illustrates subcellular distribution of CNI93(SEQ ID NO: 220)-biotin in mouse macrophages treated with 25 µM CNI93-biotin for 5 min

As CN and NFAT are both intracellular proteins, effective cellular uptake is critical for targeting the calcineurin-NFATc3 interaction. Primary mouse macrophages were treated in vitro with 25 µM biotinylated CNI93 for 5 min and the intracellular distribution of CNI93 was determined by subcellular proteome fractionation (ProteoExtract subcellular proteome extraction kit) and immunoblotting for biotin. Within 5 min of treatment, significant CNI93 concentrations were found in the cytoplasm, organelles, cytoskeleton and nuclear compartments of mouse macrophages (FIG. 9).

Figure 10:
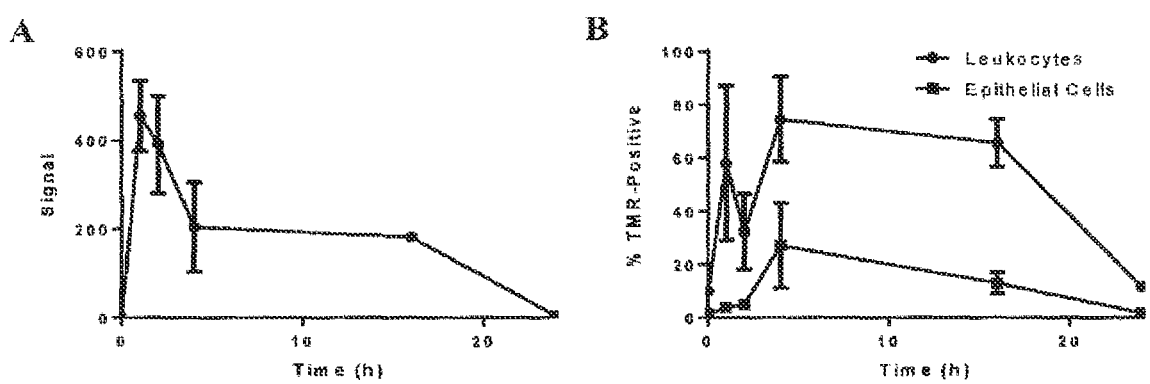
FIG. 10A illustrates time-dependent distribution of CNI93 (SEQ ID NO: 220)-TMR in mouse lung tissues following intranasal administration of CNI93 (5 mg/kg; n=4) as measured by TMR fluorescence in BALF.
FIG. 10B illustrates time-dependent distribution of CNI93-TMR in mouse lung tissues following intranasal administration of CNI93 (5 mg/kg; n=4) as measured by TMR fluorescence in leukocytes (all $CD45^+$ cells) and $CD31^+/CD45^-$ epithelial cells.

Next, TMR-labelled CNI93 was delivered intranasally to mice (5 mg/kg) and the CNI93-TMR level in the lungs was monitored from 1 to 24 h. The CNI93-TMR concentration in the bronchoalveolar lavage fluid (BALF) peaked at ~2 h, followed by slow declination and eventual clearance at between 16 and 24 h (FIG. 10A). Flow cytometry analysis of the single-cell suspension isolated by collagenase/DNase digestion from the lungs showed time-dependent distribution of CNI93-TMR in both leukocyte and non-leukocyte populations, which peaked at 4 h and declined by 24 h (FIG. 10B). Interestingly, the CNI93-TMR concentration in leukocytes is consistently 3- to 5-fold higher than non-leukocytes, likely due to the higher endocytosis rates of leukocytes (e.g., macrophages) compared to structural lung cells. It is worth noting that the blood plasma levels of CNI93-TMR were negligible throughout the 24-h time course. The cellular contents of BALF from the control mice that were treated with CNI93-TMR were analyzed by staining with Hema 3 and showed no increase in the neutrophilic population, indicating that CNI93 by itself does not cause neutrophilic infiltration.

Cells. Bone marrow cells from wild type C57BL/6 mice were isolated and allowed to differentiate into mature bone marrow derived macrophages (BMDMs) as described earlier. BMDM were gown in Dulbecco Modified Eagle Medium (DMEM) supplemented with 10% FBS, 1% penicillin/streptomycin. Mouse total lung macrophages were isolated by collagenase digestion, purified by adherence for 1 hour, plated in RPMI supplemented with 10% FBS, 1% penicillin/streptomycin.

Peptide delivery in to mouse lungs. Mice were anesthetized with Ketamine/Xylazine mixture and checked for anesthesia levels by toe pinch. Control CPP9(SEQ ID NO. 76)-VAVAA or calcineurin inhibitor CNI93 peptides reconstituted in 25 µL 10% DMSO were delivered intranasally to anesthetized mice.

In vivo uptake of CNI93 peptide. 10% DMSO or CNI93 (SEQ ID NO. 220)-TMR at 5 mg/kg body weight was delivered by intranasal insufflation and mouse lungs were harvested at 1, 2, 4, 16 and 24 hours. Single cell suspension was prepared by collagenase/DNase digestion and stained by CD45. Total lung cells from different treatment periods were analyzed by flow cytometry for CD45 positive, negative and TMR positive population. BALF fluid from another parallel set of treated mice groups is used for measuring cellular influx (cytospin slides) and measuring BALF TMR levels.

Western Blot Analysis. BMDMs or total lung macrophages from wild type mice were harvested, treated with peptides and/or LPS, and cell extracts were prepared in 1×RIPA buffer supplemented with protease inhibitors. An equal amount of protein was analyzed by Western blotting for the protein of interest using its specific antibodies according to standard protocols.

Example 8. CNI93 Attenuates Acute Lung Injury in Mice

Figure 11:
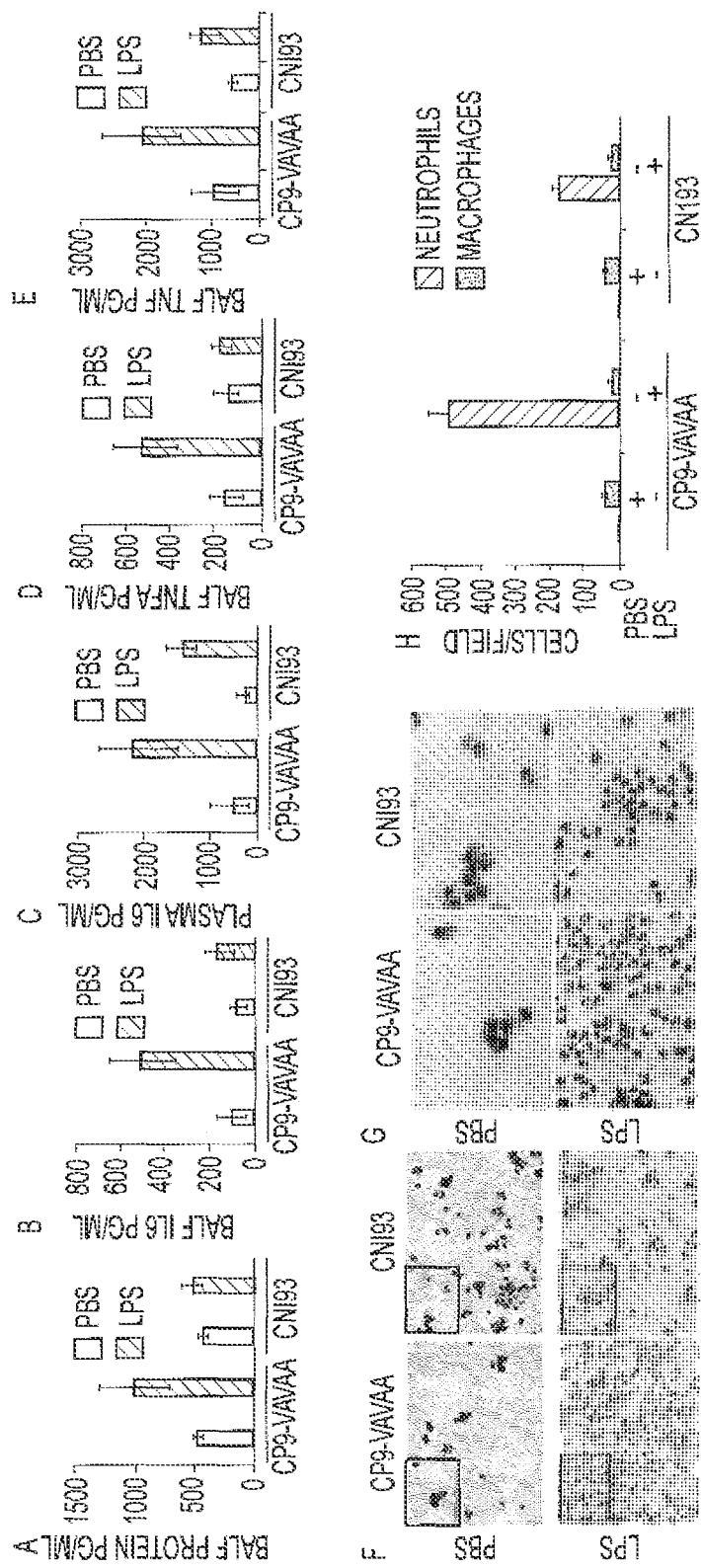
FIG. 11A illustrates BALF protein levels after the CNI93 (SEQ ID NO: 220) or CPP9-VAVAA (i.n. 10 mg/kg) were delivered to mice and after 1 h injected with LPS (i.p 10 mg/kg).
FIG. 11B illustrates BALF IL-6 levels after the CNI93 (SEQ ID NO: 220) or CPP9-VAVAA (i.n. 10 mg/kg) were delivered to mice and after 1 h injected with LPS (i.p 10 mg/kg).
FIG. 11C illustrates plasma levels of IL-6 after the CNI93 or CPP9-VAVAA (i.n. 10 mg/kg) were delivered to mice and after 1 h injected with LPS (i.p 10 mg/kg).
FIG. 11D illustrates BALF TNFα levels after the CNI93 or CPP9-VAVAA (i.n. 10 mg/kg) were delivered to mice and after 1 h injected with LPS (i.p 10 mg/kg).
FIG. 11E illustrates plasma levels of TNFα after the CNI93 or CPP9-VAVAA (i.n. 10 mg/kg) were delivered to mice and after 1 h injected with LPS (i.p 10 mg/kg).
FIG. 11F-H illustrate a reduction in the number of neutrophils in BALF in the treatment group of mice compared to the control group. CPP9 is cyclic(fΦRrRrQ) (SEQ ID NO: 76).

We next tested whether CNI93 (SEQ ID NO. 220) is capable of protection against LPS-induced acute lung injury (ALI) in mice. Healthy mice were treated intra-nasally with CPP9-VAVAA or CNI93 at 10 mg/kg body weight and an hour later were subjected to a single intraperitoneal injection of LPS (10 mg/kg body weight). As expected, LPS challenge of CPP9-VAVAA treated mice increased the total protein in BALF by ~2-fold and TNFα and IL-6 levels in BALF (FIGS. 11A, B, and D, respectively). In contrast, pretreatment with CNI93 almost completely protected the animals from LPS-induced production of cytokines and protein leakage into BALF and prevented neutrophilic infiltration into the lungs (FIG. 11F-H). Interestingly, CNI93 also decreased the plasma levels of TNFα and IL6 by ~4-fold in LPS sepsis mice (FIGS. 11C and E, respectively). The decreased cytokine storm, BALF protein and cytokine levels and neutrophilic infiltration clearly indicate the protective effect of CNI93 on LPS induced ALI in mouse models.

Mouse models of LPS sepsis. Mouse LPS sepsis-induced acute lung injury models were established by intraperitoneal injection of LPS at 10 mg/kg body weight. Acute lung injury was assessed by measuring secretion of TNFα, IL6 in to broncho alveolar lavage fluid (BALF), plasma levels of IL6 and TNFα, and neutrophilic infiltration. Pulmonary edema was measured by increased protein levels in BALF. Neutrophilic infiltration in to bronchoalveolar lavage fluid is determined by Hema 3.0 staining and number of neutrophils in BALF is quantitated.

Neutrophilic inflammation. BALF fluid from different treatment groups of mice was used to prepare Cytospin slides, stained using Hema 3 and number of neutrophils and macrophages per field view of microscopic view were counted and differences among groups calculated.

Example 9. Maximum Tolerated Dose

Figures 12A, 12B, 12C:
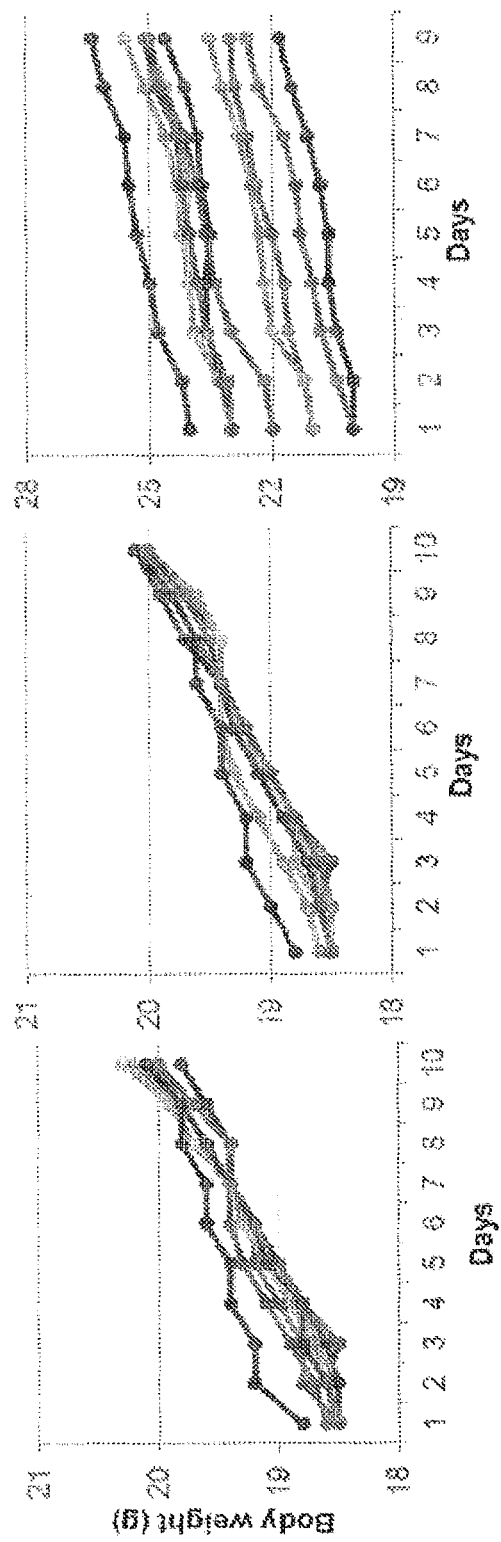
FIG. 12A graphically represents the determination of maximum tolerated dose of CNI93 (SEQ ID NO: 220) in mice, based on changes in body weight over a period of 10 days, for 10 mg/kg CPP9-VAVAA.
FIG. 12B graphically represents the determination of maximum tolerated dose of CNI93 in mice for 10 mg/kg CNI93.
FIG. 12C graphically represents the determination of maximum tolerated dose of CNI93 in mice for 50 mg/kg CNI93. CPP9 is cyclic (fΦRrRrQ) (SEQ ID NO: 76).

Three groups of mice were treated intranasally with 10 mg/kg body weight of CPP9-VAVAA, 10 mg/kg of CNI93 (SEQ ID NO. 220), or 50 mg/kg CNI93 and their body weights were monitored for 10 days. All of the treated animals survived and showed no visible sign of distress. All three groups showed steady increase in body weight similar to healthy controls (FIG. 12A-C). In the 50 mg/kg CNI93 group, the mice used for the study were of different ages, indicating that even at the highest dose, weight gain was not affected by age.

Respiratory Toxicity. Respiratory toxicity of CNI93 will be evaluated in mice by measuring breaths/min using STARR life sciences Pulse Oximeter.

Neurotoxicity. Following peptide delivery in to mice, after 4 hours, neurotoxicity due to CNI93 will be determined by measuring open field activity, general sensorimotor, cognitive and pain functions at the Institute for Behavioral Medicine Research, OSU.

In Vivo Uptake and Distribution in Lung Cells. CNI93-TMR peptide (5 mg/kg) or 10% DMSO in saline was delivered intranasally into anesthetized mice. After 1, 2, 4, 16 and 24 h, mice were euthanized and total lung cells were isolated by collagenase/DNase digestion to obtain single cell suspension as described in methods. Total lung cells were stained with PerCP/Cy5.5 anti-mouse CD45 Antibody and analyzed by flow cytometry.

Example 10. Development of CN Inhibitor CNI95

Figure 13:
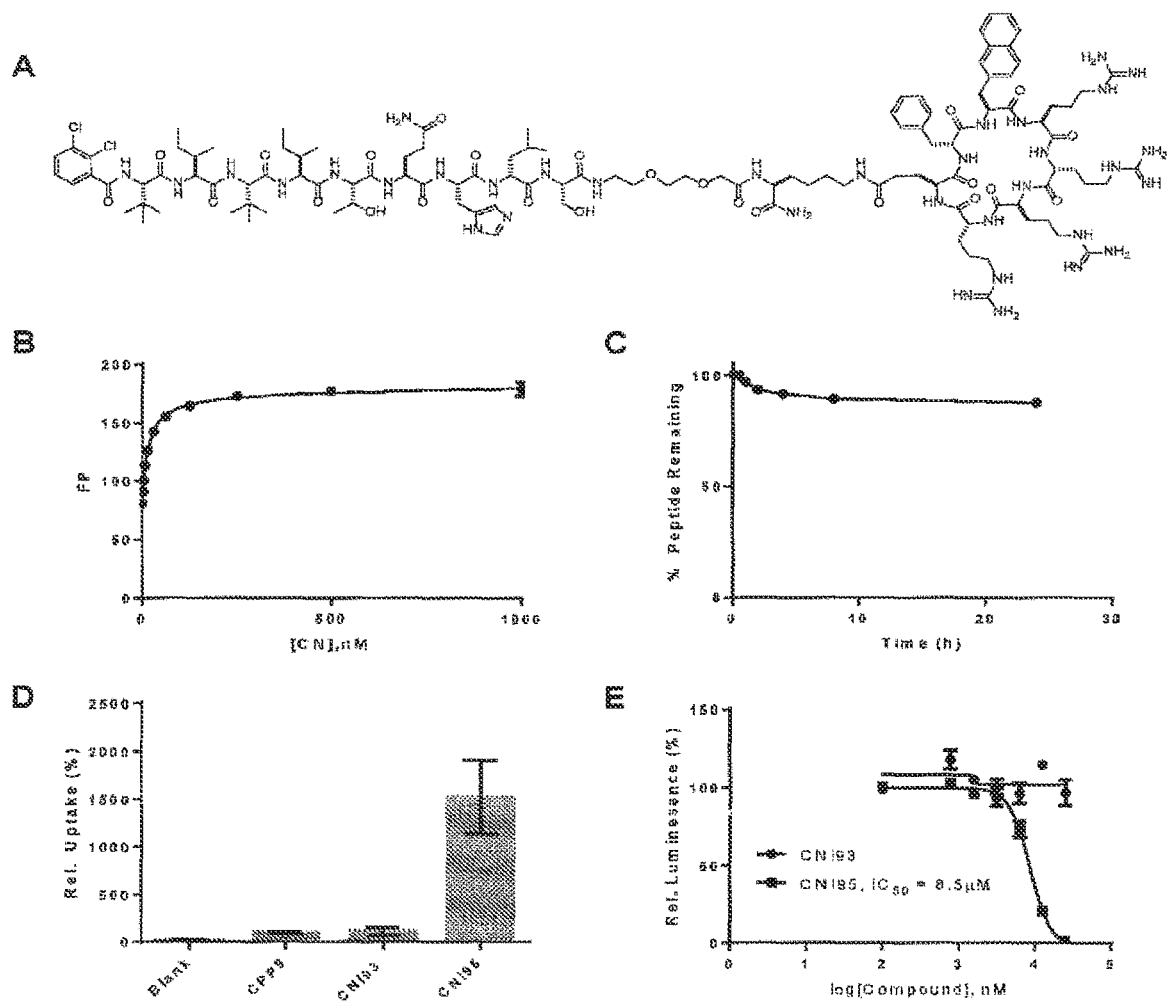
FIG. 13A illustrates the structure of CNI95 (SEQ ID NO: 221).
FIG. 13B graphically illustrates binding of FITC-labeled CNI95 to CN as monitored by FA ($K_D$=17 nM).
FIG. 13C graphically illustrates the stability of CNI95 in human serum at 37° C.
FIG. 13D depicts a graphical comparison of the cytosolic entry efficiency of NF-labeled CPP9, CNI93, and CNI95 (each at 5 µM) into HeLa cells after 2 h treatment as monitored by flow cytometry. Blank, no peptide added.
FIG. 13E graphically illustrates dose-dependent inhibition of NFAT-mediated luciferase expression in Jurkat cells by CNI93 (SEQ ID NO: 220) and CNI95 (SEQ ID NO: 221).
Figure 14A:
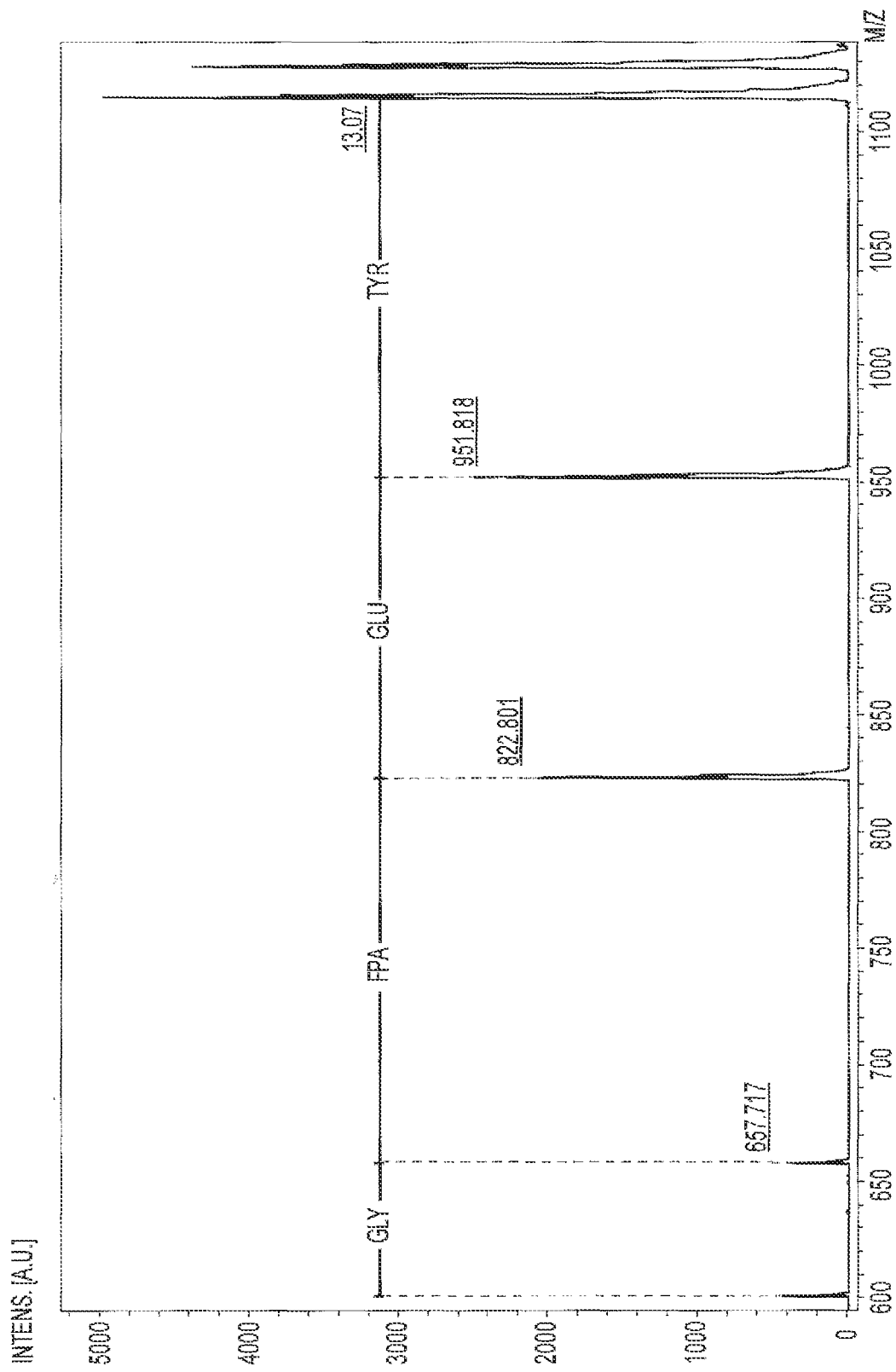
FIG. 14A depicts a MALDI-TOF mass spectra of peptide sequence: Dcb-Tle-Ile-Tle-Ile-Thr-Tyr-glu-Fpa-Gly-Linker (SEQ ID NO:10, underlined portion) synthesized in the library.
Figure 14B:
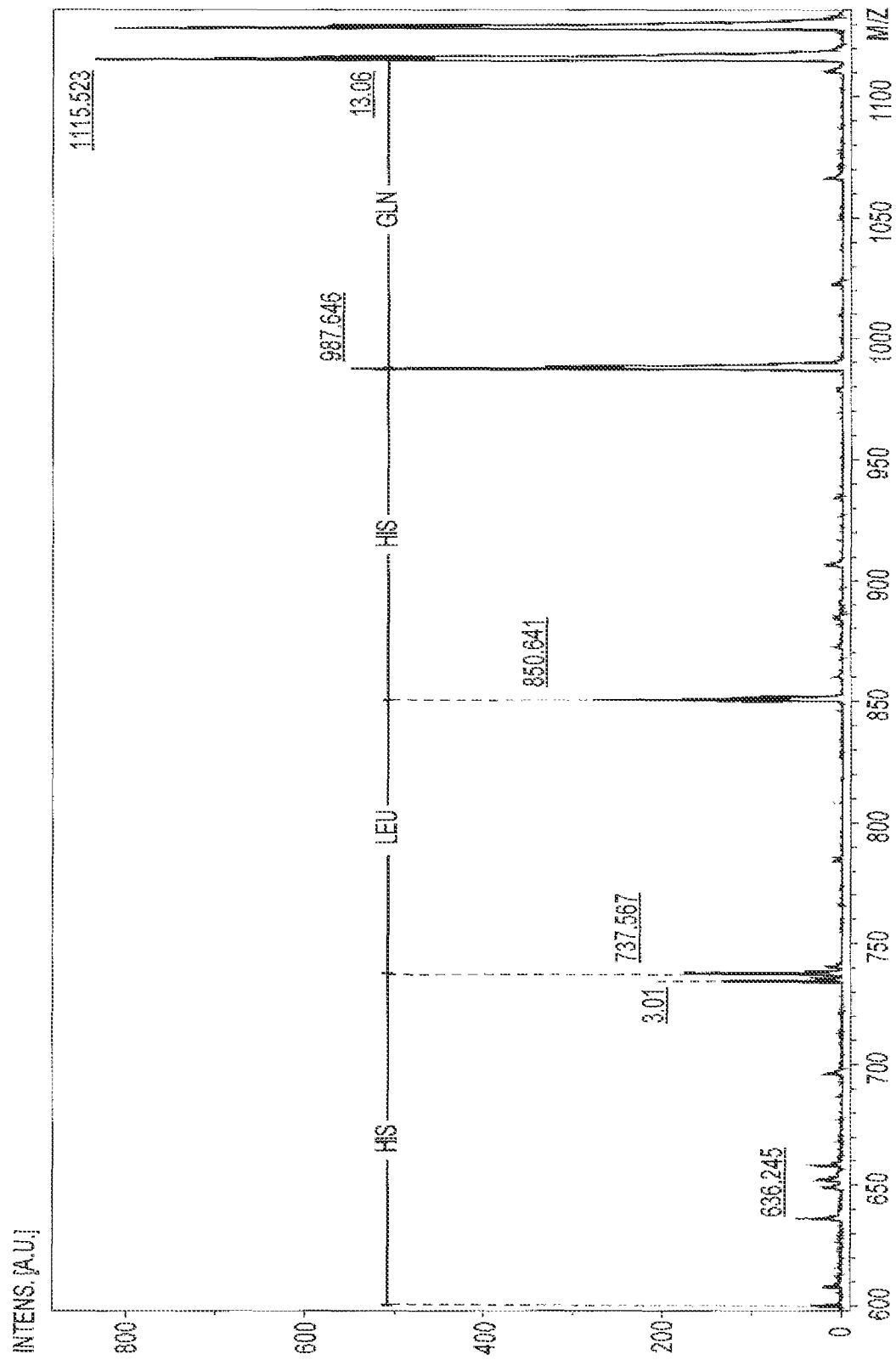
FIG. 14B depicts a MALDI-TOF mass spectra of peptide sequence: Dcb-Tle-Ile-Tle-Ile-Thr-Gln-His-leu-His-Linker (SEQ ID NO:11, underlined portion) synthesized in the library.
Figure 14C:
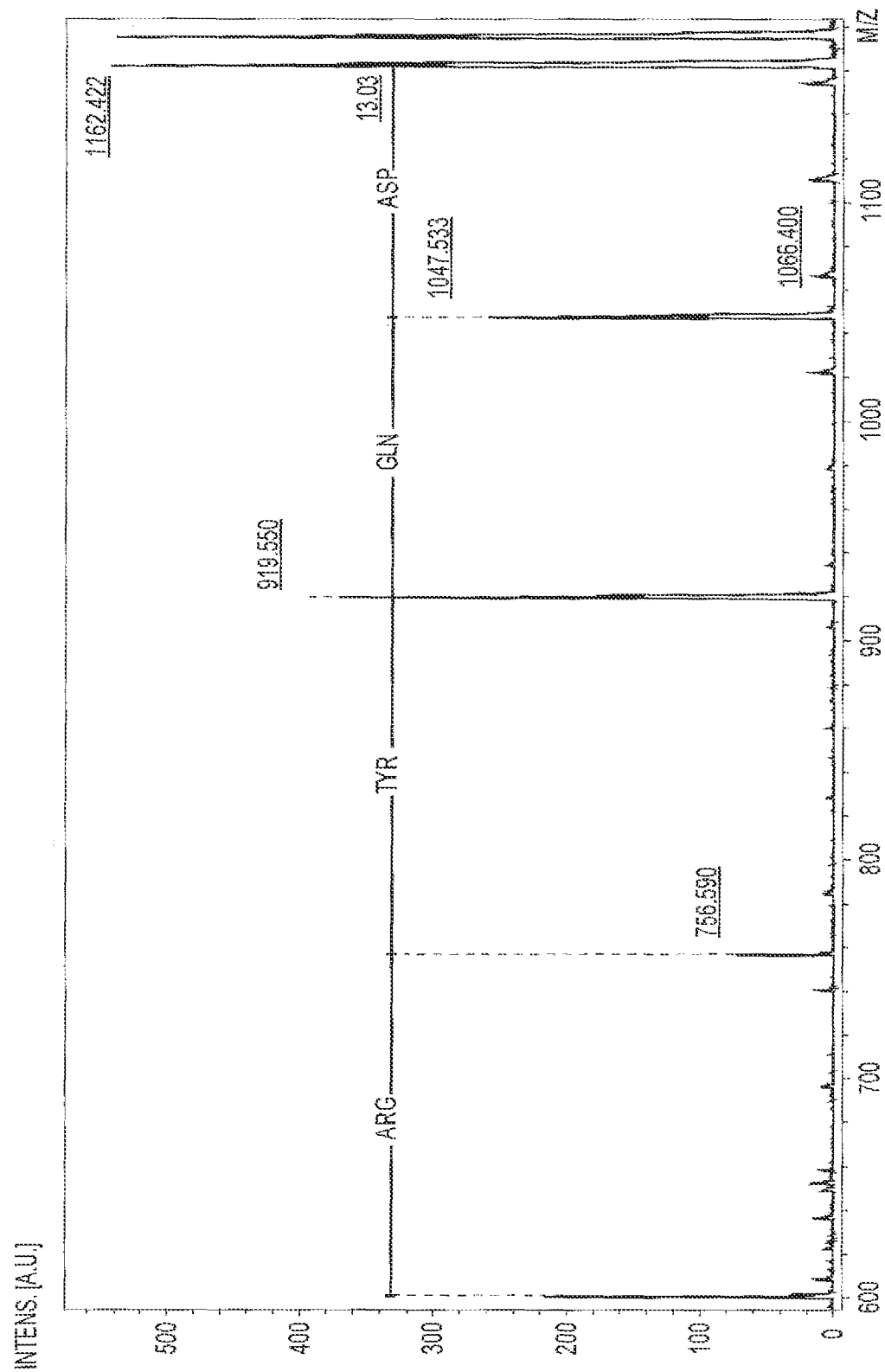
FIG. 14C depicts a MALDI-TOF mass spectra of peptide sequence: Dcb-Tle-Ile-Tle-Ile-Thr-Asp-Gln-Tyr-Arg-Linker (SEQ ID NO:12, underlined portion) synthesized in the library.
Figure 14D:
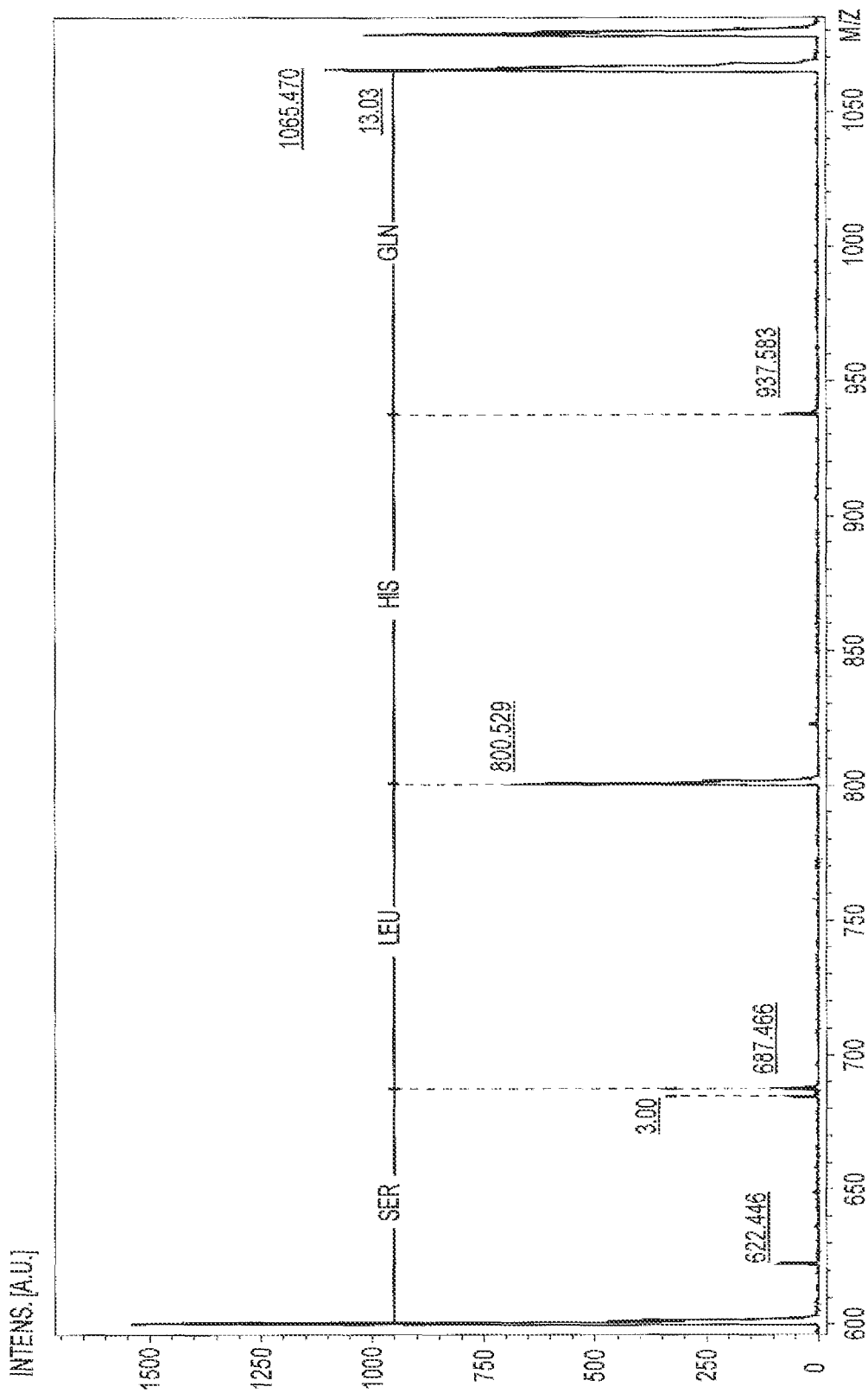
FIG. 14D depicts a MALDI-TOF mass spectra of peptide sequence: Dcb-Tle-Ile-Tle-Ile-Thr-Gln-His-leu-Ser-Linker (SEQ ID NO:13, underlined portion) synthesized in the library.
Figure 14E:
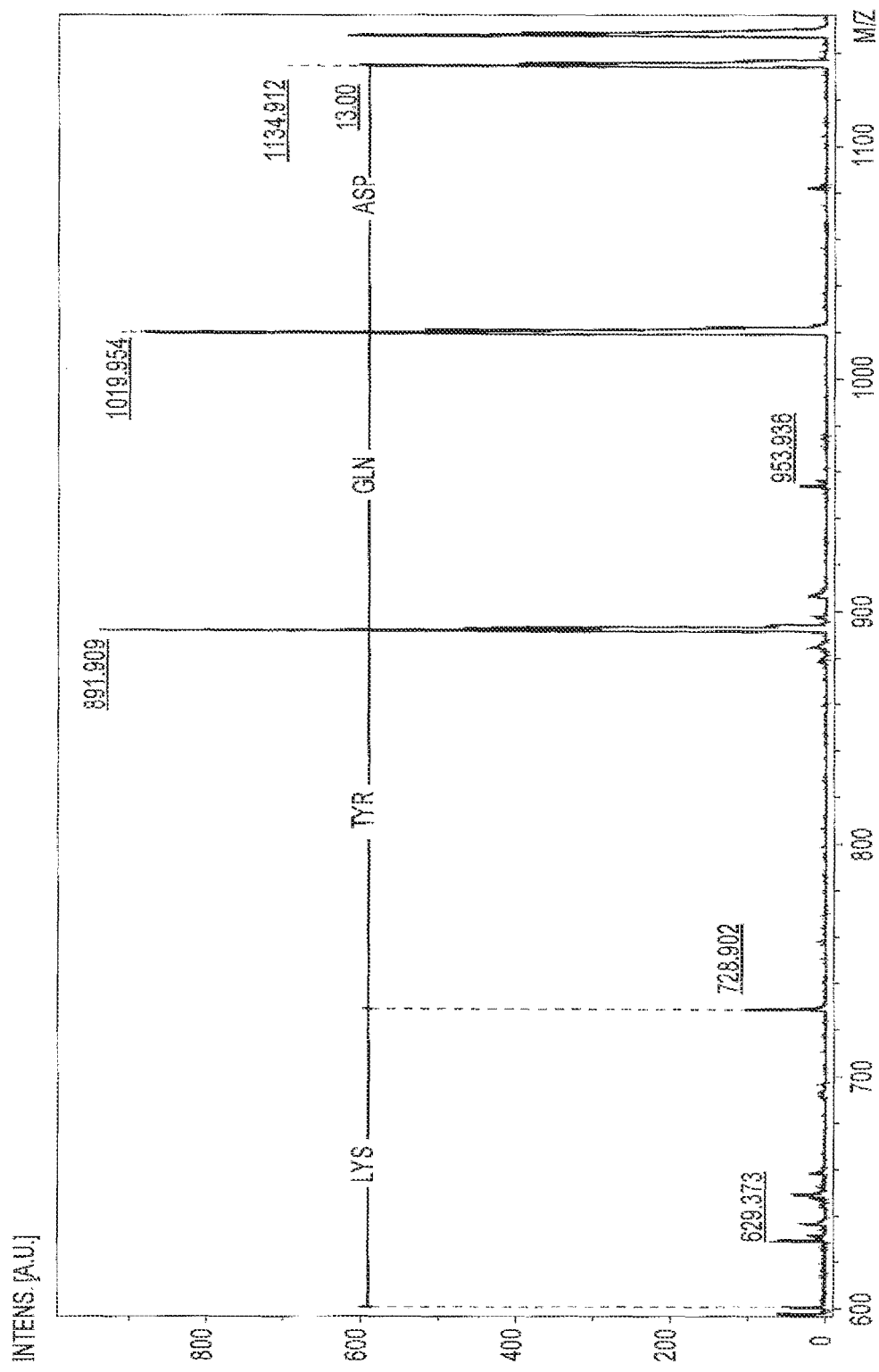
FIG. 14E depicts a MALDI-TOF mass spectra of peptide sequence: Dcb-Tle-Ile-Tle-Ile-Thr-Asp-Gln-Tyr-lys-Linker (SEQ ID NO:14, underlined portion) synthesized in the library.
Figure 15:
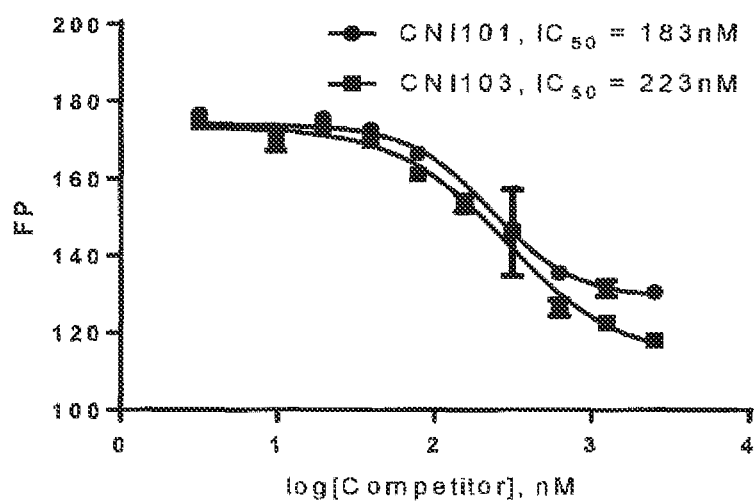
FIG. 15 graphically illustrates binding curves for CNI101 (SEQ ID NO: 206) and CNI103 (SEQ ID NO: 208).
Figure 16:
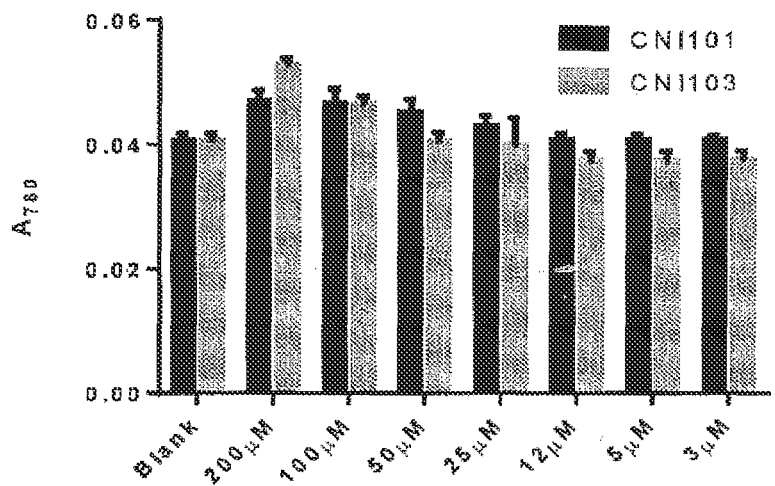
FIG. 16 graphically illustrates the solubility of serial dilutions of CNI101 (SEQ ID NO: 206) and CNI103 (SEQ ID NO: 208), respectively, in phosphate buffered saline (PBS) at pH 7.4.
Figure 17:
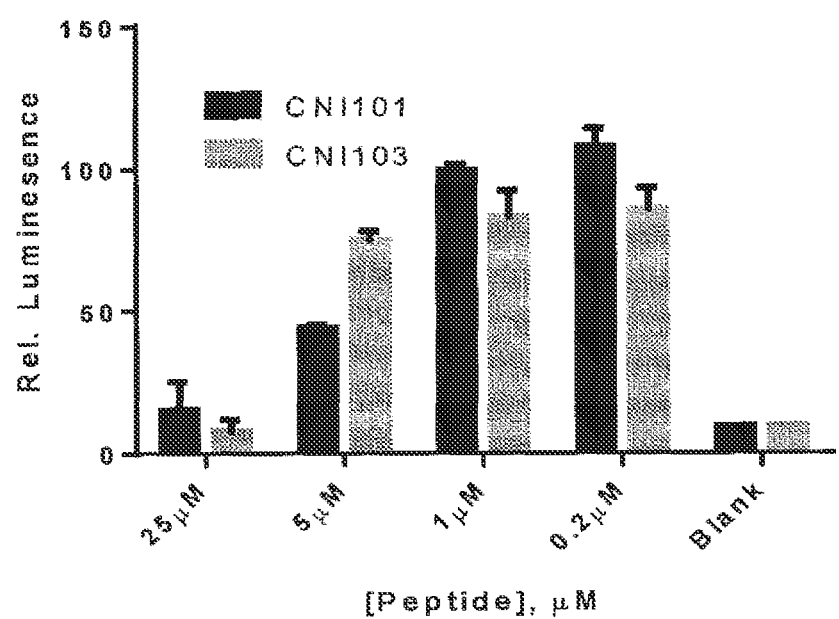
FIG. 17 graphically illustrates NFAT activity of HeLa-NFAT-Luciferase cells in the presence of increasing concentrations CNI101 (SEQ ID NO: 206) and CNI103 (SEQ ID NO: 208), respectively, as measured with a luciferase assay.

The 8-fold lower CN-binding affinity of CNI93 (relative to peptide 14) is likely caused by interference with CN binding by the CPP moiety. To minimize the interference, we conjugated CPP9 to peptide 14 through a longer and more flexible linker, miniPEG-Lys (FIG. 13A). The resulting conjugate (CNI95) (SEQ ID NO: 221), when labeled at the C-terminus with FITC, bound to CN with a $K_D$ value of 17 nM (FIG. 13B). CNI95 (unlabeled) also showed ~5-fold higher potency than CNI93 in an FA-based competition assay, for inhibition of the binding of peptide 14 to CN. Like CNI93, CNI95 has excellent proteolytic stability, incubation of CNI95 in human serum at 37° C. for 24 h resulted in only ~12% degradation (FIG. 13C). Surprisingly, CNI95 also has greatly improved cell-permeability relative to CNI93. As a result, CNI95 is vastly superior to CNI93 for attenuating the NFAT activity in Jurkat cells, which express a luciferase under the transcriptional control of NFAT (FIG. 13E). CNI95 decreased the viability of HeLa and Jurkat cells at concentrations ≥25 μM (Figure S7). Additional characterization of CNI95 (including in vivo evaluation) is currently ongoing.

NFAT Luciferase Assay. Jurkat-Lucia cells maintained in RPMI-1640 supplemented with 10% FBS, 1% penicillin/streptomycin (v/v/v) and 100 μg/mL normocin were harvested after a passage with 50 μg/mL selective antibiotic Zeocin at 300×RCF for 5 mM. Cells were resuspended in warm RPMI-1640 with antibiotics but without FBS to a final density of $2 \times 10^6$ cells/mL and seeded into white-on-white cell-culture treated 96-well plates. To each well was added 10 μL of DPBS containing compounds which dilute to the desired concentrations followed by 170 μL of cell suspension ($4 \times 10^5$ cells/well) and incubated at 37° C. for 2 h. The cells were induced by treatment with 50 ng/mL PMA and 3 μg/mL ionomycin, $Ca^{2+}$ salt in FBS to achieve a final FBS concentration of 10% in each well (with FBS only as control). The plate was incubated for an additional 4 h at 37° C., when 20 μL of each sample was withdrawn and mixed with 50 μL of Quanti-Luc assay solution. The luminescence of the mixture was immediately measured on a Tecan Infinite M1000 plate reader.

Example 11. Peptide Conjugates Comprising Pyridinyl Groups

Binding Affinity. Condition E (denoted with superscript e): 50 nM probe was incubated with 50 nM CN-GST in pH 7.4 PBS supplemented with 5 mM DTT and 0.01% Triton-X100 for 1 hr at RT. Serial dilutions of each unlabeled compound were prepared in pH 7.4 PBS containing 0.01% Triton-X100, to which was added the incubation solution and mixed for 1 hr at RT after which 20 μL sample was pipetted into 384-well black-on-black microplates and fluorescence polarization was measured using a TECAN Infinite M1000 plate reader. $IC_{50}$ values were calculated using GraphPad PRISM v. 6.0, and are reported below in Table 8.

Solubility. Peptides were diluted from a DMSO stock into PBS, pH 7.4 and then serially diluted in identical buffer to standardize DMSO concentration in clear, 96-well plates. The solutions were allowed to stand for 1 h at RT without mixing and then turbidity was measured at 780 nm using a Tecan Infinite M1000 plate reader.

Luciferase. Stably transfected HeLa-NFAT-Luciferase cells (Signosis, Inc. Santa Clara, Calif.) maintained in DMEM supplemented with 10% FBS and 1% penicillin/streptomycin (v/v/v) were harvested through the addition of 0.025% Trypsin/EDTA, followed by centrifugation at 300× RCF for 5 min Cells were resuspended in warm DMEM supplemented with 10% FBS and 1% penicillin/streptomycin (v/v/v) and seeded into white-on-white cell-culture treated 96-well plates to a final density of $1 \times 10^4$ cells/well and incubated overnight at 37° C., 5% $CO_2$. The next day, the seeding media was aspirated and the wells rinsed with DPBS. Compounds were serially diluted from DMSO stocks into DMEM containing 0.1% FBS and 1% penicillin/streptomycin (v/v/v) and added to each well. The cells were then incubated at 37° C. for 2 hr. After 2 hr, NFAT activity was induced through the addition of 10 ng/mL PMA and 1 µM ionomycin to each well and then incubated for 6 hr at 37° C. Following induction, the media was aspirated and the cells gently washed with DPBS, then 20 µL of passive lysis buffer was added to each well and incubated at RT for 20 min After lysis, 100 µL of luciferase substrate was added to each well, gently mixed and then luminescence immediately measured using a Tecan Infinite M1000 Pro plate reader using a 1 second integration.

TABLE 8

Binding Affinity

| Peptide | Structure | IC50 (nM) |
|---|---|---|
| control | (DCB)-Tle-Ile-Tle-Ile-Thr-Gln-His-(D-Leu)-Ser-(β-Ala)-Lys{[cyclo-(Gln-(D-Arg)-Arg-(D-Arg)-Arg-(2-Nal)-(D-Phe)]}-NH$_2$ | 857 ± 35 (IC$_{50}$)$^e$ |
| CNI101 | (DCN)-Tle-Ile-Tle-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 184 ± 10 (IC$_{50}$)$^e$ |
| CN103 | (DCN)-Tle-Ile-Hva-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 223 ± 10 (IC$_{50}$)$^e$ |

DCN, 2,3-dichloro-4-pyridinyl

Example 12. Further Peptide Conjugates

In an attempt to further improve the potency of CNI103 (IC50=223 nM), we replaced the first tert-Leu residue of the ZIZIT motif with L-cyclohexylglycine, with the guide of in silico modeling. The resulting compound 44 (CNI104) indeed exhibited ~5-fold higher potency than CNI103 (Table 9). However, the more hydrophobic cyclohexyl group rendered CNI104 less soluble. Replacing the miniPEG-Lys linker with β-Ala-Lys linker did not improve the solubility. We next replaced the hydroxyvaline residues of CNI103 with L-penicillaminesulfonic acid (PsA), which contains a permanent negative charge at the physiological pH. We also replaced the N-terminal dichloronicotinyl group with difluoronicotinyl group. Overall, substitution of cyclohexylglycine improves the potency, but reduces aqueous solubility. We therefore chose CNI103 for further evaluation. The compounds are provided in Table 9.

Binding Affinity Assay Conditions: FITC-labeled compound 35 (15 nM) was used as a probe and incubated with 15 nM recombinant GST-CN in PBS (pH 7.4) containing 5 mM DTT and 0.01% Triton-X100 for 1 h at RT. Serial dilutions of unlabeled inhibitor were prepared in pH 7.4 PBS containing 0.01% Triton-X100, to which was added the incubation solution and mixed for 1 h at RT. 20 µL aliquots from each concentration were added into 384-well black-on-black microplates and fluorescence polarization was measured using a TECAN Infinite M1000 plate reader. IC50 values were calculated using GraphPad PRISM v. 7.

Figure 18:
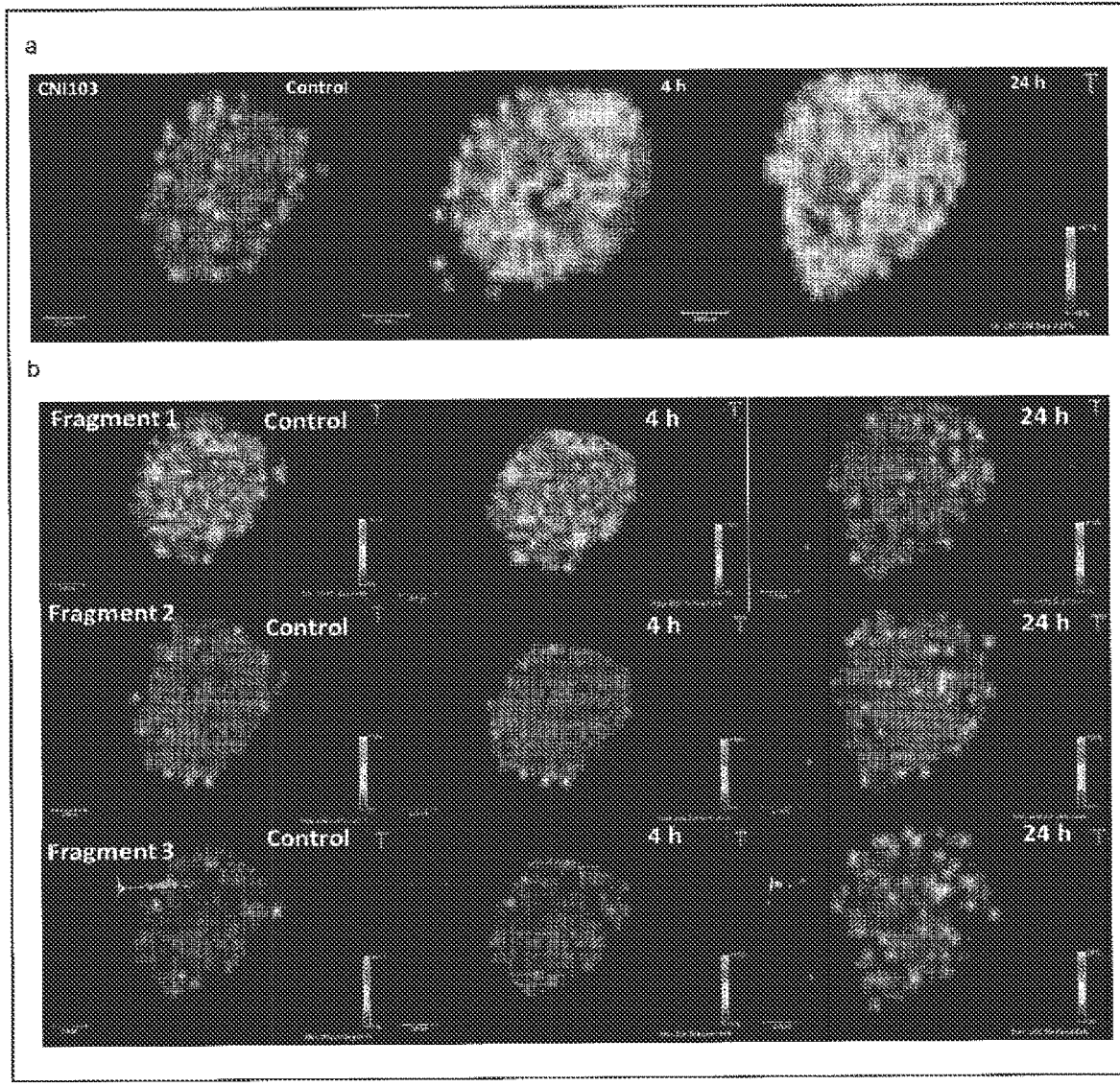
FIG. 18 depicts cellular entry and intracellular stability of CNI103 (SEQ ID NO: 208) as determined by MALDI-TOF MS imaging. (a) Heatmaps showing the comparison of CNI103 intensity in control (untreated) or HCT116 colorectal cancer cells treated with 5 µM CNI103 for 4 or 24 h. (b) Heatmaps showing the ion intensities of three predicted proteolytic degradation products (compounds 52, 53, 54 in FIG. 11) at 0 (control), 4, or 24 h of incubation.

Intracellular Stability. HCT116 cell spheroids in RPMI-1640 medium supplemented with 10% FBS and 1% penicillin/streptomycin were treated with 5 µM CNI103 for 4 or 24 h. Spheroids were washed three times with warm DPBS, quickly frozen, embedded in a solid support and cryo-sectioned. Prior to analysis, sinapinic acid was sublimed onto individual slides, which were subsequently imaged using a Bruker ultrafleXtreme MALDI-TOF-TOF mass spectrometer. The spectra were analyzed for intact CNI103 as well as proteolytic degradation fragments of interest. The MS signal intensity data were used to generate Heatmaps, scaled relative to the most intense signal, for each time point and fragment. The results indicate that CNI103 entered spheroids in a time-dependent manner and accumulated in the cells (FIG. 18a). No significant degradation product signal was observed after 24 h of incubation, suggesting that CNI103 does not undergo significant intracellular degradation (FIG. 18b).

TABLE 9

Sequences and Calcineurin Binding Affinities of Compounds in this Work

| Cmpnd | Sequence | Affinity (nM) |
|---|---|---|
| 41 | (DCNA)-Tle-Ile-Tle-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 184 (IC$_{50}$) |
| 42 | (DCB)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | N.D. |
| 43 | (DCNA)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 223 (IC$_{50}$) |
| 44 | (DCNA)-Tle-Chg-Bhv-Ile-Thr-Gln-His-(D-Leu)-Ser-βAla-Lys{[cyclo-(Gln-(D-Arg)-Arg-(D-Arg)-Arg-(2-Nal)-(D-Phe)]}-NH$_2$ | 44.9 (IC$_{50}$) |
| 45 | (DCNA)-Tle-Chg-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 45.6 (IC$_{50}$) |
| 46 | (DCNA)-Tle-Ile-Psa-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 107 (IC$_{50}$) |
| 47 | (DCNA)-Tle-Chg-Psa-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH2 | N.D. |
| 48 | (DFNA)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 73.5 (IC$_{50}$) |

TABLE 9 -continued

Sequences and Calcineurin Binding Affinities
of Compounds in this Work

| Cmpnd | Sequence | Affinity (nM) |
|---|---|---|
| 49 | (DFNA)-Tle-Cpg-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | N.D. |
| 50 | (DFNA)-Tle-Chg-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | N.D. |
| 51 | (DFNA)-Tle-Chg-Psa-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ | 96.5 (IC$_{50}$) |

Where Bhv=L-β-hydroxyvaline, Chg=L-cyclohexylglycine, Cpg=L-cyclopentylglycine, Psa=L-penicillamine sulfonic acid, DCB=2,3-dichlorobenzamide, DCNA=2,3-dichlorisonicotinamide, DFNA=2,3-difluoroisonicotinamide, miniPEG=2-(2-(2-aminoethoxy)ethoxy)acetamide, βAla=beta-alanine.

The structure of the compounds in Table 9 is shown in FIG. 29.

Example 13. Cytotoxicity by MTT Assay

Figure 19:
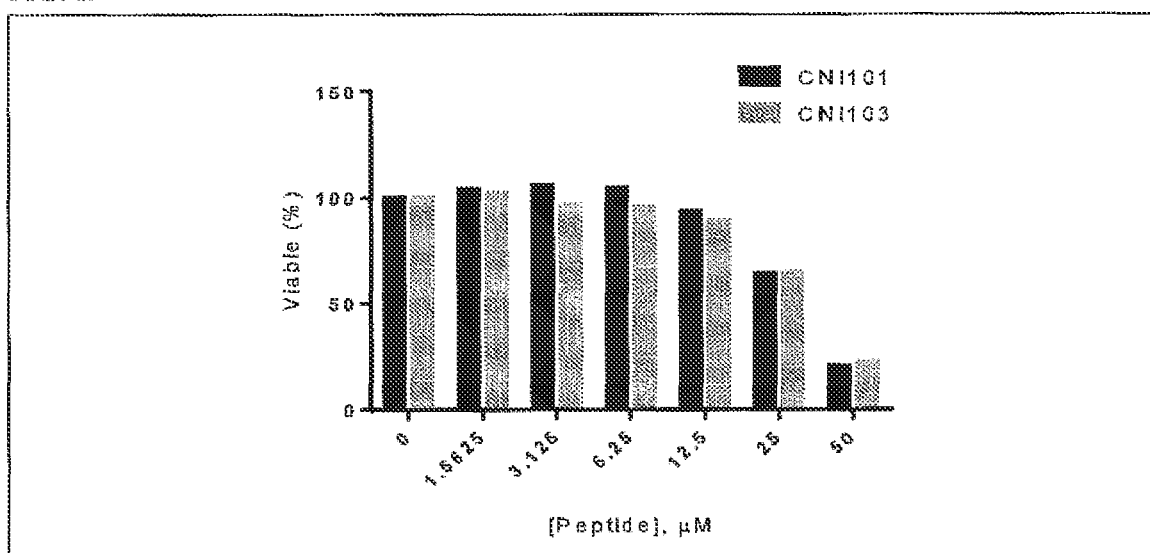
FIG. 19 shows that effect of CNI103 (SEQ ID NO: 208) on the viability of HeLa cells as measured by the MTT assay.

Potential cytotoxicity of CNI101 and CNI103 was tested on HeLa cells by the MTT proliferation assay. HeLa cells were seeded into a 96-well microplate (5000 cells per well) in full growth media and incubated at 37° C. overnight. A serial dilution of each inhibitor was prepared in DPBS and then added to each well. The treated cells were incubated at 37° C. with 5% CO$_2$ for 72 h. Following compound treatment, 10 μL of MTT stock solution was added to each well. After an additional 4 h at 37° C., 100 μL of SDS-HCl solubilizing solution was added to each well and the plate was returned to the incubator overnight at 37° C. A Tecan Infinite M1000 Pro microplate reader was used the following morning to measure the absorbance of the formazan product at 565 nm. CNI101 and CNI103 had no significant effect on cell viability at ≤12.5 μM, but reduced the viability at ≥25 μM (FIG. 19).

Example 14. Inhibition of TNFα and IL-6 Secretion by Macrophage

Figure 20:
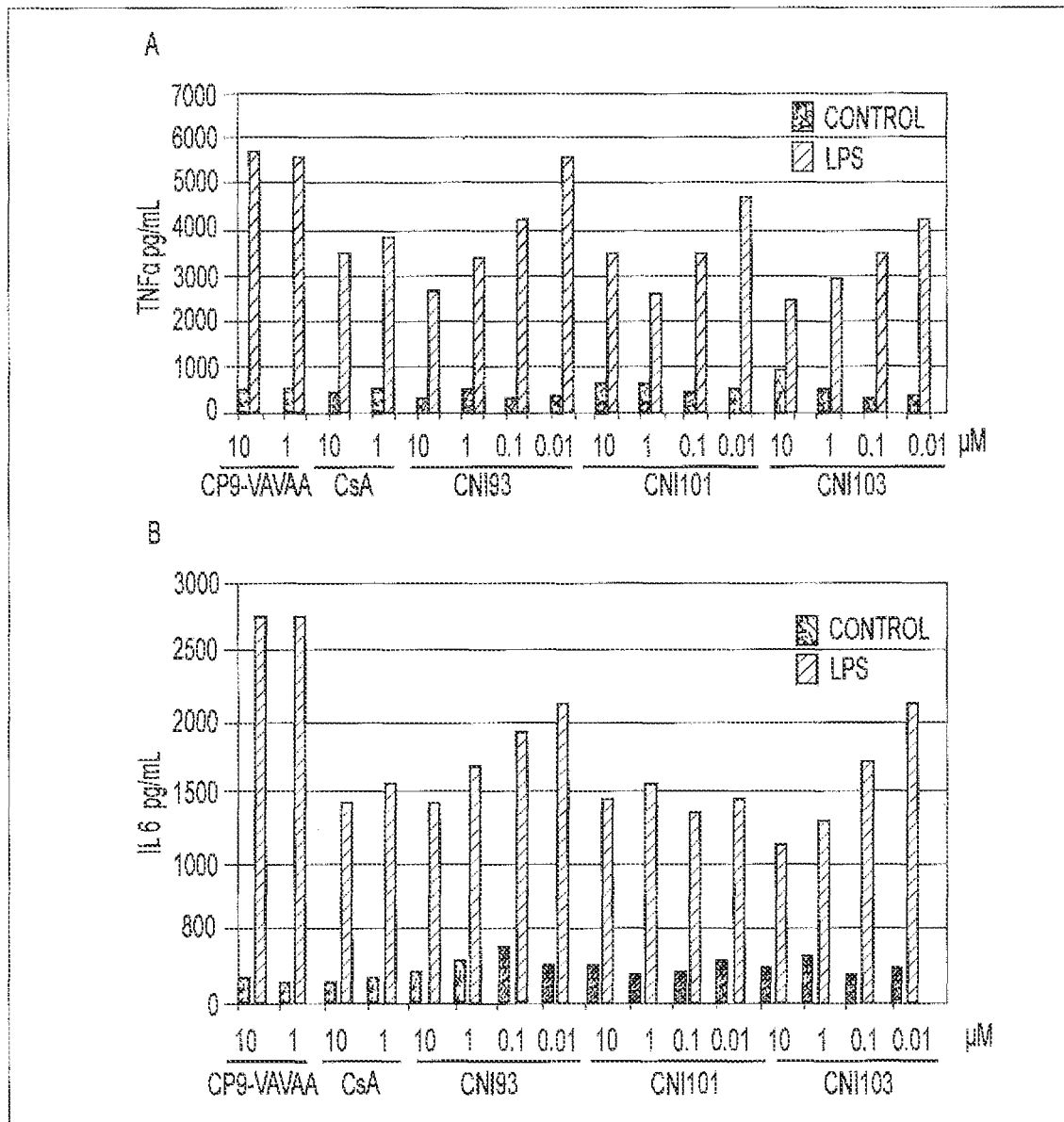
FIG. 20 shows that effect of different calcineurin inhibitors on cytokine secretion by mouse primary macrophage cells. Control (blue bars), no LPS. (a) Shows TNFα levels. (b) Shows IL6 levels.

Mouse total lung macrophages were obtained from 5 mice and pooled. Macrophages were pretreated with 100 nM, 1 μM, or 10 μM inhibitor for 2 h and stimulated with LPS (10 mg/mL) or PBS for 6 h. Cell supernatants were collected and analyzed for TNFα levels (FIG. 20a) or IL-6 levels (FIG. 20b) by R&D Systems TNFα ELISA kit and R&D Systems IL-6 ELISA kit. CNI93 (SEQ ID NO: 220), CNI101 (SEQ ID NO: 206), and CNI103 (SEQ ID NO: 208) dose-dependently reduced the secreted amounts of TNFα and IL6, with CNI103 being the most potent. Cyclosporine A also showed activity in this assay, but was less effective, whereas the negative control, CPP9-VAVAA, had no effect.

Example 15. Pharmacokinetics and Biodistribution of CNI103

Figure 21:
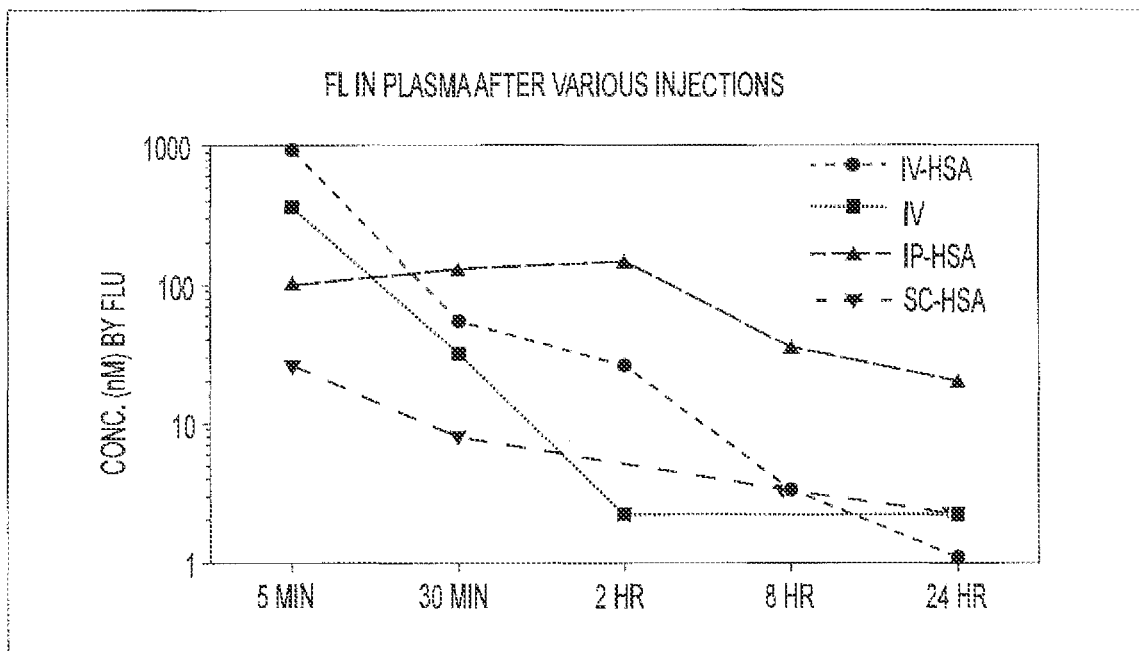
FIG. 21 shows the plasma concentration of CNI103-Cy5 as a function of time after intravenous (IV), intraperitoneal (IP), and subcutaneous (SC) administration with and without human serum albumin (HAS) as excipient. CNI103-Cy5 is Cy5-labeled CNI103 (SEQ ID NO: 208).
Figure 22:
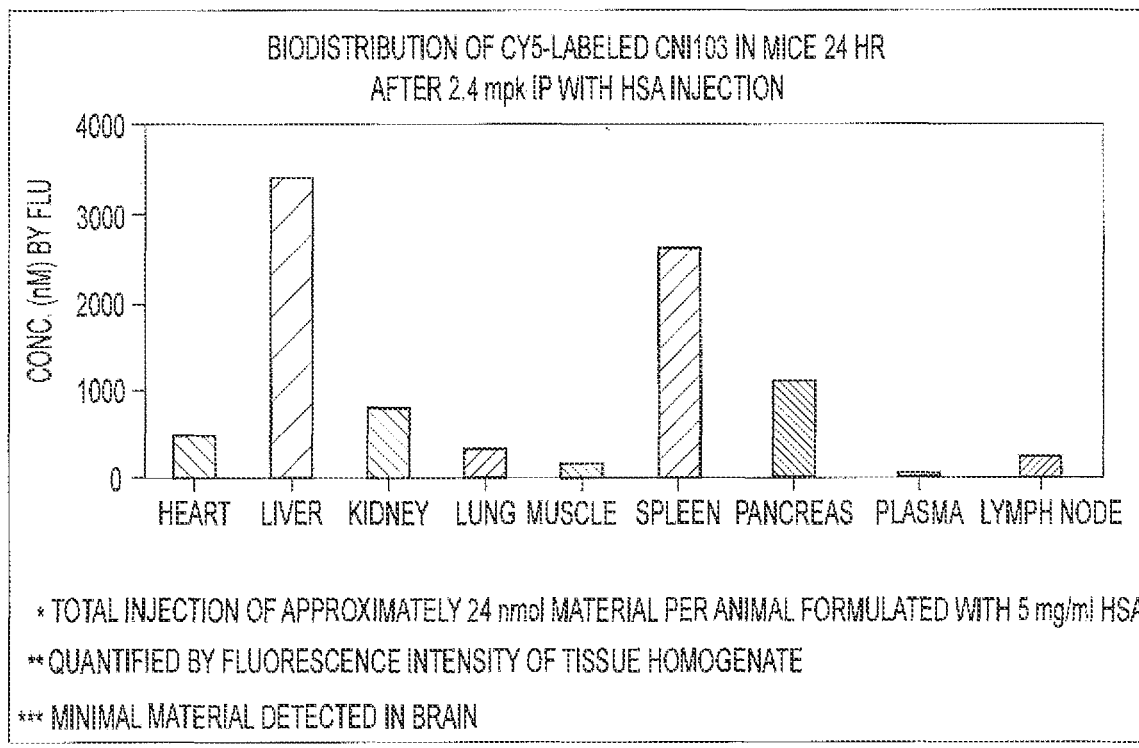
FIG. 22 shows tissue distribution of CNI103-Cy5 (2.4 mg/kg) 24 h after IP administration with HAS as excipient. CNI103-Cy5 is Cy5-labeled CNI103 (SEQ ID NO: 208).
Figure 23:
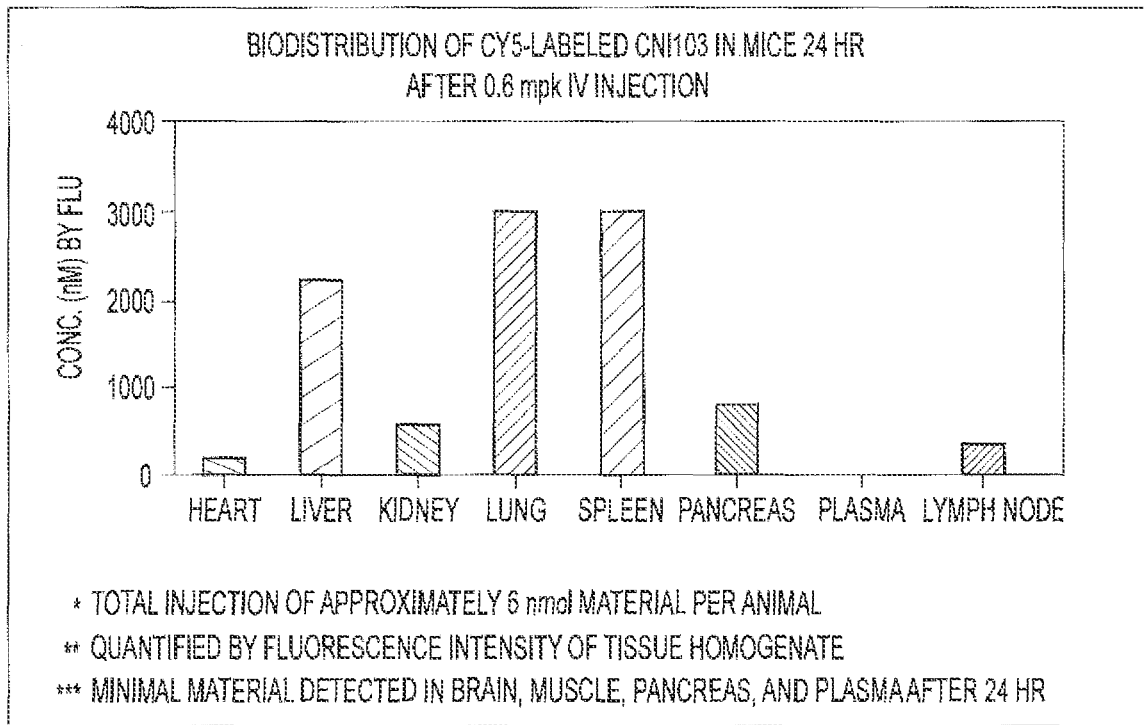
FIG. 23 shows tissue distribution of CNI103-Cy5 (0.6 mg/kg) 24 h after IV administration. CNI103-Cy5 is Cy5-labeled CNI103 (SEQ ID NO: 208).
Figure 24:
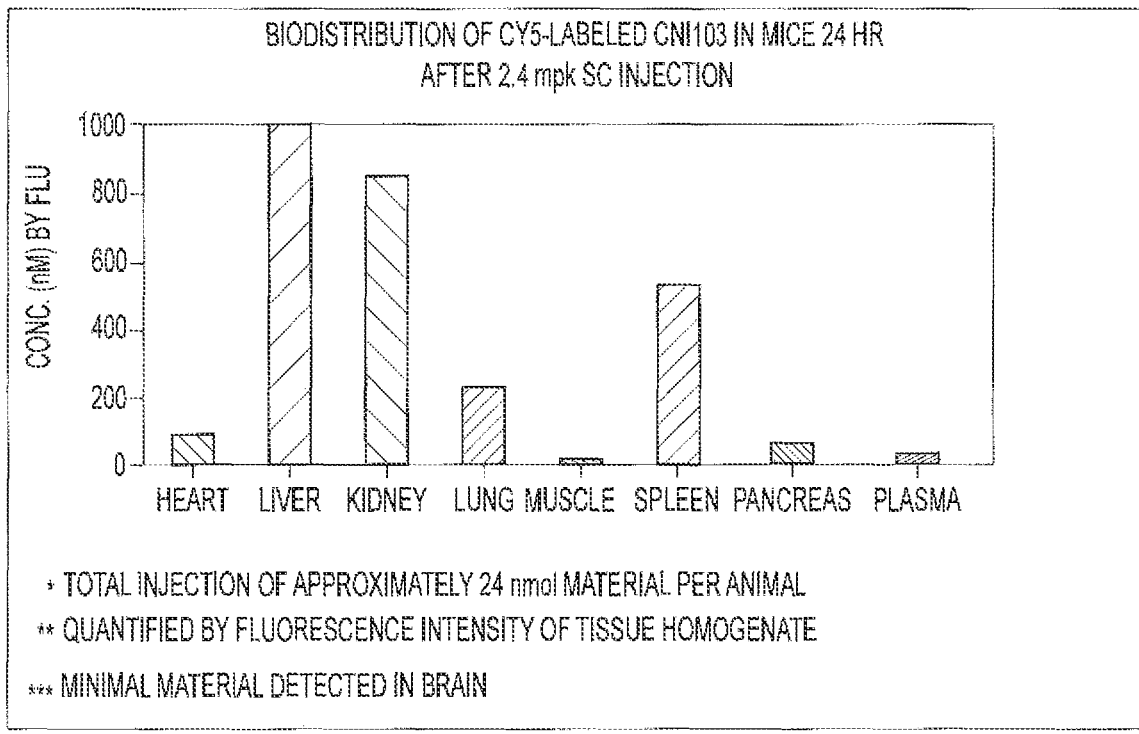
FIG. 24 shows tissue distribution of CNI103-Cy5 (2.4 mg/kg) 24 h after subcutaneous administration. CNI103-Cy5 is Cy5-labeled CNI103 (SEQ ID NO: 208).

Anesthetized mice were administered Cy5-labeled CNI103 (SEQ ID NO: 208) via three different routes (intravenous (IV), intraperitoneal (IP), and subcutaneous (SC)) with or without human serum albumin (HSA) added as an excipient. Plasma samples were obtained at indicated time points through retro-orbital bleeding. End-point tissue peptide concentration was determined following homogenization by fluorescent intensity and standardized to a peptide signal of known concentration. Following IV injection, CNI103-Cy5 reached high plasma concentrations, which rapidly declines over time. On the other hand, IP or SC administration resulted in lower peak concentrations, but much slower clearance (FIG. 21). CNI103-Cy5 showed broad tissue distribution, with highest concentrations typically found in liver, kidney, lungs, and spleen (FIGS. 22-24).

Example 16. In Vivo Efficacy in Mouse Model of LPS-Induced Acute Lung Injury

Figure 25:
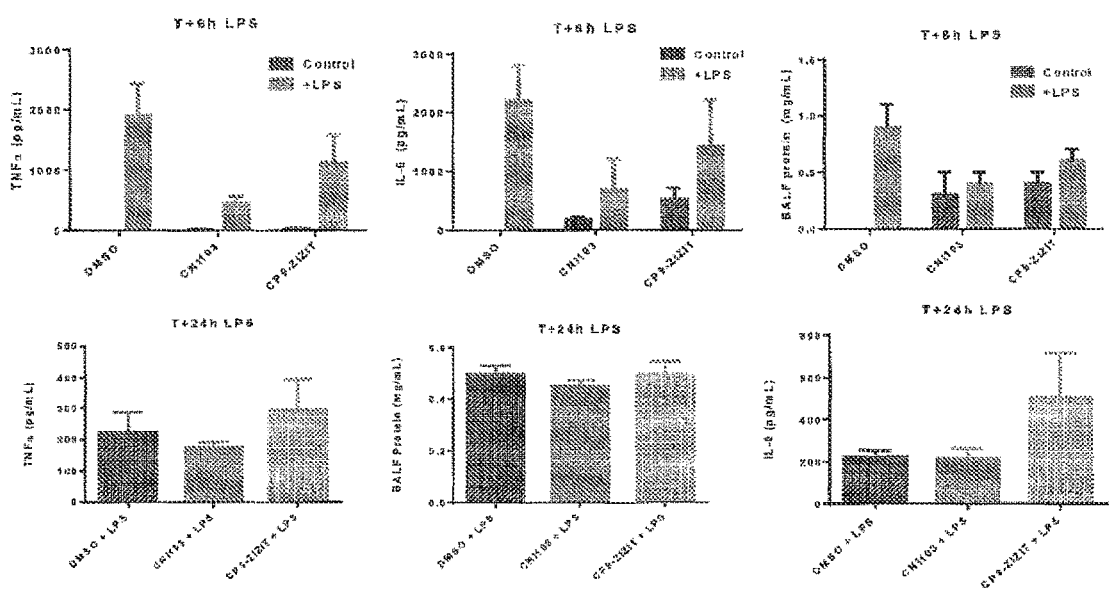
FIG. 25 Reduction of LPS-induced cytokine secretion in mice dosed intranasally with CNI103 (SEQ ID NO: 208) or CPP9(SEQ ID NO: 76)-ZIZIT(SEQ ID NO: 1) (3 mg/kg.

Following Intranasal Delivery. Anesthetized mice were treated with compound (intranasal, 3 mg/kg) and after 2 h were injected with LPS (IP, 10 mg/kg). After 6 or 24 h, mice were euthanized using Ketamine/Xylazine and acute lung inflammation was measured in terms of increased bronchoalveolar lavage fluid levels of protein, IL6, and TNFα. CNI103 (SEQ ID NO: 208) at 3 mpk was highly effective in preventing LPS-induced cytokine production and total protein release into BALF (FIG. 25). CPP9-ZIZIT, a tool compound of lower potency and metabolic stability, was efficacious but less effective than CNI103

Dose Dependent Response Observed with Intranasal Delivery. Anesthetized mice (n=5) were dosed intranasally with CNI103 at 0.3, 1, and 3 mpk and after 2 h injected with LPS (IP 10 mg/kg). Six hours after LPS administration, mice were euthanized using Ketamine/Xylazine and acute lung inflammation was assessed by measuring the increased levels of protein, IL-6, and TNFα in bronchoalveolar lavage fluid. Dose-dependent reduction of protein levels was observed, with 3 mpk being most effective (FIG. 26).

Following Systemic Delivery. Anesthetized mice (n=5 per group) were intravenously dosed with CNI103 at 5 mg/kg in sterile saline containing 0.1 mg/kg DMSO and after 4 h injected with LPS (i.p 10 mg/kg). After 18 h, mice were euthanized using Ketamine/Xylazine and the levels of total protein, IL-6, TNFα in bronchoalveolar lavage fluid, as well as the serum levels of IL-6 and TNFα were quantitated. CNI103 greatly reduced the cytokine and protein levels in BALF and serum (FIG. 27).

Example 17. In Vitro DMPK Assays of CNI103

Caco-2 permeability assay. To assay the permeability of test compounds by Caco-2 cell model, Caco-2 cells were cultured to confluency before being trypsinized and seeded onto filter transwell inserts at a density of 30,000 cells/well in DMEM medium. Cells were cultured in a humidified atmosphere with 5% $CO_2$ at 37° C. After overnight attachment, cell medium was replaced with fresh medium at both apical and basolateral sides every other day. The cell monolayers are ready for the assay 20 days post seeding. CNI103 was first dissolved in DMSO to obtain a 10 mM stock solution. The dosing solution at 10 µM was obtained by diluting 10 mM stock solution in HBSS medium (pH 7.4, 25 mM HEPES) freshly before the assay. Terfenadine (25 ng/mL) and Tolbutamide (50 ng/mL) were added into dosing solution as internal standards. Before treating the cells, transepithelial electrical resistance (TEER) values of each well were tested, the wells can be used only when TEER values are greater than 600 Ohms/cm². The culture medium from either the basolateral side (plate B) or apical side (plate A) were aspirated and then rinsed with HBSS medium once. Afterwards, the dosing medium was added to either basolateral or apical side. Following the incubation, 100 microliter samples from both sides were harvested at time 0 and time 90 mM Samples were quenched with acetonitrile/methanol (1:1 v/v), centrifuged, and analyzed on a Shimadzu reversed-phase HPLC and Sciex API4500 Q trap instrument.

Permeability parameters were calculated using the following equations and shown in Table 10:

$$P_{app} = (Conc._{receiver, 90\ mM} * Volume_{receiver}) / (Time * Membrane\ Area * Conc._{donor, 0\ min})$$

$$Efflux\ Ratio = P_{app}[B\ to\ A] / P_{app}[A\ to\ B]$$

TABLE 10

Determination of the permeability coefficient (Papp) of CNI103 and other control compounds across Caco-2 cell monolayers grown on filters

| Compounds ID | Papp (×10 −6 cm/s) (N = 2) | | Efflux Ratio | Pgp Substrate |
|---|---|---|---|---|
| | A → B | B → A | | |
| Atenolol | 0.4 | 0.6 | 1.5 | No |
| Propranolol | 35.0 | 26.0 | 0.7 | No |
| Amprenavir | 15.5 | 49.6 | 3.2 | Yes |
| CNI103 | 7.5 | 2.1 | 0.3 | No |

Liver microsome stability assay. Liver microsome stability was assessed using mouse microsome (cat. M1000, XenoTech). Ten mM stock solution of CNI103 was similarly prepared in DMSO. One hundred micromolar of CNI103 solution was prepared by diluting the DMSO stock in phosphate buffer (50 mM potassium phosphate, pH 7.4). To assay the stability, liver microsomes (final concentration 0.5 mg/mL) were mixed with testing samples gently and incubated at 37° C. for 5 min. At varying time points post reaction (0, 5, 15, 30, and 60 min), 25 microliter aliquots were withdrawn and each aliquot (25 microliter) was quenched with 300 µL of an internal standard solution (25 ng/mL terfenadine in 1:1 v/v methanol/acetonitrile) followed by vigorous vortexing and centrifugation. To assess metabolism by P450 enzymes, the microsome degradation reaction was supplemented with NADPH (final 1 mM) followed by gentle mixing. 100 µL aliquots of the reaction mixture were withdrawn at 0, 30, or 60 mM, diluted two fold with distilled water, and subjected to LC-MS/MS analysis on a reversed-phase HPLC coupled with Sciex 4500 Q-trap based quantification. The results are presented in Table 11.

TABLE 11

Percentage of CNI103 remaining after incubation in mouse liver microsome with and without NADPH supplements

| Time (min) | % remaining (−NADPH) | % remaining (+NADPH) |
|---|---|---|
| 0 | 100.0 | 100.0 |
| 5 | ND | 131.1 |
| 15 | ND | 95.8 |
| 30 | 113.6 | 76.0 |
| 60 | 70.8 | 75.1 |

Stability of CNI103 in mouse hepatocytes. Hepatocyte stability was assessed by using mouse hepatocyte (cat. M005052, BioIVT). Mouse hepatocytes were revived following manufacturer's procedure with Cryopreserved Hepatocyte Recovery Medium and used for the assay when cell viability was greater than 70%. Testing compound (at 2 µM) was mixed with mouse hepatocytes at 37° C. in a humidified incubator with 5% $CO_2$. Final hepatocyte cell density was 2 million per mL. At varying time points (0, 15, 30, 60, and 90 min) post reaction, 30 µL aliquots of the reaction mixture were withdrawn and mixed with 200 µL of an internal standard solution (25 ng/mL terfenadine in 1:1 v/v methanol/acetonitrile) followed by vigorous vortexing and centrifugation. One hundred mL of the resulting supernatant was diluted two fold with distilled water and analyzed by reversed-phase HPLC coupled with Sciex 4500 Q-trap based quantification. The results are presented in Table 12 and FIG. 28.

TABLE 12

Percentage of CNI103 remaining after incubation in mouse hepatocytes

| Time (min) | % remaining CNI103 |
|---|---|
| 0 | 100.00 |
| 15 | 103.38 |
| 30 | 100.84 |
| 60 | 119.83 |
| 90 | 141.77 |
| 120 | 124.89 |

Example 18. Plasma Protein Binding by CNI103

Plasma binding was assessed using mouse plasma obtained from in-life studies. CNI103 was diluted to 5 mM in pre-warmed mouse plasma. The solution was added to the left chamber of a commercial plate based RED (rapid equilibrium dialysis) device. Isotonic sodium phosphate buffer (100 mM sodium phosphate, 100 mM sodium chloride, pH 7.4) was added to the outer chamber of the RED device and the plate was incubated at 37° C. for five hours. Aliquots of the buffer and the plasma were withdrawn before and after the incubation and the concentrations of free and bound test compound were determined by LC/MS/MS analysis. To test for plasma stability, the dosing solution was also incubated at 37° C. for 5 hours and the concentration of CNI103 was determined by LC/MS/MS analysis as described above.

The calculation of percentage binding is calculated using the following equations and the results are presented in Table 13:

Binding % = $(C_{pe} - C_b)/C_{pe} \times 100$ $C_{pe}$ = Conc. of test compound in plasma at equilibrium
$C_b$ = Conc. of test compound in buffer at equilibrium % Stability of test compound = (Conc. of stability sample/Conc. of time zero sample) × 100%

% Recovery = $(C_{pe} + C_b)$/Conc. of stability sample × 100

TABLE 13

Plasma stability and plasma protein binding of CNI103 after incubation with mouse plasma at 37° C. for 5 hours (n = 2).

| Compound Type | Compounds ID | % Binding | Plasma Stability @ 5 hr (% remaining) | % Recovery |
|---|---|---|---|---|
| Control | Phenacetine | 36.5 | 73.8 | 73.3 |
| | Quinidine | 75.7 | 107 | 102 |
| | Warfarin | 91.4 | 101 | 103 |
| Test Compound | CNI103 | 97.6 | 110 | 130 |

Example 19. Stability of CNI103 in Simulated Gastric and Intestinal Fluid

Stability of CNI103 in simulated gastric fluid (SGF) was evaluated by diluting CNI103 (final 5 µM) in FaSSGF buffer (pH 1.2), which was prepared from FaSSGF powder (cat no. FFF01, BioRelavant). The results are provided in Table 14. Similarly, stability of CNI103 in simulated intestinal fluid (SIF) was evaluated by diluting CNI103 (final 5 µM) in FaSSIF buffer (pH 6.5), which was prepared from FaSSIF powder (cat no. FFF-1017-B, BioRelavant) supplemented with Lecithin and maleic acid. The results are provided in Table 15. The solutions were incubated at 37° C. for 5, 15, 30, 60, or 120 min, and the concentration of remaining CNI103 was determined by LC/MS/MS analysis as described above.

TABLE 14

The amount of remaining CNI103 after incubation in SGF (n = 2).

| Time (min) | 0 | 5 | 15 | 30 | 60 | 120 |
|---|---|---|---|---|---|---|
| % remaining | 100.00 | 93.69 | 87.39 | 88.29 | 105.86 | 103.15 |

TABLE 15

The remaining percentage of CNI103 after incubation in SIF (n = 2).

| Time (min) | 0 | 5 | 15 | 30 | 60 | 120 |
|---|---|---|---|---|---|---|
| % remaining | 100.00 | 92.27 | 108.85 | 108.85 | 95.93 | 75.58 |

The invention claimed is:

1. A polypeptide conjugate, comprising Formula I, II, or III

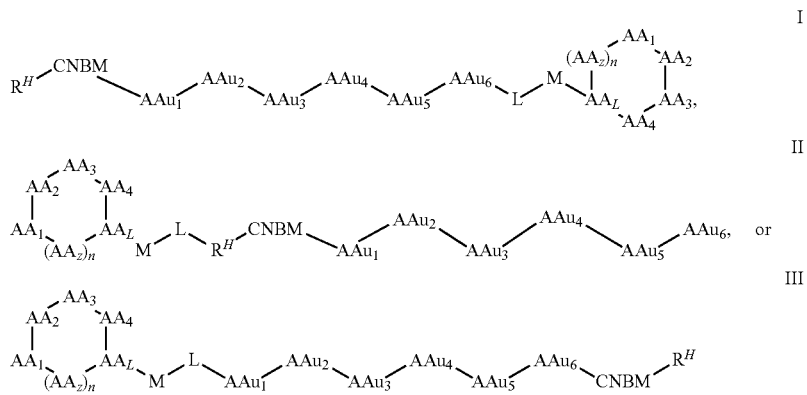

wherein:
each of $AA_1$, $AA_2$, $AA_3$, $AA_4$, $AA_L$ and $AA_Z$ are independently an amino acid which is optionally substituted;
n is an integer from 0 to 6;
M is a bonding moiety;
L is a linking moiety;
each of $AA_{U1}$, $AA_{U2}$, $AA_{U3}$, $AA_{U4}$, $AA_{U5}$, and $AA_{U6}$, is optional and independently selected from an amino acid which is optionally substituted;
calcineurin (CN) binding motif (CNBM) comprises a sequence selected from the group consisting of: (i) Tle-Ile-Tle-Ile-Thr (ZIZIT) (SEQ ID NO:1); (ii) Val-Ile-Val-Ile-Thr (VIVIT) (SEQ ID NO:2); (iii) Val-Ile-Tle-Ile-Thr (VIZIT) (SEQ ID NO:3); (iv) Tle-Ile-Hva-Ile-Thr (SEQ ID NO:4); (v) Tle-Ile-Val-Ile-Thr (ZIVIT) (SEQ ID NO:5); (vi) Tle-Ile-Bhv-Ile-Thr (SEQ ID NO:6); (vii) Tle-Chg-Bhv-Ile-Thr (SEQ ID NO:7); (viii) Tle-Ile-Psa-Ile-Thr (SEQ ID NO:8); or (ix) Tle-Chg-Psa-Ile-Thr (SEQ ID NO:9);

$R^H$ is a hydrophobic non-peptidyl moiety which interacts with the hydrophobic pocket in a CN protein;

wherein:
at least two of $AA_1$, $AA_2$, $AA_3$, $AA_4$ and $AA_Z$ are arginines; and
at least two of $AA_1$, $AA_2$, $AA_3$, $AA_4$ and $AA_Z$ are independently amino acids having a hydrophobic side chain.

2. The polypeptide conjugate of claim 1, wherein the amino acids having a hydrophobic side chain are independently 3-benzothienyl-L-alanine, phenylalanine, naphthylalanine, or tryptophan, each of which is optionally substituted.

3. The polypeptide conjugate of claim 1, wherein M is a covalent bond, a disulfide, an amide, a thioether, or a triazolyl.

4. The polypeptide conjugate of claim 1, wherein L is a linking moiety comprising at least one amino acid, alkylene, alkenylene, alkynylene, aryl, cycloalkyl, cycloalkenyl, cycloalkynyl, heterocyclyl, heteroaryl, ether, βAla-Lys, mini-PEG-Lys, or combinations thereof, each of which are optionally substituted.

5. The polypeptide conjugate of claim 1, wherein $R^H$ is acyl, carbocyclyl, heterocyclyl, formyl, acetyl, aryl, heteroaryl, pyridinyl, benzoyl, cyclopentylcarbonyl, or cyclohexylcarbonyl, each of which are optionally substituted.

6. The polypeptide conjugate of claim 1, wherein $R^H$ is 2,3-dichlorobenzoyl, 3-chloro-4-methylbenzoyl, 2,6-dichloro-3-fluorobenzoyl, 2-trifluoromethylbenzoyl, formyl, 2-fluoro-6-methylbenzoyl, acetyl, 4-chloro-2-methylbenzoyl, 3-chloro-5-methylbenzoyl, 3-(1-chloromethyl)benzoyl, 3,5-dibromobenzoyl, 4-tertbutylbenzoyl, 3-methylbenzoyl, 2-chlorobenzoyl, 3-iodobenzoyl, 2-chloro-4-iodobenzoyl, 4-methylbenzoyl, 2-bromobenzoyl, 2-fluorobenzoyl, 2,4,6-trimethylbenzoyl, 2-chloro-5-fluorobenzoyl, 2-chlorobenzoyl, 2-bromo-4-chlorobenzoyl, 2-fluoro-4-methylbenzoyl, 4-isopropylbenzoyl, 4-fluoro-2-methylbenzoyl, 4-(1-bromomethyl)benzoyl, 2-methylbenzoyl, 4-bromobenzoyl, 4-trifluoromethylbenzoyl, 2-fluoro-4-chlorobenzoyl, 2,6-dimethylbenzoyl, 4-butylbenzoyl, 3-bromobenzoyl, 3,5-dimethylbenzoyl, 2-iodobenzoyl, cyclopropylcarbonyl, 2-chloro-3-methylbenzoyl, 3-ethynylbenzoyl, 2,4-dimethylbenzoyl, 3,5-trifluoromethylbenzoyl, 2-chloro-4-fluorobenzoyl, 4-fluorobenzoyl, 5-chloro-2-methylbenzoyl, 2-(1-chloromethyl)benzoyl, 4-(2-chloroethyl)benzoyl, 2-chloro-6-fluorobenzoyl, 4-chloro-2-methylbenzoyl, 3-fluorobenzoyl, cyclohexylcarbonyl, 2-naphthoic acid, 4-iodobenzoyl, 3,4-dimethylbenzoyl, 2,4-dichloro-3-fluorobenzoyl, 2,3,4-trifluorobenzoyl, 4-ethynylbenzoyl, 2-chloro-4-iodobenzoyl, or 2,3-dichloro-4-pyridinyl.

7. The polypeptide conjugate of claim 1, wherein $R^H$ is 2,3-dichlorobenzoyl or 2,3-dichloro-4-pyridinyl.

8. The polypeptide conjugate of claim 1, wherein each of $AA_{U1}$, $AA_{U2}$, $AA_{U3}$, $AA_{U4}$, $AA_{U5}$, and $AA_{U6}$, when present, are independently:

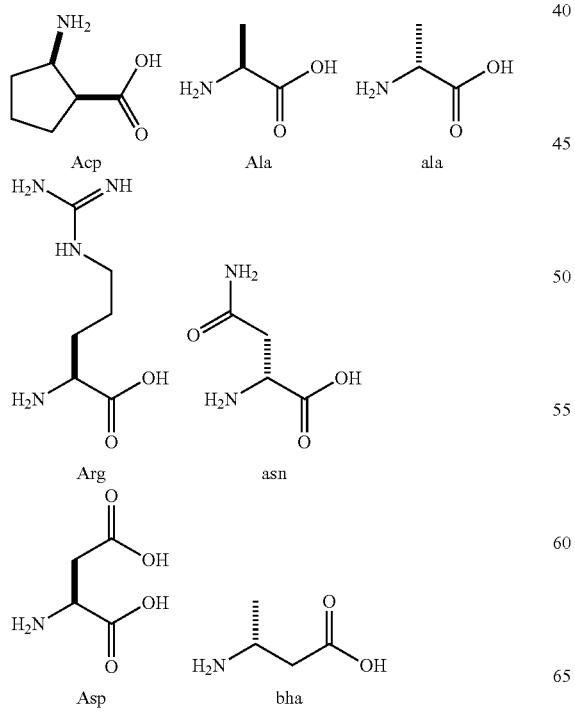

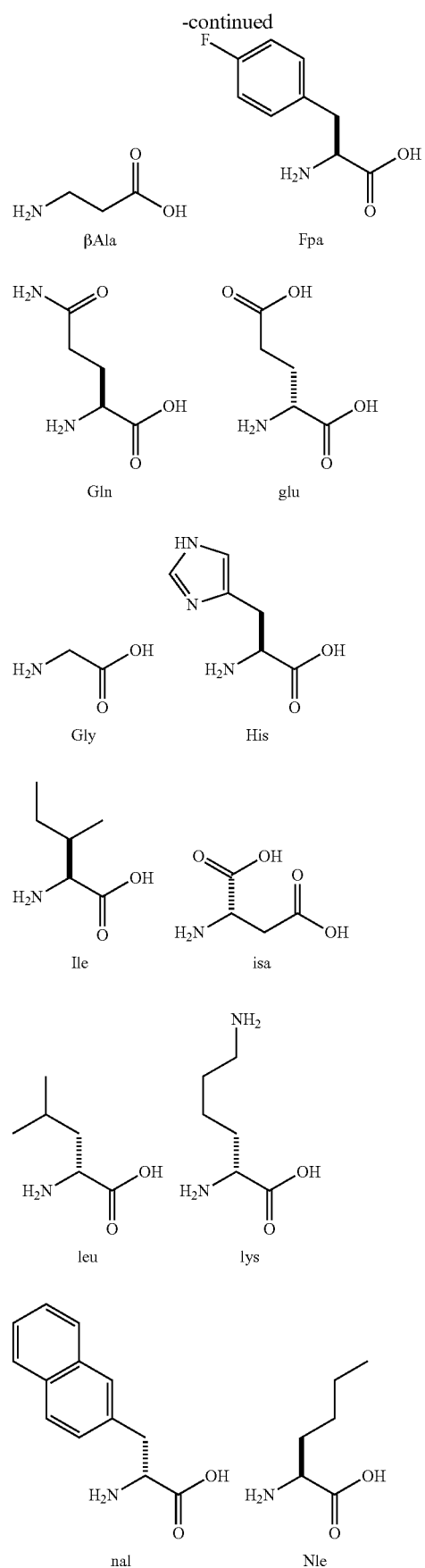

-continued

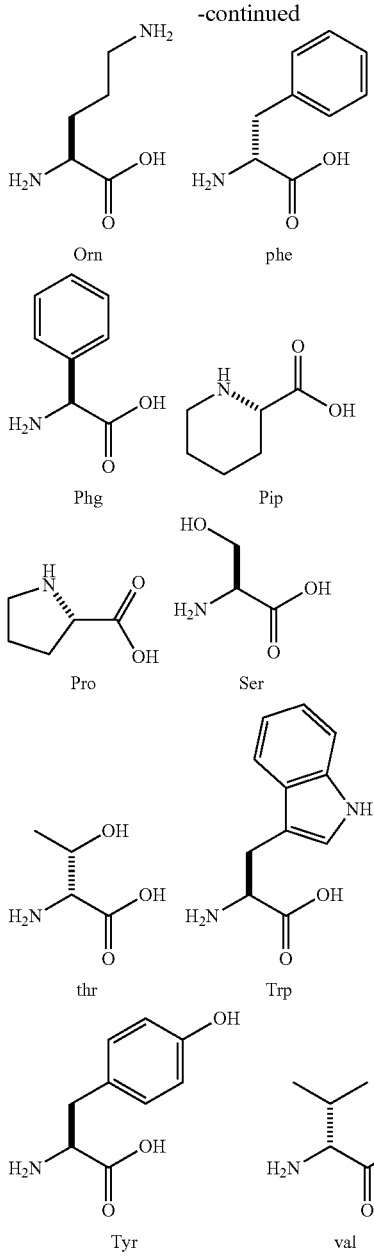

where abbreviations starting with a capital letter refer to L-amino acids and abbreviations starting with a lowercase letter refer to D-amino acids, and
   wherein at least one of the N-terminus and the C-terminus forms a peptide bond.

9. The polypeptide conjugate of claim 1, wherein $AA_{U1}$ on the C-terminus of CNBM in Formula I or II is an L-amino acid selected from the group consisting of glutamine, tyrosine, aspartic acid, and histidine.

10. The polypeptide conjugate of claim 1, wherein $AA_{U2}$ is histidine, tyrosine, or glutamic acid.

11. The polypeptide conjugate of claim 1, wherein at least one of the $AA_{U3}$ and $AA_{U4}$ is an aromatic hydrophobic amino acid.

12. The polypeptide conjugate of claim 1, wherein at least one of $AA_{U1}$, $AA_{U2}$, $AA_{U3}$, $AA_{U4}$, $AA_{U5}$, and $AA_{U6}$ is a D-amino acid.

13. The polypeptide conjugate of claim 1, wherein $AA_{U1}$, $AA_{U2}$, $AA_{U3}$, and $AA_{U4}$ are selected from No. 1-47 below, and each of $AA_{U5}$ and $AA_{U6}$ are absent.

| No. | $AA_{U1}$ | $AA_{U2}$ | $AA_{U3}$ | $AA_{U4}$ |
|---|---|---|---|---|
| 1 | Asp | Gly | Trp | leu |
| 2 | Tyr | glu | Fpa | His |
| 3 | Tyr | Trp | Bha | Pro |
| 4 | Nal | Gln | AcP | Trp |
| 5 | Gln | Tyr | asn | Nal |
| 6 | Gln | His | leu | His |
| 7 | Asp | Gln | Tyr | Arg |
| 8 | Ias | Gln | Trp | Arg |
| 9 | Tyr | Acp | Gly | Trp |
| 10 | Ser | Gly | His | Nal |
| 11 | Pro | Nal | Arg | Bha |
| 12 | His | glu | Orn | ala |
| 13 | Gln | His | leu | Ser |
| 14 | Nle | Ala | Nal | Tyr |
| 15 | lys | His | Nal | Asp |
| 16 | Orn | Nle | His | Nal |
| 17 | Tyr | asn | Ser | Nal |
| 18 | Gly | Tyr | Gly | Nal |
| 19 | Asp | His | lys | Tyr |
| 20 | Gln | Tyr | βAla | Nal |
| 21 | His | His | phe | Trp |
| 22 | Arg | Tyr | glu | Tyr |
| 23 | Ala | His | Nal | Bha |
| 24 | Pro | βAsp | His | Nal |
| 25 | Gln | His | Tyr | Nle |
| 26 | Gln | phe | Arg | Asp |
| 27 | Trp | glu | Gly | Arg |
| 28 | Pro | glu | Nal | Arg |
| 29 | Gln | His | Gly | βAla |
| 30 | Tyr | glu | Fpa | Gly |
| 31 | Ala | His | Nal | Phg |
| 32 | Nal | His | Tyr | Acp |
| 33 | His | ala | Ser | Tyr |
| 34 | βAla | glu | Nal | Arg |
| 35 | thr | Pro | ala | Nal |
| 36 | Ile | His | Nal | His |
| 37 | Asp | Gln | Tyr | lys |
| 38 | βAla | glu | Arg | Tyr |
| 39 | thr | leu | Tyr | phe |
| 40 | Tyr | His | Pro | Trp |
| 41 | asn | Pro | Tyr | Trp |
| 42 | Ser | Tyr | Ser | Trp |
| 43 | Gln | Tyr | Nal | Ser |
| 44 | Tyr | His | Gly | phe |
| 45 | Acp | Gly | Nal | His |
| 46 | glu | Pip | Nal | His |
| 47 | Gln | His | Leu | Ser |

14. The polypeptide conjugate of claim 1, wherein the polypeptide conjugate has an increased resistance to proteolytic degradation compared to an otherwise identical polypeptide conjugate lacking the $R^H$ moiety.

15. The polypeptide conjugate of claim 1, having a dissociation constant ($K_D$) for CN that is less than 50 nM.

16. A polypeptide conjugate of claim 1, having one of the following structures:
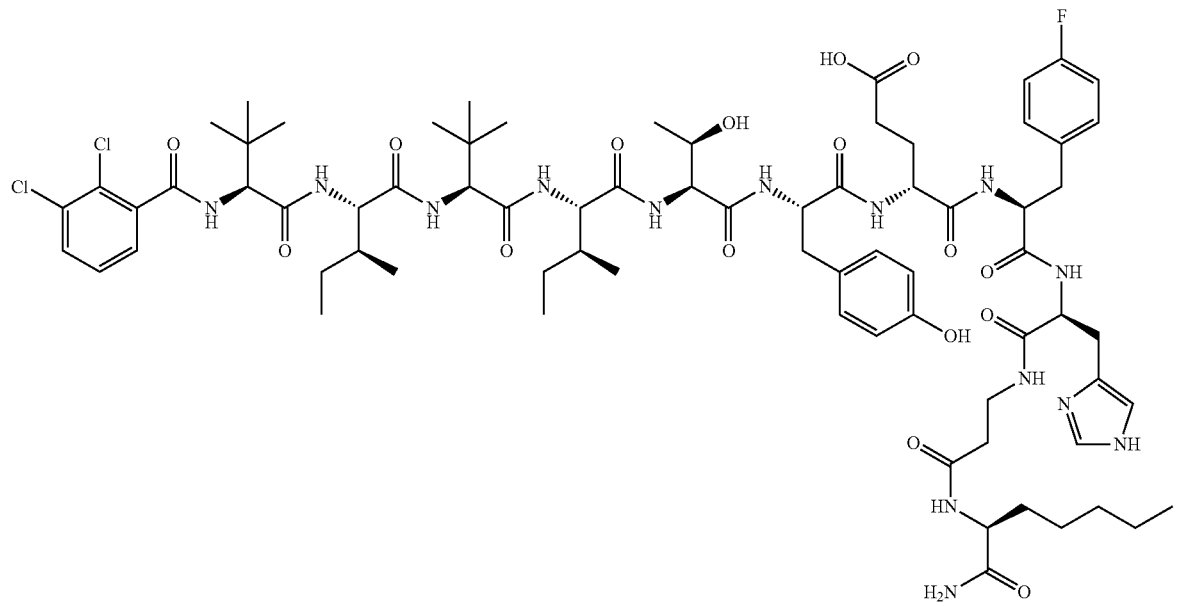
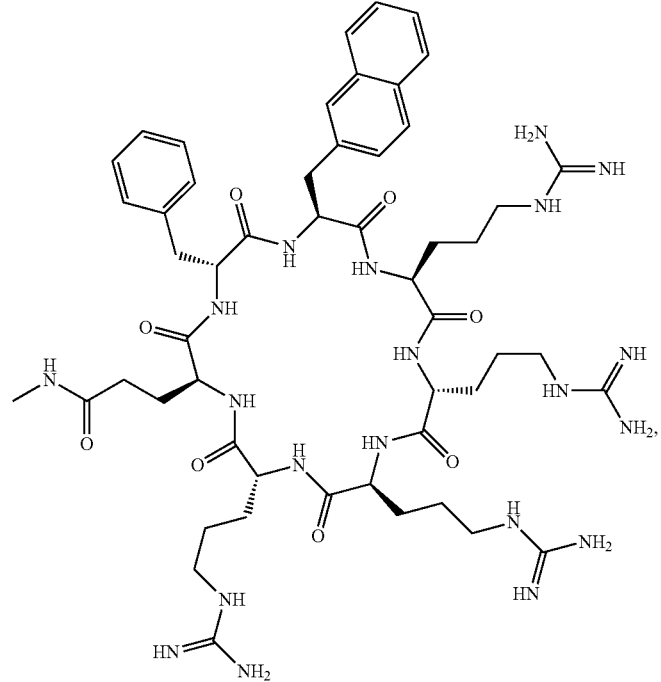

which corresponds to $R^H$ is 2,3-dichlorobenzoyl, CNBM is ZIZIT (SEQ ID NO: 1), $AA_{U1}$, $AA_{U2}$, $AA_{U3}$, and $AA_{U4}$ together are Tyr-glu-Fpa-His (SEQ ID NO: 30), L is βAla-Lys, and $AA_1$, $AA_2$, $AA_3$, $AA_4$, $AA_L$ and $AA_z$ together are CPP9 (SEQ ID NO: 76)),

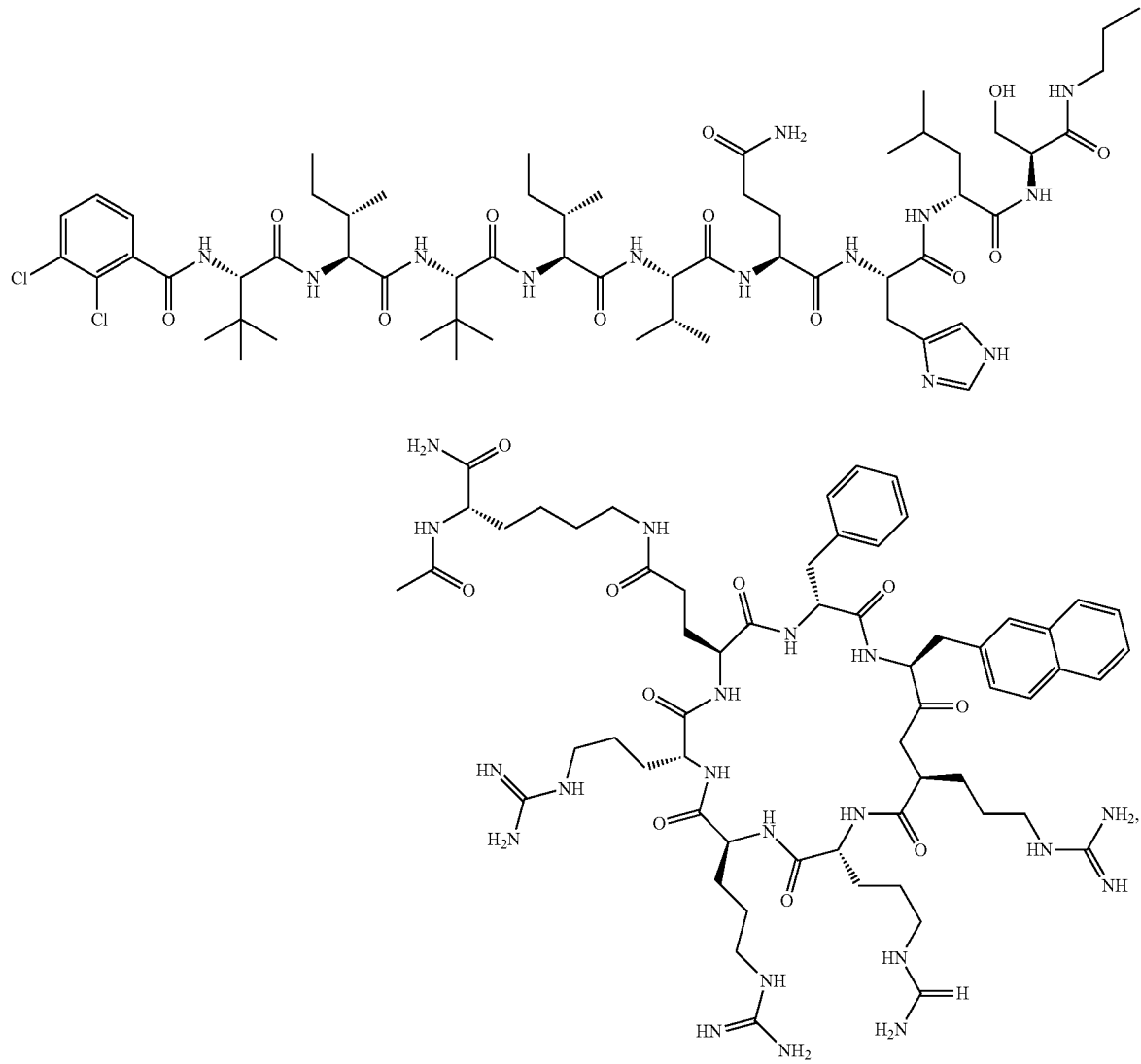

50 which corresponds to $R^H$ is 2,3-dichlorobenzoyl, CNBM is ZIZIT (SEQ ID NO: 1), $AA_{U1}$, $AA_{U2}$, $AA_{U3}$, and $AA_{U4}$ together are Gln-His-leu-Ser (SEQ ID NO: 41), L is βAla-Lys, and $AA_1$, $AA_2$, $AA_3$, $AA_4$, $AA_L$ and $AA_z$ together are CPP9 (SEQ ID NO: 76)),

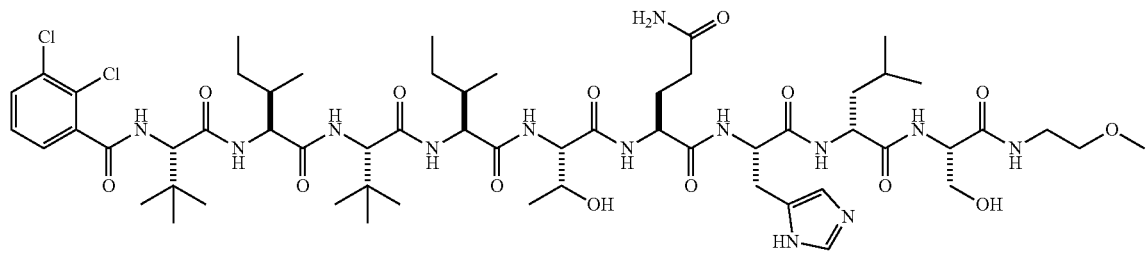

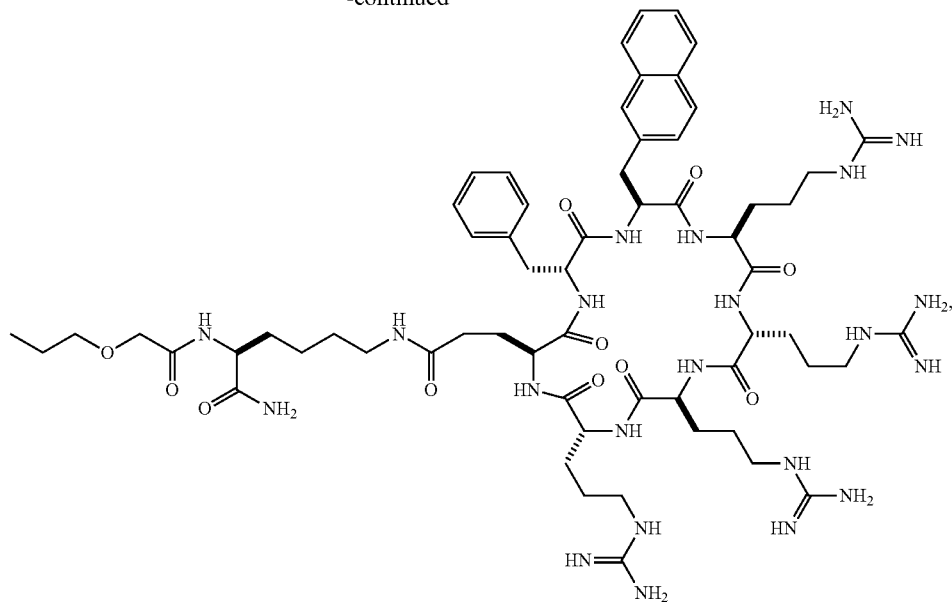
which corresponds to $R^H$ is 2,3-dichlorobenzoyl, CNBM is ZIZIT (SEQ ID NO: 1), $AA_{U1}$, $AA_{U2}$, $AA_{U3}$, and $AA_{U4}$ is Gln-His-leu-Ser (SEQ ID NO: 41), L is miniPEG-Lys, and $AA_1$, $AA_2$, $AA_3$, $AA_4$, $AA_L$ and $AA_z$ is CPP9 (SEQ ID NO: 76)),
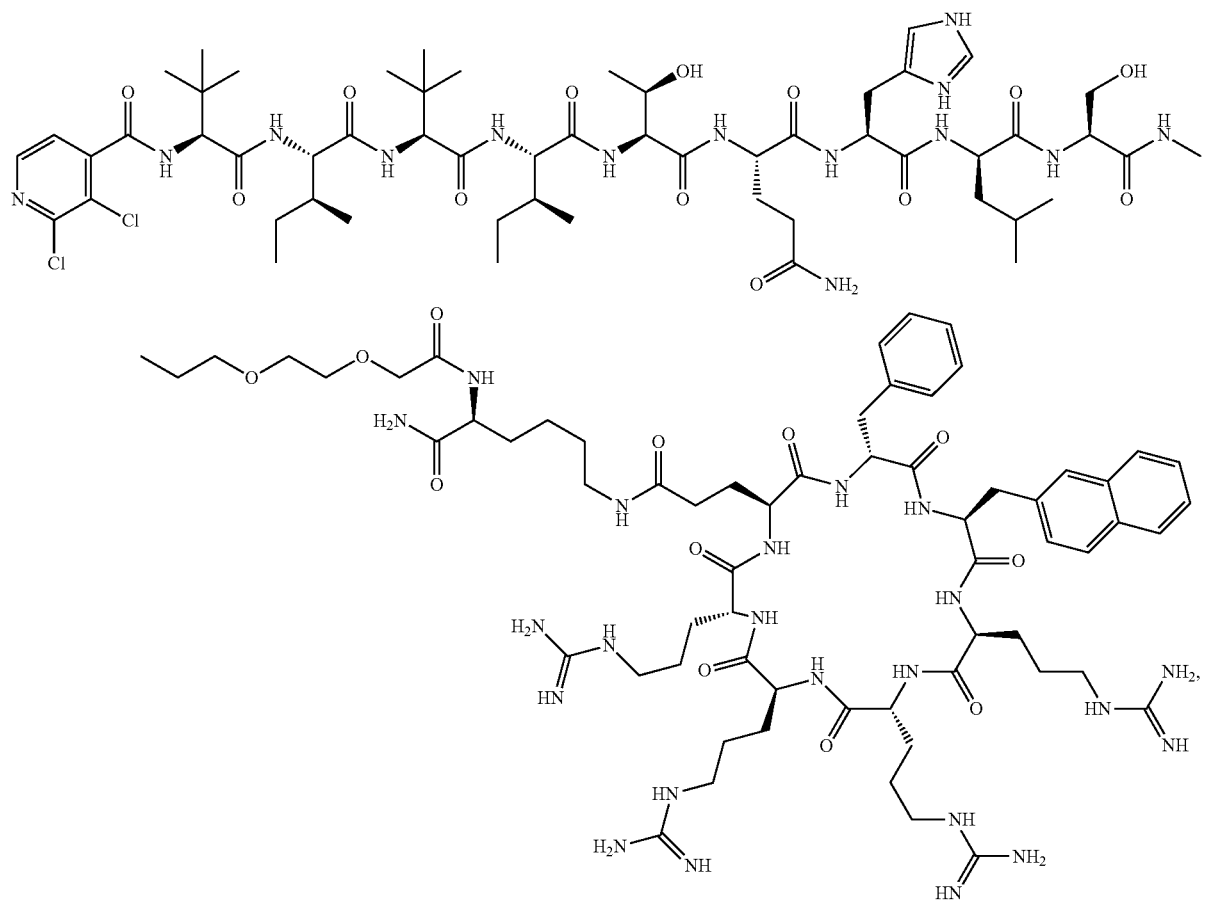

which corresponds to (DCNA)-Tle-Ile-Tle-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH₂(SEQ ID NO: 206),
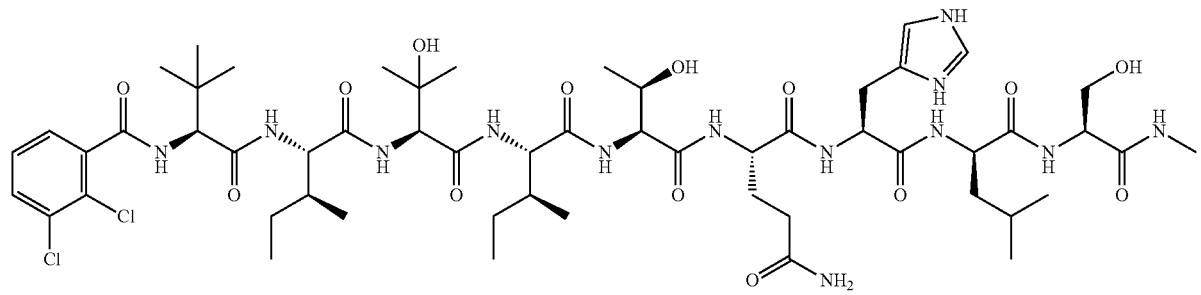
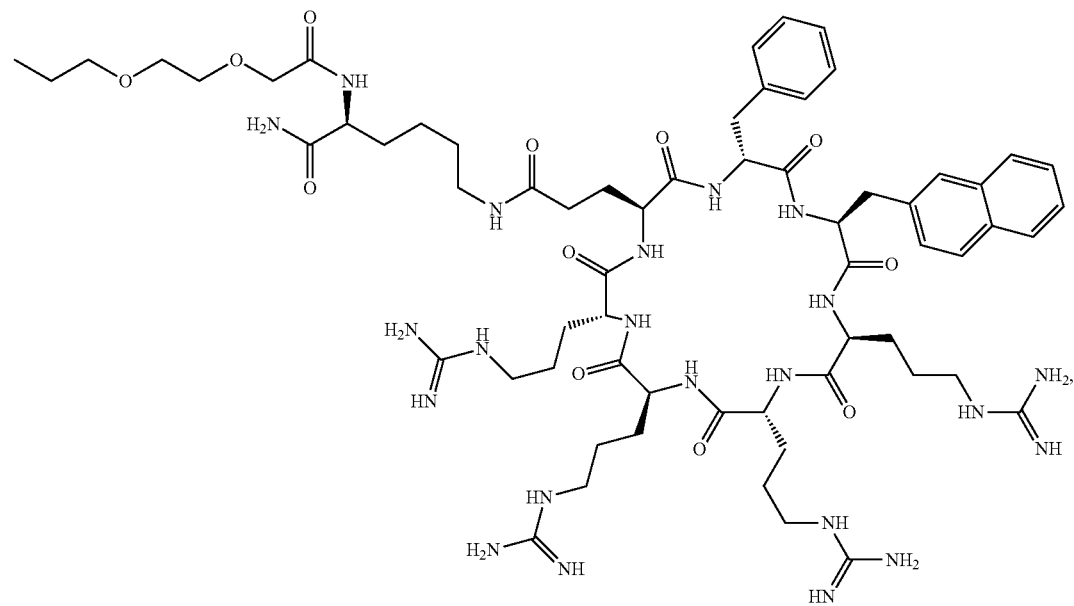

which corresponds to (DCB)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ (SEQ ID NO: 207),
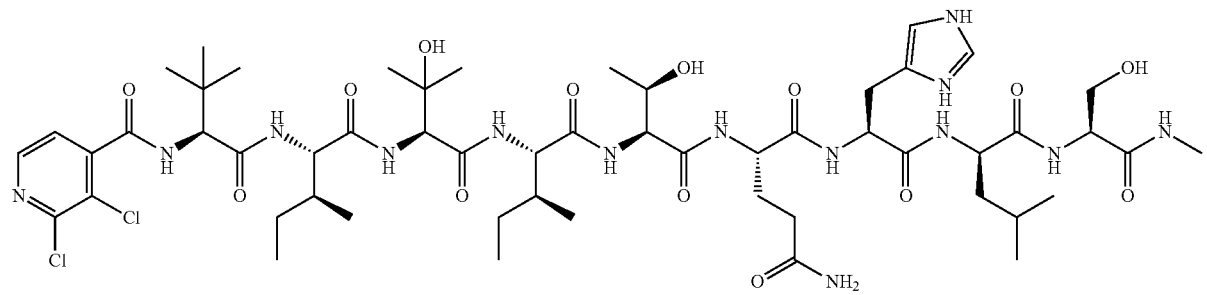
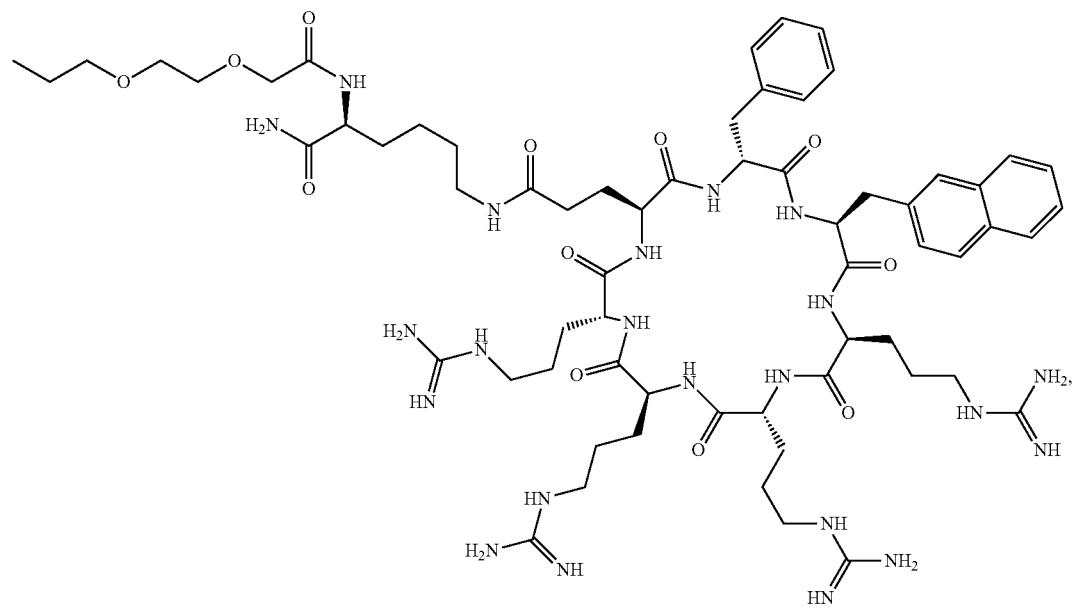

which corresponds to (DCNA)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH₂ (SEQ ID NO: 208),
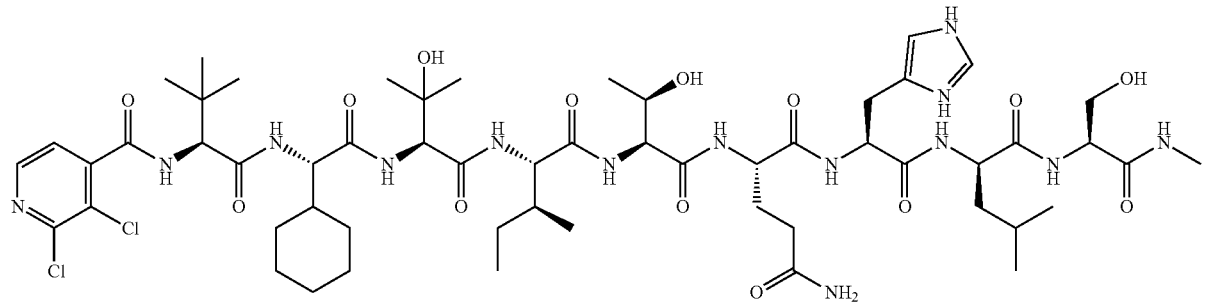
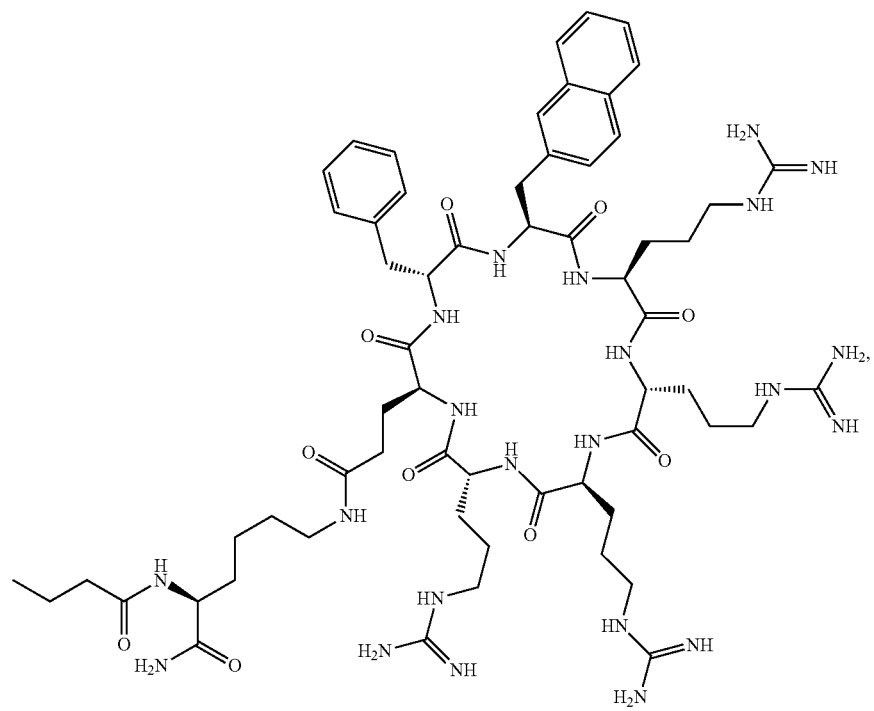
which corresponds to (DCNA)-Tle-Chg-Bhv-Ile-Thr-Gln-His-(D-Leu)-Ser-βAla-Lys{[cyclo-(Gln-(D-Arg)-Arg-(D-Arg)-Arg-(2-Nal)-(D-Phe)]}-NH₂ (SEQ ID NO: 209),
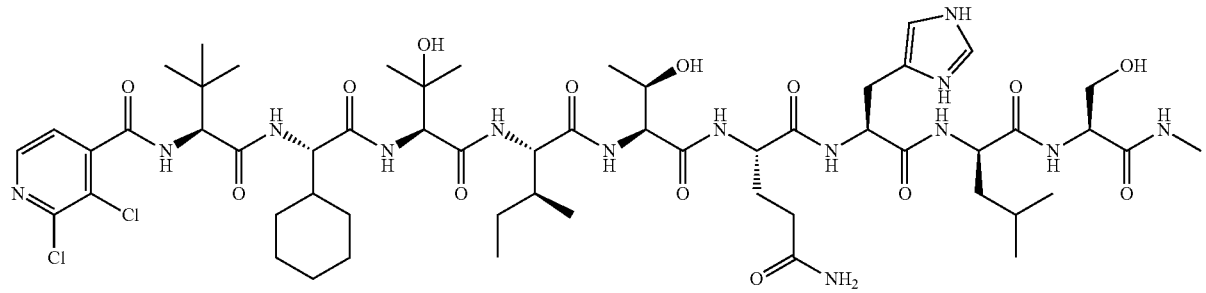

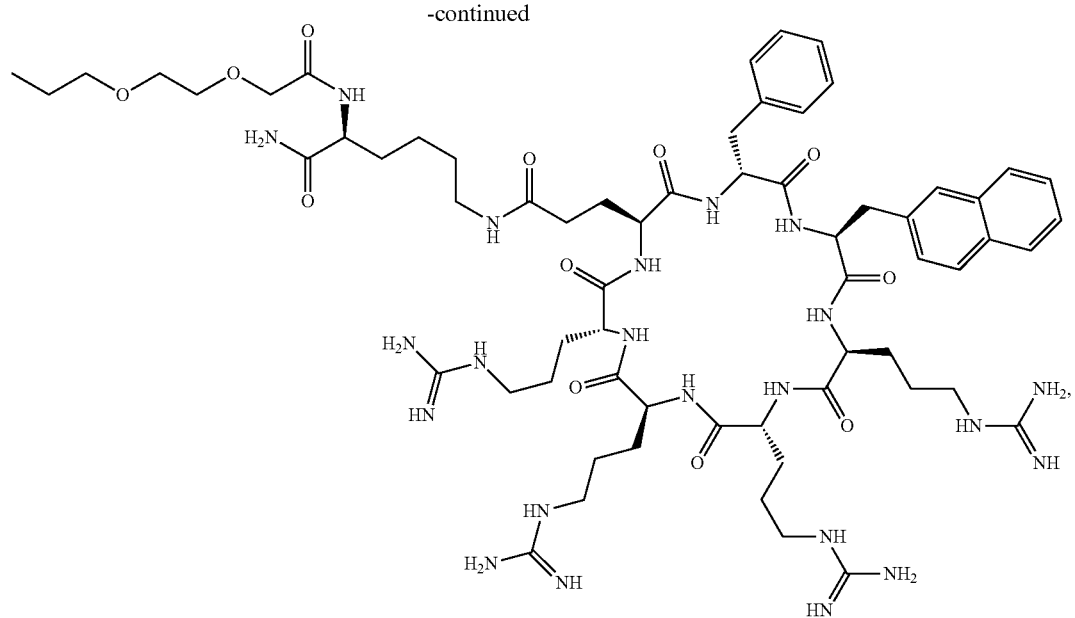
which corresponds to (DCNA)-Tle-Chg-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH₂ (SEQ ID NO: 210),
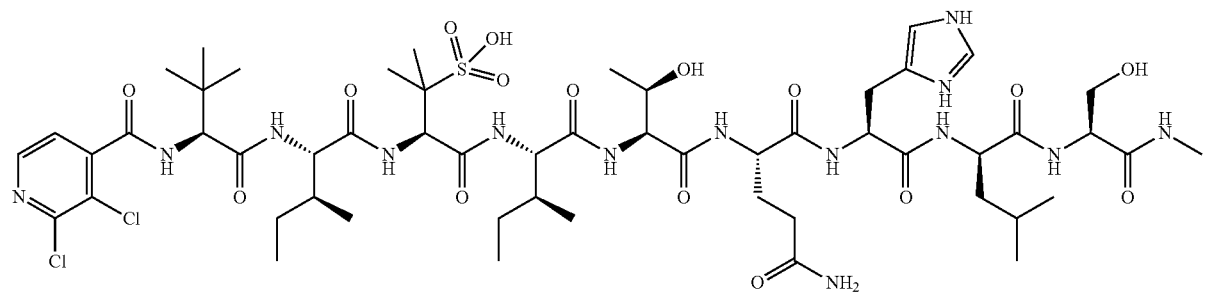
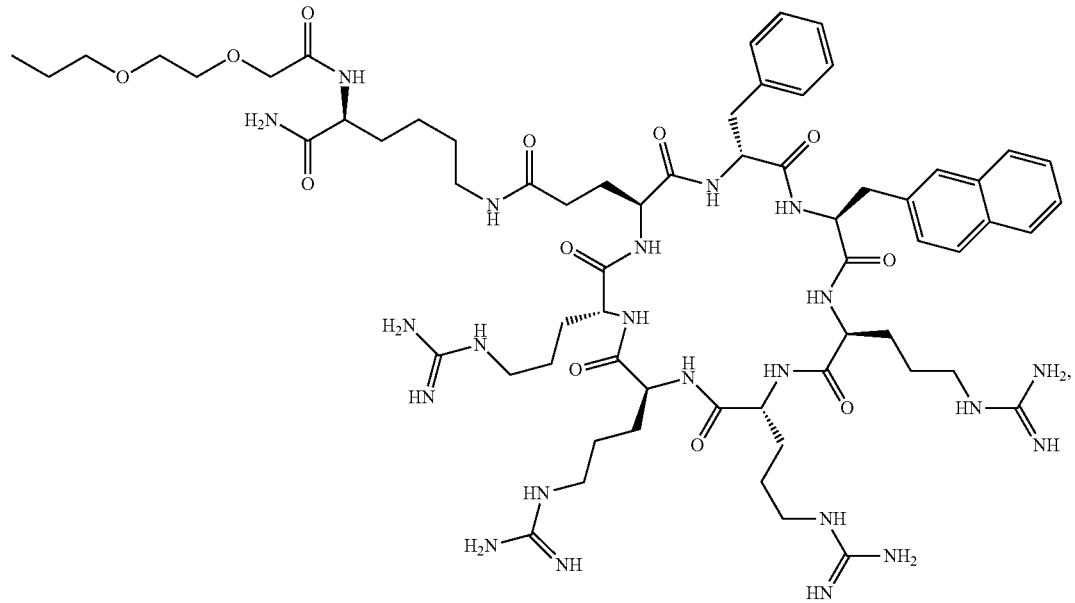

which corresponds to (DCNA)-Tle-Ile-Psa-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ (SEQ ID NO: 211),
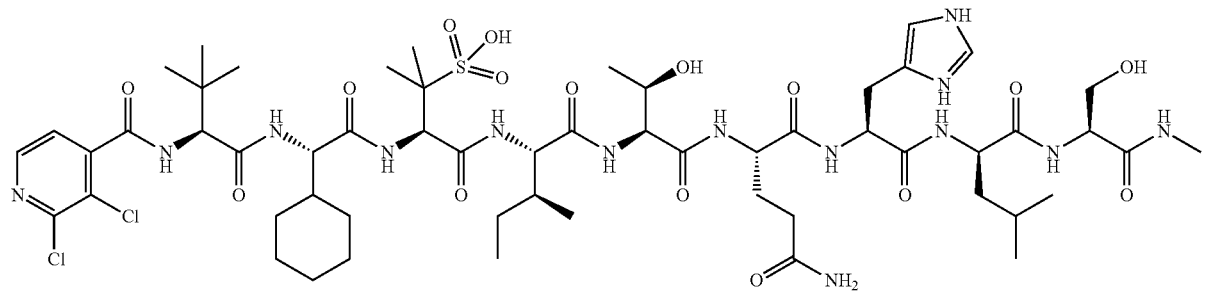
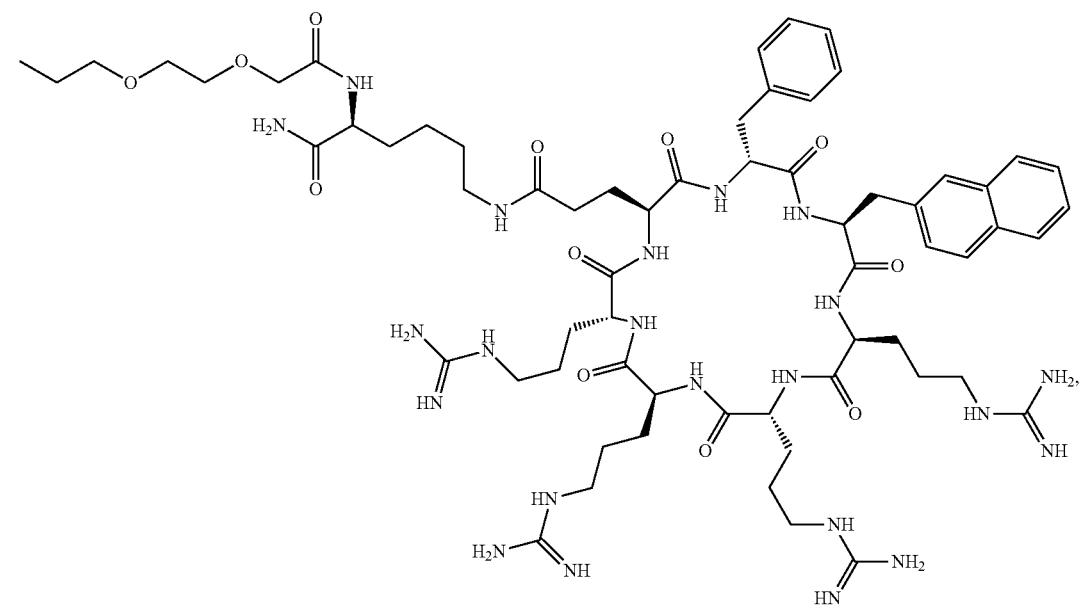
50
which corresponds to (DCNA)-Tle-Chg-Psa-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ (SEQ ID NO: 212),
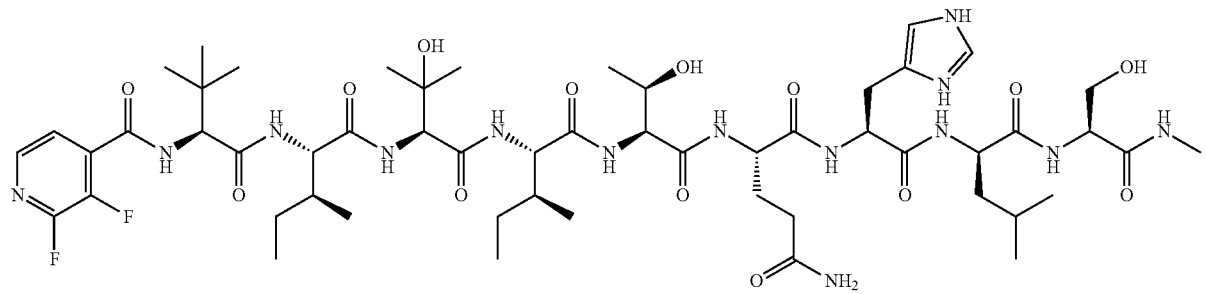

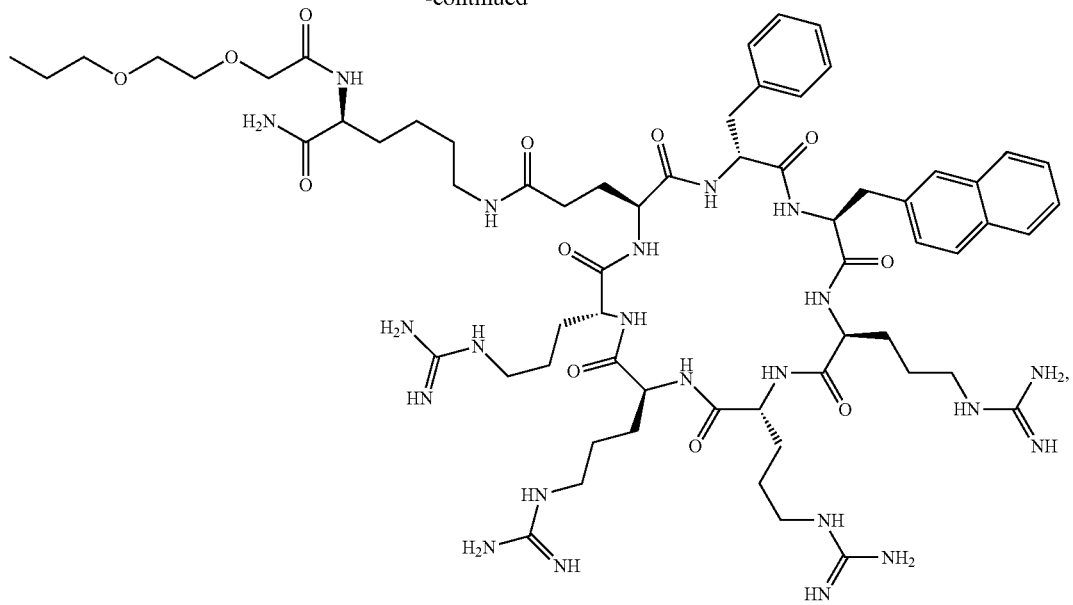
which corresponds to (DFNA)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH₂ (SEQ ID NO: 213),
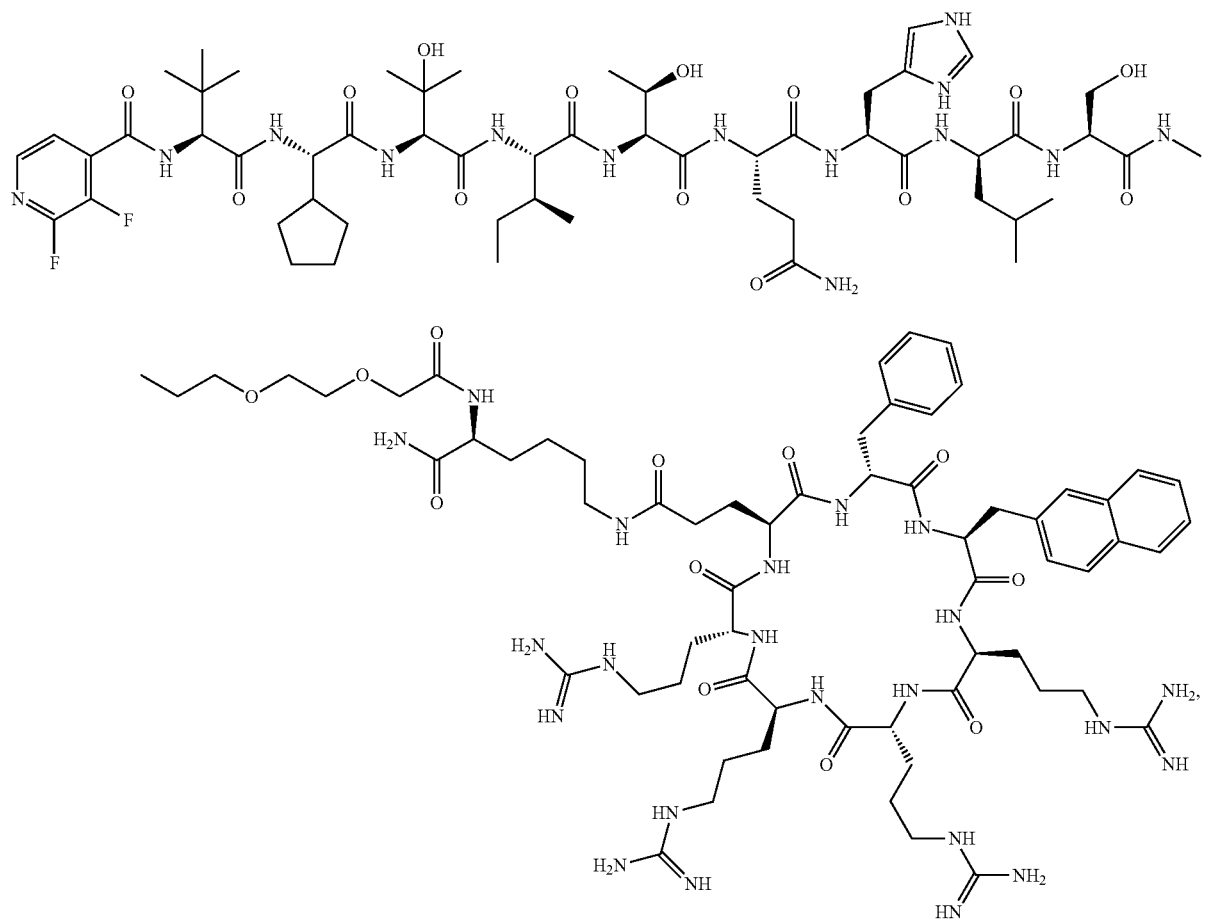

which corresponds to (DFNA)-Tle-Cpg-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$(SEQ ID NO: 214),
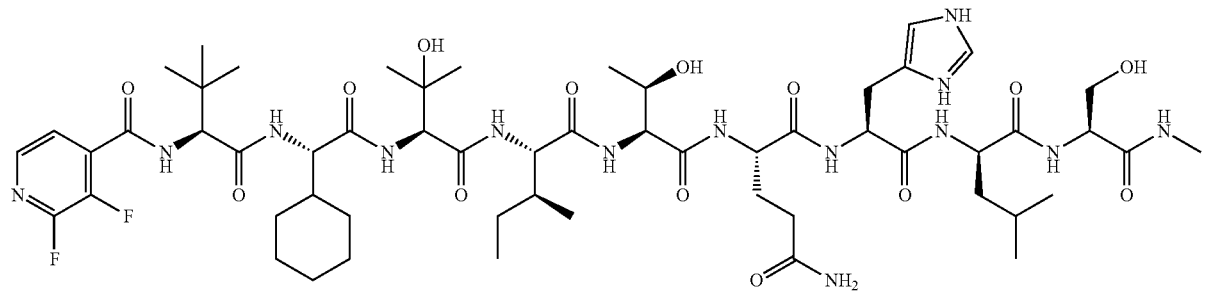
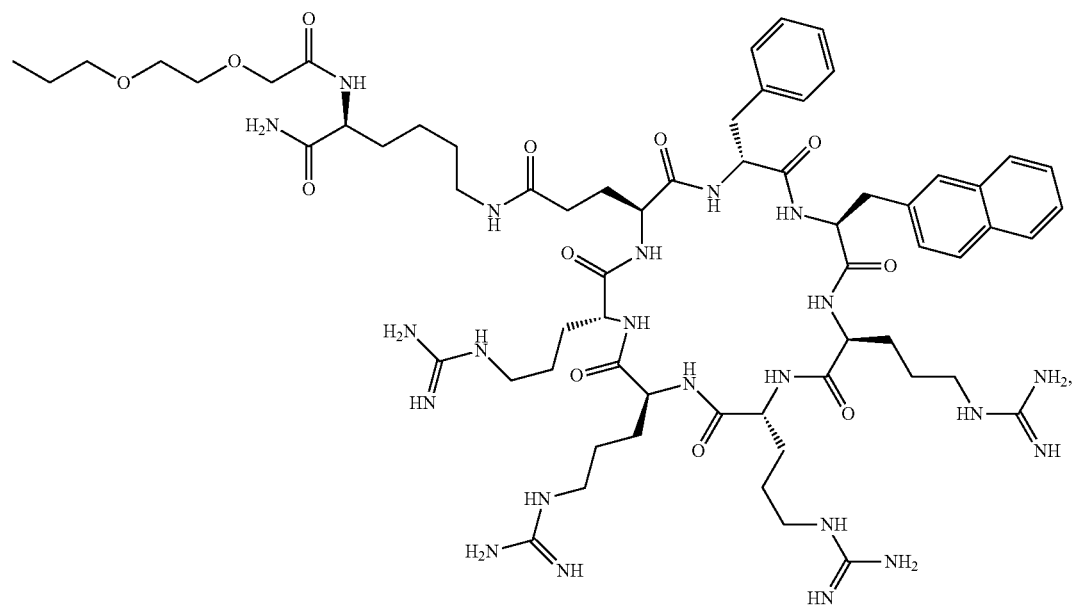
which corresponds to (DFNA)-Tle-Chg-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$ (SEQ ID NO: 215), or
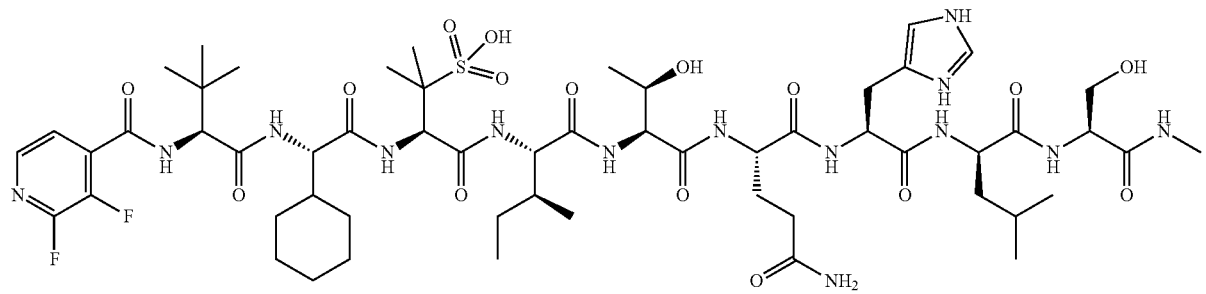

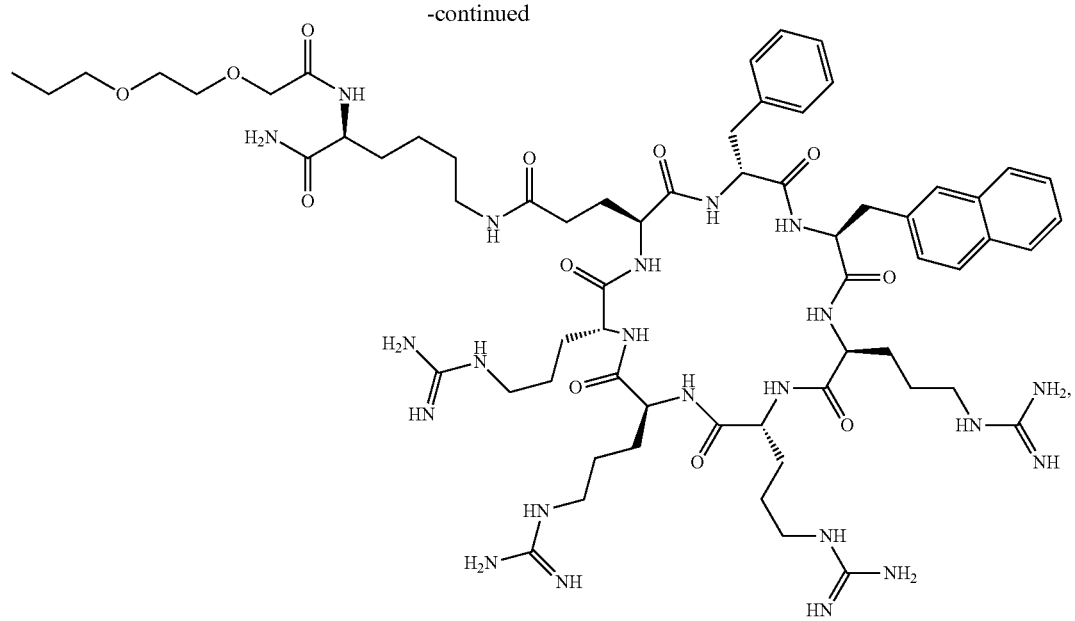
which corresponds to (DFNA)-Tle-Chg-Psa-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH₂ (SEQ ID NO: 216).
17. The polypeptide conjugate of claim 1, having the following structure:
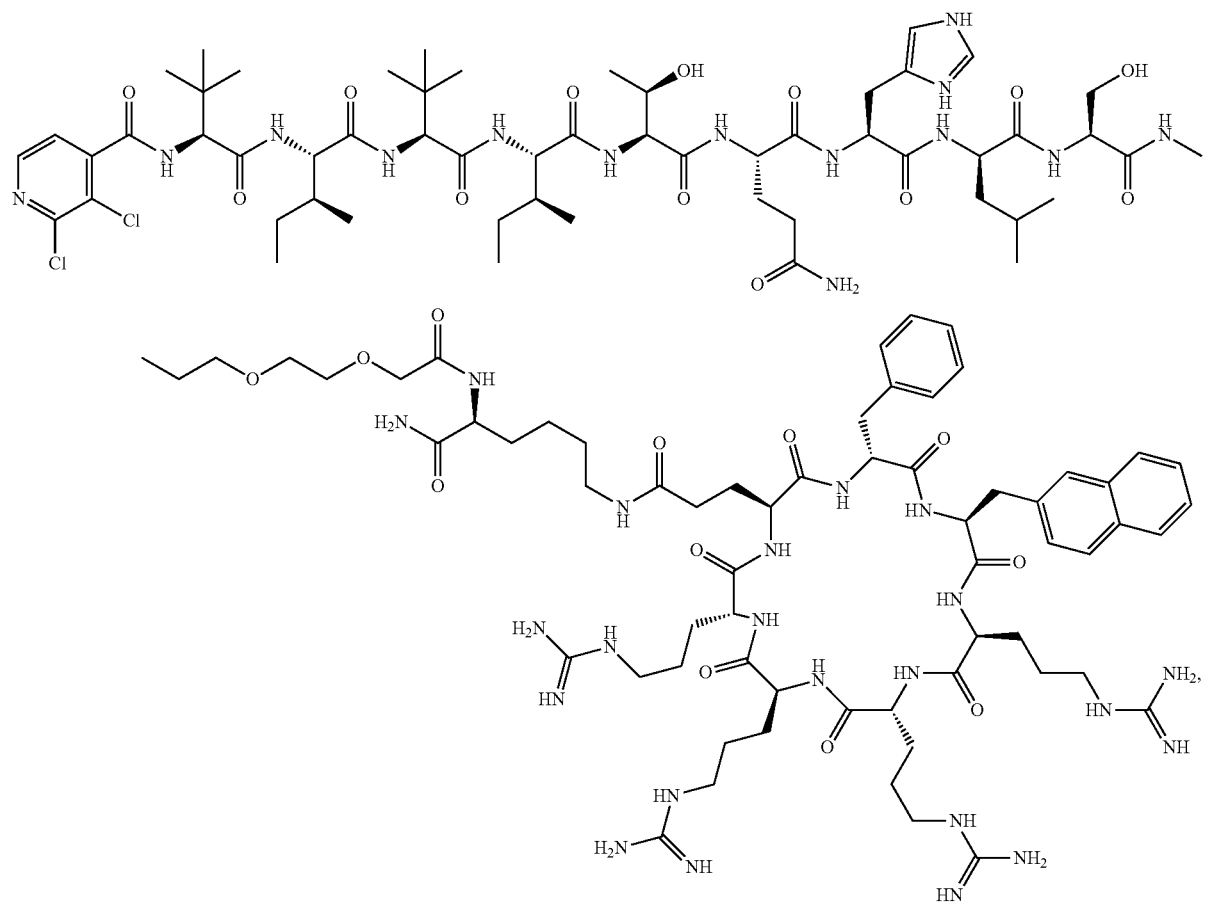

which corresponds to (DCNA)-Tle-Ile-Tle-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$(SEQ ID NO: 206).

18. The polypeptide conjugate of claim 1, having the following structure:

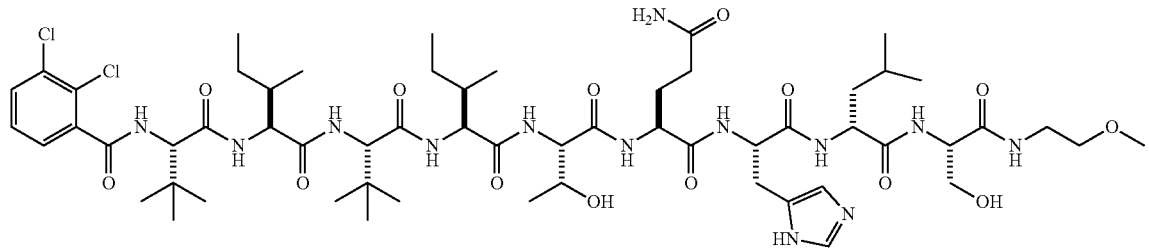

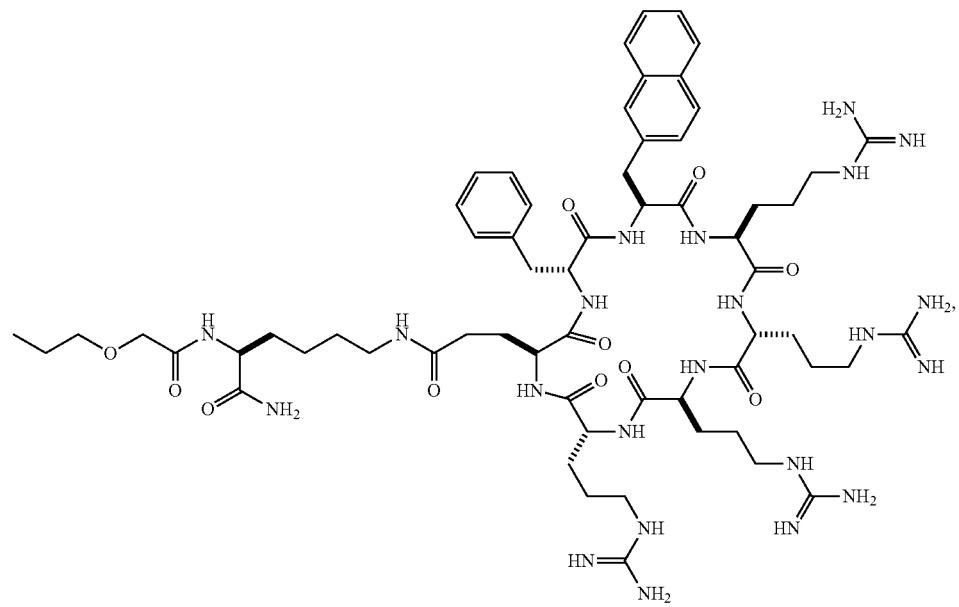

which corresponds to (DCB)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$(SEQ ID NO: 207).

19. The polypeptide conjugate of claim 1, having the following structure:

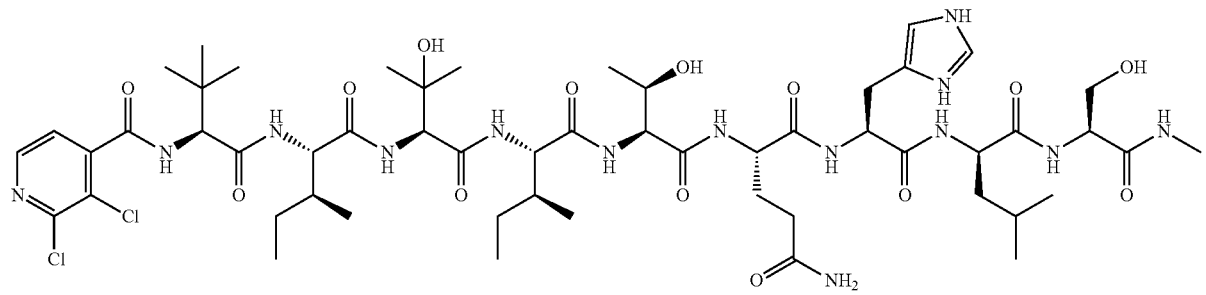

which corresponds to (DCNA)-Tle-Ile-Bhv-Ile-Thr-Gln-His-(D-Leu)-Ser-miniPEG-Lys{[cyclo-(Gln-(D-Arg)-Arg-(D-Arg)-Arg-(2-Nal)-(D-Phe)]}-NH$_2$(SEQ ID NO: 208).

20. A method for inhibiting the binding between CN and one or more ligands, comprising contacting the CN with the polypeptide conjugate of claim 1.

21. A method for treating a subject having acute respiratory distress syndrome (ARDS) comprising administering a therapeutically effective amount of a polypeptide conjugate of claim 1.

* * * * *

UNITED STATES PATENT AND TRADEMARK OFFICE
CERTIFICATE OF CORRECTION

Page 1 of 1

PATENT NO. : 11,576,946 B2
APPLICATION NO. : 16/965718
DATED : February 14, 2023
INVENTOR(S) : Dehua Pei et al.

It is certified that error appears in the above-identified patent and that said Letters Patent is hereby corrected as shown below:

On the Title Page

Item (57) ABSTRACT, approximately Line 60, "conjugated to the N- or C terminus of the CNBM. In some..." should read --conjugated to the N- or C-terminus of the CNBM. In some--

In the Claims

In Column 223, Line 5 of Claim 16, delete "76))," and insert --76),--

In Column 223, Line 55 of Claim 16, delete "76))," and insert --76),--

In Column 225, Line 30 of Claim 16, delete "76))," and insert --76),--

In Column 227, Line 3 of Claim 16, delete "NH$_2$(SEQ" and insert --NH$_2$ (SEQ--

In Column 239, Line 3 of Claim 16, delete "NH$_2$(SEQ" and insert --NH$_2$ (SEQ--

In Column 243, Line 3 of Claim 17, delete "NH$_2$(SEQ" and insert --NH$_2$ (SEQ--

In Column 243, Line 51 of Claim 18, delete "NH$_2$(SEQ" and insert --NH$_2$ (SEQ--

In Column 245, Line 29 of Claim 19, delete "NH$_2$(SEQ" and insert --NH$_2$ (SEQ--

Signed and Sealed this
Twenty-seventh Day of August, 2024

Katherine Kelly Vidal
*Director of the United States Patent and Trademark Office*